(12) United States Patent
Hanazawa et al.

(10) Patent No.: US 7,622,589 B2
(45) Date of Patent: Nov. 24, 2009

(54) SUBSTITUTED SULFONYLAMINOARYLMETHYL CYCLOPROPANECARBOXAMIDE AS VR1 RECEPTOR ANTAGONISTS

(75) Inventors: Takeshi Hanazawa, Aichi-ken (JP); Misato Hirano, Aichi-ken (JP); Tadashi Inoue, Aichi-ken (JP); Satoshi Nagayama, Aichi-ken (JP); Kazunari Nakao, Aichi-ken (JP); Yuji Shishido, Aichi-ken (JP); Hirotaka Tanaka, Aichi-ken (JP)

(73) Assignee: Pfizer Inc., New York, NY (US)

( * ) Notice: Subject to any disclaimer, the term of this patent is extended or adjusted under 35 U.S.C. 154(b) by 417 days.

(21) Appl. No.: 11/384,127

(22) Filed: Mar. 17, 2006

(65) Prior Publication Data

US 2006/0211741 A1 Sep. 21, 2006

Related U.S. Application Data

(60) Provisional application No. 60/733,651, filed on Nov. 4, 2005, provisional application No. 60/699,800, filed on Jul. 15, 2005, provisional application No. 60/663,374, filed on Mar. 17, 2005.

(51) Int. Cl.
*C07D 213/02* (2006.01)
*A61K 31/44* (2006.01)
*A61K 31/445* (2006.01)

(52) U.S. Cl. .......... 546/309; 546/268.1; 546/276.4; 546/336; 514/318; 514/352; 514/357

(58) Field of Classification Search .......... 546/268.1, 546/276.4, 309, 336; 514/318, 352, 357
See application file for complete search history.

(56) References Cited

U.S. PATENT DOCUMENTS

| | | | |
|---|---|---|---|
| 4,681,952 A | 7/1987 | Lantzsch et al. | |
| 4,786,646 A | 11/1988 | Guthrie et al. | 514/346 |
| 4,927,826 A | 5/1990 | Guthrie et al. | 514/256 |
| 4,988,734 A | 1/1991 | Kraatz et al. | 514/624 |
| 5,082,852 A | 1/1992 | Kardorff et al. | 514/351 |
| 5,286,736 A | 2/1994 | Soyka et al. | 514/357 |
| 5,633,239 A | 5/1997 | Englert et al. | 514/83 |
| 2003/0153596 A1 | 8/2003 | Suh et al. | |
| 2004/0110754 A1* | 6/2004 | Wu et al. | 514/237.8 |
| 2004/0204341 A1* | 10/2004 | Allen et al. | 514/2 |
| 2005/0004122 A1 | 1/2005 | Brown et al. | 514/241 |

FOREIGN PATENT DOCUMENTS

| | | |
|---|---|---|
| CA | 1314563 | 3/1993 |
| DE | 1108213 | 6/1961 |
| DE | 102005011056 | 10/2005 |
| GB | 1086191 | 10/1967 |
| GB | 1086192 | 10/1967 |
| JP | 56-005435 | 1/1981 |
| JP | 8245555 | 9/1996 |
| JP | 2005-314407 | 11/2005 |
| RU | 2293080 | 7/2004 |
| WO | WO9406761 | 3/1994 |
| WO | WO9427947 | 12/1994 |
| WO | WO9748397 | 12/1997 |
| WO | WO9748695 | 12/1997 |
| WO | WO9926927 | 6/1999 |
| WO | WO9931060 | 6/1999 |
| WO | WO9931064 | 6/1999 |
| WO | WO0021910 | 4/2000 |
| WO | WO0111966 | 2/2001 |
| WO | WO0155146 | 8/2001 |
| WO | WO0202522 | 1/2002 |
| WO | WO 02/16318 A1 | 2/2002 |
| WO | WO03082190 | 10/2003 |
| WO | WO 2004/047738 | 6/2004 |
| WO | WO2004108133 | 12/2004 |
| WO | WO 2005/003084 A1 | 1/2005 |
| WO | WO 2005/007614 A1 | 1/2005 |
| WO | WO2005051890 | 6/2005 |
| WO | WO2005068468 | 7/2005 |
| WO | WO2006098554 | 9/2006 |

OTHER PUBLICATIONS

Hee-Doo Kim, et al., "Chain-branched 1, 3-dibenzylthioureas as Vanilloid Receptor 1 Antagonists", Bioorganic Medicinal Chemistry Letters, 2004, pp. 1751-1755, vol. 14, No. 7.

Jeewoo Lee, et al., "N-(3-Acyloxy-2-benzylpropyl)-N'-[4-(methylsulfonylamino)benzyl]thiourea Analogues: Novel Potent and High Affinity Antagonists and Partial Antagonists of the Vanilloid Receptor", J Med Chem, 2003, pp. 3116-3126, vol. 46, No. 14.

Jeewoo Lee, et al., 'Analysis of Structure-activity Relationships with the N-(3-Acyloxy-2-benzylpropyl)-N'-[4-(methylsulfonylamino)benzyl]thiourea Template for Vanilloid Receptor 1 Antagonism, Bioorganic & Medicinal Chemistry, 2004, p. 3411-3420, vol. 12, No. 13.

(Continued)

*Primary Examiner*—Shailendra Kumar
(74) *Attorney, Agent, or Firm*—Gregg C. Benson; A. Dean Olson

(57) ABSTRACT

This invention provides a compound of the formula (I):

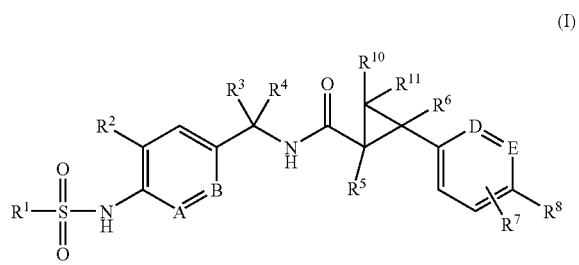

wherein, variables A, B, D, E, and $R^1$ to $R^{11}$ are as defined in the specification.

10 Claims, No Drawings

OTHER PUBLICATIONS

"Rodriques et al: ""A Novel route toCycloPropyl Ketones, Aldehydes, andCarboxylic acids""", Tetrahedron Letters, 1991, pp. 1275-1278, vol. 32, No. 10".

Young-Ger Suh, et al., "Novel non-Vanilloid VR1 Antagonis of High Analgesic Effects and its Structural Requirement for VR1 Antagonistic Effects", Bioorganic & Medicinal Chemistry Letters, 2003, pp. 4389-4398, vol. 13, No. 24.

"Susanna Tchilibon, et al., ""ExploringDistal Regions of the A3 AdenosineReceptor Binding Site: StericallyConstrained N6-(2-phenylethyl)adenosineDerivatives as Potent Ligands""", Bioorganic & Medicinal Chemistry, 2004, pp. 2021-2034, vol. 12, No. 9".

PCT International Search Report for PCT/IB2006/000557 Dated Jul. 5, 2006.

Dutch Industrial Property Office Search Report for Application No. 1031385, Dated Aug. 30, 2006.

C. Deal, et al., "Treatment of Arthritis with Topical Capsaicin:Double-Blind Trial", Clin Ther, 1991, pp. 383-395, vol. 13, No. 3.

J. Fernihough, et al, "Regulation of Calcitonin Gene-related Peptide and TRPV1 in a Rat Model of Osteoarthritis", Neuroscience Letters, Nov. 2005, pp. 75-80, vol. 388, No. 2.

P. Honore, et al., "A-425619 [1-Isoquinolin-5-yl-3-(4-trifluoromethyl-benzyl)-urea], a Novel Transient Receptor Potential Type V1 Receptor Antagonist, Relieves Pathophysiological Pain Associated with Inflammation and Tissue Injury in Rats", J Pharmacol Exp Ther, 2005, pp. 410-421, vol. 314 No. 1.

R. Planells-Cases, et al., Functional Aspects and Mechanisms of TRPV1 Involvement in Neurogenic Inflammation that Leads to Thermal Hyperalgesia, Eur J Physiol, 2005, pp. 151-159, vol. 451.

* cited by examiner

SUBSTITUTED SULFONYLAMINOARYLMETHYL CYCLOPROPANECARBOXAMIDE AS VR1 RECEPTOR ANTAGONISTS

This application is a United States utility application, which claims the benefit of priority to U.S. Provisional Application No. 60/663,374, filed Mar. 17, 2005, U.S. Provisional Application No. 60/699,800, filed Jul. 15, 2005, and U.S. Provisional Application No. 60/733,651, filed Nov. 4, 2005.

TECHNICAL FIELD

This invention relates to novel substituted N-(N-sulfonylaminoarylmethyl)cyclopropanecarboxamide compounds and to their use in therapy. These compounds are particularly useful as antagonists of the VR1 (Type I Vanilloid) receptor, and are thus useful for the treatment of pain, neuralgia, neuropathies, a m nerve injury, burns, migraine, carpal tunnel syndrome, fibromyalgia, neuritis, sciatica, pelvic hypersensitivity, bladder disease, inflammation, or the like in mammals, especially humans. The present invention also relates to a pharmaceutical composition comprising the above compounds and to intermediate compounds useful for preparing the above compounds.

BACKGROUND ART

The Vanilloid receptor 1 (VR1) is a ligand gated non-selective cation channel. It is believed to be a member of the transient receptor potential super family. VR1 is recognized as a polymodal nociceptor that integrates multiple pain stimuli, e.g., noxious heat, protons, and vanilloids (European Journal of Physiology 451:151-159, 2005). A major distribution of VR1 is in the sensory (Aδ- and C-) fibers, which cu are bipolar neurons having somata in sensory ganglia. The peripheral fibers of these neurons innervate the skin, the mucosal membranes, and almost all internal organs. It is also recognized that VR1 exists in bladder, kidney, brain, pancreas, and various kinds of organs. A body of studies using VR1 agonists, e.g., capsaicin or resiniferatoxin, have suggested that VR1 positive nerves are thought to participate in a variety of physiological responses, including nociception (Clinical Therapeutics. 13(3): 338-395, 1991, Journal of Pharmacology and Experimental Therapeutics 314:410-421, 2005, and Neuroscience Letter 388: 75-80, 2005). Based on both the tissue distribution and the roles of VR1, VR1 antagonists would have good therapeutic potential.

International Patent Application Number WO-A-2005003084 discusses 4-(methylsulfonylamino)phenyl analogues which are stated to have activity as VR1 antagonists. International Patent Application Number WO200216318 discloses a variety of sulfonylaminobenzylthiourea derivatives and N-sulfonylaminobenzyl-2-phenoxyacetamide derivatives as modulators for vanilloid receptor. International Patent Application Number WO2004047738 discloses a variety of arylcyclopropylcarboxylic amides as potassium channel openers.

It would be desirable if there were provided improved VR1 selective antagonist with enhanced binding activity with the VR1 receptor by systemic administration and with a good half-life. Other potential advantages include less toxicity, good absorption, good solubility, low protein binding affinity, less drug-drug interaction, a reduced inhibitory activity at HERG channel, reduced QT prolongation and good metabolic stability.

BRIEF DISCLOSURE OF THE INVENTION

It has now been found that substituted N-(N-sulfonylaminoarylmethyl)cyclopropanecarboxamide compounds are potent VR1 antagonists with analgesic activity by systemic administration. The compounds of the present invention may show less toxicity, good absorption, good half-life, good solubility, low protein binding affinity, less drug-drug interaction, a reduced inhibitory activity at HERG channel, reduced QT prolongation and good metabolic stability.

The present invention provides a compound of the following formula (I):

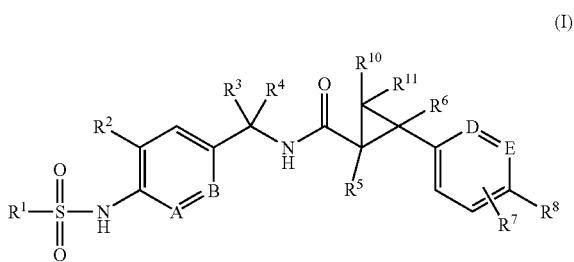

(I)

wherein
A and B are independently $CR^{12}$ or N;
D and E are each independently $CR^9$ or N;
$R^1$ represents $(C_1-C_6)$alkyl;
$R^2$ represents hydrogen, halogen, hydroxy, $(C_1-C_6)$alkyl, halo$(C_1-C_6)$alkyl, hydroxy$(C_1-C_6)$alkyl, $(C_1-C_6)$alkoxy or $(C_1-C_6)$alkoxy-$(C_1-C_6)$alkyl;
$R^3$, $R^4$, $R^5$, $R^6$, $R^{10}$ and $R^{11}$ each independently represent hydrogen, halogen, $(C_1-C_6)$alkyl, halo$(C_1-C_6)$alkyl, $(C_1-C_6)$alkoxy, hydroxy$(C_1-C_6)$alkyl or $(C_1-C_6)$alkoxy-$(C_1-C_6)$alkyl; or
$R^3$ and $R^4$ are taken together with the carbon atom to which they are attached to form a 3- to 7-membered carbocyclic ring or heterocyclic ring in which one or two non-adjacent carbon atoms are optionally replaced by an oxygen atom, a sulfur atom or NH;
$R^7$ and $R^9$ each independently represent hydrogen, halogen, $(C_1-C_6)$alkyl, halo$(C_1-C_6)$alkyl, hydroxy$(C_1-C_6)$alkyl, $(C_1-C_6)$alkoxy, hydroxy$(C_1-C_6)$alkoxy, $(C_1-C_6)$alkoxy-$(C_1-C_6)$alkyl, $(C_1-C_6)$alkoxy, $(C_1-C_6)$alkylthio, $(C_1-C_6)$alkylsulfinyl, $(C_1-C_6)$alkylsulfonyl, $NH_2$, $[(C_1-C_6)$alkyl]NH—, $[(C_1-C_6)$alkyl$]_2$N—, $H_2$N—$(C_1-C_6)$alkoxy, $(C_1-C_6)$alkyl-NH—$(C_1-C_6)$alkoxy, $[(C_1-C_6)$alkyl$]_2$N$(C_1-C_6)$alkoxy; $H_2$N—$(C_1-C_6)$alkoxy-$(C_1-C_6)$alkyl, $(C_1-C_6)$alkyl-NH—$(C_1-C_6)$alkoxy-$(C_1-C_6)$alkyl, $[(C_1-C_6)$alkyl$]_2$N$(C_1-C_6)$alkoxy-$(C_1-C_6)$alkyl or 5- or 6-membered heterocyclic ring containing at least one nitrogen atom;
$R^8$ represents halogen, $(C_1-C_6)$alkyl, halo$(C_1-C_6)$alkyl, hydroxy$(C_1-C_6)$alkyl, $(C_1-C_6)$alkoxy, hydroxy$(C_1-C_6)$alkoxy, $(C_1-C_6)$alkoxy-$(C_1-C_6)$alkyl, $(C_1-C_6)$alkoxy-$(C_1-C_6)$alkoxy, halo$(C_1-C_6)$alkylsulfonyl, halo$(C_1-C_6)$alkylsulfinyl, halo$(C_1-C_6)$alkoxy, halo$(C_1-C_6)$alkylthio, $[(C_1-C_6)$alkyl]NH— or $[(C_1-C_6)$alkyl$]_2$N—; or
$R^7$ and $R^8$, when E is $CR^9$, are taken together with the carbon atoms to which they are attached form a 5-8 membered carbocyclic or heterocyclic ring, in which one or two non-adjacent carbon atoms are optionally replaced by oxygen, sulfur, N or NH groups, wherein the carbocyclic ring or the heterocyclic ring is unsubstituted or substituted with one or more substituents each independently selected from the group consisting of hydroxy, $(C_1-C_6)$alkyl, $(C_1-C_6)$alkoxy and hydroxy$(C_1-C_6)$alkyl; and $R^{12}$ represents hydrogen, halogen, $(C_1-C_6)$alkyl or hydroxy $(C_1-C_6)$alkyl;

or a pharmaceutically acceptable salt or solvate thereof.

DETAILED DESCRIPTION OF THE INVENTION

As used herein, the term "halogen" means a fluoro, a chloro, a bromo or an iodo atom, preferably a fluoro or a chloro atom.

As used herein, the terms "$(C_1-C_6)$alkyl" and "$(C_1-C_3)$alkyl" mean straight or branched chain saturated radicals having the required number of carbon atoms, including, but not limited to methyl, ethyl, n-propyl, iso-propyl, n-butyl, iso-butyl, secondary-butyl, tert-butyl and 2-methylbutyl groups. Preferred alkyl groups are methyl, ethyl, n-propyl, f-butyl, tert-butyl and 2-methylbutyl groups.

As used herein, the term "hydroxy$(C_1-C_6)$alkyl" means $(C_1-C_6)$alkyl radical as defined above which is substituted by at least one hydroxy group including, but not limited to, hydroxymethyl, hydroxyethyl, hydroxy n-propyl, hydroxy iso-propyl (e. g. 2-hydroxy-1,1-dimethylethyl), hydroxy n-butyl, hydroxy iso-butyl, hydroxy secondary-butyl and hydroxy tert-butyl. Preferred hydroxyalkyl groups are hydroxymethyl, hydroxyethyl, hydroxy n-propyl, hydroxy iso-propyl (e. g. 2-hydroxy-1,1-dimethylethyl) and hydroxy n-butyl.

As used herein, the term "$(C_1-C_6)$alkoxy" means $(C_1-C_6)$alkyl-O— wherein $(C_1-C_6)$alkyl radical is as defined above, including, but not limited to methoxy, ethoxy, n-propoxy, iso-propoxy, n-butoxy, iso-butoxy, sec-butoxy and tert-butoxy. Preferred alkoxy groups are methoxy, ethoxy, n-propoxy, n-butoxy and tert-butoxy.

As used herein, the term "hydroxy$(C_1-C_6)$alkoxy" means $(C_1-C_6)$alkoxy radical as defined above which is substituted by hydroxy group including, but not limited to, hydroxymethoxy, hydroxyethoxy, hydroxy n-propoxy, hydroxy iso-propoxy, hydroxy n-butoxy, hydroxy iso-butoxy, hydroxy sec-butoxy and hydroxy tert-butoxy. Preferred hydroxyalkoxy groups are hydroxymethoxy, hydroxyethoxy, hydroxy n-propoxy and hydroxy n-butoxy.

As used herein, the term "$(C_1-C_6)$alkoxy-$(C_1-C_6)$alkyl" means $(C_1-C_6)$alkyl radical as defined above which is substituted by $(C_1-C_6)$alkoxy group as defined above.

As used herein, the term "$(C_1-C_6)$alkoxy-$(C_1-C_6)$alkoxy" means $(C_1-C_6)$alkoxy radical as defined above which is substituted by $(C_1-C_6)$alkoxy as defined above. Preferred alkoxy-alkoxy groups are methoxy methoxy, methoxy ethoxy or ethoxy ethoxy groups.

As used herein the term "halo$(C_1-C_6)$alkyl", means $(C_1-C_6)$alkyl radical which is substituted by one or more halogen atoms as defined above including, but not limited to, fluoromethyl, difluoromethyl, trifluoromethyl, 2-fluoroethyl, 2,2-difluoroethyl, 2,2,2-trifluoroethyl, 2,2,2-trifluoro-1,1-dimethylethyl, 2,2,2-trichloroethyl, 3-fluoropropyl, 4-fluorobutyl, chloromethyl, trichloromethyl, iodomethyl, bromomethyl and 4,4,4-trifluoro-3-methylbutyl groups. Preferred halo$(C_1-C_6)$alkyl groups are fluoromethyl, difluoromethyl, trifluoromethyl, 2-fluoroethyl, 2,2-difluoroethyl, 2,2,2-trifluoroethyl and 2,2,2-trifluoro-1,1-dimethylethyl groups.

As used herein the terms "halo$(C_1-C_6)$alkoxy", and "halo$(C_1-C_3)$alkoxy" mean $(C_1-C_6)$alkyl-O— or $(C_1-C_3)$alkyl-O—, which is substituted by one or more halogen atoms as defined above including, but not limited to, fluoromethoxy, difluoromethoxy, trifluoromethoxy, 2-fluoroethoxy, 2,2-difluoroethoxy, 2,2,2-trifluoroethoxy, 2,2,2-trifluoro-1,1-dimethylethoxy, 2,2,2-trichloroethoxy, 3-fluoropropoxy, 4-fluorobutoxy, chloromethoxy, trichloromethoxy, iodomethoxy, bromomethoxy and 4,4,4-trifluoro-3-methylbutoxy groups. Preferred halo$(C_1-C_6)$alkyl-O— or halo$(C_1-C_3)$alkyl-O— groups are fluoromethoxy, difluoromethoxy, trifluoromethoxy, 2-fluoroethoxy, 2,2-difluoroethoxy, 2,2,2-trifluoroethoxy and 2,2,2-trifluoro-1,1-dimethylethoxy groups.

As used herein, the terms "halo$(C_1-C_6)$alkylthio" and "halo$(C_1-C_3)$alkylthio" mean $(C_1-C_6)$alkyl-S— or $(C_1-C_3)$alkyl-S—, which is substituted by one or more halogen atoms as defined above, including, but not limited to fluoromethylthio, difluoromethylthio, trifluoromethylthio, 2-fluoroethylthio, 2,2-difluoroethylthio, 2,2,2-trifluoroethylthio, 2,2,2-trifluoro-1,1-dimethylethylthio, 2,2,2-trichloroethylthio, 3-fluoropropylthio, 4-fluorobutylthio, chloromethylthio, trichloromethylthio, iodomethylthio, bromomethylthio and 4,4,4-trifluoro-3-methylbutylthio groups. Preferred halo$(C_1-C_6)$alkylthio or halo$(C_1-C_3)$alkylthio groups are fluoromethylthio, difluoromethylthio, trifluoromethylthio, 2-fluoroethylthio, 2,2-difluoroethylthio, 2,2,2-trifluoroethylthio and 2,2,2-trifluoro-1,1-dimethylethylthio groups.

As used herein, the terms "halo$(C_1-C_6)$alkylsulfinyl" and "halo$(C_1-C_3)$alkylsulfinyl" mean $(C_1-C_6)$alkyl-SO— or $(C_1-C_3)$alkyl-SO—, which is substituted by one or more halogen atoms as defined above, including, but not limited to fluoromethylsulfinyl, difluoromethylsulfinyl, trifluoromethylsulfinyl, 2-fluoroethylsulfinyl, 2,2-difluoroethylsulfinyl, 2,2,2-trifluoroethylsulfinyl, 2,2,2-trifluoro-1,1-dimethylethylsulfinyl, 2,2,2-trichloroethylsulfinyl, 3-fluoropropylsulfinyl, 4-fluorobutylsulfinyl, chloromethylsulfinyl, trichloromethylsulfinyl, iodomethylsulfinyl, bromomethylsulfinyl and 4,4,4-trifluoro-3-methylbutylsulfinyl groups. Preferred halo$(C_1-C_6)$alkylsulfinyl or halo$(C_1-C_3)$alkylsulfinyl groups are fluoromethylsulfinyl, difluoromethylsulfinyl, trifluoromethylsulfinyl, 2-fluoroethylsulfinyl, 2,2-difluoroethylsulfinyl, 2,2,2-trifluoroethylsulfinyl and 2,2,2-trifluoro-1,1-dimethylethylsulfinyl groups.

As used herein, the terms "halo$(C_1-C_6)$alkylsulfonyl" and "halo$(C_1-C_3)$alkylsulfonyl" mean $(C_1-C_6)$alkyl-SO$_2$— or $(C_1-C_3)$alkyl-SO$_2$—, which is substituted by one or more halogen atoms as defined above, including, but not limited to fluoromethylsulfonyl, difluoromethylsulfonyl, trifluoromethylsulfonyl, 2-fluoroethylsulfonyl, 2,2-difluoroethylsulfonyl, 2,2,2-trifluoroethylsulfonyl, 2,2,2-trifluoro-1,1-dimethylethylsulfonyl, 2,2,2-trichloroethylsulfonyl, 3-fluoropropylsulfonyl, 4-fluorobutylsulfonyl, chloromethylsulfonyl, trichloromethylsulfonyl, iodomethylsulfonyl, bromomethylsulfonyl and 4,4,4-trifluoro-3-methylbutylsulfonyl groups. Preferred halo$(C_1-C_6)$alkylsulfonyl or halo$(C_1-C_3)$alkylsulfonyl groups are fluoromethylsulfonyl, difluoromethylsulfonyl, trifluoromethylsulfonyl, 2-fluoroethylsulfonyl, 2,2-difluoroethylsulfonyl, 2,2,2-trifluoroethylsulfonyl and 2,2,2-trifluoro-1,1-dimethylethylsulfonyl groups.

As used herein, the term "3 to 7 membered carbocyclic ring" and "5 to 8 membered carbocyclic ring" means a saturated carbocyclic ring having the required number of carbon atoms including, but not limited to, cyclopropyl, cyclobutyl, cyclopentyl, cyclohexyl and cycloheptyl. Preferred carbocyclic rings are cyclopropyl, cyclopentyl and cyclohexyl.

As used herein the term "3 to 7 membered heterocyclic ring" and "5 to 8 membered heterocyclic ring" means a carbocyclic ring having the required number of carbon atoms in which one or two non-adjacent carbon atoms are replaced by oxygen, sulfur or NH. Examples of such heterocyclic rings include, but are not limited to, tetrahydrofuran, tetrahydrothiophen, tetrahydrothiazole, tetrahydropyrrole, tetrahydropyran, tetrahydropyridine, tetrahydroprazine, tetrahydropyrimidine and 3,4-dihydro-2H-pyran. Preferred heterocyclic rings are tetrahydrofuran, tetrahydrothiophen, tetrahydropyrrole, tetrahydropyridine and 3,4-dihydro-2H-pyran.

As used herein the term "5- or 6-membered heterocyclic ring containing at least one nitrogen atom" means 5- or 6-membered heterocyclic ring containing either from 1 to 3 nitrogen heteroatoms, or 1 or 2 nitrogen heteroatoms and 1 oxygen or 1 sulphur heteroatom including, but are not limited to, 1H-pyrrole, 2-pyridyl, 3-pyridyl, 4-pyridyl, pyrrolidino, 2-pyrrolidyl, 3-pyrrolidyl, piperidino, 2-piperidyl, 3-piperidyl, 4-piperidyl, morpholino and thiomorpholino. Preferred 5- or 6-membered heterocyclic rings are 2-pyridyl, 4-pyridyl, pyrrolidino, piperidino, morpholino and thiomorpholino.

As used herein, the term "$[(C_1-C_6)alkyl]NH-$" means alkyl-NH— wherein alkyl is defined above, including, but not limited to methylamino, ethylamino, n-propylamino, iso-propylamino, n-butylamino, iso-butylamino, secondary-butylamino, tert-butylamino. Preferred alkylamino groups are methylamino, ethylamino, n-propylamino, n-butylamino.

As used herein, the term "$[(C_1-C_6)alkyl]_2N-$" means dialkyl-N— wherein alkyl is defined above, including, but not limited to dimethylamino, diethylamino, methylethylamino, di n-propylamino, methyl n-propylamino, ethyl n-propylamino di iso-propylamino, di n-butylamino, methyl n-butylamino di iso-butylamino, di secondary-butylamino, di tert-butylamino. Preferred dialkylamino groups are dimethylamino, diethylamino, di n-propylamino, di n-butylamino.

Preferably A is $CR^{12}$, B is $CR^{12}$ or N, D is $CR^9$, and E is $CR^9$ or N; more preferably A is $CR^{12}$, B is $CR^{12}$ or N, D is $CR^9$, and E is $CR^9$ or N, wherein B and E are not N at the same time; still more preferably A is $CR^{12}$, B is $CR^{12}$ or N, D is $CR^9$, and E is $CR^9$ or N, except when B is N, and $R^8$ is trifluoromethyl; or E is N, and $R^2$ is fluoro; most preferably A is $CR^{12}$, B is $CR^{12}$, D is $CR^9$, and E is $CR^9$.

Preferably $R^1$ is $(C_1-C_3)$alkyl; more preferably methyl.

Preferably $R^2$ is hydrogen, halogen, $(C_1-C_6)$alkyl, or hydroxy$(C_1-C_6)$alkyl; more preferably hydrogen, fluoro, methyl, ethyl, hydroxymethyl or hydroxyethyl.

Preferably $R^3$ is hydrogen or $(C_1-C_3)$alkyl; still more preferably hydrogen, methyl or ethyl; most preferably methyl or ethyl.

Preferably $R^4$ is hydrogen or $(C_1-C_3)$alkyl; still more preferably hydrogen, methyl or ethyl; most preferably hydrogen.

Preferably $R^5$, $R^6$, $R^{10}$ and $R^{11}$ are each independently hydrogen, halogen, $(C_1-C_3)$alkyl or hydroxy$(C_1-C_3)$alkyl, more preferably $R^5$ is hydrogen; more preferably $R^6$ is hydrogen, $(C_1-C_3)$alkyl, $(C_1-C_3)$alkoxy or hydroxy$(C_1-C_3)$alkyl; still more preferably hydrogen, methyl, ethyl, methoxy or hydroxymethyl; most preferably methyl, ethyl or methoxy; more preferably $R^{10}$ and $R^{11}$ are each independently hydrogen.

Preferably $R^7$ and $R^9$ are each independently hydrogen, halogen, hydroxy$(C_1-C_6)$alkyl, $[(C_1-C_6)alkyl]_2N-$, pyridyl, piperidino, pyrrolidino or morpholino ; more preferably hydrogen, fluoro, chloro, hydroxymethyl, dimethylamino, 4-pyridyl(4-yl-pyridine), piperidino, pyrrolidino or morpholino; most preferably hydrogen or fluoro.

Preferably $R^8$ is $(C_1-C_6)$alkyl, halo$(C_1-C_6)$alkyl, hydroxy$(C_1-C_6)$alkyl, $(C_1-C_3)$alkoxy, $(C_1-C_6)$alkoxy-$(C_1-C_6)$alkyl, halo$(C_1-C_3)$alkoxy, halo$(C_1-C_3)$alkylthio or halo$(C_1-C_3)$alkylsulfonyl; more preferably $(C_1-C_6)$alkyl halo$(C_1-C_6)$alkyl, halo$(C_1-C_3)$alkoxy, hydroxy$(C_1-C_6)$alkyl, $(C_1-C_6)$alkoxy-$(C_1-C_6)$alkyl, halo$(C_1-C_3)$alkylthio or halo$(C_1-C_3)$alkylsulfonyl; still more preferably tert-butyl, trifluoromethyl, 2,2,2-trifluoro-1,1-dimethylethyl, trifluoromethoxy, trifluoromethylthio, trifluoromethylsulfonyl, 2-hydroxy-1,1-dimethylethyl or 2-methoxy-1,1-dimethylethyl; most preferably tert-butyl, trifluoromethyl, 2,2,2-trifluoro-1,1-dimethylethyl, trifluoromethoxy or trifluoromethylthio.

Preferably $R^{12}$ is hydrogen, halogen, $(C_1-C_6)$alkyl, or hydroxy$(C_1-C_6)$alkyl; more preferably hydrogen, fluoro, methyl, ethyl, hydroxymethyl or hydroxyethyl.

Preferably $R^5$ and $R^6$ are trans.

Preferred compounds of the invention include those in which each variable in formula (I) is selected from the preferred groups for each variable.

Specific preferred compounds of the invention are those listed in the Examples section below and the pharmaceutically acceptable salts and solvates thereof.

The compounds of formula (I), being VR1 antagonists, are potentially useful in the treatment of a range of disorders, particularly the treatment of acute cerebral ischemia, pain, chronic pain, acute pain, nociceptive pain, neuropathic pain, inflammatory pain, post herpetic neuralgia, neuropathies, neuralgia, diabetic neuropathy, HIV-related neuropathy, nerve injury, rheumatoid arthritic pain, osteoarthritic pain, burns, back pain, visceral pain, cancer pain, dental pain, headache, migraine, carpal tunnel syndrome, fibromyalgia, neuritis, sciatica, pelvic hypersensitivity, pelvic pain, menstrual pain, bladder disease, such as incontinence, micturition disorder, renal colic and cystitis, inflammation, such as burns, rheumatoid arthritis and osteoarthritis, neurodegenerative disease, such as stroke, post stroke pain and multiple sclerosis, pulmonary disease, such as asthma, cough, chronic obstructive pulmonary disease (COPD) and broncho constriction, gastrointestinal disorders, such as gastroesophageal reflux disease (GERD), dysphagia, ulcer, irritable bowel syndrome (IBS), inflammatory bowel disease (IBD), colitis and Crohn's disease, ischemia, such as cerebrovascular ischemia, emesis, such as cancer chemotherapy-induced emesis, and obesity, or the like in mammals, especially humans. The treatment of pain, particularly neuropathic pain, is a preferred use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:

pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;

heart and vascular pain, including pain caused by angina, myocardical infarction, mitral stenosis, pericarditis, Raynaud's phenomenon, scleredoma and skeletal muscle ischemia;

head pain, such as migraine (including migraine with aura and migraine without aura), cluster headache, tension-type headache mixed headache and headache associated with vascular disorders; and orofacial pain, including dental pain, otic pain, burning mouth syndrome and temporomandibular myofascial pain.

The present invention provides a pharmaceutical composition including a compound of formula (I), or a pharmaceutically acceptable salt or solvate thereof, together with a pharmaceutically acceptable excipient. The composition is preferably useful for the treatment of the disease conditions defined above.

The present invention further provides a compound of formula (I), or a pharmaceutically acceptable salt or solvate thereof, for use as a medicament.

Further, the present invention provides a method for the treatment of the disease conditions defined above in a mammal, preferably a human, which includes administering to said mammal a therapeutically effective amount of a compound of formula (I), or a pharmaceutically acceptable salt or solvate thereof.

Yet further, the present invention provides the use of a compound of formula (I), or a pharmaceutically acceptable salt or solvate thereof, in the manufacture of a medicament for the treatment of the disease conditions defined above.

Yet further, the present invention provides a combination of a compound of the formula (I), or a pharmaceutically acceptable salt or solvate thereof, and another pharmacologically active agent.

Yet further, the present invention provides an intermediate compound of the formula (Ia):

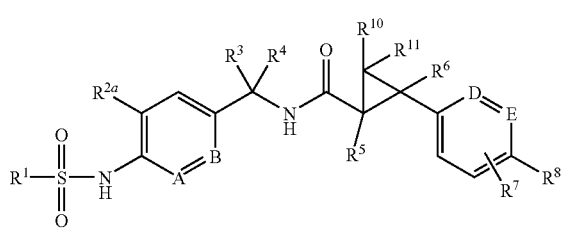

wherein A, B, D, E, $R^1$, $R^3$, $R^4$, $R^5$, $R^6$, $R^7$, $R^8$, $R^{10}$, $R^{11}$ and $R^{12}$ are as defined in the above; and $R^{2a}$ represents $(C_1-C_6)$ alkoxycarbonyl; or a pharmaceutically acceptable salt or solvate thereof.

Preferably $R^{2a}$ is $(C_1-C_3)$ alkoxycarbonyl; more preferably methoxycarbonyl or ethoxycarbonyl.

Yet further, the present invention provides an intermediate compound of the formula (III):

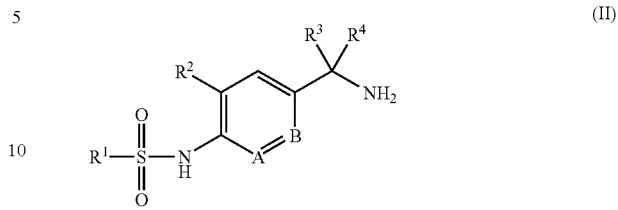

wherein A, B, $R^1$, $R^2$, $R^3$ and $R^4$ are as defined in the above; or a pharmaceutically acceptable salt or solvate thereof.

Yet further, the present invention provides an intermediate compound of the formula (III):

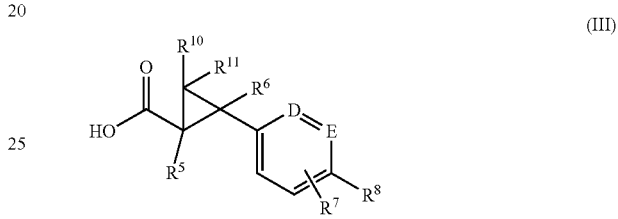

D, E, $R^5$, $R^6$, $R^8$, $R^7$, $R^{10}$ and $R^{11}$ are as defined in the above; or a pharmaceutically acceptable salt or solvate thereof.

Preferred intermediate compounds of the invention include those in which each variable in Formula (Ia), (II) or (III) is selected from the above mentioned preferred groups for each variable.

In this specification, especially in "General Synthesis" and "Examples", the following abbreviations can be used:

BEP 2-bromo-1-ethylpyridinium tetrafluoroborate
BOP benzotriazol-1-yloxy-tris(dimethylamino)phosphonium hexafluorophosphate
CDI 2-chloro-1,3-dimethylimidazolinium chloride
Co(TPP) 5, 10, 15, 20 tetraphenyl-21H,23H porphine Co(II)
DCC dicyclohexylcarbodiimide
DCM dichloromethane
DME 1,2-dimethoxyethane, dimethoxyethane
DMF N,N-dimethylformamide
DMSO dimethyl sulfoxide
EDC 1-ethyl-3-(3'-dimethylaminopropyl)carbodiimide hydrogen chloride)
EtOAc ethyl acetate
EtOH ethanol
HOBt 1-hydroxybenzotriazole
MeOH methanol
NMP N-methyl-2-pyrroliidone
$PdCl_2$ (pddf).$CH_2Cl_2$ palladiumdichloro-1,1'-bis(diphenylphosphino)ferrocene-dichloromethane complex
THF tetrahydrofuran
TFA trifluoroacetic acid General Synthesis The compounds of the present invention may be prepared by a variety of processes well known for the preparation of compounds of this type, for example as shown in the following reaction Schemes. The term "protecting group", as used hereinafter, means a hydroxy or amino protecting group which is selected from typical hydroxy or amino protecting groups described in Protective Groups in Organic Synthesis edited by T. W. Greene et al. (John Wiley & Sons, 1999). In the following general methods, A, B, D, E, $R^1$, $R^2$, $R^3$, $R^4$, $R^5$, $R^6$, $R^7$, $R^8$, $R^9$, $R^{10}$, $R^{11}$ and $R^{12}$ are as previously defined for the formula (I) unless otherwise stated.

The following reaction scheme illustrates the preparation of compounds of formula (I).

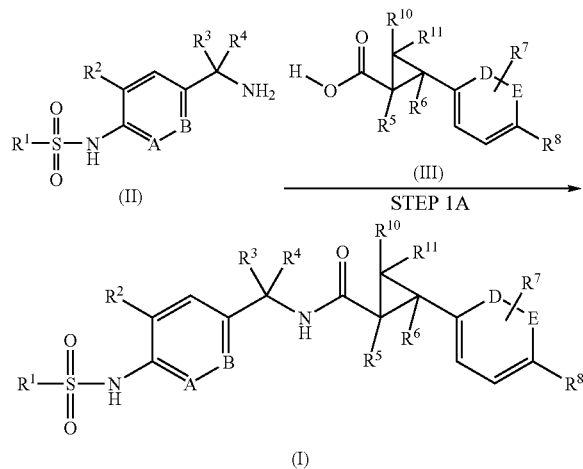

Step 1A

In this Step, an amide compound of formula (I) can be prepared by the coupling reaction of an amine compound of formula (II) with the acid compound of formula (III) in the presence or absence of a coupling reagent in an inert solvent. This reaction can be also carried out via activated carboxylic derivatives. Suitable coupling reagents are those typically used in peptide synthesis including, for example, diimides (e.g., DCC, EDC), 2-ethoxy-N-ethoxycarbonyl-1,2-dihydroquinoline, BEP, CDI, BOP, diethyl azodicarboxylate-triphenylphosphine, diethylcyanophosphate, diethylphosphorylazide, 2-chloro-1-methylpyridinium iodide, N,N'-carbonyldiimidazole, benzotriazole-1-yl diethyl phosphate, ethyl chloroformate and isobutyl chloroformate.

The reaction can be carried out in the presence of a base such as, HOBt, N,N-diisopropylethylamine, N-methylmorpholine or triethylamine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: acetone; nitromethane; DMF; NMP; sulfolane; DMSO; 2-butanone; acetonitrile; halogenated hydrocarbons, such as DCM, dichloroethane, chloroform; and ethers, such as THF and 1,4-dioxane.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 100° C., more preferably from about 0° C. to 60° C. The time required for the reaction can also vary widely, depending on many factors, notably the reaction temperature and the nature of the reagents and solvent employed. However, provided that the reaction is effected under the preferred conditions outlined above, a period of from 5 minutes to 1 week, more preferably from 30 minutes to 24 hours, will usually suffice.

Alternatively, the compound of formula (III) can first be converted to an acylhalide derivative by reaction with halogenating agents such as oxalylchloride, phosphorus oxychloride and thionyl chloride. The resulting acylhalide derivative can then be reacted with a compound of formula (II) as described above to provide a compound of formula (I).

Scheme 2

This illustrates preparation of compounds of formula (II).

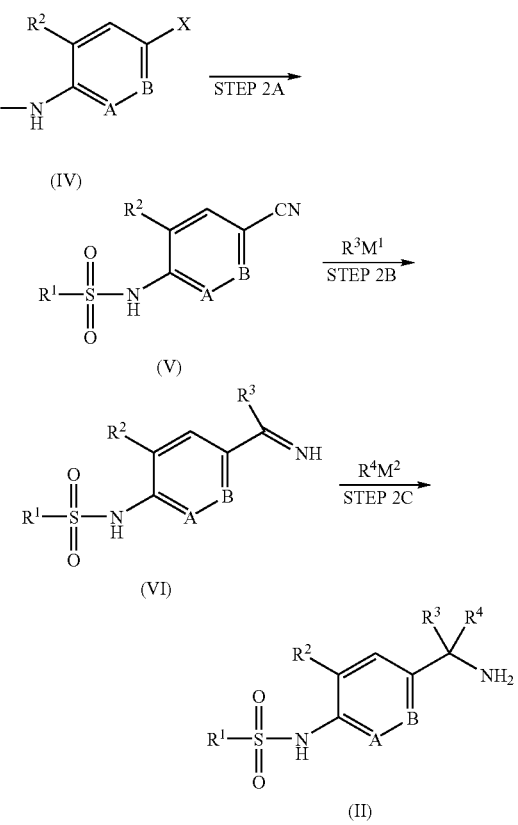

wherein X is a suitable leaving group such as sulfoxy or halogen, for examole chloro;

$M^1$ is a metal, such as lithium, or MgY, wherein Y represents hydrogen or halogen such as fluorine, chlorine, bromine or iodine; and $M^2$ is a metal, such as lithium, or MgY, wherein Y represents hydrogen or halogen such as, fluorine, chlorine, bromine or iodine.

Step 2A

In this step, the compound of formula (V) can be prepared by the cyanating the compound of formula (IV) with a metal cyanide reagent in the presence of a transition metal catalyst in an inert solvent.

Examples of suitable solvents include: THF; 1,4-dioxane; DMF; acetonitrile; alcohols, such as MeOH or ethanol; halogenated hydrocarbons, such as DCM, 1,2-dichloroethane, chloroform or carbon tetrachloride; and DME. Suitable metal cyanide reagents include, for example: alkalimetal cyanide such as lithium cyanide, sodium cyanide or potassium cyanide; transition metal cyanide such as ferric(II) cyanide, cobalt(II) cyanide, copper(I) cyanide, copper(II) cyanide or zinc(II) cyanide; sodium cyanide borohydride cyanide; and trimethylsilyl cyanide.

This reaction can be carried out in the presence of a suitable transition metal catalyst. There is likewise no particular restriction on the nature of the catalysts used, and any catalysts commonly used in reactions of this type can equally be used here. Examples of such catalysts include: tetrakis(triphenylphosphine)-palladium, bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, copper(II) trifluoromethanesulfonate, palladium(II) acetate, palladium(II) chloride, bisacetonitriledichloropalladium(0), bis(dibenzylideneacetone)palladium(0), tris(dibenzylideneacetone)dipalladium(0) and [1,1'-bis(diphenylphosphino)ferrocene]palladium(II) dichloride. Preferred catalysts are tetrakis(triphenylphosphine)-palladium, bis(triphenylphosphine)palladium(II) chloride, palladium(II) acetate, palladium(II) chloride, bisacetonitriledichloropalladium(0), bis(dibenzylideneacetone)palladium(0), tris(dibenzylideneacetone)dipalladium(0) and [1,1'-bis(diphenylphosphino)ferrocene]palladium(II) dichloride This reaction can be carried out in the presence of a suitable additive agent. Examples of such additive agents include: triphenylphosphine, tri-tert-butylphosphine, 1,1'-bis(diphenylphosphino)ferrocene, tri-2-furylphosphine, tri-o-tolylphosphine, 2-(dichlorohexylphosphino)biphenyl and triphenylarsine.

The reaction can be carried out at a temperature of from 0° C. to 200° C., more preferably from 20° C. to 120° C. Reaction times are, in general, from 5 minutes to 48 hours, more preferably from 30 minutes to 24 hours.

Step 2B

In this Step, an imine compound of formula (VI) can be prepared by the nucleophilic addition of a cyano compound of formula (V) with the organometallic compound of formula $R^3M^1$. The reaction may be carried out in the presence of a solvent. Examples of suitable solvents include for example: hydrocarbons, such as hexane; ethers, such as diethyl ether, diisopropyl ether, DME THF and 1,4-dioxane; or mixtures thereof. Reaction temperatures are generally in the range of from −100 to 50° C., preferably in the range of from −100° C. to room temperature. Reaction times are, in general, from 1 minute to a day, preferably from 1 hour to 10 hours.

The organometallic compound of formula $R^3M^1$ can be prepared by reaction of a halide compound of $R^3$. This reaction may be carried out in the presence of an organometallic reagent or a metal. Examples of suitable organometallic reagents include; alkyllithiums such as n-butyllithium, sec-butyllithium and tert-butyllithium; and aryllithiums such as phenyllithium and lithium naphthylide. Examples of suitable metals include magnesium. Preferred inert solvents include, for example: hydrocarbons, such as hexane; ethers, such as diethyl ether, diisopropyl ether, DME, THF and 1,4-dioxane; or mixtures thereof. Reaction temperatures are generally in the range of from −100° C. to 50° C., preferably in the range of from −100° C. to room temperature. Reaction times are, in general, from 1 minute to a day, preferably from 1 hour to 10 hours.

Step 2C

In this step, an amine of compound of formula (II) can be prepared by the nucleophilic addition of an imine compound of formula (VI) with the organometallic compound of formula $R^4M^2$. The reaction may be carried out in the presence of a solvent. Examples of suitable solvents include for example: hydrocarbons, such as hexane; ethers, such as diethyl ether, diisopropyl ether, DME, THF and 1,4-dioxane; or mixtures thereof. Reaction temperatures are generally in the range of from −100 to 50° C., preferably in the range of from −100° C. to room temperature. Reaction times are, in general, from 1 minute to a day, preferably from 1 hour to 10 hours.

The organometallic compound of formula $R^4M^2$ can be prepared by reaction of a halide compound of $R^4$. This reaction may be carried out in the presence of an organometallic reagent or a metal. Examples of suitable organometallic reagents include; alkyllithiums such as n-butyllithium, sec-butyllithium and tert-butyllithium; and aryllithiums such as phenyllithium and lithium naphtilide. Examples of suitable metals include magnesium. Preferred inert solvents include, for example: hydrocarbons, such as hexane; ethers, such as diethyl ether, diisopropyl ether, DME, THF and 1,4-dioxane; or mixtures thereof. Reaction temperatures aregenerally in the range of from −100 to 50° C., preferably in the range of from −100° C. to room temperature. Reaction times are, in general, from 1 minute to a day, preferably from 1 hour to 10 hours.

When $R^3$ and $R^4$ are both hydrogen, a compound of formula (II) may be prepared from a compound of formula (V) as illustrated in Scheme 3.

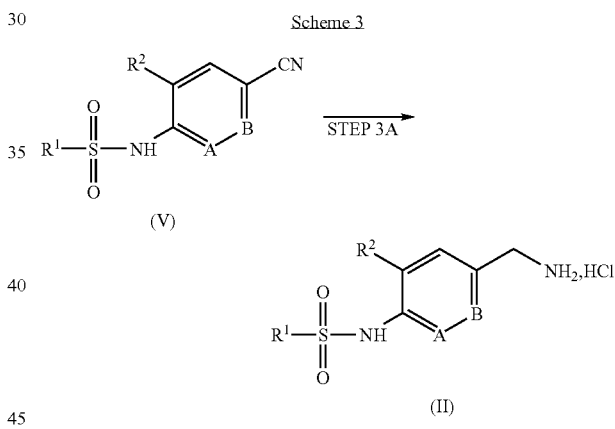

Step 3A

In this step, the compounds of formula (II) can be prepared by hydrogenation of a compound of formula (V) under, for example, known hydrogenolysis conditions in the presence of a metal catalyst under a hydrogen atmosphere, or in the presence of hydrogen sources such as formic acid or ammonium formate, in an inert solvent. If desired, the reaction may be carried out under acidic conditions, for example, in the presence of hydrochloric acid or acetic acid. A preferred metal catalyst is selected from, for example: nickel catalysts such as Raney nickel; Pd—C; palladiumhydroxide-carbon; platinumoxide; platinum-carbon; ruthenium-carbon; rhodium-aluminumoxide; and tris[triphenyphosphine]rhodiumchloride. Example of suitable inert aqueous or non-aqueous organic solvents include: alcohols, such as methanol and ethanol; ethers, such as THF or 1,4-dioxane; acetone; dimethylformamide; halogenated hydrocarbons, such as DCM, dichloroethane or chloroform; and acetic acid; or mixtures thereof. The reaction can be carried out at a temperature in the range of from 20° C. to 100° C., preferably in the range of from 20° C.

to 60° C. Reaction times are, in general, from 10 minutes to 4 days, preferably from 30 minutes to 24 hours. This reaction can be carried out under a hydrogen atmosphere at a pressure ranging from 1 to 100 atom, preferably from 1 to 10 atom.

Scheme 4

This illustrates preparation of compounds of formula (III).

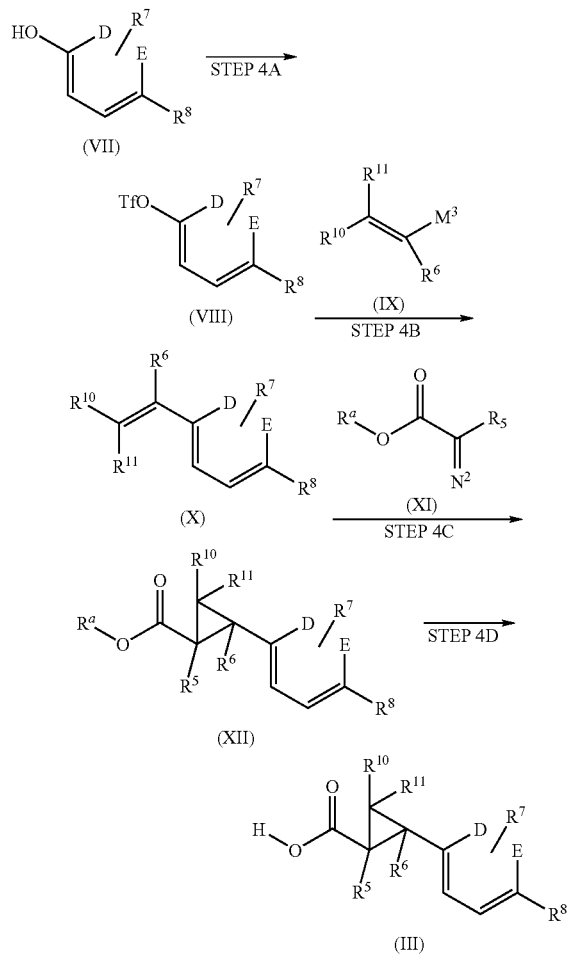

$R^a$ is a suitable protecting group such as $(C_1-C_4)$alkyl or benzyl; and
$M^3$ is tributylstannane, trimethylstannane, triphenylstannane, tributylsilane, trimethylsilane, triphenylsilane, diphenylborane, dimethylboronate, magnesium bromide or the like.

Step 4A

In this step, the compound of formula (VII) can be prepared by trifluoromethane sulfonation reaction of the compound of formula (VII) using trifluoromethane sulfonic acid anhydrate under basic conditions in an inert solvent. A preferred base is selected from, for example, but not limited to: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride; or an amine such as triethylamine, tributylamine, diisopropylethylamine, 2,6-lutidine, pyridine or dimethylaminopyridine. Examples of suitable solvents include: toluene; xylene; DME; DMSO; THF; 1,4-dioxane; DMF; acetonitrile; halogenated hydrocarbons, such as DCM, 1,2-dichloroethane, chloroform or carbon tetrachloride; and diethylether. Reaction temperatures are generally in the range of from −78° C. to 200° C., preferably in the range of from 0° C. to room temperature. Reaction times are, in general, from 1 minute to a day, preferably from 1 hour to 20 hours.

Step 4B

In this step, the compound of formula (X) can be prepared by olefinating the compound of formula (VIII) with the compound of formula (IX) with a vinyl metal, vinyl acetate or vinyl methyl ether reagent under olefination conditions in the presence of a transition metal catalyst in an inert solvent. Examples of suitable solvents include: THF; 1,4-dioxane; DMF; acetonitrile; alcohols, such as methanol or ethanol; halogenated hydrocarbons, such as DCM, 1,2-dichloroethane, chloroform or carbon tetrachloride; and diethylether; in the presence or absence of an aqueous base such as aqueous KOH, NaOH, LiOH or $K_2CO_3$. Suitable vinyl reagents include, for example, metal vinyl reagents such as tributylvinylstannane, potassium isopropenyltrifluoroborate, trimethylvinylstannane, triphenylvinylstannane, tributylvinylsilane, trimethylvinylsilane, triphenylvinylsilane, diphenylvinylborane, dimethylvinylboronate and vinylmagnesium bromide.

This reaction can be carried out in the presence of a suitable transiaiton metal catalyst. There is likewise no particular restriction on the nature of the catalysts used, and any catalysts commonly used in reactions of this type can equally be used here. Examples of such catalysts include: tetrakis(triphenylphosphine)-palladium, bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, copper(II) trifluoromethanesulfonate, palladium(II) acetate, palladium(II) chloride, bisacetonitriledichloropalladium(0), bis(dibenzylideneacetone)palladium(0), tris(dibenzylideneacetone)dipalladium (0) and [1,1'-bis(diphenylphosphino)ferrocene]palladium(II) dichloride. Preferred catalysts are tetrakis(triphenylphosphine)-palladium, bis(triphenylphosphine)palladium(II) chloride, palladium(II) acetate, palladium(II) chloride, bisacetonitriledichloropalladium(0), bis(dibenzylideneacetone) palladium(0), tris(dibenzylideneacetone)dipalladium(0) and [1,1'-bis(diphenylphosphino)ferrocene]palladium(II) dichloride This reaction can be carried out in the presence of a suitable additive agent. Examples of such additive agents include: triphenylphosphine, tri-tert-butylphosphine, 1,1'-bis(diphenylphosphino)ferrocene, tri-2-furylphosphine, tri-o-tolylphosphine, 2-(dichlorohexylphosphino)biphenyl, triphenylarsine, tetrabutylammonium chloride, tetrabutylammonium fluoride, lithium acetate, lithium chloride, triethylamine, potassium sodium methoxide, sodium hydroxide, sodium carbonate, sodium bicarbonate and/or sodium iodide. The reaction can be carried out at a temperature of from 0° C. to 200° C., more preferably from 20° C. to 120° C. Reaction times are, in general, from 5 minutes to 96 hours, more preferably from 30 minutes to 24 hours.

Step 4C

In this step, the compound of formula (XII) can also be prepared by the olefinating the compound of formula (X) with the compound of formula (XI) and a diazo reagent in an inert solvent.

Examples of suitable solvents include: diglyme; DMSO; DME; THF; 1,4-dioxane; DMF; acetonitrile; halogenated hydrocarbons, such as DCM, 1,2-dichloroethane, chloroform or carbon tetrachloride; and acetic acid. Suitable diazo reagents include, for example, diazonium esters such as methyl diazoacetate, ethyl diazoacetate, benzyldiazoacetate and tert-butyl diazoacetate.

This reaction can be carried out in the presence of a suitable catalyst. Examples of such catalysts include: Rh(II)acetate, $Ru_2(OAc)_4Cl$, $RuCl_2(PPh_3)$(p-cymene), Cu(0), Cu(acetylacetonate)$_2$, Co(TPP) and $Pd(OAc)_2$. This reaction can be carried out in the presence of a suitable additive agent. Examples of such additive agents include: triphenylphosphine, tri-tert-butylphosphine, 1,1'-bis(diphenylphosphino)ferrocene, tri-2-furylphosphine, tri-o-tolylphosphine, 2-(dichlorohexylphosphino)biphenyl, triphenylarsine, tetrabutylammonium chloride, tetrabutylammonium fluoride, lithium acetate, lithium chloride, N-methylimidazole, triethylamine, potassium sodium methoxide, sodium hydroxide, sodium carbonate, sodium bicarbonate and/or sodium iodide. The reaction can be carried out at a temperature of from 0° C. to 200° C., more preferably from 20° C. to 120° C. Reaction times are, in general, from 5 minutes to 96 hours, more preferably from 30 minutes to 24 hours,.

Step 4D

In this Step, an acid compound of formula (III) can be prepared by hydrolysis of the ester compound of formula (XII) in an inert solvent.

The hydrolysis can be carried out by conventional procedures. In a typical procedure, the hydrolysis is carried out under basic conditions, e.g. in the presence of sodium hydroxide, potassium hydroxide or lithium hydroxide. Suitable solvents include, for example: alcohols such as methanol, ethanol, propanol, butanol, 2-methoxyethanol, and ethylene gylcol; ethers such as THF, DME, and 1,4-dioxane; amides such as DMF and hexamethylphospholictriamide; and sulfoxides such as DMSO. Preferred solvents are methanol, ethanol, propanol, THF, DME, 1,4-dioxane, DMF, and DMSO. This reaction can be carried out at a temperature in the range of from −20° C. to 100° C., usually from 20° C. to 65° C. for from 30 minutes to 24 hours, usually from 60 minutes to 10 hours.

The hydrolysis can alternatively be carried out under acidic conditions, e.g. in the presence of hydrogen halides, such as hydrogen chloride and hydrogen bromide; sulfonic acids, such as p-toluenesulfonic acid and benzenesulfonic acid; pyridium p-toluenesulfonate; or carboxylic acids, such as acetic acid and TFA. Suitable solvents include, for example: alcohols such as methanol, ethanol, propanol, butanol, 2-methoxyethanol, and ethylene gylcol; ethers such as THF, DME, and 1,4-dioxane; amides such as DMF and hexamethylphospholictriamide; and sulfoxides such as DMSO. Preferred solvents are methanol, ethanol, propanol, THF, DME, 1,4-dioxane, DMF, and DMSO. This reaction can be carried out at a temperature in the range of from −20° C. to 100° C., usually from 20° C. to 65° C. for from 30 minutes to 24 hours, usually from 60 minutes to 10 hours.

Scheme 5

This illustrates the preparation of compounds of formula (X).

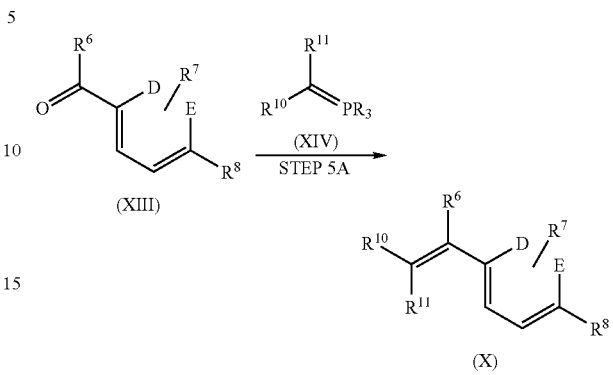

Step 5A

In this step, the compound of formula (X) can be prepared by olefinating the compound of formula (XIII) using a phosphinilide of formula (XIV) prepared in situ from a suitable phosphine reagent and a methylene halide reagent or phosphorane under olefination conditions or basic conditions in an inert solvent.

Examples of suitable solvents include: toluene; benzene; xylene; diglyme; DMSO; DME; THF; diethylether; 1,4-dioxane; DMF; acetonitrile; alcohols such as methanol or ethanol; halogenated hydrocarbons such as DCM, 1,2-dichloroethane, chloroform or carbon tetrachloride; and acetic acid. Suitable phosphine reagents include, for example, triphenylphosphine and tributylphosphine. Suitable methylene halide reagents include, for example, methyl bromide, ethyl bromide, methyl iodide, ethyl idolide, methyl chloride, ethyl chloride, methyl bromoacetate, bromoacetonitrile, 1-bromoacetone, ethylidene(triphenyl)phosphorane, (triphenylphosphoranylidene)acetonitrile and methyl (triphenylphosphoranylidene)acetate.

A preferred base is selected from, for example, but not limited to: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride; or an amine such as triethylamine, tributylamine, diisopropylethylamine, 2,6-lutidine, pyridine or dimethylaminopyridine.

The reaction can be carried out at a temperature of from 0° C. to 300° C., more preferably from 20° C. to 200° C. Reaction times are, in general, from 5 minutes to 96 hours, more preferably from 30 minutes to 24 hours.

When $R^{10}$ and $R^{11}$ are both fluoro, compounds of formula (III) may be prepared from compounds of formula (XV) as illustrated in Scheme 6.

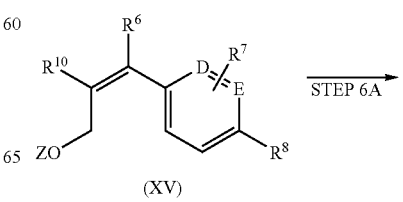

-continued

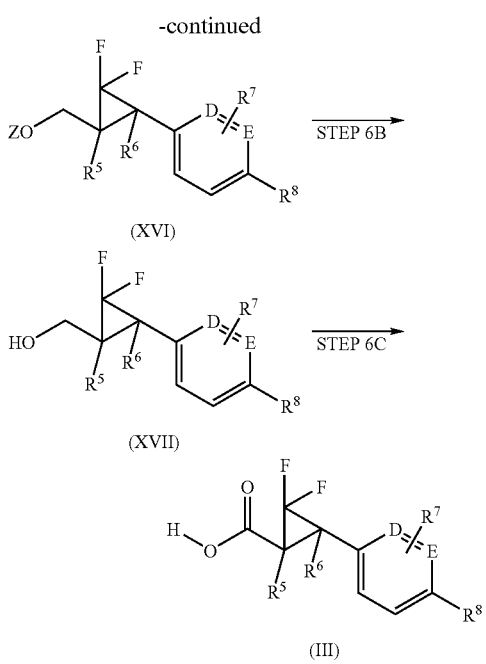

Z is a suitable hydroxy protecting group such as ($C_1$-$C_6$)alkyl, ($C_1$-$C_{10}$)alkanoyl, or benzyl.

Step 6A

In this step, the compound of formula (XVI) can be prepared by cyclopropanating the compound of formula (XV) with sodium chlorodifluoroacetic acid using a carbene reagent prepared in situ under cyclopropanation conditions in an inert solvent. Examples of suitable solvents include: diglyme; DMSO; DME; ethers such as THF, diethylether, or 1,4-dioxane; DMF; acetonitrile; alcohols, such as methanol or ethanol; halogenated hydrocarbons, such as DCM, 1,2-dichloroethane, chloroform or carbon tetrachloride; and acetic acid. Suitable carbine reagents include, for example, $CH_2I_2$, $CHCl_3$, sodium chlorodifluoroacetate, trimethylsilyl fluorosulfonyidifluoroacetate, trimethylsulfoxonium iodide and diazomethane.

This reaction can be carried out in the presence or absence of a suitable catalyst. There is likewise no particular restriction on the nature of the catalysts used, and any catalysts commonly used in reactions of this type can equally be used here. Examples of such catalysts include: Zn(0), Cu(0), Cu(acetylacetonate)$_2$, Co(TPP) and Pd(OAc)$_2$.

This reaction can be carried out in the presence of a suitable additive agent. Examples of such additive agents include: acetylchloride, methylbenzoate, sodium fluoride, triphenylphosphine, tri-tert-butylphosphine, 1,1'-bis(diphenylphosphino)ferrocene, tri-2-furylphosphine, tri-o-tolylphosphine, 2-(dichlorohexylphosphino)biphenyl, triphenylarsine, sodium hydride, potassium hydride, sodium methoxide and lithium diisopropyl amide. The reaction can be carried out at a temperature of from 0° C. to 300° C., more preferably from 20° C. to 200° C. Reaction times are, in general, from 5 minutes to 96 hours, more preferably from 30 minutes to 24 hours.

Step 6B

In this step, the compound of formula (XVII) can be prepared by deprotection of the compound of formula (XVI) under acidic conditions or by hydrogenation.

When acidic conditions are used, reaction temperatures are generally in the range of from 0 to 200° C., preferably room temperature. Reaction times are, in general, from 1 minute to 24 hours, preferably from 5 minutes to 1 hour. Suitable reagents include, for example, hydrochloric acid, trifluoromethane sulfonic acid, methansulfonic acid, p-toluene sulfonic acid and acetic acid. Examples of suitable solvents include: THF; 1,4-dioxane; DMF; acetonitrile; alcohols, such as methanol or ethanol; halogenated hydrocarbons, such as DCM, 1,2-dichloroethane, chloroform or carbon tetrachloride; and acetic acid.

Hydrogenation is carried out, for example, using known hydrogenolysis conditions in the presence of a suitable metal catalyst under a hydrogen atmosphere, or in the presence of hydrogen sources such as formic acid or ammonium formate, in an inert solvent. If desired, the reaction is carried out under acidic conditions, for example, in the presence of hydrochloric acid or acetic acid. A preferred metal catalyst is selected from, for example: nickel catalysts such as Raney nickel; Pd—C; palladiumhydroxide-carbon; platinumoxide; platinum-carbon; ruthenium-carbon; rhodium-aluminumoxide; and tris[triphenyphosphine] rhodiumchloride. Examples of suitable inert aqueous or non-aqueous organic solvents include: alcohols, such as methanol or ethanol; ethers, such as THF or 1,4-dioxane; acetone; dimethylformamide; halogenated hydrocarbons, such as DCM, dichloroethane or chloroform; and acetic acid; or mixtures thereof. The reaction can be carried out at a temperature in the range of from 20° C. to 100° C., preferably in the range of from 20° C. to 60° C. Reaction times are, in general, from 10 minutes to 4 days, preferably from 30 minutes to 24 hours. This reaction can be carried out under a hydrogen atmosphere at a pressure ranging from 1 to 100 atom, preferably from 1 to 10 atom.

Step 6C

In this Step, the compound of formula (III) can be prepared by oxidation of the compound of formula (XVII) using an oxidizing agent in an inert solvent. Examples of oxidizing agents include oxalyl chloride-DMSO (Swern oxidation condition), pyridinium chlorochromate (PCC), pyridinium dichromate (PDC), manganese dioxide and tetrapropylammonium perruthenate (TPAP). This reaction can be carried out in a suitable inert solvent such as halogenated hydrocarbons, for example, chloroform, dichloroethane and 1,2-dichloroethane. This reaction may be carried out at a temperature in the range of from −100 to 80° C., usually from −80 to 50° C. for from 5 minutes to 30 hours, usually from 15 minutes to 20 hours.

When $R^{10}$ and $R^{11}$ are both hydrogen, compounds of formula (III) may be prepared from compounds of formula (XVII) as illustrated in Scheme 7.

Scheme 7

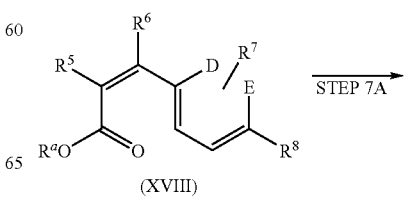

(XVIII)

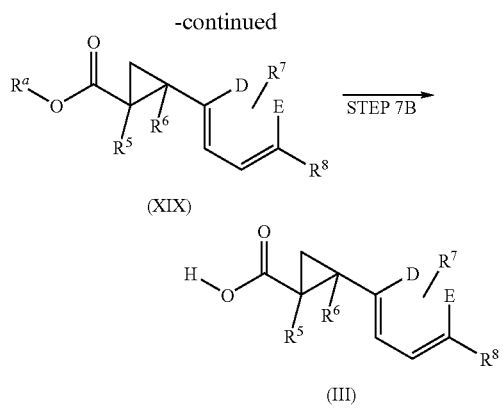

(XIX)

(III)

$R^a$ is a suitable protecting group such as $(C_1$-$C_4)$alkyl or benzyl.

Step 7A

In this Step, the compound of formula (XIX) can be prepared by cyclopropanating the compound of formula (XVIII) using a carbene prepared in situ under cyclopropanation conditions in an inert solvent. Examples of suitable solvents include: diglyme; DMSO; DME; THF; diethylether; 1,4-dioxane; DMF; acetonitrile; alcohols, such as methanol or ethanol; halogenated hydrocarbons, such as DCM, 1,2-dichloroethane, chloroform or carbon tetrachloride; and acetic acid. Suitable reagents include, for example, $CH_2I_2$, $CHCl_3$, sodium chlorodifluoroacetate, trimethylsilyl fluorosulfonyldifluoroacetate, trimethylsulfoxonium iodide and diazomethane.

This reaction can be carried out in the presence or absence of a suitable catalyst. There is likewise no particular restriction on the nature of the catalysts used, and any catalysts commonly used in reactions of this type can equally be used here. Examples of such catalysts include: Zirconium(0), Copper(0), Copper(acetylacetone)$_2$, Co(TPP) and Pd(OAc)$_2$.

This reaction can be carried out in the presence of a suitable additive agent. Examples of such additive agents include: acetylchloride, methylbenzoate, sodium fluoride, triphenylphosphine, tri-tert-butylphosphine, 1,1'-bis(diphenylphosphino)ferrocene, tri-2-furylphosphine, tri-o-tolylphosphine, 2-(dichlorohexylphosphino)biphenyl, triphenylarsine, sodium hydride, potassium hydride, sodium methoxide and lithium diisopropyl amide. The reaction can be carried out at a temperature of from 0° C. to 300° C., more preferably from 20° C. to 200° C. Reaction times are, in general, from 5 minutes to 96 hours, more preferably from 30 minutes to 24 hours,.

Step 7B

In this step, the compound of formula (III) can be prepared by hydrolysis of the ester compound of formula (XIX) as described in Step 4D.

When $R^4$ is hydrogen, compounds of formula (II) may be prepared from compounds of formula (XX) as illustrated in Scheme 8.

Scheme 8

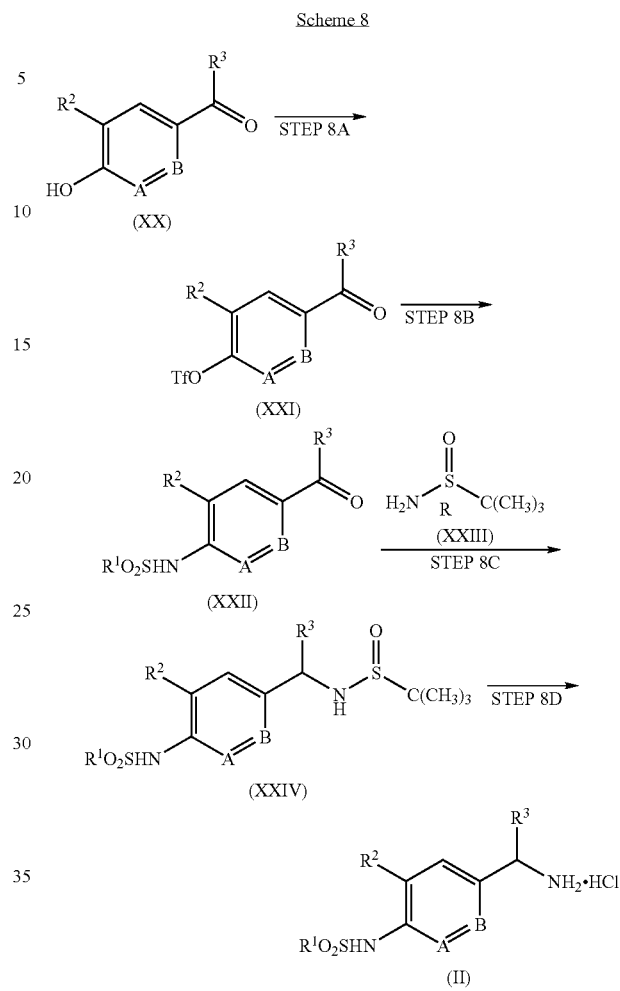

Step 8A

In this Step, the compound of formula (XXI) can be prepared by triflic reaction of the compound of formula (XX) using triflic anhydrate under basic conditions in an inert solvent.

A preferred base is selected from, for example, but not limited to: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride; or an amine such as triethylamine, tributylamine, diisopropylethylamine, 2,6-lutidine, pyridine or dimethylaminopyridine. Examples of suitable solvents include: THF; 1,4-dioxane; DMF; acetonitrile; alcohols, such as methanol or ethanol; halogenated hydrocarbons, such as DCM, 1,2-dichloroethane, chloroform or carbon tetrachloride; and acetic acid. Reaction temperatures are generally in the range of from −78° C. to 200° C., preferably in the range of from 0° C. to room temperature. Reaction times are, in general, from 1 minute to a day, preferably from 1 hour to 20 hours.

Step 8B

In this Step, the compound of formula (XXII) can be prepared by coupling the compound of formula (XXI) with alkyl sulfonamide in the presence of a catalyst and 4,5-bis(diphenylphosphino)-9,9-demethylxanthene (Xantphos) under basic conditions in an inert solvent, as described in Buchwald, S. L. Journal of American chemical society, 2002, 124, 6043-6048. Examples of suitable catalysts include tris(dibenzylidenacetone)dipalladium (0) and palladium reagents, such as palladium acetate and palladium dibenzylacetone. A preferred base is selected from, for example, but not limited to: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, cesium carbonate, potassium fluoride, sodium hydride or potassium hydride; or an amine such as triethylamine, tributylamine, diisopropylethylamine, 2,6-lutidine, pyridine or dimethylaminopyridine. Examples of suitable solvents include: THF; 1,4-dioxane; DMF; acetonitrile; alcohols, such as methanol or ethanol; halogenated hydrocarbons, such as DCM, 1,2-dichloroethane, chloroform or carbon tetrachloride; and acetic acid. Reaction temperatures aregenerally in the range of from 0 to 200° C., preferably in the range of from 100° C. to 140° C. Reaction times are, in general, from 1 minute to a day, preferably from 5 minutes to 1 hour.

Step 8C

In this Step, the compound of formula (XXIV) can be prepared by dehydration and reduction of the compound of formula (XXII) and sulfinamide of formula (XXIII) in the presence of a catalyst and reducing agent in an inert solvent. Dehydration is conducted in the presence of a dehydrating agent. Examples of a suitable dehydrating agents include: hydrogen halides such as hydrogen chloride and hydrogen bromide; sulfonic acids such as p-toluenesulfonic acid and benzenesulfonic acid; sulfonylchlorides such as methansulfonylchloride and p-toluenesulfonylchloride; methoxycarbonylsulfamoyltriethylammonium hydroxide; p-toluenesulfonylisocyanate; and titanium(IV) ethoxide. Reaction temperatures are generally in the range of from 0 to 200° C., preferably in the range of from 50° C. to 100° C. Reaction times are, in general, from 1 minute to 48 hours, preferably from 12 hours to 24 hours. The reduction may be carried out in the presence of a suitable reducing agent in an inert solvent or without solvent. A preferred reducing agent is selected from, for example, but not limited to, $NaBH_4$, $LiAlH_4$, $LiBH_4$, Fe, Sn or Zn. Reaction temperatures are generally in the range of from $-78°$ C. to room temprature, preferably in the range of from $-70°$ C. to 0° C. Reaction times are, in general, from 1 minute to a day, preferably from 3 hours to 6 hours. Examples of suitable solvents include: THF; 1,4-dioxane; DMF; acetonitrile; alcohols, such as methanol or ethanol; halogenated hydrocarbons, such as DCM, 1,2-dichloroethane, chloroform or carbon tetrachloride; and acetic acid.

Step 8D

In this Step, the compound of formula (II) can be prepared by deprotection and salt formation of the compound of formula (XXIV) under acidic conditions in an inert solvent, using the method of D. Cogan et. al., Journal of American Chemical Society, 1999, 121, 268-269. Reaction temperatures are generally in the range of from 0 to 200° C., preferably room temperature. Reaction times are, in general, from 1 minute to 24 hours, preferably from 5 minutes to 1 hour. Examples of suitable solvents include: THF; 1,4-dioxane; DMF; acetonitrile; alcohols, such as methanol or ethanol; halogenated hydrocarbons, such as DCM, 1,2-dichloroethane, chloroform or carbon tetrachloride; and acetic acid.

Scheme 9

This illustrates an alternative preparation of compounds of formula (XXII).

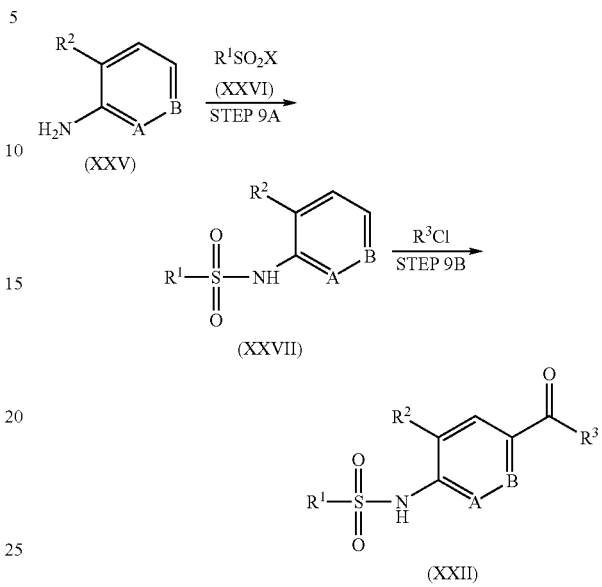

X is halogen, such as bromine or chlorine

Step 9A

In this Step, the compounds of formula (XXVII) can be prepared by sulfonylation of the compound of formula (XXV) with the compound of formula (XXVI) under, for example, known sulfonylation conditions in the presence of a base in an inert solvent. A preferred base is selected from, for example, but not limited to: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride; or an amine such as triethylamine, tributylamine, diisopropylethylamine, 2,6-lutidine, pyridine or dimethylaminopyridine. Examples of suitable inert aqueous or non-aqueous organic solvents include: alcohols, such as methanol or ethanol; ethers, such as THF or 1,4-dioxane; acetone; dimethylformamide; halogenated hydrocarbons, such as DCM, dichloroethane or chloroform; and acetic acid; or mixtures thereof. The reaction can be carried out at a temperature in the range of from 20° C. to 100° C., preferably in the range of from 20° C. to 60° C. Reaction times are, in general, from 10 minutes to 4 days, preferably from 30 minutes to 24 hours.

Step 9B

In this step, the compounds of formula (XXII) can be prepared by Friedal-Crafts acylation of the compound of formula (XXVII) with $R^3Cl$ under, for example, known Friedal-Crafts acylation conditions in the presence of a metal and acylhalide. This reaction may be carried out in an inert solvent. Examples of suitable solvents include: halogenated hydrocarbons, such as DCM, dichloroethane or chloroform; and aromatic hydrocarbons, such as nitrobenzene and chlorobenzene. Examples of suitable catalysts include aluminum halides, such as aluminum chloride and aluminum bromide. This reaction can be carried out at temperature of from $-50°$ C. to 200° C., preferably from about $-10°$ C. to 150° C. for from 5 minutes to 48 hours, preferably 30 minutes to 24 hours.

When R⁴ is hydrogen, compounds of formula (II) may be prepared from compounds of formula (XXVII) as illustrated in Scheme 10.

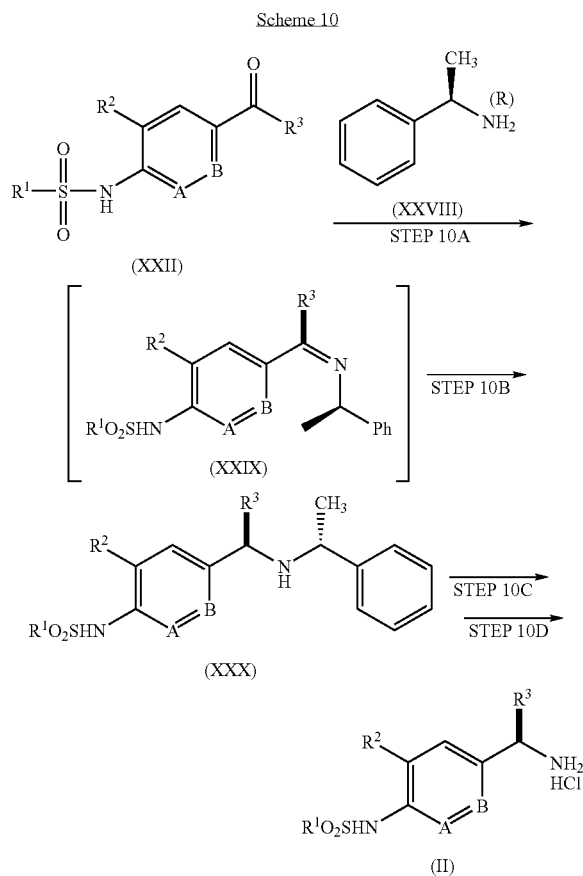

Step 10A

In this step, the compound of formula (XXIX) can be prepared by dehydration of the compound of formula (XXII) using a Lewis acid under basic conditions in an inert solvent. A preferred Lewis acid is selected from, for example, but not limited to, titanium tetrachloride, aluminium tetrachloride or zirconium tetrachloride. A preferred base is selected from, for example, but not limited to: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride; or an amine such as triethylamine, tributylamine, diisopropylethylamine, 2,6-lutidine, pyridine or dimethylaminopyridine. Examples of suitable solvents include: THF; 1,4-dioxane; DMF; acetonitrile; alcohols, such as methanol or ethanol; halogenated hydrocarbons, such as DCM, 1,2-dichloroethane, chloroform or carbon tetrachloride; and acetic acid. Reaction temperatures are generally in the range of from −78 to 200° C., preferably in the range of from 0° C. to room temperature. Reaction times are, in general, from 1 minute to a day, preferably from 1 hour to 20 hours.

Step 10B

In this Step, the compound of formula (XXX) can be prepared by the reduction of the compound of formula (XXIX) in the presence of a suitable reducing agent in an inert solvent or without solvent. A preferred reducing agent is selected from, for example, but not limited to, $NaBH_4$, $LiAlH_4$, $LiBH_4$, Fe, Sn or Zn. Reaction temperatures are generally in the range of from −78° C. to room temprature, preferably in the range of from −70° C. to 0° C. Reaction times are, in general, from 1 minute to a day, preferably from 3 hours to 6 hours. Examples of suitable solvents include: THF; 1,4-dioxane; DMF; acetonitrile; alcohols, such as methanol or ethanol; halogenated hydrocarbons, such as DCM, 1,2-dichloroethane, chloroform or carbon tetrachloride; and acetic acid.

The reduction may also be carried out in the presence of a suitable metal catalyst under a hydrogen atmosphere in an inert solvent. A preferred metal catalyst is selected from, for example: nickel catalysts such as Raney nickel; Pd—C; palladiumhydroxide-carbon; platinumoxide; platinum-carbon; ruthenium-carbon; rhodium-aluminumoxide; and tris[triphenyphosphine] rhodiumchloride. Examples of suitable inert aqueous or non-aqueous organic solvents include: alcohols, such as methanol or ethanol; ethers, such as THF or 1,4-dioxane; acetone; dimethylformamide; halogenated hydrocarbons, such as DCM, dichloroethane or chloroform; and acetic acid; or mixtures thereof. The reaction can be carried out at a temperature in the range of from 20° C. to 100° C., preferably in the range of from 20° C. to 60° C. Reaction times are, in general, from 10 minutes to 4 days, preferably from 30 minutes to 24 hours. This reaction can be carried out under a hydrogen atmosphere at a pressure ranging from 1 to 100 atoms, preferably from 1 to 10 atom.

Step 10C

In this step, the compounds of formula (II) can be prepared by hydrogenation of the compound of formula (XXX) under, for example, known hydrogenolysis conditions in the presence of a metal catalyst under hydrogen atmosphere, or in the presence of hydrogen sources such as formic acid or ammonium formate, in an inert solvent. If desired, the reaction is carried out under acidic conditions, for example, in the presence of hydrochloric acid or acetic acid. A preferred metal catalyst is selected from, for example: nickel catalysts such as Raney nickel; Pd—C; palladiumhydroxide-carbon; platinumoxide; platinum-carbon; ruthenium-carbon; rhodium-aluminumoxide; and tris[triphenyphosphine] rhodiumchloride. Examples of suitable inert aqueous or non-aqueous organic solvents include: alcohols, such as methanol or ethanol; ethers, such as THF or 1,4-dioxane; acetone; dimethylformamide; halogenated hydrocarbons, such as DCM, dichloroethane or chloroform; and acetic acid; or mixtures thereof. The reaction can be carried out at a temperature in the range of from 20° C. to 100° C., preferably in the range of from 20° C. to 60° C. Reaction times are, in general, from 10 minutes to 4 days, preferably from 30 minutes to 24 hours. This reaction can be carried out under a hydrogen atmosphere at a pressure ranging from 1 to 100 atom, preferably from 1 to 10 atom.

Step 10D

In this step, the compounds of formula (II) can be prepared from the compound of formula (XXX) by salt formation with, for example, hydrogen-chloride methanol solution, 1,4-dioxane solution and aqueous solution. The reaction can be carried out at a temperature in the range from of from 20° C. to 100° C., preferably in the range of from 20° C. to 60° C. Reaction times are, in general, from 10 minutes to 4 days, preferably from 30 minutes to 24 hours.

Scheme 11

This illustrates the preparation of compounds of formula (X).

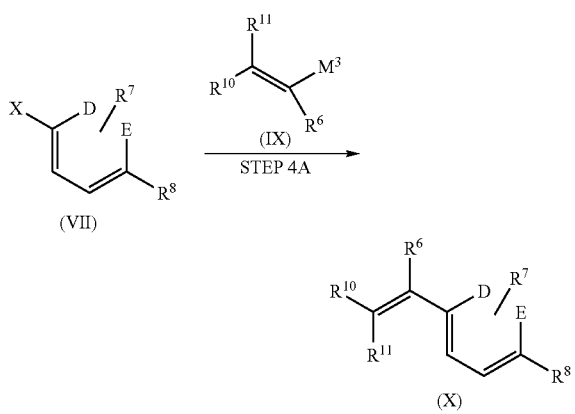

X: halogen
$M^3$: tributylstannane, trimethylstannane, triphenylstannane, tributylsilane, trimethylsilane, triphenylsilane, diphenylborane, dimethylboronate, magnesium bromide, pottasium trifluoroborate or the like.

Step 11A

In this step, a compound of formula (X) can be prepared by the olefinating a compound of formula (VII) with a compound of formula (IX) under olefination conditions with a vinyl metal, vinyl acetate or vinyl methyl ether reagent in the presence of a transition metal catalyst in an inert solvent. Examples of suitable solvents include: THF; 1,4-dioxane; DMF; acetonitrile; alcohols, such as methanol or ethanol; halogenated hydrocarbons, such as DCM, 1,2-dichloroethane, chloroform or carbon tetrachloride; and diethylether; in the presence or absence of an aqueous base such as aqueous KOH, NaOH, LiOH or $K_2CO_3$. Suitable vinyl reagents include, for example, metal vinyl reagents such as tributylvinylstannane, trimethylvinylstannane, triphenylvinylstannane, tributylvinylsilane, trimethylvinylsilane, triphenylvinylsilane, diphenylvinylborane, dimethylvinylboronate, potassium vinyl trifluoroborate or vinylmagnesium bromide. Examples of suitable transition metal catalysts include: tetrakis(triphenylphosphine)-palladium, bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper (II) acetate, copper(II) bromide, copper(II) chloride, copper (II) iodide, copper(II) oxide, copper(II) trifluoromethanesulfonate, palladium(II) acetate, palladium (II) chloride, bisacetonitriledichloropalladium(0), bis(dibenzylideneacetone)palladium(0), tris(dibenzylideneacetone) dipalladium(0) and [1,1'-bis(diphenylphosphino)ferrocene] palladium (II) dichloride. Preferred catalysts are tetrakis (triphenylphosphine)-palladium, bis(triphenylphosphine) palladium(II) chloride, palladium(II) acetate, palladium(II) chloride, bisacetonitriledichloropalladium(0), bis(dibenzylideneacetone)palladium(0), tris(dibenzylideneacetone) dipalladium(0) and [1,1'-bis(diphenylphosphino)ferrocene] palladium(II) dichloride. This reaction can be carried out in the presence of a suitable additive agent. Examples of such additive agents include: triphenylphosphine, tri-tert-butylphosphine, 1,1'-bis(diphenylphosphino)ferrocene, tri-2-furylphosphine, tri-tolylphosphine, 2-(dichlorohexylphosphino)biphenyl, triphenylarsine, tetrabutylammonium chloride, tetrabutylammonium fluoride, lithium acetate, lithium chloride, triethylamine, potassium sodium methoxide, sodium hydroxide, carbonate, sodium bicarbonate and/or sodium iodide. The reaction can be carried out at a temperature of from 0° C. to 200° C., more preferably from 20° C. to 120° C. Reaction times are, in general, from 5 minutes to 96 hours, more preferably from 30 minutes to 24 hours.

When $R^4$, $R^5$, $R^6$, $R^{10}$ and $R^{11}$ are all hydrogen; D is $CR^9$, wherein $R^9$ is H; E is N; and $R^7$ is $NH_2$, $(C_1$-$C_6)$alkylNH or $[(C_1$-$C_6)$alkyl$]_2$N, compounds of formula (I) may be prepared from compounds of formula (XXXI) as illustrated in Scheme 12.

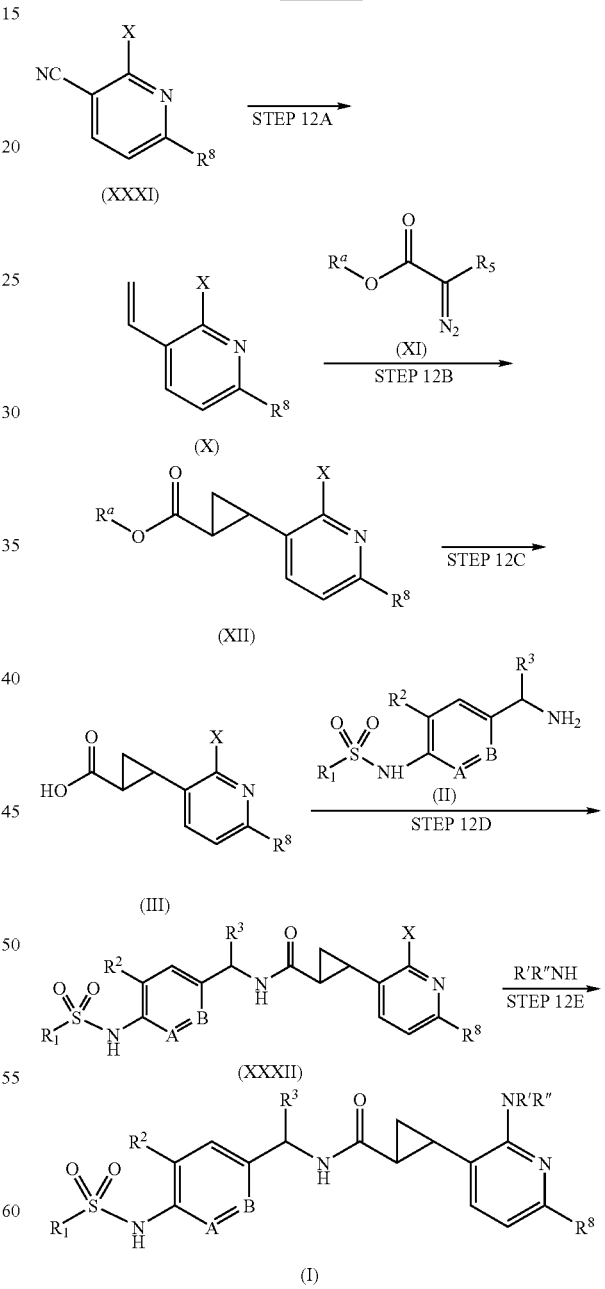

$R^a$ is a suitable protecting group such as $(C_1$-$C_4)$alkyl or benzyl;
X is halogen; and
R' and R" are each independently $(C_1$-$C_6)$alkyl or hydrogen.

Step 12A

In this Step, the compound of formula (X) can be prepared by reduction of formula (XXXI) under reduction conditions with a reducing reagent in an inert solvent following olefination using a compound of formula (XI) prepared in situ or phosphorane under olefination condition in an inert solvent or under base condition in an inert solvent. The reduction may be carried out in the presence of a suitable reducing agent in an inert solvent or without solvent. A preferred reducing agent is selected from, for example, but not limited to, sodiumborohydride, lithium aluminium hydride or lithium borohydride. Examples of suitable solvents include: THF, 1,4-dioxane, DMF, acetonitrile; alcohols, such as MeOH or ethanol; halogenated hydrocarbons, such as DCM, 1,2-dichloroethane, chloroform or carbon tetrachloride and acetic acid. Reaction temperature is generally in the range of −78° C. to room temprature, preferably in the range of from −70° C. to 0° C. Reaction time is, in general, from 1 minute to a day, preferably from 3 hours to 6 hours.

Step 12B

Compounds of formula (XII) can be prepared from compounds of formula (X) by the reaction described in Step 4C above.

Step 12C

Compounds of formula (III) can be prepared from compounds of formula (XII) by the reaction described in Step 4D above.

Step 12D

Compounds of formula (XXXII) can be prepared from compounds of formula (III) by the reaction described in Step 1A above.

Step 12E

In this step, the compound of formula (I) can be prepared by coupling a compound of formula (XXXII) with the amine HNR'R" in an inert solvent or without solvent. Examples of suitable solvents include: THF; 1,4-dioxane; DMF; acetonitrile; alcohols, such as methanol or ethanol; and halogenated hydrocarbons, such as DCM, 1,2-dichloroethane, chloroform or carbon tetrachloride. The reaction can be carried out at a temperature of from 0° C. to 200° C., more preferably from 20° C. to 120° C. Reaction times are, in general, from 5 minutes to 96 hours, more preferably from 30 minutes to 24 hours,.

When D and E are both $CR^9$, and $R^8$ is tert-butyl or 2,2,2-trifluoro-1,1-methylethyl, compounds of formula (VII) can be prepared from compounds of formula (XXXIII) as illustrated in Scheme 13.

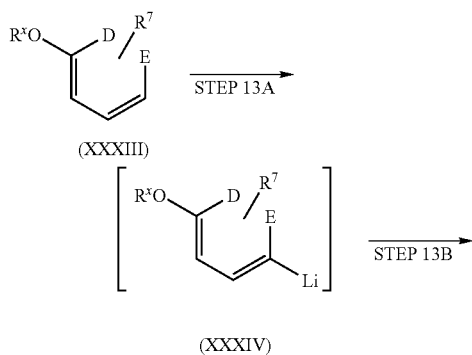

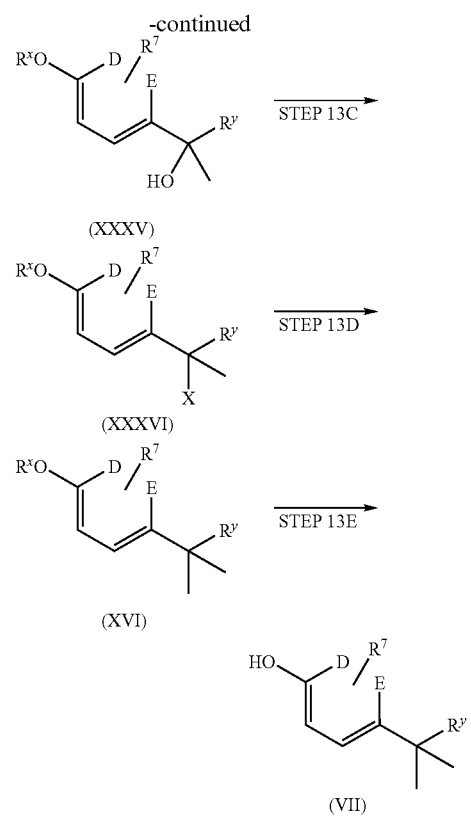

$R^x$ is a suitable protecting group such as $(C_1-C_4)$alkyl or benzyl;
$R^y$ is methyl or trifluoromethyl; and
X is halogen.

Step 13A

In this Step, an organometalic compound of formula (XXXIV) can be prepared by directive metalation reaction of a compound of formula (XXXIII) with alkyllithium. This reaction may be carried out in the presence of an organmetallic reagent or metal. Examples of suitable organometallic reagents include; alkyllithiums such as n-butyllithium, sec-butyllithium and tert-butyllithium; and aryllithiums such as phenyllithium and lithium naphtilide. Preferred reaction inert solvents include, for example: hydrocarbons, such as hexane; ethers, such as diethyl ether, diisopropyl ether, DME, THF and 1,4-dioxane; or mixtures thereof. Reaction temperatures are generally in the range of from −100° C. to 50° C., preferably in the range of from −100° C. to room temperature. Reaction times are, in general, from 1 minute to a day, preferably from 1 hour to 10 hours.

Step 13B

In this step, a compound of formula (XXXV) can be prepared by nucleophilic addition of the compound of formula (XXXIV) with a ketone reagent. Examples of suitable ketone reagents include; dialkylketones such as acetone; and haloalkylketones such as 1,1,1-trifluoroacetone. Preferred reaction inert solvents include, for example: hydrocarbons, such as hexane; ethers such as diethyl ether, diisopropyl ether, DME, THF and 1,4-dioxane; or mixtures thereof. Reaction temperatures are generally in the range of from −100 to 50° C., preferably in the range of from −100° C. to room temperature. Reaction times are, in general, from 1 minute to a day, preferably from 1 hour to 10 hours.

Step 13C

In this step, a compound of formula (XXXVI) can be prepared by halogenation of a compound of formula (XXXV) with a halogenating agent. The halogenation may be carried out in the presence of a suitable halogenating agent in an inert solvent or without solvent. Preferred reaction inert solvents include, for example: hydrocarbons, such as benzene, toluene or xylene; halogenated hydrocarbons, such as DCM, 1,2-dichloroethane, chloroform or carbon tetrachloride; or mixtures thereof. A preferred halogenating agent is selected from the following examples, but not limited to: thionyl chloride, oxalyl chloride, phosphorus oxychloride, titanium chloride and phosphorus pentachloride, optionally combined with catalytic pyridine, and is most preferably the combination of thionyl chloride and catalytic pyridine. Reaction temperatures are generally in the range of from −100 to 200° C., preferably in the range of from −40° C. to 100° C. Reaction times are, in general, from 1 minute to a day, preferably from 1 hour to 10 hours.

Step 13D

In this Step, a compound of formula (XXXVII) can be prepared by a substitution reaction of the compound of formula (XXXVI) with n alkylating agent in an inert solvent. A preferred alkylating agent is selected from the following examples, but not limited to: trialkylmetals such as trimethylaluminum, triethylaluminum; alkylmagnesium halides such as methylmagnesium bromide in the presence of additive compound such as lithium bromide; dialkylzinc halides such as dimethylzinc dichloride prepared by dimethylzinc and titanium chloride; and is most preferably trimethylaluminum. Preferred reaction inert solvents include, for example: halogenated hydrocarbons, such as DCM, 1,2-dichloroethane, chloroform or carbon tetrachloride; ethers, such as diethyl ether, diisopropyl ether, DME, THF and 1,4-dioxane; hydrocarbons, such as n-hexane, cyclohexane, benzene and toluene; or mixtures thereof. Reaction temperatures are generally in the range of from −100 to 200° C., preferably in the range of from −40° C. to 100° C. Reaction times are, in general, from 1 minute to a day, preferably from 1 hour to 10 hours.

Step 13E

In this Step, the compound of formula (VII) can be prepared by dealkylation of the compound of formula (XXXVII) with a dealkylating agent in an inert solvent. Examples of suitable dealkylating agents include: boron halides such as boron tribromide or boron trichloride; and hydrogen halides, such as hydrogen bromide. Preferred reaction inert solvents include, for example: halogenated hydrocarbons such as DCM, 1,2-dichloroethane, chloroform or carbon tetrachloride; and acetic acid. Reaction temperatures are generally in the range of from −100 to 200° C., preferably in the range of from −80° C. to 80° C. Reaction times are, in general, from 1 minute to a day, preferably from 1 hour to 10 hours.

When B is N and A is CH or $CR^{12}$, compounds of formula (XXII) can be prepared from compounds of formula (XXXVIII) as illustrated by Scheme 14.

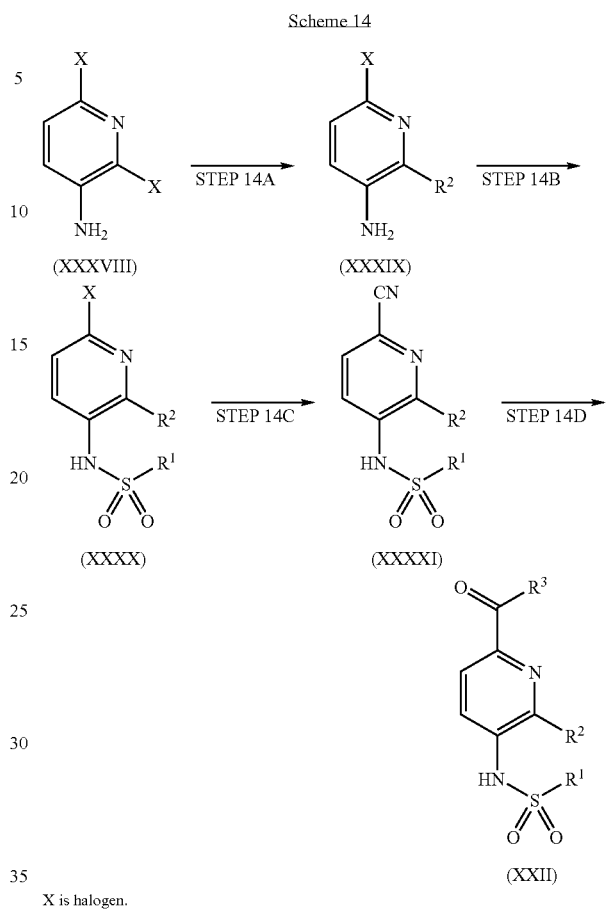

X is halogen.

Step 14A

In this Step, a compound of formula (XXXIX) can be prepared by alkylation of a compound of formula (XXXVIII) with an alkylating agent in the presence of a suitable metal catalyst in an inert solvent. A preferred alkylating agent is selected from, but not limited to: trialkylmetals such as trimethylaluminum or triethylaluminum; and alkylmagnesium halides such as methylmagnesium bromide. The reaction can be carried out in the presence of an additive compound such as lithium bromide or a dialkylzinc halide such as dimethylzinc dichloride prepared by dimethylzinc and titanium chloride, preferably trimethylaluminum. Examples of suitable metal catalysts include: tetrakis(triphenylphosphine)-palladium, bis(triphenylphosphine)palladium(II) chloride, copper (0), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, copper(II) trifluoromethanesulfonate, palladium(II) acetate, palladium(II) chloride, bisacetonitriledichloropalladium(0), bis(dibenzylideneacetone)palladium(0), tris(dibenzylideneacetone)dipalladium(0) and [1,1'-bis(diphenylphosphino)ferrocene]palladium (II) dichloride. Preferred catalysts are tetrakis(triphenylphosphine)-palladium, bis(triphenylphosphine)palladium(II) chloride, palladium(II) acetate, palladium(II) chloride, bisacetonitriledichloropalladium(0), bis(dibenzylideneacetone)palladium(0), tris(dibenzylideneacetone)dipalladium(0) and

[1,1'-bis(diphenylphosphino)ferrocene]palladium(II) dichloride. Preferred reaction inert solvents include, for example: halogenated hydrocarbons such as DCM, 1,2-dichloroethane, chloroform or carbon tetrachloride; acetic acid; 1,4-dioxane; THF; DMF; dimethylsulfoxide; and dyglime.

This reaction can be carried out in the presence of a suitable additive agent. Examples of such additive agents include: triphenylphosphine, tri-tert-butylphosphine, 1,1'-bis(diphenylphosphino)ferrocene, tri-2-furylphosphine, tri-o-tolylphosphine, 2-(dichlorohexylphosphino)biphenyl, triphenylarsine, tetrabutylammonium chloride, tetrabutylammonium fluoride, lithium acetate, lithium chloride, triethylamine, potassium sodium methoxide, sodium hydroxide, sodium carbonate, sodium bicarbonate and/or sodium iodide.

Reaction temperatures are generally in the range of from −100° C. to 200° C., preferably in the range of from −40° C. to 100° C. Reaction times are, in general, from 1 minute to a day, preferably from 1 hour to 10 hours.

Step 14B

In this Step, a compound of formula (XXXX) can be prepared from a compound of formula (XXXIX) by the method described in Step 9A above.

Step 14C

In this Step, a compound of formula (XXXXI) can be prepared from a compound of formula (XXXX) by the method described in Step 2A above.

Step 14D

In this Step, a compound of formula (XXII) can be prepared by alkylation of the compound of formula (XXXI) with an alkylating agent in an inert solvent. Preferred alkylating agents and inert solvents are the same as those of Step 14A. The reaction can be carried out at a temperature of from 0° C. to 200° C., more preferably from 20° C. to 120° C. Reaction times are, in general, from 5 minutes to 96 hours, more preferably from 30 minutes to 24 hours.

Step 15A

In this Step, a compound of formula (XXXXIII) can be prepared from a compound of formula (XXXXII) by acetal formation in the presence of a suitable catalyst in an inert solvent or without solvent. Dialkyl acetal formation may be carried out in the presence of a suitable acetal formation agent and catalyst in an inert solvent.

Examples of preferred acetal formation agents include trimethylorthoformate and triethylorthoformate. Examples of preferred catalysts include: tetrabutylammonium tribromide; tetrabutylammonium trichloride; hydrogenchloride; and metal chlorides such as aluminium(III) chloride, zinc chloride or boron(III) trichloride. Examples of suitable solvents include: THF; 1,4-dioxane; DMF; acetonitrile; alcohols such as methanol or ethanol; halogenated hydrocarbons such as DCM, 1,2-dichloroethane, chloroform or carbon tetrachloride; and acetic acid. Reaction temperatures are generally in the range of from −78° C. to room temprature, preferably in the range of from −70° C. to 0° C. Reaction times are, in general, from 1 minute to a day, preferably from 3 hours to 6 hours.

Step 15B

In this step, a compound of formula (X) can be prepared by olefination of a compound of formula (XXXXIII) under in the presence of a catalyst in an inert solvent or without solvent. The olefination reaction may be carried out in the presence of a suitable agent and additive in an inert solvent. A preferred agent is selected from, for example, but not limited to: succinic anhydride and triethylamine; and succinic anhydride and pyridine. A preferred additive is selected from, for example, but not limited to, benzoic acid, trifluoromethane sulfonic acid and p-toluenesulfonic acid. Examples of suitable solvents include: THF; 1,4-dioxane; DMF; acetonitrile; alcohols, such as methanol or ethanol; halogenated hydrocarbons, such as DCM, 1,2-dichloroethane, chloroform or carbon tetrachloride; and acetic acid.

Reaction temperatures are generally in the range of from −78° C. to room temprature, preferably in the range of from −70° C. to 0° C. Reaction times are, in general, from 1 minute to a day, preferably from 3 hours to 6 hours.

When $R^3$ is methyl, compounds of formula (XXII) may be prepared from compounds of formula (XXXXIV) as illustrated in Scheme 16.

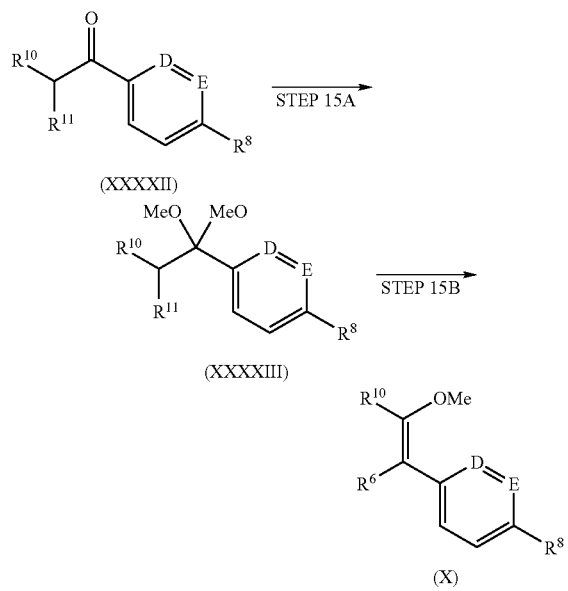

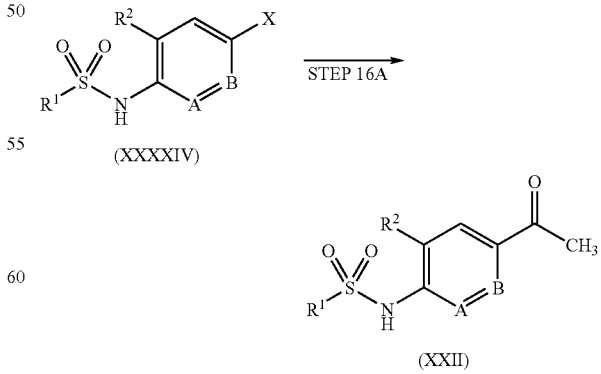

X represents halogen such as iodide, bromide, chloride or fluoride.

Step 16A

In this step, a compound of formula (XXII) can be prepared by acylation of a compound of formula (XXXXIV) under acylating conditions using n-buthyl vinyl ether as a reagent in water-organic co-solvent mixture in the presence of a suitable transition metal catalyst and in the presence or absence of a base, followed by hydrolysis under acidic condition.

Examples of suitable organic solvents include: THF; 1,4-dioxane; DMF; acetonitrile; alcohols, such as methanol or ethanol; halogenated hydrocarbons, such as DCM, 1,2-dichloroethane, chloroform or carbon tetrachloride; and diethylether in the presence or absence of an aqueous base such as aqueous KOH, NaOH, LiOH or $K_2CO_3$. Examples of suitable catalysts include: tetrakis(triphenylphosphine)-palladium, bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, copper(II) trifluoromethanesulfonate, palladium(II) acetate, palladium(II) chloride, bisacetonitriledichloropalladium(0), bis(dibenzylideneacetone)palladium(0), tris(dibenzylideneacetone)dipalladium(0) and [1,1'-bis(diphenylphosphino)ferrocene]palladium (II) dichloride. Preferred catalysts are tetrakis(triphenylphosphine)-palladium, bis(triphenylphosphine)palladium(II) chloride, palladium(II) acetate, palladium(II) chloride, bisacetonitriledichloropalladium(0), bis(dibenzylideneacetone)palladium(0), tris(dibenzylideneacetone)dipalladium(0) and [1,1'-bis(diphenylphosphino)ferrocene]palladium(II) dichloride.

This reaction can be carried out in the presence of a suitable additive agent. Examples of such additive agents include: triphenylphosphine, tri-tert-butylphosphine, 1,1'-bis(diphenylphosphino)ferrocene, tri-2-furylphosphine, tri-o-tolylphosphine, 2-(dichlorohexylphosphino)biphenyl, triphenylarsine, tetrabutylammonium chloride, tetrabutylammonium fluoride, lithium acetate, lithium chloride, triethylamine, potassium sodium methoxide, sodium hydroxide, sodium carbonate, sodium bicarbonate, and/or sodium iodide.

This reaction can be acidified with a suitable acid. Examples of such acid agents include: concentrated hydrogen chloride aqueous solution, sulfonic acid in the presence of water.

The reaction can be carried out at a temperature of from 0° C. to 200° C., more preferably from 20° C. to 120° C. Reaction times are, in general, from 5 minutes to 96 hours, more preferably from 30 minutes to 24 hours.

Scheme 17:

This illustrates the preparation of compounds of formula (XIII).

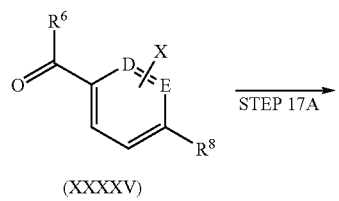

(XXXXV)

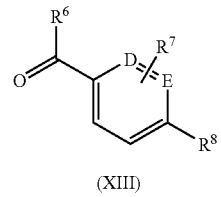

(XIII)

X is halogen.

Step 17A

In this Step, the compound of formula (XIII) can be prepared by coupling a compound of formula (XXXXV) with alkyl or aryl metal reagent in water-organic co-solvent mixture under coupling conditions in the presence of a suitable transition metal catalyst and in the presence or absence of a base.

Examples of suitable transition metal catalysts include: tetrakis(triphenylphosphine)-palladium, bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper (II) acetate, copper(II) bromide, copper(II) chloride, copper (II) iodide, copper(II) oxide, copper(II) trifluoromethanesulfonate, palladium(II) acetate, palladium (II) chloride, bisacetonitriledichloropalladium(0), bis(dibenzylideneacetone)palladium(0), tris(dibenzylideneacetone) dipalladium(0) and [1,1'-bis(diphenylphosphino)ferrocene] palladium (II) dichloride. Preferred catalysts are tetrakis (triphenylphosphine)-palladium, bis(triphenylphosphine) palladium(II) chloride, palladium(II) acetate, palladium(II) chloride, bisacetonitriledichloropalladium(0), bis(dibenzylideneacetone)palladium(0), tris(dibenzylideneacetone) dipalladium(0) and [1,1'-bis(diphenylphosphino)ferrocene] palladium(II) dichloride.

Examples of suitable alkyl or aryl metal reagents include, but not limited to, boronic acids such as phenyl boronic acid, 4-pyridinyl boronic acid, cyclopropyl boronic acid, and methyl boronic acid.

Examples of suitable organic solvent for the water-organic co-solvent mixture include: THF; 1,4-dioxane; DMF; acetonitrile; alcohols, such as methanol or ethanol; halogenated hydrocarbons, such as DCM, 1,2-dichloroethane, chloroform or carbon tetrachloride; and diethylether; in the presence or absence of an aqueous base such as aqueous KOH, NaOH, LiOH or $K_2CO_3$.

This reaction can be carried out in the presence of a suitable additive agent. Examples of such additive agents include: triphenylphosphine, tri-tert-butylphosphine, 1,1'-bis(diphenylphosphino)ferrocene, tri-2-furylphosphine, tri-tolylphosphine, 2-(dichlorohexylphosphino)biphenyl, triphenylarsine, tetrabutylammonium chloride, tetrabutylammonium fluoride, lithium acetate, lithium chloride, triethylamine, potassium sodium methoxide, sodium hydroxide, sodium carbonate, sodium bicarbonate, and/or sodium iodide. The reaction can be carried out at a temperature of from 0° C. to 200° C., more preferably from 20° C. to 120° C. Reaction times are, in general, from 5 minutes to 96 hours, more preferably from 30 minutes to 24 hours.

When $R^3$ and $R^4$ are taken together with the carbon atoms to which they are attached to form a cyclopropane ring, compounds of formula (II) can be prepared from compounds of formula (XXXXV) as illustrated in Scheme 18.

Scheme 18

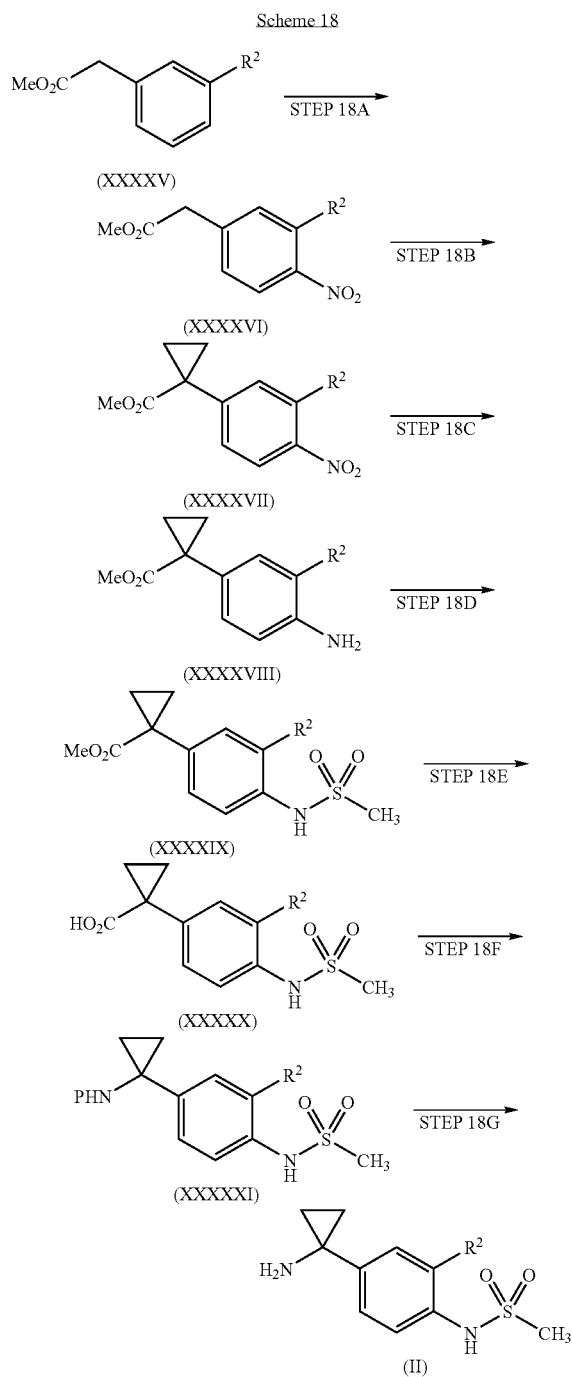

wherein, P represents a suitable amine protective group such as benzoyl or tert-methoxycarbonyl.

Step 18A

In this Step, a compound of formula (XXXXVII) can be prepared by nitration of a compound of formula (XXXXVI) under acidic conditions in an inert solvent. Nitration may be carried out in the presence of a suitable nitrating agent and acid in an inert solvent.

Examples of preferred nitrating agents include, but are not limited to, nitric acid, potassium nitrate and copper (II) nitrate. Examples of preferred acids include, but are not limited to, acetic acid, acetic acid anhydride and sulfuric acid. Examples of suitable solvents include THF; 1,4-dioxane; DMF; acetonitrile; water; ethylacetate; alcohols such as methanol or ethanol; and halogenated hydrocarbons such as DCM, 1,2-dichloroethane, chloroform or carbon tetrachloride. Reaction temperatures are generally in the range of from −78° C. to 100° C., preferably in the range of from −15° C. to 50° C. Reaction times are, in general, from 1 minute to a day, preferably from 3 hours to 6 hours.

Step 18B

In this Step, a compound of formula (XXXXVIII) can be prepared by cyclopropane formation of a compound of formula (XXXXVII) under alkylation conditions in an inert solvent. Alkylation may be carried out in the presence of a suitable alkylating agent and metal hydride in an inert solvent.

Examples of preferred alkylating agents include, but are not limited to, dibromoethane, diiodoethane and dichloroethane. Examples of preferred metal hydrides include, but are not limited to, sodium hydride, potassium hydride and lithium hydride. Examples of suitable solvents include THF; 1,4-dioxane; and DMF. Reaction temperatures are generally in the range of from -78° C. to 100° C., preferably in the range of from −78° C. to room temperature. Reaction times are, in general, from 1 minute to a day, preferably from 3 hours to 6 hours.

Step 18C

In this Step, a compound of formula (XXXXIX) can be prepared by hydrogenation of a compound of formula (XXXXVIII) under, for example, known hydrogenolysis conditions in the presence of a suitable metal catalyst under a hydrogen atmosphere, or in the presence of hydrogen sources such as formic acid or ammonium formate, in an inert solvent. If desired, the reaction is carried out under acidic conditions, for example, in the presence of hydrochloric acid or acetic acid. A preferred metal catalyst is selected from, for example, nickel catalysts such as Raney nickel; Pd—C; palladiumhydroxide-carbon; platinumoxide; platinum-carbon; ruthenium-carbon; rhodium-aluminumoxide; tris[triphenyphosphine] rhodiumchloride; Fe; Zn; Sn; and SnCl$_2$. Examples of suitable inert aqueous or non-aqueous organic solvents include: alcohols, such as methanol or ethanol; ethers, such as THF or 1,4-dioxane; acetone; dimethylformamide; halogenated hydrocarbons, such as DCM, dichloroethane or chloroform; and acetic acid; or mixtures thereof. The reaction can be carried out at a temperature in the range of from 20° C. to 100° C., preferably in the range of from 20° C. to 60° C. Reaction times are, in general, from 10 minutes to 4 days, preferably from 30 minutes to 24 hours. This reaction can be carried out under a hydrogen atmosphere at a pressure ranging from 1 to 100 atoms, preferably from 1 to 10 atom.

Step 18D

In this Step, a compound of formula (XXXXIX) can be prepared from a compound of formula (XXXXVIII) by the method described in Step 9A above.

Step 18E

In this Step, a compound of formula (XXXXX) can be prepared from a compound of formula (XXXXIX) by the methods decribed in Step 4D above.

Step 18F

In this Step, a compound of formula (XXXXXI) can be prepared by conversion of the carboxylic acid of formula (XXXXX) to the corresponding amine derivative under known Curtius conditions in an inert solvent. The Curtius reaction may be carried out in the presence of a suitable phosphinic azide agent and base in an inert solvent, following alcohol addition. Examples of preferred phosphinic azide agents include, but are not limited to, diphenylphosphorylazide. Examples of preferred bases include, but are not limited to, triethylamine, diisopropylamine, sodium methoxide and tert-butyl ethoxide. Examples of preferred alcohols include, but are not limited to, benzyl alcohol and tert-butanol. Examples of suitable solvents include THF; 1,4-dioxane; DMF; DMSO; and Diglyme. Reaction temperatures are generally in the range of from −78° C. to 200° C., preferably in the range of from 0° C. to the reflux temperature of the solvent. Reaction times are, in general, from 1 minute to a day, preferably from 3 hours to 12 hours.

Step 18G

In this Step, a compound of formula (XXXXXI) can be prepared by deprotection of a compound of formula (XXXXX) under known deprotection conditions. Hydrogenation conditions may be used, as described in Step 10C above. Alternatively, other deprotecting conditions which may be used to convert a carbamate such as tert-butyl carbamate to a primary amine include basic conditions under inert solvent. A preferred base includes, for example, but is not limited to, potassium hydroxide, sodium hydroxide and lithium hydroxide. Examples of suitable inert aqueous or non-aqueous organic solvents include: alcohols, such as methanol or ethanol; ethers, such as THF or 1,4-dioxane; acetone; dimethylformamide; halogenated hydrocarbons, such as DCM, dichloroethane or chloroform; and acetic acid; or mixtures thereof. The reaction can be carried out at a temperature in the range of from 20° C. to 100° C., preferably in the range of from 20° C. to 60° C. Reaction times are, in general, from 10 minutes to 4 days, preferably from 30 minutes to 24 hours.

When $R^{10}$ and $R^{11}$ are both hydrogen, a compound of formula (X) may be prepared from a compound of formula (XXXXXII) as illustrated in Scheme 19.

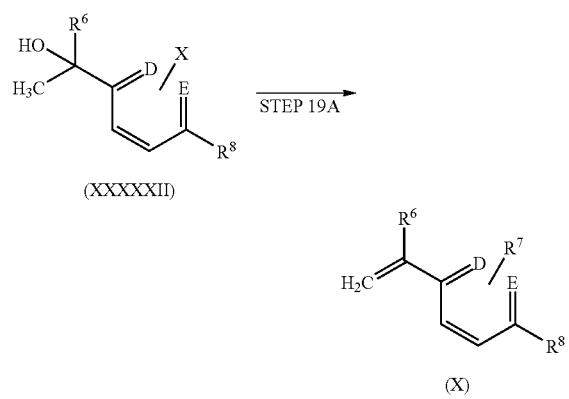

Step 19A

In this step, the compound of formula (X) can be prepared by dehydration of a compound of formula (XXXXXII) under acidic conditions in an inert solvent. Examples of preferred acids include, but are not limited to, p-toluene sulfonic acid, hydrogen chloride and trifluoro acetic acid. Examples of preferred solvents include, but are not limited to: alcohols, such as methanol or ethanol; ethers, such as THF or 1,4-dioxane; acetone; dimethylformamide; halogenated hydrocarbons, such as DCM, dichloroethane or chloroform; and acetic acid; or mixtures thereof. The reaction can be carried out at a temperature in the range of from 20° C. to 100° C., preferably in the range of from 20° C. to 60° C. Reaction times are, in general, from 10 minutes to 4 days, preferably from 30 minutes to 24 hours.

When B is $CR^{12}$; $R^2$ is hydrogen, halogen, $(C_1-C_6)$alkyl, $(C_1-C_6)$alkoxy or $(C_1-C_6)$alkoxy-$(C_1-C_6)$alkyl; and $R^{12}$ is hydrogen or $(C_1-C_6)$alkyl, a compound of formula (XXII) may be prepared from a compound of formula (XXV) as illustrated in Scheme 20.

Scheme 20

This illustrates an improved method of Scheme 9 to prepare compounds of formula (XXII) from compounds of formula (XXV). The compounds of formula (XXII and formula (XXV) are included in the compounds of formula (XXII) and formula (XXV), respectively.

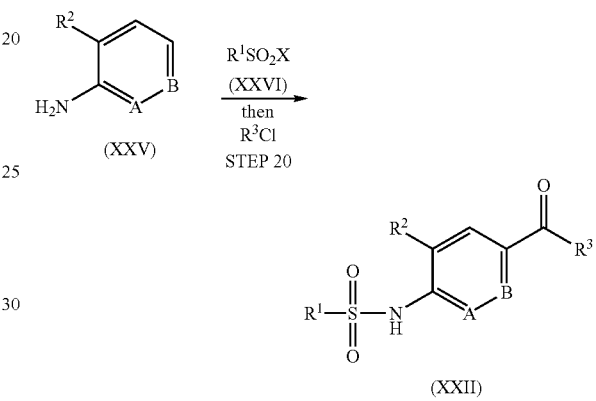

X: halogen atoms such as bromine and chloride
A, B: CH, $CR^{12}$, N
$R^2$: hydrogen, (C1-C6) alkyl, halo (C1-C6)alkyl, (C1-C6) alkoxy group or (C1-C6) alkoxy-(C1-C6) alkyl
$R^{12}$: hydrogen or (C1-C6) alkyl Step 20

In this step, the compounds of formula (XXII) can be prepared by one-pot process of sulfonylation reaction of the compound of formula (XXV) with the compound of formula (XXVI) and subsequent Friedel-Crafts acylation reaction with $R^3Cl$. The formation of undesirable N-acylated products is substantially suppressed by the one-pot procedure. The sulfonylation reaction is carried out under, for example, known sulfonylation conditions in the presence of a base in an inert solvent. The reaction may be carried out without the use of a solvent. Examples of preferred base and suitable inert organic solvents are the same as Step 9A. The reaction can be carried out at a temperature in the range from of 20° C. to 100° C., preferably in the range of −20° C. to 40° C. Reaction time is, in general, from 5 minutes to 4 days, preferably 10 minutes to 3 hours. After the completion of the sulfonylation, Friedel-Crafts acylation reaction with $R^3Cl$ should follow without any work-up procedure for the preceding reaction. Friedel-Crafts acylation reaction with $R^3Cl$ is carried out under, for example, known Friedel-Crafts acylation in the presence of a metal and acylhalide. This reaction may be carried out in an inert solvent. Examples of suitable solvents and suitable catalysts are the same as Step 9B. This reaction can be carried out at temperature of −50° C. to 200° C., preferably from about −10° C. to 150° C. for 5 minutes to 48 hours, preferably 10 minutes to 24 hours.

According to this Scheme, the compounds of formula (XXIId) can be prepared more selectively with a small amount of by-product materials. In other words, the yield of the compounds of formula (XXIId) can be improved effectively compared with known methods such as the method described in the above Scheme 9 or in Kostsova, A. G.; Tkachenko, N. N.; Eveseeva, I. I.; *Zhurnal Obshchei Khimii*, 1961, 31, 2241-6.

When $R^3$ is methyl; and $R^{12}$ is hydroxy($C_1$-$C_6$)alkyl, a compound of formula (II) may be prepared from a compound of formula (XXXXXII) as illustrated in Scheme 21.

Scheme 21

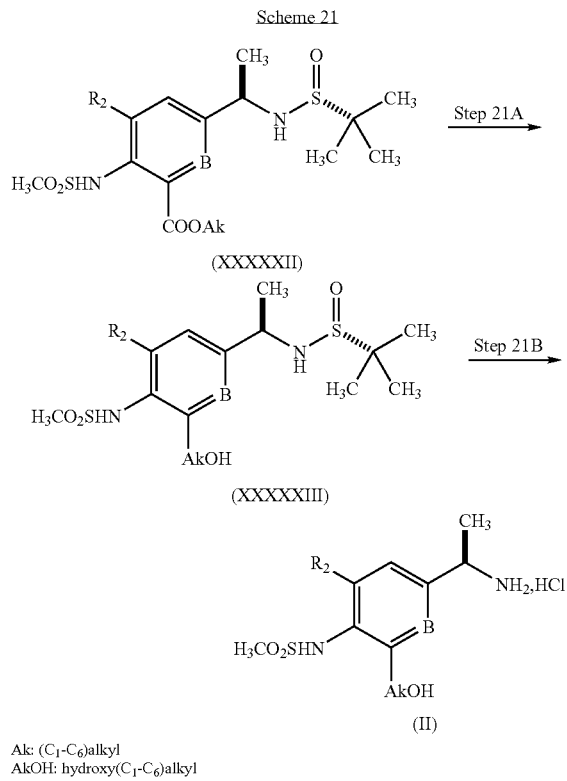

Ak: ($C_1$-$C_6$)alkyl
AkOH: hydroxy($C_1$-$C_6$)alkyl

Step 21A

In this step the compounds of formula (XXXXXIII) can be prepared by reduction of the compound of formula (XXXXXII) under the condition of Step 8C.

Step 21B

In this step the compounds of formula (II) can be prepared by deprotection of the compound of formula (XXXXXIII) under the condition of Step 8D.

When $R^{12}$ is hydroxy($C_1$-$C_6$)alkyl, a compound of formula (I) may be prepared from a compound of formula (Ia) as illustrated in Scheme 22.

Scheme 22

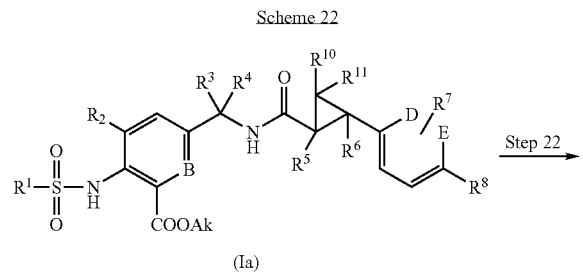

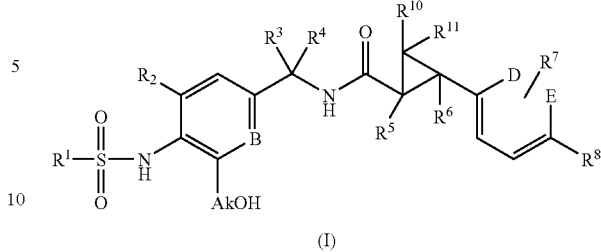

Ak: ($C_1$-$C_6$)alkyl
AkOH: hydroxy($C_1$-$C_6$)alkyl

Scheme 22

In this step, the compounds of formula (I) can be prepared by reduction of the compound of formula (Ia) under the condition described in Step 8C.

The starting materials in the aforementioned general syntheses are commercially available or may be obtained by conventional methods known to those skilled in the art.

The compounds of formula (I), and the intermediates above-mentioned preparation methods can be isolated and purified by conventional procedures, such as recrystallization or chromatographic purification.

The various general methods described above may be useful for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

Method for Assessing Biological Activities:

Human VR1 Antagonist Assay

VR1 antagonistic activity can be determined by the $Ca^{2+}$ imaging assay using human VR1 highly expressing cells. The cells that highly express human VR1 receptors are obtainable from several different conventional methods. The one standard method is cloning from human Dorsal Root Ganglion (DRG) or kidney according to the methods such as described in the journal article; Nature, 389, pp 816-824, 1997. Alternatively VR1 receptors highly expressing human keratinocytes are also known and published in the journal article (Biochemical and Biophysical Research Communications, 291, pp 124-129, 2002). In this article, human keratinocytes demonstrated VR1 mediated intracellular $Ca^{2+}$ increase by addition of capsaicin. Further more, the method to up regulate human VR1 gene, which is usually a silent gene or don't produce detectable level of VR1 receptors, is also available to obtain propriety cells. Such genetic modification method was described in detail; Nat. Biotechnol., 19, pp 440-445, 2001.

The cells that express human VR1 receptors were maintained in culture flask at 37° C. in an environment containing 5% $CO_2$ until use in the assay. The intracellular $Ca^{2+}$ imaging assay to determine VR1 antagonistic activities were done by following procedures.

The culture medium was removed from the flask and fura-2/AM fluorescent calcium indicator was added to the flask at a concentration of 5 μM in the medium. The flask was placed in $CO_2$ incubator and incubated for 1 hour. Then the cells expressing the human VR1 receptors were detached from the flask follow by washing with phosphate buffer saline, PBS(−) and re-suspended in assay buffer. The 80 μl of aliquot of cell suspension ($3.75 \times 10^5$ cells/ml) was added to the assay plate and the cells were spun down by centrifuge (950 rpm, 20° C., 3 minutes).

Capsaicin Stimulation Assay:

The capsaicin-induced changes in the intracellular calcium concentration were monitored using FDSS 6000 (Hamamatsu Photonics, Japan), a fluorometric imaging system. The cell suspension in Krebs-Ringer HEPES (KRH) buffer (115 mM NaCl, 5.4 mM KCl, 1 mM $MgSO_4$, 1.8 mM $CaCl_2$, 11 mM D-Glucose, 25 mM HEPES, 0.96 mM $Na_2HPO_4$, pH 7.3) were pre-incubated with varying concentrations of the test compounds or KRH buffer (buffer control) for 15 minutes at room temperature under the dark condition. Then capsaicin solution, which gives 300 nM in assay mixture, was automatically added to the assay plate by the FDSS 6000.

Acid Stimulation Assay:

The Acid-induced changes in the intracellular calcium concentration were monitored using FDSS 6000 (Hamamatsu Photonics, Japan), a fluorometric imaging system. The cell suspension in resting buffer (HBSS supplemented with 10 mM HEPES, pH 7.4) were pre-incubated with varying concentrations of the test compounds or resting buffer (buffer control) for 15 minutes at room temperature under the dark condition. The cells were automatically added the stimulating solution (HBSS supplemented with MES, final assay buffer pH5.8) by the FDSS 6000. The $IC_{50}$ values of VR1 antagonists were determined from the half of the increase demonstrated by buffer control samples after acidic stimulation.

Determination of Antagonist Activity

The monitoring of the changes in the fluorescence signals ($\lambda$ex=340 nm/380 nm, $\lambda$em=510–520 nm) was initiated at 1 minute prior to the addition of capsaicin solution or acidic buffer and continued for 5 minute. The $IC_{50}$ values of VR1 antagonists were determined from the half of the increase demonstrated by buffer control samples after agonist stimulation.

Chronic Contriction Injury Model (CCI Model):

Male Sprague-Dawley rats (270-300 g; B.W., Charles River, Tsukuba, Japan) were used. The chronic constriction injury (CCI) operation was performed according to the method described by Bennett and Xie (Bennett, G. J. and Xie, Y. K. Pain, 33:87-107, 1988). Briefly, animals were anesthetized with sodium pentobarbital (64.8 mg/kg, i.p.) and the left common sciatic nerve was exposed at the level of the middle of the thigh by blunt dissection through biceps femoris. Proximal to the sciatic's trifurcation was freed of adhering tissue and 4 ligatures (4-0 silk) were tided loosely around it with about 1 mm space. Sham operation was performed as same as CCI surgery except for sciatic nerve ligation. Two weeks after surgery, mechanical allodynia was evaluated by application of von Frey hairs (VFHs) to the plantar surface of the hind paw. The lowest amount of force of VFH required to elicit a response was recorded as paw withdrawal threshold (PWT). VFH test was performed at 0.5, 1 and 2 hr post-dosing. Experimental data were analyzed using Kruskal-Wallis test followed by Dunn's test for multiple comparisons or Mann-Whitney U-test for paired comparison.

Caco-2 Permeability

Caco-2 permeability was measured according to the method described in Shiyin Yee, *Pharmaceutical Research*, 763 (1997).

Caco-2 cells were grown on filter supports (Falcon HTS multiwell insert system) for 14 days. Culture medium was removed from both the apical and basolateral compartments and the monolayers were preincubated with pre-warmed 0.3 ml apical buffer and 1.0 ml basolateral buffer for 0.75 hour at 37° C. in a shaker water bath at 50 cycles/min. The apical buffer consisted of Hanks Balanced Salt Solution, 25 mM D-glucose monohydrate, 20 mM MES Biological Buffer, 1.25 mM $CaCl_2$ and 0.5 mM $MgCl_2$ (pH 6.5). The basolateral buffer consisted of Hanks Balanced Salt Solution, 25 mM D-glucose monohydrate, 20 mM HEPES Biological Buffer, 1.25 mM $CaCl_2$ and 0.5 mM $MgCl_2$ (pH 7.4). At the end of the preincubation, the media was removed and test compound solution (10 µM) in buffer was added to the apical compartment. The inserts were moved to wells containing fresh basolateral buffer and incubated for 1 hr. Drug concentration in the buffer was measured by LC/MS analysis.

Flux rate (F, mass/time) was calculated from the slope of cumulative appearance of substrate on the receiver side and apparent permeability coefficient ($P_{app}$) was calculated from the following equation.

$$P_{app}(\text{cm/sec})=(F*VD)/(SA*MD)$$

where SA is surface area for transport (0.3 $cm^2$), VD is the donor volume (0.3 ml), MD is the total amount of drug on the donor side at t=0. All data represent the mean of 2 inserts. Monolayer integrity was determined by Lucifer Yellow transport.

Human Dofetilide Binding

Cell paste of HEK-293 cells expressing the HERG product can be suspended in 10-fold volume of 50 mM Tris buffer adjusted at pH 7.5 at 25° C. with 2 M HCl containing 1 mM $MgCl_2$, 10 mM KCl. The cells were homogenized using a Polytron homogenizer (at the maximum power for 20 seconds) and centrifuged at 48,000 g for 20 minutes at 4° C. The pellet was resuspended, homogenized and centrifuged once more in the same manner. The resultant supernatant was discarded and the final pellet was resuspended (10-fold volume of 50 mM Tris buffer) and homogenized at the maximum power for 20 seconds. The membrane homogenate was aliquoted and stored at –80° C. until use. An aliquot was used for protein concentration determination using a Protein Assay Rapid Kit and ARVO SX plate reader (Wallac). All the manipulation, stock solution and equipment were kept on ice at all time. For saturation assays, experiments were conducted in a total volume of 200 µl. Saturation was determined by incubating 20 µl of [$^3$H]-dofetilide and 160 µl of membrane homogenates (20-30 µg protein per well) for 60 min room temperature in the absence or presence of 10 µM dofetilide at final concentrations (20 µl) for total or nonspecific binding, respectively. All incubations were terminated by rapid vacuum filtration over polyetherimide (PEI) soaked glass fiber filter papers using Skatron cell harvester followed by two washes with 50 mM Tris buffer (pH 7.5 at 25° C.). Receptor-bound radioactivity was quantified by liquid scintillation counting using Packard LS counter.

For the competition assay, compounds were diluted in 96 well polypropylene plates as 4-point dilutions in semi-log format. All dilutions were performed in DMSO first and then transferred into 50 mM Tris buffer (pH 7.5 at 25° C.) containing 1 mM $MgCl_2$, 10 mM KCl so that the final DMSO concentration became equal to 1%. Compounds were dispensed in triplicate in assay plates (4 µl). Total binding and nonspecific binding wells were set up in 6 wells as vehicle and 10 µM dofetilide at final concentration, respectively. The radioligand was prepared at 5.6× final concentration and this solution was added to each well (36 µl). The assay was initiated by addition of YSi poly-L-lysine Scintillation Proximity Assay (SPA)

beads (50 µl, 1 mg/well) and membranes (110 µl, 20 µg/well). Incubation was continued for 60 min at room temperature. Plates were incubated for a further 3 hours at room temperature for beads to settle. Receptor-bound radioactivity was quantified by counting Wallac MicroBeta plate counter.

$I_{HERG}$ Assay

HEK 293 cells which stably express the HERG potassium channel were used for electrophysiological study. The methodology for stable transfection of this channel in HEK cells can be found elsewhere (Z. Zhou et al., 1998, Biophysical Journal, 74, pp 230-241). Before the day of experimentation, the cells were harvested from culture flasks and plated onto glass coverslips in a standard Minimum Essential Medium (MEM) medium with 10% Fetal Calf Serum (FCS). The plated cells were stored in an incubator at 37° C. maintained in an atmosphere of 95% $O_2$/5% $CO_2$. Cells were studied between 15-28 hrs after harvest.

HERG currents were studied using standard patch clamp techniques in the whole-cell mode. During the experiment the cells were superfused with a standard external solution of the following composition (mM); NaCl, 130; KCl, 4; $CaCl_2$, 2; $MgCl_2$, 1; Glucose, 10; HEPES, 5; pH 7.4 with NaOH. Whole-cell recordings was made using a patch clamp amplifier and patch pipettes which have a resistance of 1-3 MOhm when filled with the standard internal solution of the following composition (mM); KCl, 130; MgATP, 5; $MgCl_2$, 1.0; HEPES, 10; EGTA 5, pH 7.2 with KOH. Only those cells with access resistances below 15MΩ and seal resistances >1 GΩ was accepted for further experimentation. Series resistance compensation was applied up to a maximum of 80%. No leak subtraction was done. However, acceptable access resistance depended on the size of the recorded currents and the level of series resistance compensation that can safely be used. Following the achievement of whole cell configuration and sufficient time for cell dialysis with pipette solution (>5 min), a standard voltage protocol was applied to the cell to evoke membrane currents. The voltage protocol is as follows. The membrane was depolarized from a holding potential of −80 mV to +40 mV for 1000 ms. This was followed by a descending voltage ramp (rate 0.5 mV msec$^{-1}$) back to the holding potential. The voltage protocol was applied to a cell continuously throughout the experiment every 4 seconds (0.25 Hz). The amplitude of the peak current elicited around −40 mV during the ramp was measured. Once stable evoked current responses were obtained in the external solution, vehicle (0.5% DMSO in the standard external solution) was applied for 10-20 min by a peristalic pump. Provided there were minimal changes in the amplitude of the evoked current response in the vehicle control condition, the test compound of either 0.3, 1, 3, 10 µM was applied for a 10 min period. The 10 min period included the time which supplying solution was passing through the tube from solution reservoir to the recording chamber via the pump. Exposing time of cells to the compound solution was more than 5 min after the drug concentration in the chamber well reached the attempting concentration. There was a subsequent wash period of a 10-20 min to assess reversibility. Finally, the cells was exposed to high dose of dofetilide (5 µM), a specific IKr blocker, to evaluate the insensitive endogenous current.

All experiments were performed at room temperature (23±1° C.). Evoked membrane currents were recorded on-line on a computer, filtered at 500-1 KHz (Bessel −3 dB) and sampled at 1-2 KHz using the patch clamp amplifier and a specific data analyzing software. Peak current amplitude, which occurred at around −40 mV, was measured off line on the computer.

The arithmetic mean of the ten values of amplitude was calculated under vehicle control conditions and in the presence of drug. Percent decrease of $I_N$ in each experiment was obtained by the normalized current value using the following formula: $I_N=(1-I_D/I_C)\times100$, where $I_D$ is the mean current value in the presence of drug and $I_C$ is the mean current value under control conditions. Separate experiments were performed for each drug concentration or time-matched control, and arithmetic mean in each experiment is defined as the result of the study.

Drug-Drug Interaction Assay

This method essentially involves determining the percent inhibition of product formation from fluorescence probe at 3 µM of the each compound.

More specifically, the assay is carried out as follows. The compounds were pre-incubated with recombinant CYPs, 100 mM potassium phosphate buffer and fluorescence probe as substrate for 5min. Reaction was started by adding a warmed NADPH generating system, which consist of 0.5 mM NADP (expect; for 2D6 0.03 mM), 10 mM $MgCl_2$, 6.2 mM DL-isocitric acid and 0.5 U/ml Isocitric Dehydrogenase (ICD). The assay plate was incubated at 37° C. (expect; for 1A2 and 3A4 at 30° C.) and taking fluoresce reading every minutes over 20 to 30 min.

Data calculations were preceded as follows;
1. The slope (Time vs. Fluorescence units) was calculated at the linear region
2. The percentage of inhibition in compounds was calculated by the equation $\{(v_o-v_i)/v_o\}\times100=\%$ inhibition Wherein
$v_o$=rate of control reaction (no inhibitor)
$v_i$=rate of reaction in the presence of compounds.

TABLE 1

| Condition for drug-drug interaction assay. | | | | | |
|---|---|---|---|---|---|
| | 1A2 | 2C9 | 2C19 | 2D6 | 3A4 |
| Substrate | Vivid blue (Aurora) | MFC (Gentest) | Vivid blue (Aurora) | AMMC (Gentest) | Vivid red (Aurora) |
| Substrate (µM) | 10 | 30 | 10 | 1 | 2 |
| Enzyme (pmol) | 50 | 50 | 5 | 50 | 5 |
| EX./Em(λ) | 408/465 | 408/535 | 408/465 | 400/465 | 530/595 |

Half-Life in Human Liver Microsomes (HLM)

Test compounds (1 µM) were incubated with 3.3 mM $MgCl_2$ and 0.78 mg/mL HLM (HL101) in 100 mM potassium phosphate buffer (pH 7.4) at 37° C. on the 96-deep well plate. The reaction mixture was split into two groups, a non-P450 and a P450 group. NADPH was only added to the reaction mixture of the P450 group. An aliquot of samples of P450 group was collected at 0, 10, 30, and 60 min time point, where 0 min time point indicated the time when NADPH was added into the reaction mixture of P450 group. An aliquot of samples of non-P450 group was collected at −10 and 65 min time point. Collected aliquots were extracted with acetonitrile solution containing an internal standard. The precipitated protein was spun down in centrifuge (2000 rpm, 15 min). The compound concentration in supernatant was measured by LC/MS/MS system.

The half-life value was obtained by plotting the natural logarithm of the peak area ratio of compounds/internal standard versus time. The slope of the line of best fit through the points yields the rate of metabolism (k). This was converted to a half-life value using following equations:

Half-life=ln2/k

Mono-Iodoacetate (MIA)-Induced OA Model

Male 6-weeks-old Sprague-Dawley (SD, Japan SLC or Charles River Japan) rats were anesthetized with pentobarbital. Injection site (knee) of MIA was shaved and cleaned with 70% ethanol. Twenty-five μl of MIA solution or saline was injected in the right knee joint using a 29 G needle. The effect of joint damage on the weight distribution through the right (damaged) and left (untreated) knee was assessed using an incapacitance tester (Linton Instrumentation, Norfolk, UK). The force exerted by each hind limb was measured in grams. The weight-bearing (WB) deficit was determined by a difference of weight loaded on each paw. Rats were trained to measure the WB once a week until 20 days post MIA-injection. Analgesic effects of compounds were measured at 21 days after the MIA injection. Before the compound administration, the "pre value" of WB deficit was measured. After the administration of compounds, attenuation of WB deficits was determined as analgesic effects.

Complete Freund's Adjuvant (CFA) Induced Thermal and Mechanical Hyperalgesia in Rats Thermal Hyperalgesia Male 6-week-old SD rats were used. Complete Freund's adjuvant (CFA, 300 μg of *Mycobacterium Tuberculosis* H37RA (Difco, Mich.) in 100 μL of liquid paraffin (Wako, Osaka, Japan)) was injected into the plantar surface of hind paw of the rats. Two days after CFA-injection, thermal hyperalgesia was determined by method described previously (Hargreaves et al., 1988) using the plantar test apparatus (Ugo-Basil, Varese, Italy). Rats were adapted to the testing environment for at least 15 min prior to any stimulation. Radiant heat was applied to the plantar surface of hind paw and paw withdrawal latencies (PWL, seconds) were determined. The intensity of radiant heat was adjusted to produce the stable PWL of 10 to 15 seconds. The test compound was administered in a volume of 0.5 mL per 100 g body weight. PWL were measured after 1, 3 or 5 hours after drug administration.

Mechanical Hyperalgesia

Male 4-week-old SD rats were used. CFA (300 μg of *Mycobacterium Tuberculosis* H37RA (Difco, Mich.) in 100 μL of liquid paraffin (Wako, Osaka, Japan)) was injected into the plantar surface of hind paw of the rats. Two days after CFA-injection, mechanical hyperalgesia was tested by measuring paw withdrawal threshold (PWT, grams) to pressure using the analgesy-Meter (Ugo-Basil, Varese, Italy). The animals were gently restrained, and steadily increasing pressure was applied to the dorsal surface of a hind paw via a plastic tip. The pressure required to elicit paw withdrawal was determined. The test compound was administered in a volume of 0.5 mL per 100 g body weight. PWT were measured after 1, 3 or 5 hours after drug administration.

The compounds of the examples were tested in the Human VR1 antagonist assy and HLM Half-life test methods described above. The $IC_{50}$ and $T_{1/2}$ values are presented in the following table.

TABLE 2

| Example # | $IC_{50}$(nM) | $T_{1/2}$(minutes) |
|---|---|---|
| 1 | 330 | 13 |
| 2 | 11.2 | 32 |
| 3 | 885 | |
| 4 | 190 | 9 |
| 5 | 40 | 5 |
| 6 | 18.3 | 18 |
| 7 | 15 | 33 |
| 8 | 38 | 37 |
| 9 | 171 | 42 |
| 10 | 3.59 | 22 |
| 11 | 3.59 | 22 |
| 12 | 27 | 83 |
| 13 | 146 | 12 |
| 14 | 203 | >120 |
| 15 | 0.71 | 38 |
| 16 | 6.59 | 53 |
| 17 | 10.3 | 51 |
| 18 | 282 | 119 |
| 19a | 23 | >120 |
| 19b | 71 | >120 |
| 20 | 47 | >120 |
| 21 | 20.1 | >120 |
| 22 | 1.2 | 37 |
| 23 | 10.9 | >120 |
| 24 | 19.3 | 23 |
| 25 | 26.6 | 30 |
| 26 | 78.3 | 38 |
| 27 | 7.83 | 25 |
| 28 | 12.3 | 61 |
| 29 | 17.9 | 19 |
| 30 | 138 | 32 |
| 31 | 192 | >120 |
| 32 | 0.934 | 10.8 |
| 33 | 56.2 | 39 |
| 34 | 4.72 | >120 |
| 35 | 156 | 25 |
| 36 | 19 | 23 |
| 37 | 197 | 41 |
| 38 | 70.9 | 40 |
| 39 | 9.12 | 15 |
| 40 | 32.5 | 35 |
| 41 | 0.234 | 21 |
| 42 | 0.713 | 19.7 |
| 43 | 20.7 | 41 |
| 44 | 2 | 29 |
| 45 | 5.84 | 29 |
| 46 | 12.6 | 23 |
| 47 | 7.64 | 11 |
| 48 | 203 | 21 |
| 49 | 125 | 3 |
| 50 | 239 | 4 |
| 51 | 15.6 | 5 |
| 52 | 1150 | |
| 53 | 125 | 44 |
| 54 | 234 | 96 |
| 55 | 297 | 42 |
| 56 | 1251 | >120 |
| 57 | 30.5 | 91 |
| 58 | 39.6 | 34 |
| 59 | 263 | 22 |
| 60 | 25.1 | >120 |
| 61 | 3.17 | >120 |
| 62 | 7.79 | 6 |
| 63 | 6.66 | 35.6 |
| 64 | 4.62 | 14 |
| 65 | 1043 | |
| 66 | 0.421 | 34 |
| 67 | 5.64 | 95 |
| 68 | 62 | 18 |
| 69 | 212 | 30 |
| 70 | 0.83 | 38 |
| 71 | 0.48 | 15.8 |
| 72 | 8.5 | 52.6 |
| 73 | 0.76 | >120 |
| 74 | 21 | >120 |
| 75 | 11.8 | 10 |
| 76 | 26.3 | 33 |

TABLE 2-continued

| Example # | IC$_{50}$(nM) | T$_{1/2}$(minutes) |
|---|---|---|
| 77 | 50.5 | 50 |
| 78 | <3 | |
| 79 | 20.5 | 22 |
| 80 | 3.01 | 117 |
| 81 | 42.2 | >120 |
| 82 | 62 | 26 |
| 83 | 63.8 | 65 |
| 84 | 24.5 | 3 |
| 85 | 52.7 | Not Calculated |
| 86 | 4.8 | |
| 87 | 19.9 | |
| 88 | <3 | |
| 89 | <3 | |
| 90 | 86.3 | |
| 91 | <3 | |
| Capsazepine (control) | 237-455 | |

Drug Substance

Pharmaceutically acceptable salts of the compounds of formula (I) include the acid addition and base salts thereof.

Suitable acid addition salts are formed from acids which form non-toxic salts. Examples include acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975).

Hereinafter all references to compounds of formula (I) include references to salts, solvates and complexes thereof and to solvates and complexes of salts thereof.

The compounds of the invention include compounds of formula (I) as hereinbefore defined, polymorphs, prodrugs, and isomers thereof (including optical, geometric and tautomeric isomers) as hereinafter defined and isotopically-labeled compounds of formula (I).

As stated, the invention includes all polymorphs of the compounds of formula (I) as hereinbefore defined.

Also within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985).

Some examples of prodrugs in accordance with the invention include:

(i) where the compound of formula (I) contains a carboxylic acid functionality (—COOH), an ester thereof, for example, replacement of the hydrogen with (C$_1$-C$_8$)alkyl;

(ii) where the compound of formula (I) contains an alcohol functionality (—OH), an ether thereof, for example, replacement of the hydrogen with (C$_1$-C$_6$)alkanoyloxymethyl; and (iii) where the compound of formula (I) contains a primary or secondary amino functionality (—NH$_2$ or —NHR where R≠H), an amide thereof, for example, replacement of one or both hydrogens with (C$_1$-C$_{10}$)alkanoyl.

Further examples of replacement groups in accordance with the foregoing examples and examples of other prodrug types may be found in the aforementioned references.

Finally, certain compounds of formula (I) may themselves act as prodrugs of other compounds of formula (I).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, N.Y., 1994).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colorants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

Solid formulations for oral administration may be formulated to be immediate and/or modified controlled release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14(2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably. to a pH of from 3 to 9), but, for some applications, they may be more suitably formulated as a sterile non-aqueous solution or as powdered a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for use with needle-free injection administration comprise a compound of the invention in powdered form in conjunction with a suitable vehicle such as sterile, pyrogen-free water.

Formulations for parenteral administration may be formulated to be immediate and/or modified controlled release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified controlled release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified controlled release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 μg to 10 mg of the compound of formula (I). The overall daily dose will typically be in the range 1 μg to 10 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified controlled release. Modified release formulations include delayed-, sustained-, pulsed-, controlled-, targeted and programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Dosage

For administration to human patients, the total daily dose of the compounds of the invention is typically in the range 0.1 mg to 3000 mg, preferably from 1 mg to 500 mg, depending, of course, on the mode of administration. For example, oral administration may require a total daily dose of from 0.1 mg to 3000 mg, preferably from 1 mg to 500 mg, while an intravenous dose may only require from 0.1 mg to 1000 mg, preferably from 0.1 mg to 300 mg. The total daily dose may be administered in single or divided doses.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

A VR1 antagonist may be usefully combined with another pharmacologically active compound, or with two or more other pharmacologically active compounds, particularly in the treatment of pain. For example, a VR1 antagonist, particularly a compound of formula (I), or a pharmaceutically acceptable salt or solvate thereof, as defined above, may be administered simultaneously, sequentially or separately in combination with one or more agents selected from:

- an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
- a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;
- a barbiturate sedative, e.g. amobarbital, aprobarbital, butabarbital, butabital, mephobarbital, metharbital, methohexital, pentobarbital, phenobartital, secobarbital, talbutal, theamylal or thiopental;
- a benzodiazepine having a sedative action, e.g. chlordiazepoxide, clorazepate, diazepam, flurazepam, lorazepam, oxazepam, temazepam or triazolam;
- an $H_1$ antagonist having a sedative action, e.g. diphenhydramine, pyrilamine, promethazine, chlorpheniramine or chlorcyclizine;
- a sedative such as glutethimide, meprobamate, methaqualone or dichloralphenazone;
- a skeletal muscle relaxant, e.g. baclofen, carisoprodol, chlorzoxazone, cyclobenzaprine, methocarbamol or orphrenadine;
- an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;
- an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl)quinazoline;
- a tricyclic antidepressant, e.g. desipramine, imipramine, amitriptyline or nortriptyline;
- an anticonvulsant, e.g. carbamazepine, lamotrigine, topiratmate or valproate;
- a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a 5-HT$_{1B/1D}$ agonist such as eletriptan, sumatriptan, naratriptan, zolmitriptan or rizatriptan;

a 5-HT$_{2A}$ receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4] triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-pyridinyl)-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid, (3R,4R,5R)-3-amino-4,5-dimethyl-octanoic acid, (2S)-2-Amino-4-ethyl-2-methylhexanoic acid and (2S)-2-aminomethyl-5-ethyl-heptanoic acid;

a cannabinoid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl] thio]-5-thiazolebutanol, 2-[[(1R,3S)-3-amino-4-hydroxy-1-(5-thiazolyl)butyl]thio]-6-(trifluoromethyl)-3pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyldisulfide;

an acetylcholinesterase inhibitor such as donepezil;

a prostaglandin E$_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,
5-trimethyl-6-(3-pyridylmethyl), 1,4-benzoquinone
(CV-6504);

a sodium channel blocker, such as lidocaine;

a 5-HT3 antagonist, such as ondansetron;

and the pharmaceutically acceptable salts and solvates thereof.

In as much as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

EXAMPLES

The invention is illustrated in the following non-limiting examples in which, unless stated otherwise: all operations were carried out at room or ambient temperature, that is, in the range of 18-25° C.; evaporation of solvent was carried out using a rotary evaporator under reduced pressure with a bath temperature of up to 60° C.; reactions were monitored by thin layer chromatography (TLC) and reaction times are given for illustration only; melting points (mp) given are uncorrected (polymorphism may result in different melting points); the structure and purity of all isolated compounds were assured by at least one of the following techniques: TLC (Merck silica gel 60 $F_{254}$ precoated TLC plates), mass spectrometry, nuclear magnetic resonance spectra (NMR), infrared red absorption spectra (IR) or microanalysis. Yields are given for illustrative purposes only. Flash column chromatography was carried out using Merck silica gel 60 (230-400 mesh ASTM) or Fuji Silysia amino bounded silica (Chromatorex, 30-50 uM) or Biotage amino bounded silica (35-75 μm, KP-NH) or Biotage silica (32-63 μm, KP-Sil). The purification using HPLC was perfomed by the following apparatus and conditions. Apparatus: UV-trigger preparative HPLC system, Waters (Column: XTerra MS C18, 5 um, 19×50 mm or 30×50 mm), Detector: UV 254 nm Conditions: $CH_3CN$/0.05% HCOOH aqueous solution or $CH_3CN$/0.01% $NH_3$ aqueous solution; 20 ml/min (19×50 mm) or 40 ml/min (30×50 mm) at ambient temperature.

Microwave apparatus used in the reaction was Emrys optimizer (Personal chemistry). Optical rotation was measured by P-1020 (Jasco). Low-resolution mass spectral data (EI) were obtained on a Integrity (Waters) mass spectrometer. Low-resolution mass spectral data (ESI) were obtained on a ZMD (Micromass) mass spectrometer. NMR data was determined at 270 MHz (JEOL JNMLA 270 spectrometer) or 300 MHz (JEOL JNMLA300 spectrometer) using deuterated chloroform (99.8% D) or DMSO (99.9% D) as solvent unless indicated otherwise, relative to tetramethylsilane (TMS) as internal standard in parts per million (ppm); conventional abbreviations used are: s=singlet, d=doublet, t=triplet, q=quartet, quint=quintet, m=multiplet, br.=broad, etc. IR spectra were measured by a Shimazu infrared spectrometer (IR-470). Chemical symbols have their usual meanings; bp (boiling point), mp (melting point), L (liter(s)), ml (milliliter(s)), g (gram(s)), mg (milligram(s)), mol (moles), mmol (millimoles), eq. (equivalent(s)), quant. (quantitative yield), sat.(saturated), aq (aqua).

In the following Examples, the term "the compound of Example XX" means the title compound of Example XX.

Example 1

2-(4-tert-Butylphenyl)-N-{3-fluoro-4-[(methylsulfonyl)amino]benzyl}cyclopropanecarboxamide

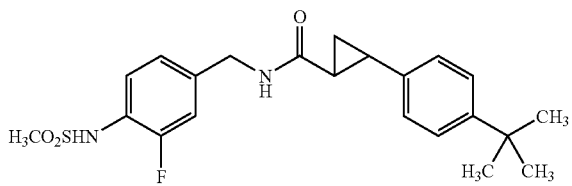

To a DMF (10 ml) solution of trans-2-(4-tert-butylphenyl) cyclopropanecarboxylic acid (435 mg, 1.89 mmol)) [Journal of medicinal chemistry, 2005, vol. 48, 71-90], EDC (572 mg, 3.0 mmol), DMAP (73 mg, 0.6 mmol), triethylamine (0.836 ml) and N-[4-(aminomethyl)-2-fluorophenyl]methanesulfonamide hydrochloride (507 mg, 1.89 mmol) were added and the mixture was stirred for 5 hours at room temperature. Then, the reaction was quenched with saturated sodium bicarbonate aqueous solution and the whole was extracted with EtOAc/hexane (3:1), and dried over sodium sulfate. Then, filtration, evaporation, and purification by silica gel column chromatography, eluting with hexane/EtOAc (1:2), gave title compound (75 mg, 9% yield) as white solids.

$^1$H NMR (300 HMz, CDCl$_3$) δ ppm 1.30 (9H, s), 1.59-1.69 (3H, m), 2.48-2.55 (1H, m), 3.02 (3H, s), 4.45 (2H, d, J=5.9 Hz), 5.98 (1H, brs), 6.49 (1H, brs), 7.03-7.12 (4H, m), 7.31 (2H, d, J=8.1 Hz), 7.53 (1H, t, J=8.4 Hz). MS (ESI) : m/z 419 (M+H)$^+$.

Example 2

2-(4-tert-Butyl-3-fluorophenyl)-N-((1R)-1-{3-methyl-4-[(methylsulfonyl)amino]phenyl}ethyl)cyclopropanecarboxamide

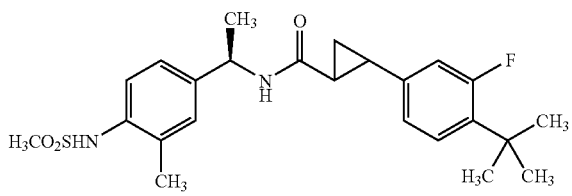

2A) 4-Acetyl-2-methylphenyl trifluoromethanesulfonate

To a stirred solution of 1-(4-hydroxy-3-methylphenyl) ethanone (6.0 g, 40 mmol) in DCM (100 ml) was added triflic anhydride (8.7 ml, 52 mmol) and triethylamine (10 ml) successively. The mixture was stirred at room temperature for 16 hours, quenched with water and extracted with DCM. The organic layer was dried over sodium sulfate and concentrated in vacuo. The crude material was purified by silica gel column chromatography eluting with DCM/EtOAc (5:1) to afford 9.6 g (85% yield) of the title compound as a yellow oil.

$^1$H NMR (270 MHz, CDCl$_3$) δ ppm 2.45 (3H, s), 2.62 (3H, s), 7.35 (1H, d, J=8.6 Hz), 7.86 (1H, dd, J=8.6, 2.5 Hz), 7.92 (1H, s).

2B) N-(4-Acetyl-2-methylphenyl)methanesulfonamide

A test tube suitable for microwave reaction was charged with tris(dibenzylideneacetone)dipalladium (0) chloroform adduct (205 mg, 0.20 mmol), the compound of Example 2A (1.41 g, 5.0 mmol), methanesulfonamide (570 mg, 6.0 mmol), and cesium carbonate (1.63 g, 7.0 mmol). The mixture was subjected to microwave irradiation at 120° C. with stirring for 10 minutes. The reaction mixture was filtered and the filtrate was concentrated in vacuo. The crude material was purified by silica gel column chromatograph eluting with hexane/ethylacetate (2:1) to afford 390 mg (34% yield) of the title compound as yellow solids.

$^1$H NMR (270 MHz, CDCl$_3$) δ ppm 2.34 (3H, s), 2.59 (3H, s), 3.11 (3H, s), 6.47 (1H, br.s), 7.58 (1H, d, J=8.1 Hz), 7.84 (2H, m). MS (ESI): m/z 228 (M+H)$^+$, 226 (M−H)$^−$.

2C) N-[4-((1R)-1-{[(R)-tert-Butylsulfinyl]amino}ethyl)-2-methylphenyl]methanesulfonamide To a solution of titanium(IV) ethoxide (1.32 g, 5.8 mol) and the compound of Example 2B (800 mg, 3.5 mmol) in THF (20 ml), (R)-(+)-tert-butanesulfinamide was added under nitrogen atmosphere and the mixture was heated at 70° C. for 16 hours. The reaction was quenched with water and the resulting white precipitates were filtered off. The filtrate was partitioned between EtOAc and water. Then the organic layer was separated, dried over sodium sulfate and concentrated in vacuo. The crude product was purified by silica gel column chromatography eluting with hexane/EtOAc (4:1). The resulting yellow oil was dissolved in THF (10 ml) and the solution was added to sodium borohydride (242 mg, 6.4 mmol) in THF (10 ml) at −70° C. The mixture was stirred at −70° C. for 5 hours and then quenched with MeOH. After stirring at room temperature for 1 hour, the mixture was concentrated in vacuo to afford 530 mg (45% yield) of the title compound as pale yellow solids.

MS (ESI) : m/z 333 (M+H)$^+$, 331 (M−H)$^−$.

2D) N-{4-[(1R)-1-Aminoethyl]-2-methylphenyl}methanesulfonamide hydrochloride To the compound of Example 2C (530 mg, 1.60 mmol) was added hydrogenchloride-MeOH (2.0 M, 5.0 ml) and 1,4-dioxane (5.0 ml). The solution was stirred at room temperature for 30 minutes and then concentrated in vacuo. Diethyl ether was added to precipitate the amine hydrochloride. The precipitates were then filtered and washed with diethyl ether to give 450 mg (quant.) of the title compound as white solids. The enantiomeric purity (>99%ee) was determined by Daicel Chiralcel OD-H (4.6×250 mm) eluting with 0.1% diethylamine in hexane/ethylalcohol (80:20 by volume) at column temperature of 40° C. Retension time: 10.2 min (R-form), 12.8 min (S-form).

$^1$H NMR (270 MHz, DMSO-d$_6$) δ ppm 1.45 (3H, m), 2.31 (3H, s), 2.98 (3H, s), 4.27 (1H, m), 7.31-7.38 (3H, m). MS (ESI): m/z 227 (M−H)$^−$.

2E) 4-tert-Butyl-3-fluorophenol

Zirconiumtetrachloride (11.7 g, 50 mmol) in DCM (130 ml), tert-butylmethylether (4.44 g, 50 mmol), and 3-fluorophenol (5.6 g, 50 mmol) were mixed at room temperature and the reaction mixture was stirred for 2 hours at 50° C. The reaction was quenched with water and the whole was extracted with ethylacetate and dried over magnesium sulfate. After filtration, evaporation gave a crude residue, which was purified by silica gel column chromatography, eluting with gradually from hexane only to hexane/ethylacetate (9:1), to afford 4.25 g (51% yield) of the title compound as white solids.

$^1$H NMR (CDCl$_3$) δ ppm 1.34 (9H, s), 4.97 (1H, brs), 6.56-6.50 (2H, m), 7.13 (1H, t, J=8.7 Hz).

2F) 4-tert-Butyl-3-fluorophenyl trifluoromethanesulfonate

To a pyridine (30 ml) and DCM (50 ml) solution of the compound of Example 2E (4.25 g, 25 mmol), triflic acid anhydride (10.6 g, 37.5 mmol) and DMAP (30 mg, 0.25 mmol) were added and the mixture was stirred for 2 hours at 0° C. After quenching with water, the mixture was extracted with hexane. The extract was concentrated in vacuo and the crude product was purified by silica gel column chromatography with graduate elution from hexane only to hexane/ethylacetate (9:1) to afford 6.7 g (88% yield) of the title compound as a colorless oil.

$^1$H NMR (CDCl$_3$) δ ppm 1.38 (9H, s), 6.95-7.03 (2H, m), 7.37 (1H, t, J=8.1 Hz). MS (ESI): m/z 301 (M+H)$^+$.

2G) 1-tert-Butyl-2-fluoro-4-vinylbenzene

To a DMF (100 ml) solution of the compound of Example 2F (3.27 g, 10.9 mmol), vinyltributylstannane (3.8 g, 12.0 mmol), lithium chloride (4.62 g, 108 mmol) and palladium-dichlorobistriphenylphosphine (0.383 g, 0.54 mmol) were added and the mixture was stirred for 30 minutes at room temperature. After stirring at 30° C. for additional 20 hours, the reaction was quenched with water and the whole was extracted with hexane. Afrer evaporation of the solvent, the residue was purified by silica gel column chromatography eluting with hexane to afford the title compound (1.87 g, 96%) as a colorless oil.

$^1$H NMR (CDCl$_3$) δ ppm 1.33 (s, 9H), 5.25 (1H, d, J=10.8 Hz), 5.72 (1H, d, J=18.9 Hz), 6.65 (1H, dd, J=10.8, 18.9 Hz), 7.03-7.09 (2H, m), 7.16-7.36 (1H, m).

2H) Ethyl 2-(4-tert-butyl-3-fluorophenyl)cyclopropanecarboxylate

To a toluene (12 ml) solution of the compound of Example 2G (1.86 g, 10.4 mmol), Co(TPP) (0.21 g, 0.3 mmol) and 1-methyl-1H-imidazole (2.56 g, 31 mmol), ethyl diazoacetate (1.66 g, 14.5 mmol) was added and the mixture was stirred for 5 minutes at room temperature. Then the mixuture was stirred for an additional 1 hour at 80° C. After evaporation of the solvent, the residue was purification by silica gel column chromatography eluting with gradually from hexane to hexane/ethylacetate (10:1) to afford the title compound (2.13 g, 77%, trans) as a colorless oil.

$^1$H NMR (CDCl$_3$) δ ppm 0.88 (3H, t, J=8.1 Hz), 1.24-1.30 (1H, m), 1.35 (9H, s), 1.55-1.62 (1H, m), 1.84-1.90 (1H, m), 2.43-2.50 (1H, m), 4.17 (2H, q, J=8.1 Hz), 6.73 (1H, br, J=8.1 Hz), 6.82 (1H, d, J=8.1 Hz), 7.19(1H, t, J=8.1 Hz). MS (ESI): m/z 265 (M+H)$^+$.

2I) 2-(4-tert-Butyl-3-fluorophenyl)cyclopropanecarboxylic acid

To a THF (5 ml) solution of the compound of Example 2H (2.13 g, 6.8 mmol), 2M sodium hydroxide aqueous solution (10 ml) and MeOH (10 ml) were added and the mixture was stirred for 30 min at 80° C. After the reaction was completed, the basic mixture was acidified with a 2M HCl aqueous solution and the whole was extracted with EtOAc. Evaporation of the solvent gave 1.63 g (89% yield) of the title compound as white solids.

MS (ESI): m/z 235 (M−H)⁻.

2J) 2-(4-tert-Butyl-3-fluorophenyl)-N-((1R)-1-{3-methyl-4-[(methylsulfonyl) amino]phenyl}ethyl)cyclopropanecarboxamide To a THF (0.5 ml) solution of the compound of Example 21 (33 mg, 0.14 mmol) was added CDI (22.7 mg, 0.14 mmol) at room temperature and the mixture was stirred for 1 hour at room temperature and then, to this reaction was added triethylamine (0.5 ml) and the compound of Example 2D (37 mg, 0.14 mmol). After the mixture was stirred for 3 hours, filtration, evaporation, and purification by silica gel column chromatography, eluting with hexane/ethylacetate/methylene chloride (1:2:2), gave the title compound (7.5 mg, 12%) as white solids.

$^1$H NMR (CDCl$_3$) δ ppm 1.30 (9H, br), 1.16-1.38 (5H, m), 1.84-1.96 (1H, m), 2.18-2.29 (1H, m), 2.28 (3H, br), 2.95 (3H, br), 4.83-4.94 (1H, m), 6.83-6.93 (2H, m), 7.12-7.23 (4H, m), 8.51-8.55 (1H, m), 9.01 (1H, br). MS (ESI): m/z 447 (M+H)⁺.

Example 3

2-[4-(1-Hydroxy-1-methylethyl)phenyl]-2-methyl-N-((1R)-1-{3-methyl-4-[(methylsulfonyl)amino]phenyl}ethyl)cyclopropanecarboxamide

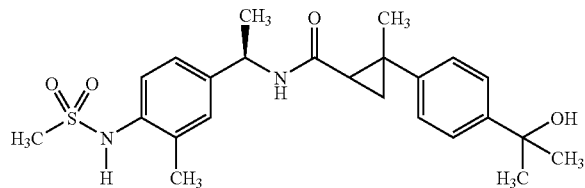

3A) Ethyl 2-(4-acetylphenyl)-2-methylcyclopropanecarboxylate

To a stirred solution of 1-[4-(1-methylethenyl)phenyl]ethanone (711 mg, 4.44 mmol, trans) (Org. Lett., 2002, 4(1), 107-109), N-methylimidazole (1.06 ml, 13.3 mmol) and Co(TPP)(89 mg, 0.13 mmol) in toluene (10 ml) was added ethyl diazoacetate (0.65 ml, 6.21 mmol) in one portion at ambient temperature. The same procedure as described in Example 2H was performed to give the title compound (236 mg, 22%) as dark yellow oil.

$^1$H NMR (270 MHz, CDCl$_3$) δ 1.31 (3H, t, J=6.8 Hz), 1.42-1.60 (5H, m), 1.95-2.02 (1H, m), 2.59 (3H, s), 4.14-4.27 (2H, m), 7.35-7.41 (2H, m), 7.88-7.94 (2H, m)

3B) 2-(4-Acetylphenyl)-2-methyl-N-((1R)-1-{3-methyl-4-[(methylsulfonyl)amino]phenyl}ethyl)cyclopropanecarboxamide A mixture of the compound of Example 3A (236 mg, 0.96 mmol) in 2M sodium hydroxide aqueous solution (2 ml, 4.0 mmol) and MeOH (6 ml) was heated at 85° C. for 1.5 hours. After cooling to ambient temperature, the solvent was evaporated in vacuo and the residue was diluted with water. The aqueous solution was washed with diethyl ether, acidified to pH 1 with 2M hydrochloric acid aqueous solution and extracted with DCM. The combined solution was washed with brine, dried over sodium sulfate and concentrated in vacuo to give the crude acid compound (205 mg) as dark yellow solids. To a stirred solution of the compound of Example 2D (249 mg, 0.94 mmol), the crude acid compound (205 mg, 0.94 mmol), HOBt (144 mg, 0.94 mmol), EDC (324 mg, 0.83 mmol) in anhydrous DMF (5 ml) was added triethylamine (380 mg, 3.76 mmol) at ambient temperature. The reaction procedure as described in Example 1 was performed to give the title compound (310 mg, 81% in 2 steps) as pale yellow amorphous solids (mixture of diastereomeric products (1:1)).

$^1$H NMR (270 MHz, CDCl$_3$) δ 1.37-1.65 (8H, m), 1.70-1.82 (1H, m), 2.32 (3H, s), 2.58 (3H, m), 3.02 (3H, m), 5.06-5.20 (1H, m), 5.94-6.05 (1H, m), 6.24(1H, br.s), 7.15-7.25 (2H, m), 7.29-7.45 (3H, m), 7.86-7.92 (2H, m)

3C) 2-[4-(1-Hydroxy-1-methylethyl)phenyl]-2-methyl-N-((1R)-1-{3-methyl-4-[(methylsulfonyl)amino]phenyl}ethyl)cyclopropanecarboxamide To a stirred solution of the compound of Example 3B (245 mg, 0.57 mmol) in anhydrous THF (30 ml) was added 0.98 mol/l methyllithium in diethyl ether solution (2.92 ml, 2.85 mmol) at −78° C. After 20 minutes −78° C., the mixture was warmed to 0° C. and stirred for 40 minutes. The mixture was quenched with saturated ammonium chloride aqueous solution and extracted with DCM. The combined solution was washed with brine, dried over sodium sulfate and concentrated in vacuo to give the crude product. Purification by column chromatography on amono bounded silica gel, eluting with DCM-MeOH (30:1-20:1), gave white solids, which was recrystallized from hexane-EtOAc to afford the title compound (128 mg, 50%) as white solids (mixture of diastereomeric products (1:1)).

$^1$H NMR (270 MHz, CDCl$_3$) δ 1.32-1.80 (16H, m), 2.31 (3H, s), 3.00 (3H, s), 5.05-5.20 (1H, m), 5.85-5.96 (1H, m), 6.30 (1H, br.s), 7.14-7.26 (4H, m), 7.37-7.46 (3H, m) MS (ESI): m/z 443 (M−H)⁻, m/z 445 (M+H)⁺.

Example 4

2-(4-tert-Butyl-3-fluorophenyl)-N-{3-methyl-4-[(methylsulfonyl)amino]benzyl}cyclopropanecarboxamide

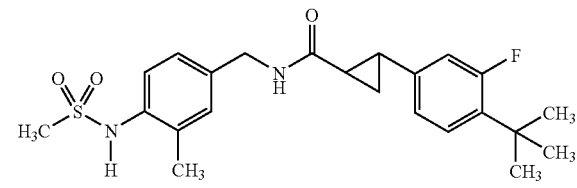

4A) 4-(4-Cyano-2-methylphenyl)methanesulfonamide

A mixture of 4-(4-iodo-2-methylphenyl)methanesulfonamide (18.0 g, 57.9 mmol), zinc cyanide (8.49 g, 74.3 mmol) and tetrakis(triphenylphosphine)palladium(0)(6.68 g, 5.78 mmol) in DMF (130 ml) was heated at 100° C. for 3 hours. The mixture was diluted with EtOAc/toluene (8:1) and the precipitates were filtered through a celite pad. The organic layer was washed with water, then brine, dried over magnesium sulfate and concentrated in vacuo to give the crude produdt. The crude product was purified by column chromatography on silica gel, eluting with hexane/EtOAc (1:1), to give white solids which was isolated from acetone-hexane to afford 10.3 g (85% yield) of the title compound as white solids.

$^1$H NMR (270 MHz, DMSO-d$_6$) δ ppm 2.31 (3H, s), 3.11 (3H, s), 7.50 (1H, d, J=8.1 Hz), 7.64-7.76 (2H, m), 9.50 (1H, s).

4B) 4-[4-(Aminomethyl)-2-methylphenyl]methanesulfonamide monohydrochloride

A mixture of the compound of Example 4A (10.0 g, 47.6 mmol) in THF (150 ml)-MeOH (100 ml)-concentrated hydrogenchloride aqueous solution (35 ml) was hydrogenated over 10% Pd—C (1.50 g) using a hydrogen balloon for 24 hours. The reaction mixture was filtered through a celite pad, and the filter cake was washed with THF/water (1:1)(300 ml). The filtrate and washings were evaporated in vacuo and the residue was diluted with EtOAc-water. The aqueous layer was separated and evaporated in vacuo to give the crude product, which was isolated from MeOH-diisopropyl ether to afford 11.5 g (95% yield) of the title compound as white solids.

$^1$H NMR (270 MHz, DMSO-d$_6$) δ ppm 2.31 (3H, s), 2.99 (3H, s), 3.95 (2H, s), 7.27-7.41 (m, 3H) , 8.66 (3H, br.s). MS (ESI): m/z 213 (M−H)$^-$.

4C) 2-(4-tert-Butyl-3-fluorophenyl)-N-{3-methyl-4-[(methylsulfonyl)amino]benzyl}cyclopropanecarboxamide To a THF (2.0 ml) solution of the compound of Example 2I (94.5 mg, 0.40 mmol) was added CDI (71 mg, 0.44 mmol) at room temperature and the mixture was stirred for 1 hour at room temperature and then, to this reaction was added triethylamine (0.5 ml) and the compound of Example 4B (120 mg, 0.48 mmol). The same procedure as described in Example 2J was performed to afford 89 mg (51% yield) of the title compound as white solids.

$^1$H NMR (DMSO-d$_6$) δ ppm 1.14-1.42 (2H, m), 1.30 (9H, s), 1.86-1.96 (1H, m), 2.20-2.31 (1H, m), 2.29 (3H, s), 2.95 (3H, s), 4.26 (2H, d, J=5.4 Hz), 6.89 (1H, d, J=8.1 Hz), 6.92 (1H, s), 7.06-7.24 (m, 4H), 8.60 (1H, t, J=5.4 Hz), 9.03 (1H, br). MS (ESI): m/z 433 (M+H)$^+$.

Example 5

2-(4-tert-Butylphenyl)-2-methyl-N-{3-methyl-4-[(methylsulfonyl)amino]benzyl}cyclopropanecarboxamide

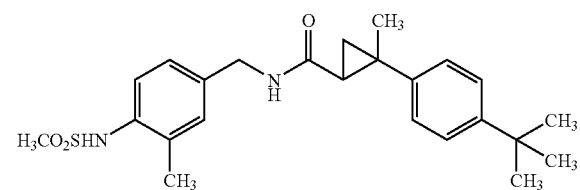

To a THF (2.0 ml) solution of trans-2-(4-tert-butylphenyl)-2-methylcyclopropane carboxylic acid (92.9 mg, 0.40 mmol) [EP 188887 A1 (1986)] was added CDI (71 mg, 0.44 mmol) at room temperature and the mixture was stirred for 1 hour at room temperature and then, to this reaction was added triethylamine (0.5 ml) and the compound of Example 4B (120 mg, 0.48 mmol). The reaction procedure as described in Example 2J was performed to afford 7 mg (4% yield) of the title compound as white solids.

$^1$H NMR (CDCl$_3$) δ ppm 1.24-1.33 (4H, m), 1.30 (9H, s), 1.41 (1H, dd, J=5.4, 8.1 Hz), 1.73 (1H, dd, J=8.1 Hz), 2.31 (3H, s), 3.01 (3H, s), 4.45 (2H, d, J=5.4 Hz), 5.95 (1H, br), 6.16-6.27 (1H, m), 7.14-7.22 (2H, m), 7.19 (2H, d, J=8.1 Hz), 7.33 (2H, d, J=8.1 Hz), 7.42 (1H, d, J=8.1 Hz). MS (ESI): m/z 429 (M+H)$^+$.

Example 6

N-{3-Methyl-4-[(methylsulfonyl)amino]benzyl}-2-[4-(2,2,2-trifluoro-1,1-dimethylethyl)phenyl]cyclopropanecarboxamide

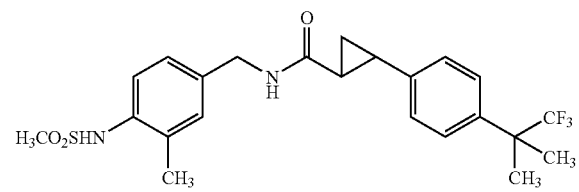

6A) 4-(2,2,2-Trifluoro-1,1-dimethylethyl)phenyl trifluoromethanesulfonate

To a pyridine (8 ml) and DCM (12 ml) solution of 4-(2,2,2-trifluoro-1,1-dimethylethyl)phenol (1.2 g, 6 mmol), triflic acid anhydride (2.54 g, 9 mmol) and DMAP (12 mg, 0.1 mmol) were added and the mixture was stirred for 3 hours at 0° C. The same procedure as described in Example 2F was purfomed to give the title compound (1.8 g, 89%) as a colorless oil.

$^1$H NMR (CDCl$_3$) δ 1.59 (6H, s), 7.28 (2H, d, J=8.1 Hz), 7.59 (2H, d, J=8.1 Hz)

6B) 1-(2,2,2-Trifluoro-1,1-dimethylethyl)-4-vinylbenzene

To a DMF (50 ml) solution of the compound of Example 6B (1.80 g, 5.3 mmol), vinyltributylstannane (1.86 g, 5.8 mmol), lithium chloride (2.25 g, 53 mmol) and palladium-dichlorobistriphenylphosphine (186 mg, 0.26 mmol) were added and the mixture was stirred for 30 minutes at room temperature followed by additional stirring for 10 hours at 28° C. The same procedure as described in Example 2G was performed to give the title compound (815 mg, 72%) as a colorless oil.

$^1$H NMR (CDCl$_3$) δ ppm 1.57 (6H, s), 5.27 (1H, d, J=10.8 Hz), 5.76 (1H, d, J=16.2 Hz), 6.71 (1H, dd, J=10.8, 16.2 Hz), 7.38-7.47 (4H, m).

6C) Ethyl 2-[4-(2,2,2-trifluoro-1,1-dimethylethyl)phenyl]cyclopropanecarboxylate To a toluene (4 ml) solution of the compound of Example 6B (0.8 g, 3.73 mmol, trans), Co(TPP) (0.075 g, 0.1 mmol) and 1-methyl-1H-imidazole (0.92 g, 11 mmol), ethyl diazoacetate (0.6 g, 5.26 mmol) was added in the same procedure as described in Example 2H to give the title compound (1.0 g, 89%) as a colorless oil.

$^1$H NMR (CDCl$_3$) δ ppm 1.28 (3H, t, J=8.1 Hz), 1.25-1.35 (1H, m), 1.55 (6H, 1.94 (1H, m), 2.47-2.54 (1H, m), 4.17 (2H, q, J=8.1 Hz), 7.10 (2H, d, j=8.1 Hz), 7.41 (2H, d, J=8.1 Hz). MS (ESI): m/z 301 (M+H)$^+$.

6D) 2-[4-(2,2,2-Trifluoro-1,1-dimethylethyl)phenyl]cyclopropanecarboxylic acid

To a THF (5 ml) solution of the compound of Example 6C (1.0 g, 3.3 mmol), 2M sodium hydroxide solution (3 ml) and MeOH (3 ml) were added in the same procedure as described in Example 2I to afford 0.82 g (90% yield) of the title compound as white solids.

MS (ESI): m/z 271 (M−H)$^-$.

6E) N-{3-Methyl-4-[(methylsulfonyl)amino]benzyl}-2-[4-(2,2,2-trifluoro-1,1-dimethyl)phenyl]cyclopropanecarboxamide To a THF (2.0 ml) solution of the compound of Example 6D (109 mg, 0.4 mmol) was CDI (71 mg, 0.44 mmol) at room temperature and the mixture was stirred for 1 hour at room temperature and then, to this reaction was added triethylamine (0.5 ml) and of the compound of Example 4B (120 mg, 0.48 mmol). The same procedure as described in Example 2J was performed to give the title compound (115 mg, 64%) as white solids.

$^1$H NMR (DMSO-d$_6$) δ ppm 1.20-1.31 (1H, m), 1.36-1.45 (1H, m), 1.52 (6H, s), 1.89-1.98 (1H, m), 2.29 (3H, s), 2.95 (3H, s), 4.26 (2H, d, J=5.4 Hz), 7.07-7.17 (2H, m), 7.16 (2H, d, J=8.1 Hz), 7.24 (1H, d, J=8.1 Hz), 7.43 (2H, d, J=8.1 Hz), 8.61 (1H, t, J=5.4 Hz), 9.03 (1H, br). MS (ESI): m/z 469 (M+H)$^+$.

Example 7

2-(4-tert-Butylphenyl)-N-((1R)-1-{3-methyl-4-[(methylsulfonyl)amino]phenyl}ethyl)cyclopropanecarboxamide

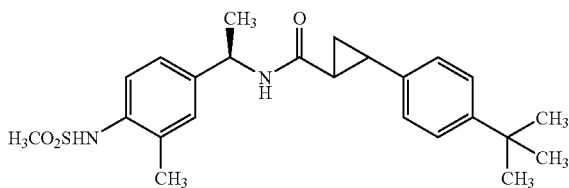

7A) 2-(4-tert-butylphenyl)cyclopropanecarboxylic acid

Racemic trans-2-[4-(1,1-dimethylethyl)phenyl]cyclopropanecarboxylic acid [Journal of medicinal chemistry, 2005, vol. 48, 71-90] was separated with DAICEL CHIRALPAK AD-H (column size: 2×25 cm, Mobile Phase: hexane/ethanol/trifluoroacetic acid=95/5/0.1, column temperature: 40° C., flow rate: 20 ml/min, detection: 220 nm, Retention time: 7.5 min and 8.6 min). The later fraction was used for the next step.

$[α]_D$=+281.1 (c=0.94, methanol, cell temperature=21.0° C.)

7B) 2-(4-tert-Butylphenyl)-N-((1R)-1-{3-methyl-4-[(methylsulfonyl)amino]phenyl}ethyl)cyclopropanecarboxamide To a stirred solution of the compound of Example 7A (276 mg, 1.26 mmol) in DCM (3 ml) was added oxalyl chloride (240 mg, 1.89 mmol) and DMF (1 drop) at 0° C. After being stirred for 1 hour at room temperature, the mixture was evaporated in vacuo and the residue was dissolved in DCM (1 ml). The above solution was added to a solution of the compound of Example 2D (288 mg, 1.26 mmol) and triethylamine (382 mg, 3.78 mmol) in DCM (5 ml) at 0° C. After being stirred for 5 hours at room temperature, the mixture was diluted with DCM and washed with 2M hydrochloric aqueous solution, brine. The organic layer was dried over sodium sulfate and concentrated in vacuo to give a crude product which was purified by an amino bound silica gel column (FUJI SILYSIA CHEMICAL LTD. size 30 to 50 μm) chromatography, eluting with DCM-MeOH (200:1), to give the desired compound. This product was isolated from hexane—EtOAc to afford 384 mg (71% yield) of the title compound as white solids.

$^1$H NMR (DMSO-d$_6$) δ ppm 1.10-1.37 (14H, m), 1.82-1.93 (1H, m), 2.14-2.25 (1H, m), 2.29 (3H, s), 2.96 (3H, s), 4.82-4.95 (1H, m), 7.00-7.33 (7H, m), 8.48-8.55 (1H, m), 9.01 (1H, br). MS (ESI): m/z 429 (M+H)$^+$.

Example 8

2-(4-tert-Butylphenyl)-N-((1R)-1-{3-fluoro-4-[(methylsulfonyl)amino]phenyl}ethyl)cyclopropanecarboxamide

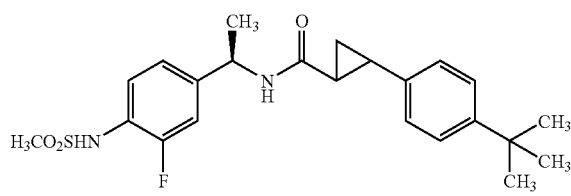

The carboxylic acid used in Example 1 (50.0 mg, 0.23 mmol) and N-{4-[(1R)-1-aminoethyl]-2-fluorophenyl}methanesulfonamide hydrochloride (50 mg, 0.23 mmol) were treated in the same procedure as Example 7B to afford 42.5 mg (38% yield) of the title compound as white solids.

$^1$H NMR (CDCl$_3$) δ ppm 1.30 (9H, s), 1.45 (3H, d, J=6.6 Hz), 1.56-1.64 (2H, m), 2.44-2.50 (1H, m), 3.02 (3H, s), 5.04-5.13 (1H, m), 5.92 (1H, d, J=7.4 Hz), 6.60 (1H, s), 7.00-7.33 (7H, m), 7.51 (1H, t, J=8.9 Hz). MS (ESI): m/z 419 (M+H)$^+$.

Example 9

2-Methyl-N-((1R)-1-{6-methyl-5-[(methylsulfonyl)amino]pyridin-2-yl}ethyl)-2-[4-(2,2,2-trifluoro-1,1-dimethylethyl)phenyl]cyclopropanecarboxamide

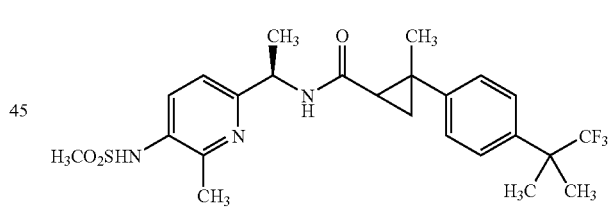

9A) N-(6-Chloro-2-methylpyridin-3-yl)methanesulfonamide

A mixture of 3-amino-6-chloro-2-picoline (2.0 g, 14.0 mmol) and methanesulfonyl chloride (1.92 g, 16.8 mmol) in pyridine (40 ml) was stirred for 1 hour at room temperature. After removal of the solvent, the resulting crude product was purified by silica gel column chromatography, eluting with hexane/EtOAc (3:2), to afford 1.70 g (55% yield) of the title compound as pale yellow solids.

$^1$H NMR (DMSO-d$_6$) δ ppm 2.47 (3H, s), 3.05 (3H, s), 7.37 (1H, d, J=8.6 Hz), 7.71 (1H, d, J=8.6 Hz), 9.47 (1H, s). MS (ESI): m/z 221 (M+H)$^+$.

9B) N-(6-Cyano-2-methylpyridin-3-yl)methanesulfonamide

A test tube suitable for microwave use was charged with the compound of Example 9A (1.66 g, 7.52 mmol), zinc cyanide (1.11 g, 9.45 mmol) and tetrakis(triphenylphosphine)

palladium(0) (872 mg, 0.754 mmol) in DMF (14.1 ml). The mixture was subjected to microwave irradiation at 100° C. with stirring for 30 minutes. Then, the mixture was diluted with toluene/EtOAc (1:10) and the precipitates were filtered off. The organic layer was washed with water, then brine, and dried over magnesium sulfate. After the filtration, the organic layer was evaporated in vacuo to give the crude product which was purified by silica gel column chromatography, eluting with hexane/EtOAc (3:2), to give the the title compound (835 mg, 53%) as pale yellow solids.

$^1$H NMR (DMSO-$d_6$) δ ppm 2.50 (3H, s), 3.15 (3H, s), 7.85 (2H, s), 9.81 (1H, s). MS (ESI): m/z 212 (M+H)$^+$.

9C) N-(6-Acetyl-2-methylpyridin-3-yl)methanesulfonamide

To a solution of the compound of Example 9B (423 mg, 2.0 mmol) in THF (9.9 ml) was added dropwise a diethyl ether solution of methyl magnesium bromide (6.7 ml, 6.0 mmol) at 0° C. with stirring. After being stirred for 2 hours at the same temperature, the reaction mixture was poured into ice cold water (10 ml) and extracted with EtOAc. The organic layer was dried over magnesium sulfate and concentrated to give dark red solids, which was isolated from EtOAc-hexane to afford 246 mg (54% yield) of the title compound as reddish solids.

$^1$H NMR (300 MHz, DMSO-$d_6$) δ ppm 2.56 (3H, s), 2.59 (3H, s), 3.13 (3H, s), 7.80-7.89 (2H, m), 9.68 (1H, s). MS (ESI): m/z 229 (M+H)$^+$.

9D) N-[2-Methyl-6-((1R)-1-{[(1R)-1-phenylethyl]amino}ethyl)pyridin-3-yl]methanesulfonamide To a solution of the compound of Example 9C (959 mg, 4.20 mmol), (1R)-1-phenylethanamine (611 mg, 5.04 mmol) and triethylamine (2.34 ml, 16.8 mmol) in DCM (30 ml) was added a solution of titanium (IV) chloride (495 mg, 2.61 mmol) in DCM (5 ml) at room temperature under N$_2$. After being stirred for 17 hours at the same temperature, the reaction volume was reduced to the extent of half by evaporation (ca. 20 m). The mixture was diluted with EtOH (40 ml) and then it was hydrogenated over Raney-Ni under H$_2$ pressure (4.3 kg/cm$_2$) at room temperature. After being stirred for 5 hours, the reaction mixture was filtered through a celite pad with DCM. The filtrate was concentrated and the residue was purified by silica gel column chromatography, eluting with acetone/hexane (1:1), to afford 0.67 g (48% yield) of the title compound as yellow viscous oil.

$^1$H NMR (300 MHz, DMSO-$d_6$) δ ppm 1.09-1.25 (6H, m), 2.45 (3H, s), 3.02 (3H, s), 3.26-3.48 (2H, m), 7.13-7.37 (6H, m), 7.61 (1H, d, J=8.1 Hz). MS (ESI): m/z 334 (M+H)$^+$.

9E) N-{6-[(1R)-1-aminoethyl]-2-methylpyridin-3-yl}methanesulfonamide hydrochloride Salt To a solution of the compound of Example 9D (0.82 g, 2.46 mmol) in EtOH (25 ml) was added 10% Pd—C (0.32 g) and ammonium formate (6.20 g, 98 mmol) at room temperature under N$_2$. The resulting mixture was stirred for 2 hours at 65° C. The reaction mixture was cooled to room temperature and filtered through a celite pad. The filtrate was treated with 10% HCl—MeOH, then concentrated and the product isolated from MeOH-ether to afford 0.54 g (83% yield) of the title compound as white solids.

$^1$H NMR (300 MHz, DMSO-$d_6$) δ ppm 1.48 (3H, d, J=6.6 Hz), 2.56 (3H, s), 3.06 (3H, s), 4.38-4.54 (1H, m), 7.40 (2H, d, J=9.0 Hz), 7.76 (1H, d, J=9.0 Hz), 8.40 (2H, br.s.), 9.50 (1H, s). MS (ESI): m/z 230 (M+H)$^+$.

9F) 2-Methyl-N-((1R)-1-{6-methyl-5-[(methylsulfonyl)amino]pyridin-2-yl}ethyl)-2-[4-(2,2,2-trifluoro-1,1-dimethylethyl)phenyl]cyclopropanecarboxamide The procedure described in Example 13C was followed using the compound of Example 13D (99.2 mg, 0.346 mmol) and the compound of Example 9E (92.1 mg, 0.35 mmol) to give solids which was isolated from DCM-hexane to afford 50.9 mg (30% yield) of the title compound as white solids.

$^1$H NMR (DMSO-$d_6$) δ ppm 1.18-1.47 (8H, m), 1.54 (6H, s), 1.94-2.10 (1H, m), 2.49 (3H, s), 3.01 (3H, s), 4.84-5.01 (1H, m), 7.13-7.23 (1H, m), 7.29-7.37 (2H, m), 7.42-7.52 (2H, m), 7.57-7.66 (1H, m), 8.53-8.71 (1H, m), 9.27 (1H, s). MS (ESI): m/z 498 (M+H)$^+$.

Example 10

2-(6-tert-Butylpyridin-3-yl)-2-methyl-N-((1R)-1-{3-methyl-4-[(methylsulfonyl)amino]phenyl}ethyl)cyclopropanecarboxamide

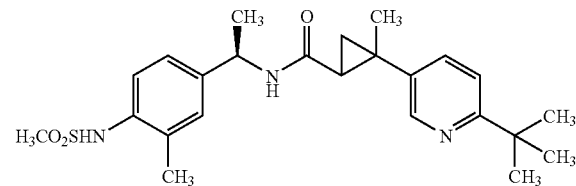

10A) 6-tert-Butylpyridin-3-yl-trifluoromethanesulfonate

To a pyridine (50 ml) and DCM (80 ml) solution of 6-tert-butylpyridin-3-ol (6.51 g, 43.1 mmol, Journal of Chemical Research, Synopses, 1978, 7, 246), trifluoromethane sulfonic anhydride (14.6 g, 51.7 mmol) and 4-(dimethylamino)pyridine (53 mg, 0.43 mmol) were added in the same procedure as described in Example 2F to afford 10.8 g (89% yield) of the title compound as a pale yellow oil.

$^1$H NMR (CDCl$_3$) δ ppm__1.38 (9H, s), 7.44 (1H, d, J=9.2 Hz), 7.54 (1H, dd, J=2.6, 9.2 Hz), 8.51 (1H, d, J=2.6 Hz)

10B) 2-tert-Butyl-5-isopropenylpyridine

A mixture of the compound of Example 10A (10.8 g, 38.2 mmol), potassium isopropenyltrifluoroborate (5.66 g, 38.2 mmol, Org. Lett. 2002, 4, 107), PdCl$_2$(dppf).CH$_2$Cl$_2$ (1.56 g, 1.91 mmol) and triethylamine (5.32 ml, 38.2 mmol) in n-propanol (400 ml) was stirred at 80° C. for 1 hour, and then stirred at 90° C. for 1 hour. The reaction was quenched with saturated aqueous sodium bicarbonate solution and the whole was extracted with hexane. The extrace was concentrated and the residue was purified by silica gel column chromatography eluting with hexane/ethylacetate=30/1 to afford the title compound (5.96 g 89%) as a colorless oil $^1$H NMR (CDCl$_3$) δ ppm 1.37 (9H, s), 2.15 (3H, s), 5.12 (1H, s), 5.39 (1H, s), 7.31 (1H, d, J=7.9 Hz), 7.68 (1H, dd, J=2.0, 7.9 Hz) 8.68 (1H, d, J=2.0 Hz)

10C) Ethyl 2-(6-tert-butylpyridin-3-yl)cyclopropanecarboxylate

To a toluene (60 ml) solution of 2-tert-butyl-5-isopropenylpyridine (5.96 g, 34 mmol), Co(TPP) (0.69 g, 1.0 mmol) and 1-methyl-1H-imidazole (8.37 g, 102 mmol), ethyl diazoacetate (5.4 g, 48 mmol) was added and the mixture was stirred for 5 minutes at room temperature followed by additional stirring for 1 hour at 80° C. Then, evaporation of the solvent and purification by silica gel column chromatography, eluting with gradually from hexane to hexane/ethylacetate (30:1), gave the title compound (3.51 g, 39%, trans) as white solids.

$^1$H NMR (CDCl$_3$) δ ppm 1.30 (3H, t, J=7.3 Hz), 1.35 (9H, s), 1.37-1.50 (2H, m), 1.53 (3H, s), 1.93 (1H, dd, J=5.9, 8.6 Hz), 4.19 (2H, q, J=7.3 Hz), 7.28 (1H, d, J=8.6 Hz), 7.51 (1H, dd, J=2.6, 8.6 Hz), 8.51 (1H, dt, J=2.5 Hz). MS (ESI): m/z 248 (M+H)$^+$.

10D) 2-(6-tert-Butylpyridin-3-yl)-2-methylcyclopropanecarboxylic acid

To a THF (25 ml) solution of the compound of Example 10C (3.51 g, 13.4 mmol), 2M sodium hydroxide aqueous solution (14 ml) and MeOH (25 ml) were added and the mixture was stirred for 16 hours at room temperature. After the reaction was completed, the basic mixture was washed with diethyl ether, and the separated aqueous layer was neutralized with 2M HCl aqueous solution to pH 5-6 and the whole was extracted with ethylacetate followed by evaporation to afford 3.22 g (quant.) of the title compound as white solids.

$^1$H NMR (CDCl$_3$) δ ppm 1.37 (9H, s), 1.45-1.60 (2H, m), 1.60 (3H, s), 1.96-2.01 (1H, m), 7.30 (1H, d, J=8.1 Hz), 7.56 (1H, dd, J=2.2, 8.1 Hz), 8.58 (1H, d, J=2.2 Hz). MS (ESI) m/z 232 (M−H)$^-$.

10E) 2-(6-tert-Butylpyridin-3-yl)-2-methyl-N-((1R)-1-{3-methyl-4-[(methylsulfonyl)amino]phenyl}ethyl)cyclopropanecarboxamide To a DMF (0.5 ml) solution of the compound of Example 10D (17 mg, 0.073 mmol), EDC (21 mg, 0.12 mmol), HOBt (12 mg, 0.080 mmol), triethylamine (0.031 ml) and the amine compound of Example 2D (19 mg, 0.073 mmol) were added in the same procedure as described in Example 1 to afford the mixture of diastereomer products (1:1) of the title compound (19 mg, 59% yield) as white solids.

$^1$H NMR (300 MHz, CDCl$_3$) δ 1.32-1.73 (18H, m), 2.32 (3H, s), 3.03 (3H, s), 5.07-5.16 (1H, m), 5.82-5.86 (1H, m), 6.10 (1H, brs), 7.18-7.30 (3H, m), 7.40-7.49 (2H, m), 8.50 (1H, d, J=2.3 Hz). MS (ESI): m/z 444 (M+H)$^+$.

Example 11

2-(6-tert-Butylpyridin-3-yl)-2-methyl-N-((1R)-1-{3-methyl-4-[(methylsulfonyl)amino]phenyl}ethyl)cyclopropanecarboxamide•monohydrochloride

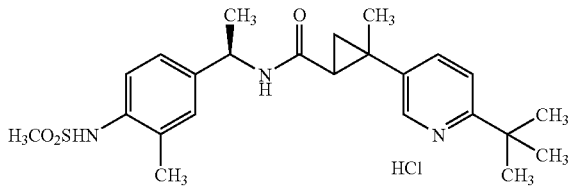

11A) 2-(6-tert-Butylpyridin-3-yl)-2-methylcyclopropanecarboxylic acid

Racemic 2-(6-tert-butylpyridin-3-yl)-2-methylcyclopropanecarboxylic acid was separated by Daicel Chiralpak AD-H (20×250 mm), eluting with n-hexane/EtOH/TFA/diethylamine=95/5/0.05/0.05 at column temperatute of 40° C. The title compound was given as a later fraction (retention time was 2.9 min).

11B) 2-(6-tert-Butylpyridin-3-yl)-2-methyl-N-((1R)-1-{3-methyl-4-[(methylsulfonyl)amino]phenyl}ethyl)cyclopropanecarboxamide To a DMF (10 ml) solution of the compound of Example 11A (600 mg, 2.57 mmol), EDC (739 mg, 3.86 mmol), HOBt (433 mg, 2.83 mmol), triethylamine (1.07 ml) and the amine of Example 2D (681 mg, 2.57 mmol) were added and the mixture was stirred for 16 hours at room temperature. Then, the reaction was quenched with saturated aqueous solution of sodium bicarbonate and the whole was extracted with EtOAc/hexane=3/1 which was dried over sodium sulfate. Then, filtration, evaporation, and purification by silica gel column chromatography, eluting with Hexane/Ethylacetate=1/1, gave 878 mg (77% yield) of the title compound as white solids.

$^1$H NMR (300 HMz, CDCl$_3$) δ ppm 1.35 (9H, s), 1.35-1.39 (1H, m), 1.49 (3H, d, J=6.6 Hz), 1.50-1.55 (1H, m), 1.55 (3H s), 1.65-1.69 (1H, m), 2.32 (3H, s), 3.02 (3H, s), 5.07-5.16 (1H, m), 5.97 (1H, d, J=7.3 Hz), 6.22 (1H, m), 7.18-7.20 (2H, m), 7.26 (1H, d, J=8.1 Hz), 7.40-7.46 (2H, m), 8.50 (1H, d, J=2.3 Hz) MS (ESI): m/z 444 (M+H)$^+$.

11C) 2-(6-tert-Butylpyridin-3-yl)-2-methyl-N-((1R)-1-{3-methyl-4-[(methylsulfonyl)amino]phenyl}ethyl)cyclopropanecarboxamide monohydrochloride A 10% HCl in MeOH (15 ml) solution of the compound of Example 11B (878 mg) was stirred at room temperature for 30 minutes. The mixture was concentrated in vacuo and diluted with diisopropylether. The resulting precipitates were filtrated and washed with diisopropylether to afford 1.0 g (100%) of the title compound as white solids.

$^1$H NMR (DMSOd-$_6$, 300 MHz): δ ppm 1.30-1.50 (2H, m), 1.34 (3H, d, J=6.6 Hz), 1.41 (9H, s), 1.46 (3H, s), 2.05-2.15 (1H, m), 2.29 (3H, s), 2.96 (3H, s), 4.90-4.94 (1H, m), 7.13-7.23 (3H, m), 7.80-7.85 (1H, m), 8.18-8.24 (1H, m), 8.55-8.68 (2H, m), 9.02 (1H, s), MS (ESI): m/z 444 (M+H)$^+$. [α]$_D$=+88.2 (c=0.48, methanol, cell temperature=21.0° C.)

Example 12

2-Methyl-N-((1R)-1-{3-methyl-4-[(methylsulfonyl)amino]phenyl}ethyl)-2-[6-(trifluoromethyl)pyridin-3-yl]cyclopropanecarboxamide

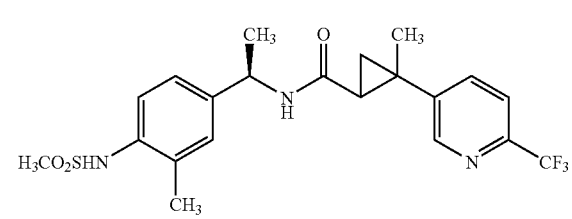

12A) 5-Isopropenyl-2-(trifluoromethyl)pyridine

A mixture of 5-bromo-2-(trifluoromethyl)pyridine (452 mg, 2.0 mmol), potassium isopropenyltrifluoroborate (355 mg, 2.4 mmol), PdCl$_2$(dppf).CH$_2$Cl$_2$ (82 mg, 0.1 mmol) and triethylamine (0.28 ml, 2.0 mmol) in n-propanol (20 ml) was treated in the same procedure as described in Example 10B. The crude residue was applied to a silica gel chromatography column and eluted with a volume mixture of hexane and EtOAc (20/1) to afford 219 mg (59% yield) of the title compound as a colorless oil.

$^1$H NMR (270 MHz CDCl$_3$) δ ppm 2.20 (3H, s), 5.32 (1H, s), 5.52 (1H, s), 7.65 (1H, d, J=8.1 Hz), 7.89 (1H, d, J=8.1 Hz), 8.83 (1H, s)

12B) Ethyl 2-methyl-2-[6-(trifluoromethyl)pyridin-3-yl]cyclopropanecarboxylate

A toluene (2 ml) solution of 5-isopropenyl-2-(trifluoromethyl)pyridine (219 mg, 1.17 mmol), Co(TPP) (26 mg, 0.039 mmol) and 1-methyl-1H-imidazole (320 mg, 3.9 mmol), ethyl diazoacetate (208 mg, 1.8 mmol) were treated in the same procedure as described in Example 2H. The crude residue (201 mg, 63% yield of the title compound as a black oil) was used in a further reaction without purification.

$^1$H NMR (300 MHz CDCl$_3$) δ ppm 1.31 (3H, t, J=6.9 Hz), 1.25-1.60 (5H, m), 1.96-2.05 (1H, m), 4.15-4.27 (2H, m), 7.58-7.80 (2H, m), 8.65-8.70 (1H, m) MS (ESI): m/z 274 (M+H)$^+$.

12C) 2-Methyl-2-[6-(trifluoromethyl)pyridin-3-yl]cyclopropanecarboxylic acid

The procedure described in Example 2I was followed using a THF (4 ml) solution of the compound of Example 12B (201 mg, 0.736 mmol), 2M sodium hydroxide aqueous solution (1 ml) and MeOH (5 ml) to afford 63 mg (35% yield, trans) of the title compound as a brown oil.

$^1$H NMR (300 MHz CDCl$_3$) δ ppm 1.53 (3H, s), 1.50-1.62 (2H, m), 1.98-2.07 (1H, m), 7.64 (1H, d, J=7.9 Hz), 7.76-7.82 (1H, m), 8.68-8.71 (1H, m), MS (ESI): m/z 246 (M+H)$^+$.

12D) 2-Methyl-N-((1R)-1-{3-methyl-4-[(methylsulfonyl)amino]phenyl}ethyl)-2-[6-(trifluoromethyl)pyridin-3-yl]cyclopropanecarboxamide The procedure described in Example 1 was followed using a DMF (2 ml) solution of the compound of Example 12C (62 mg, 0.253 mmol), EDC (73 mg, 0.38 mmol), HOBt (43 mg, 0.278 mmol), triethylamine (0.106 ml) and the compound of Example 2D (67 mg, 0.253 mmol). The crude residue was applied to a silica gel chromatography column and eluted with a volume mixture of hexane and EtOAc (1/1) to afford 31 mg (27% yield) of the title compound as white solids.

1H NMR (CDCl$_3$, 300 MHz) δ ppm 1.41-1.80 (8H, m), 2.30-2.40 (4H, m), 3.01-3.08 (3H, m), 5.08-5.20 (1H, m), 5.90-5.95 (1H, m), 6.17-6.19 (1H, m), 7.14-7.22 (2H, m), 7.38-7.54(2H, m), 7.84-7.87 (1H, m), 8.72 (1H, s). MS (ESI): m/z 456 (M+H)+.

Example 13

2-Methyl-N-((1R)-1-{3-methyl-4-[(methylsulfonyl)amino]phenyl}ethyl)-2-[6-(trifluoromethyl)pyridin-3-yl]cyclopropanecarboxamide

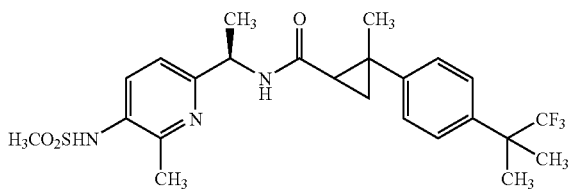

13A) 1-Isopropenyl-4-(2,2,2-trifluoro-1,1-dimethylethyl)benzene

The procedure described in Example 10B was followed using a mixture of 4-(2,2,2-trifluoro-1,1-dimethylethyl)phenyl trifluoromethanesulfonate (13.3 g, 40 mmol), potassium isopropenyltrifluoroborate (7.0 g, 47.6 mmol), PdCl$_2$(dppf).CH$_2$Cl$_2$ (1.6 g, 1.98 mmol) and triethylamine (5.5 ml, 40 mmol) in n-propanol (400 ml). The crude residue was applied to a silica gel chromatography column and eluted with a volume mixture of hexane and EtOAc (100/1) to afford 6.32 g (70% yield) of the title compound as a colorless oil.

$^1$H NMR (300 MHz CDCl$_3$) δ ppm 1.58 (6H, s), 2.16 (3H, s), 5.10 (1H, s), 5.40 (1H, s), 7.47 (4H, s)

13B) Ethyl 2-methyl-2-[4-(2,2,2-trifluoro-1,1-dimethylethyl)phenyl]cyclopropanecarboxylate The procedure described in Example 2H was followed using a toluene (50 ml) solution of the compound of Example 13A (6.32 g, 27.7 mmol), Co(TPP) (558 mg, 0.83 mmol) and 1-methyl-1H-imidazole (6.82 g, 83 mmol), ethyl diazoacetate (4.42 g, 38.8 mmol). The crude residue was applied to a silica gel chromatography column and eluted with a volume mixture of hexane and EtOAc (50/1) to afford 6.75 g (78% yield, trans) of the title compound as a colorless oil.

$^1$H NMR (300 MHz CDCl$_3$) δ ppm 1.29 (3H, t, J=7.3 Hz), 1.40-1.48 (2H, m) 1.53 (3H, s), 1.57 (6H, s), 1.96 (1H, dd, J=5.9, 8.7 Hz), 4.19 (2H, q, J=7.3 Hz), 7.24 (2H, d, J=8.1 Hz), 7.42 (2H, d, J=8.1 Hz)

13C) 2-Methyl-2-[4-(2,2,2-trifluoro-1,1-dimethylethyl)phenyl]cyclopropanecarboxylic acid The procedure described in Example 2I was followed using a THF (50 ml) solution of the compound of Example 13B (6.75 g, 21.5 mmol), 2M sodium hydroxide aqueous solution (22 ml) and MeOH (50 ml) to afford 5.16 g (84% yield) of the title compound as white solids.

$^1$H NMR (300 MHz CDCl$_3$) δ ppm 1.48-1.57 (2H, m), 1.57 (6H, s), 1.59 (3H, s), 1.99 (1H, dd, J=5.3, 7.7 Hz), 7.29 (2H, d, J=8.1 Hz), 7.43 (2H, d, J=8.1 Hz). MS (ESI): m/z 285 (M+H)$^-$.

13D) 2-Methyl-2-[4-(2,2,2-trifluoro-1,1-dimethylethyl)phenyl]cyclopropanecarboxylic acid The racemic 2-methyl-2-[4-(2,2,2-trifluoro-1,1-dimethylethyl)phenyl]cyclopropanecarboxylic acid was separated by Daicel Chiralpak OJ-H (20×250 mm), eluting with 0.1% TFA in n-hexane/EtOH (98/2) under the condition of column temperature (40° C.). The title compound was given as a later fraction (retention time was 12 minutes).

13E) 2-Methyl-N-((1R)-1-{3-methyl-4-[(methylsulfonyl)amino]phenyl}ethyl)-2-[6-(trifluoromethyl)pyridin-3-yl]cyclopropanecarboxamide To a solution of the compound of Example 13D (100 mg, 0.33 mmol) in DCM (3 ml) was added oxalyl chloride (0.087 ml, 1.0 mmol) and DMF (one drop) at room temperature under N$_2$. After being stirred for 1 hour, the resulting solution was evaporated and the residue was dissolved with toluene, followed by evaporation. The resulting material was dissolved in dry dichloromethane (3 ml), which was added to a pyridine (3 ml) solution of the compound of Example 9E (94 mg, 0.33 mmol) at room temperature. After being stirred for 1 hour, the reaction mixture was diluted with saturated aqueous solution of sodium bicarbonate and extracted with EtOAc. The organic layer was dried over magnesium sulfate, filtered and concentrated. The crude residue was applied to a silica gel chromatography column and eluted with a volume mixture of hexane and EtOAc (1/2) to afford 47 mg (29%) of the title compound as white solids.

$^1$H NMR (CDCl$_3$, 300 MHz) δ ppm 1.22-1.70 (13H, m), 1.79-1.84 (1H, m), 1.97-2.04 (1H, m), 2.57 (3H, s), 3.04 (3H, s), 5.13-5.22 (1H, m), 7.08(1H, d, J=7.3 Hz), 7.14 (1H, d, J=8.1 Hz), 7.25-7.35 (2H, m), 7.39-7.52 (3H, m), 7.72 (1H, d, J=8.8 Hz). MS (ESI): m/z 498 (M+H)+.

Example 14

(1S,2S)-2-Methyl-N-((1R)-1-{6-methyl-5-[(methyl-sulfonyl)amino]pyridin-2-yl}ethyl)-2-[4-(trifluoromethyl)phenyl]cyclopropanecarboxamide

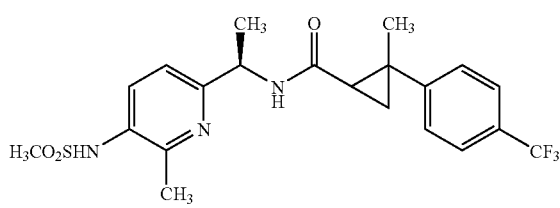

14A) Ethyl 2-methyl-2-[4-(trifluoromethyl)phenyl]cyclopropanecarboxylate

To a toluene (50 ml) solution of 1-isopropenyl-4-(trifluoromethyl)benzene (4.93 g, 26.5 mmol) [*Tetrahedron* (2003), 59(17), 2999-3002], Co(TPP) (534 g, 0.795 mmol) and 1-methyl-1H-imidazole (6.53 g, 79.5 mmol), ethyl diazoacetate (4.23 g, 37.0 mmol) was added. Then the reaction and the following work-up were carried out accridong to the procedure described in Example 2H. The crude residue was applied to a silica gel chromatography column and eluted with a volume mixture of hexane and EtOAc (20/1) to afford 5.92 g (82% yield, trans) of the title compound as a colorless oil.

$^1$H NMR (300 MHz CDCl$_3$) δ ppm 1.31 (3H, t, J=7.0 Hz) 1.40-1.54 (2H, m), 1.54 (3H, s), 1.95-2.00 (1H, m), 4.15-4.28 (2H, m), 7.41 (2H, d, J=8.1 Hz), 7.56 (2H, d, J=8.1 Hz), 14B) 2-Methyl-2-[4-(trifluoromethyl)phenyl]cyclolropanecarboxylic acid (Racemic)

The procedure described in Example 2I was followed using a THF (30 ml) solution of 14A (5.92 g, 21.7 mmol), 2M sodium hydroxide aqueous solution (22 ml) and MeOH (30 ml) to give 5.0 g (94% yield) of the title compound as white solids.

$^1$H NMR (270 MHz CDCl$_3$) δ ppm 1.50-1.57 (2H, m) 1.60 (3H, s), 2.00 (1H, dd, J=5.9, 8.1 Hz), 7.42 (2H, d, J=8.1 Hz), 7.58 (2H, d, J=8.1 Hz) MS (ESI): m/z 243 (M+H)$^-$.

14C) (1S,2S)-2-Methyl-2-[4-(trifluoromethyl)phenyl]cyclopropanecarboxylic acid

The racemic compound of Example 14B was separated by Daicel Chiralpal OJ-H (20×250 mm), eluting with n-hexane/2-propanol/TFA=97/3/0.001 at column temperatute of 40° C. The title compound was given as a later fraction (retention time was 8 minutes).

[α]$_D$=+167.5 (c=0.59, methanol, cell temperature=21.0° C.)

14D) (1S,2S)-2-Methyl-N-((1R)-1-{6-methyl-5-[(methylsulfonyl)amino]pyridin-2-yl}ethyl)-2-[4-(trifluoromethyl)phenyl]cyclopropanecarboxamide To a DMF (6.5 ml) solution of the compound of Example 14C (159 mg, 0.651 mmol), HBTU (296 mg, 0.782 mmol), triethylamine (0.27 ml, 1.95 mmol) and the compound of Example 9E (150 mg, 0.651 mmol) were added and the mixture was stirred for 2 hours at room temperature. Then the reaction was quenched with saturated aqueous sodium bicarbonate solution, and the whole was extracted with DCM. The extract was dried over magnesium sulfate, filtered and concentrated in vacuo. Purification by preparative thin layer chromatography (Merck, silica gel 60 F254, 1 mm) eluting with hexane/EtOAc (1:1) twice gave white solids, which was isolated from hexane-DCM to afford the title compound (138 mg, 46% yield) as white solids.

1H NMR (CDCl$_3$, 300M Hz) δ ppm 1.39 (1H, dd, J=8.6, 4.9 Hz), 1.47 (3H, d, J=6.6 Hz), 1.55-1.61 (4H, m), 1.81 (1H, dd, J=8.6, 5.9 Hz), 2.57 (3H, s), 3.05 (3H, s), 5.09-5.24 (1H, m), 6.24 (1H, br. s.), 6.96 (1H, d, J=7.9 Hz), 7.15 (1H, d, J=7.9 Hz), 7.41(2H, d, J=8.6 Hz), 7.59 (2H, d, J=8.6 Hz), 7.74 (1H, d, J=8.6 Hz) MS (ESI): m/z 456 (M+H)$^+$, 454 (M–H)$^-$.

Example 15

(1S,2S)-2-Methyl-N-((1R)-1-{3-methyl-4-[(methylsulfonyl)amino]phenyl}ethyl)-2-[4-(trifluoromethyl)phenyl]cyclopropanecarboxamide

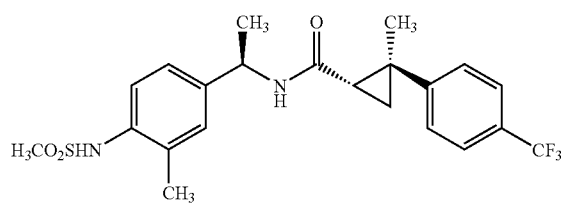

To a DMF (10 ml) solution of the compound of Example 14C (262 mg, 1.07 mmol), triethylamine (0.472 ml) and HBTU (514 mg, 1.36 mmol), the amine of Example 2D (328 mg, 1.24 mmol) was added. Then the reaction and the following work-up were carried out accridong to the procedure described in Example 14D. The crude residue was applied to a silica gel chromatography column and eluted with a volume mixture of hexane and EtOAc (1/1) to afford 481 mg (99% yield) of the title compound as white solids.

$^1$H NMR (CDCl$_3$, 300 MHz) δ ppm 1.49 (3H, d, J=7.3 Hz), 1.37-1.57 (2H, m), 1.59 (3H, s) 1.68-1.72 (1H, m), 2.31 (3H, s), 3.01 (3H, s), 5.05-5.21 (1H, m), 5.90 (1H, d, J=7.3 Hz), 6.21 (1H, s), 7.18-7.23 (2H, m), 7.35-7.45 (3H, m), 7.56 (2H, d, J=8.1 Hz). MS (ESI): m/z 455 (M+H)$^+$. [α]$_D$=+104.3 (c=0.42, methanol, cell temperature=21.0° C.)

Example 16

2-Methyl-N-((1R)-1-{3-methyl-4-[(methylsulfonyl)amino]phenyl}ethyl)-2-[4-(trifluoromethoxy)phenyl]cyclopropanecarboxamide

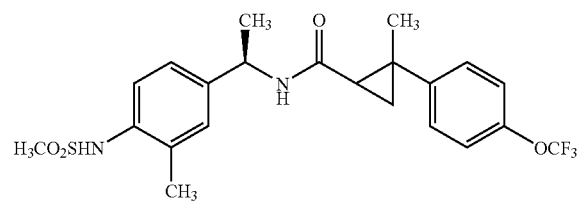

16A) 1-Isopropenyl-4-(trifluoromethoxy)benzene

To a stirred suspension of 60% sodium hydride (1.96 g, 49 mmol) was added DMSO (20 ml) dropwise at 0° C. and the mixture was stirred at 80° C. for 30 minutes. After cooling the mixture to 0° C., a sol methyltriphenylphosphonium bromide (17.5 g, 49 mmol) in DMSO (60 ml) was added dropwise at 0° C. and stirred at ambient temperature for 45 minutes. Then, to this mixture 1-[4-(trifluoromethoxy)phenyl]ethanone (5 g, 24.5 mmol) was added dropwise at ambient temperature and stirred at ambient temperature for 1 hour. The reaction was quenched with a small amount of acetone and diluted with hexane and water. The resulting precipitates were filtered and the organic layer was separated. After evaporation of the solvent, the residue was washed with hexane and concentrated in vacuo to afford 5.1 g (quant.) of the title compound as a colorless oil $^1$H NMR (270 MHz CDCl$_3$) δ ppm 2.15 (3H, s), 5.10-5.15 (1H, m), 5.36 (1H, s), 7.17 (2H, d, J=8.7 Hz), 7.44-7.52 (2H, m), 16B) Ethyl 2-methyl-2-[4-(trifluoromethoxy)phenyl]cyclopropanecarboxylate To a toluene (50 ml) solution of the compound of Example 16A (5.0 g, 24.5 mmol), Co(TPP) (494 mg, 0.735 mmol) and 1-methyl-1H-imidazole (6.0 g, 73.5 mmol), ethyl diazoacetate (3.91 g, 34.3 mmol) was added in the same procedure as described in Example 2H. The crude residue was applied to a silica gel chromatography column and eluted with a volume mixture of hexane and EtOAc (20/1), followed by dilution with hexane, standing at ~10° C. for 2hours. Then filtration and evaporation of the filtrate gave 4.25 g (60% yield, trans) of the title compound as a purple oil.

$^1$H NMR (270 MHz CDCl$_3$) δ ppm 1.30 (3H, t, J=6.1 Hz) 1.37-1.48 (2H, m), 1.52 (3H, s), 1.95 (1H, dd, J=5.9, 7.9 Hz), 4.15-4.26 (2H, m), 7.14 (2H, d, J=7.9 Hz), 7.28-7.35 (2H, m), 16C) 2-Methyl-2-[4-(trifluoromethoxy)phenyl]cyclopropanecarboxylic acid (Racemic)

The procedure described in Example 2I was followed using a THF (20 ml) solution of the compound of Example 16B (4.25 g, 14.7 mmol), 2M sodium hydroxide aqueous solution (15 ml) and MeOH (20 ml) to afford 3.82 g (quant.) of the title compound as pale brown solids.

$^1$H NMR (300 MHz CDCl$_3$) δ ppm 1.45-1.57 (2H, m) 1.58 (3H, s), 1.98 (1H, dd, J=6.6, 8.1 Hz), 7.16 (2H, d, J=8.1 Hz), 7.30-7.37 (2H, m), MS (ESI): m/z 259 (M+H)$^-$.

16D) 2-Methyl-N-((1R)-1-{3-methyl-4-[(methylsulfonyl) amino]phenyl}ethyl)-2-[4-(trifluoromethoxy)phenyl]cyclopropanecarboxamide The procedure described in Example 14D was followed using a DMF (4 ml) solution of the compound of Example 16C (100 mg, 0.384 mmol), HBTU (175 mg, 0.461 mmol), triethylamine (0.16 ml) and the compound of Example 2D (102 mg, 0.384 mmol). The crude residue was applied to a silica gel chromatography column and eluted with a volume mixture of hexane and EtOAc (1/1) to afford 151 mg (83% yield) of the title compound as white solids.

$^1$H NMR (CDCl$_3$, 270 MHz) δ ppm 1.33-1.74 (9H, m), 2.32 (3H, s), 3.02 (3H, s), 5.08-5.17 (1H, m), 5.84-5.89 (1H, m), 6.17 (1H, s), 7.13-7.29 (6H, m), 7.42 (1H, d, J=7.3 Hz), MS (ESI): m/z 471 (M+H)+.

Example 17

2-Methyl-N-((1R)-1-{3-methyloxy-4-[(methylsulfonyl)amino]phenyl}ethyl)-2-[4-(trifluoromethoxy) phenyl]cyclopropanecarboxamide

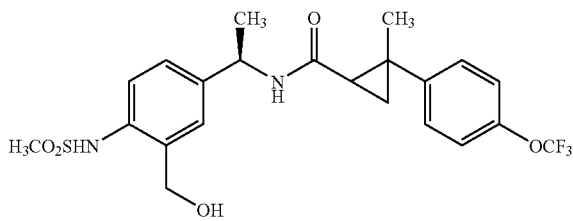

17A) Ethyl 5-((1R)-1-{[(R)-tert-butylsulfinyl]amino}ethyl)-2-[(methylsulfonyl)amino]benzoate To a mixture of methyl 5-acetyl-2-[(methylsulfonyl) amino]benzoate (13.2 g, 49 mmol, PCT Int. Appl. WO2005003084), titanium (IV) ethoxide (100 ml) and THF (100 ml) was added (R)-(+)-2-methylpropane-2-sulfinamide (5.9 g, 49 mmol, Advanced Asymmmetry) and the mixture was stirred for 16 hours at 80° C. The mixture was cooled to room temperature and then to 0° C. before it was added dropwise into a 0° C. solution of sodium borohydride (7.4 g, 195 mmol). The mixture was stirred at 0° C. for 3 hours and then warmed to room temperature. The reaction was quenched with MeOH and stirred for 30 minutes. Then to the mixuture water was added. After stirring for 10 minutes, the resulting suspension was filtered through a celite pad and the filtered cake was washed with EtOAc. The filtrate was concentrated under reduced pressure to give a residue, which was applied to a silica gel chromatography column and eluted with a volume mixture of DCM and EtOAc (1/1) to afford 4.3 g (23% yield) of the title compound as pale yellow solids.

$^1$H NMR (270 MHz, CDCl$_3$) δ ppm 1.24 (9H, s), 1.43 (3H, t, J=6.8 Hz), 1.53 (3H, d, J=6.6 Hz), 3.07 (3H, s), 3.39 (1H, br.s), 4.41 (2H, q, J=6.8 Hz), 4.55 (1H, m), 7.56 (1H, dd, J=8.6, 2.0 Hz), 7.74 (1H, d, J=9.2 Hz), 8.06 (1H, d, J=2.0 Hz), 10.49 (1H, br.s). MS (ESI): m/z 391 [M+H]$^+$, 389 [M−H]$^-$.

17B) Ethyl 5-[(1R)-1-aminoethyl]-2-[(methylsulfonyl)amino]benzoate

To a solution of the compound of Example 17A (4.3 g, 11 mmol) in MeOH (30 ml) was added 10% hydrogenchloride-MeOH solution (30 ml). The mixture was then treated accrding to the procedure described in Example 2D to afford 3.1 g (87% yield) of the title compound as white solids.

$^1$H NMR (270 MHz, DMSO-d6) δ ppm 1.34 (3H, t, J=7.3 Hz), 1.49 (3H, d, J=7.3 Hz), 3.19 (3H, s), 4.36 (2H, q, J=7.3 Hz), 4.45 (1H, m), 7.61 (1H, d, J=8.6 Hz), 7.75 (1H, dd, J=8.6, 2.0 Hz), 8.09 (1H, d, J=2.0 Hz), 8.35 (2H, br.s), 10.14 (1H, br.s).

17C) Ethyl 2-[(methylsulfonyl)amino]-5-{(1R)-1-[({2-methyl-2-[4-(trifluoromethoxy)phenyl]cyclopropyl}carbonyl) amino]ethyl}benzoate The procedure described in Example 14D was followed using a DMF (4 ml) solution of the compound of Example 16C (100 mg, 0.384 mmol), HBTU (175 mg, 0.461 mmol), triethylamine (0.16 ml) and the compound of Example 17B (124 mg, 0.384 mmol). The crude residue was applied to a silica gel chromatography column and eluted with a volume mixture of hexane and EtOAc (1/1) to afford 175 mg (86% yield) of the title compound as a colorless oil.

¹H NMR (300 MHz CDCl₃) δ ppm 1.35-1.76 (12H, m), 3.06 (3H, s), 4.39 (2H, t, J=7.3 Hz), 5.11-5.40 (1H, m), 5.90-5.94 (1H, m), 7.15 (2H, d, J=8.1 Hz), 7.25-7.35 (2H, m), 7.48-7.56 (1H, m), 7.69-7.76 (1H, m), 7.97-8.07 (1H, m), 10.45-10.54 (1H, m). MS (ESI): m/z 529 (M+H)⁺.

17D) 2-Methyl-N-((1R)-1-{3-methyl-4-[(methylsulfonyl) amino]phenyl}ethyl)-2-[4-(trifluoromethoxy)phenyl]cyclopropanecarboxamide To a mixture of lithium aluminium hydride (25 mg, 0.66 mmol) in THF (50 ml) was added a solution of Example 17C (175 mg, 0.33 mmol) at 0° C. After being stirred for 3 hours at 0° C., potassium fluoride and sodium sulfate decahydrate were added. After being stirred for 5 hours, the reaction mixture was filtered and the filtrate was evaporated under reduced pressure to give a crude residue. The crude residue was applied to a silica gel chromatography column and eluted with a volume mixture of hexane and EtOAc (1/4) to give 92 mg (57% yield) of the title compound as white solids.

¹H NMR (CDCl₃, 270 MHz) δ ppm 1.26-1.74 (8H, m), 2.36-2.43 (1H, m), 3.04 (3H, s), 4.71-4.78 (2H, m), 5.05-5.15 (1H, m), 5.85-5.97 (1H, m), 7.13-7.34 (7H, m), 7.51 (1H, d, J=7.9 Hz), 7.42-7.75 (1H, m) MS (ESI): m/z 487 (M+H)⁺.

Example 18

N-((1R)-1-{3-Fluoro-4-[(methylsulfonyl)amino] phenyl}ethyl)-2-[4-(2,2,2-trifluoro-1,1-dimethylethyl)phenyl]cyclopropanecarboxamide

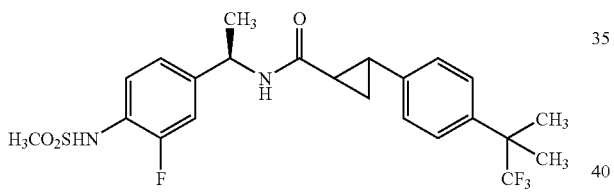

Following a procedure analogous to that described in Example 8, but using the carboxylic acid of Example 6D (50.0 mg, 0.23 mmol) instead of the carboxylic acid of Example 1, the title compound was obtained as white solids (yield 71%).

¹H NMR (DMSOd-6, 270 MHz) δ ppm 1.16-1.41 (5H, m), 1.52 (6H, s), 1.88-1.97 (1H, m), 2.14-2.27 (1H, m), 2.97-3.03 (3H, m), 4.87-4.99 (1H, m), 7.08-7.24 (4H, m), 7.27-7.38 1H, m), 7.39-7.43 (2H, m), 8.53-8.69 (1H, m), 9.54 (1H, s). MS (ESI): m/z 487 (M+H)⁺.

Example 19

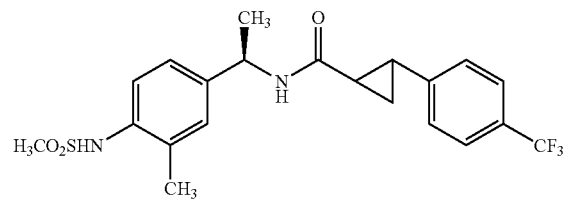

19a) N-((1R)-1-{3-Methyl-4-[(methylsulfonyl)amino] phenyl}ethyl)-2-[4-(trifluoromethyl)phenyl]cyclopropanecarboxamide (racemic)

The procedure described in Example 1 was followed, using a DMF (2 ml) solution of 2-[4-(trifluoromethyl)phenyl]cyclopropanecarboxylic acid (racemic) (100 mg, 0.434 mmol) [Journal of Organic Chemistry (1997), 62(26), 9114-9122.], EDC (125 mg, 0.651 mmol), HOBt (74 mg, 0.477 mmol), triethylamine (0.18 ml) and the compound of Example 2D (115 mg, 0.434 mmol). The crude residue was applied to a silica gel chromatography column and eluted with a volume mixture of hexane and EtOAc (1/1) and isolated from MeOH to afford 20 mg (10% yield) of the title compound as white solids.

¹H NMR (DMSOd-6, 300 MHz) δ ppm 1.32 (3H, d, J=7.3 Hz), 1.23-1.43 (2H, m), 1.99-2.05 (1H, m), 2.29 (3H, s), 2.28-2.39 (1H, m), 2.96 (3H, s), 4.85-4.96 (1H, m), 7.11-7.23 (3H, m), 7.36 (2H, d, J=8.1 Hz), 7.63 (2H, d, J=8.1 Hz), 8.56 (1H, d, J=8.1 Hz), 9.02 (1H, brs). MS (ESI): m/z 441 (M+H)⁺.

19b) N-((1R)-1-{3-Methyl-4-[(methylsulfonyl)amino] phenyl}ethyl)-2-[4-(trifluoromethyl)phenyl]cyclopropanecarboxamide (diastereomer Mixture)

Following Example 19a, the filtrate was evaporated under reduced pressure to give the title compound (80 mg, 42% yield) as the mixture of diastereomer products (1:2) as white solids.

¹H NMR (300 MHz, DMSOd-6) δ 1.24-1.43 (5H, m), 1.99-2.05 (1H, m), 2.26-2.35 (4H, m), 2.94-2.96 (3H, m), 4.85-4.94 (1H, m), 7.09-7.23 (3H, m), 7.30-7.40 (2H, m), 7.57-7.64 (2H, m), 8.53-8.62 (1H, m), 8.99 (1H, brs). MS (ESI): m/z 441 (M+H)⁺.

Example 20

N-((1R)-1-{3-(Hydroxymethyl)-4-[(methylsulfonyl) amino]phenyl}ethyl)-2-[4-(trifluoromethyl)phenyl] cyclopropanecarboxamide

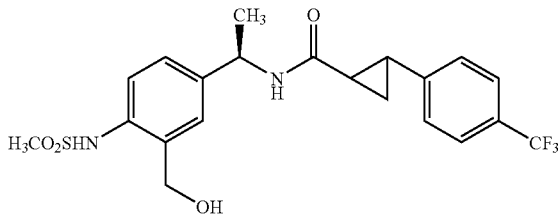

20A) N-[4-((1R)-1-{[(R)-tert-butylsulfinyl]amino}ethyl)-2-(hydroxymethyl)phenyl]methanesulfonamide To a mixture of lithium aluminium hydride (1.6 g, 43 mmol) in THF (50 ml) was added a solution of the compound of Example 17B (4.2 g, 11 mmol) in THF (100 ml) at 0° C. After being stirred for 3 hours at 0° C., potassium fluoride and sodium sulfate decahydrate were added. After being stirred for 5 hours, the reaction mixture was filtered and the filtrate was evaporated under reduced pressure to afford 3.6 g (97% yield) of the title compound as a pale yellow oil. MS (ESI): m/z 391 [M+H]⁺, 389 [M−H]⁻.

20B) N-[4-[(1R)-1-Aminoethyl]-2-(hydroxymethyl)phenyl] methanesulfonamide

To the the compound of Example 20A (3.6 g, 10 mmol) in methanol (30 ml) was added 10% hydrogenchloride-MeOH solution (30 ml) and the procedure described in Example 2D was followed to afford 2.5 g (87% yield) of the title compound as a yellow oil.

¹H NMR (270 MHz, DMSO-d6) δ ppm 1.51 (3H, t, J=6.6 Hz), 3.01 (3H, s), 4.36 (1H, m), 4.63 (2H, s), 7.34 (1H, d, J=7.9 Hz), 7.45 (1H, dd, J=7.9, 2.0 Hz), 7.58 (1H, d, J=2.0 Hz), 8.56 (2H, br.s), 9.13 (1H, br.s). MS (ESI): m/z 243 [M−H]⁻.

20C) N-((1R)-1-{3-(Hydroxymethyl)-4-[(methylsulfonyl)amino]phenyl}ethyl)-2-[4-(trifluoromethyl)phenyl]cyclopropanecarboxamide The procedure described in Example 1 was followed using a DMF (2 ml) solution of 2-[4-(trifluoromethyl)phenyl]cyclopropanecarboxylic acid (160 mg, 0.695 mmol), EDC (200 mg, 1.04 mmol), HOBt (118 mg, 0.765 mmol), triethylamine (0.29 ml) and the compound of Example 20B (197 mg, 0.695 mmol). The crude residue was applied to a silica gel chromatography column and eluted with a volume mixture of hexane and EtOAc (1/2) to afford 44 mg (14% yield) of the title compound as white solids.

¹H NMR (CDCl₃, 300 MHz) δ ppm 1.30-1.72 (5H, m), 2.43-2.72 (2H, m), 2.97 (3H, s), 4.66 (2H, s), 5.02-5.06 (1H, m), 6.22 (1H, s), 7.12-7.27 (5H, m), 7.41-7.60 (4H, m). MS (ESI): m/z 457 (M+H)⁺.

Example 21

(1S,2S)-2-Methyl-N-((1R)-1-{4-[(methylsulfonyl)amino]phenyl}ethyl)-2-[4-(trifluoromethyl)phenyl]cyclopropanecarboxamide

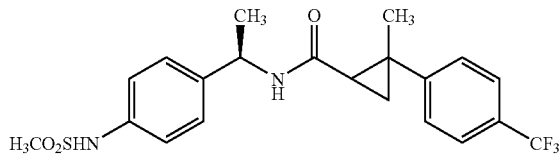

The procedure described in Example 14D was followed using a DMF (4 ml) solution of the carboxylic acid of Example 14C (112 mg, 0.459 mmol), HBTU (209 mg, 0.55 mmol), triethylamine (0.19 ml) and N-{4-[(1R)-1-aminoethyl]phenyl}methanesulfonamide hydrochloride (115 mg, 0.459 mmol). The crude residue was applied to a silica gel chromatography column and eluted with a volume mixture of hexane and EtOAc (1/1) to afford 124 mg (61% yield) of the title compound as white solids ¹H NMR (CDCl₃, 300 MHz) δ ppm 1.38-1.42 (1H, m), 1.51 (3H, d, J=6.6 Hz), 1.59 (3H, s), 1.68-1.73 (2H, m), 3.00 (3H, s), 5.11-5.20 (1H, m), 5.90 (1H, d, J=7.3 Hz), 6.52 (1H, s), 7.18 (2H, d, J=8.8 Hz), 7.32 (2H, d, J=8.8 Hz), 7.36 (2H, d, J=8.1 Hz), 7.56 (2H, d, J=8.1 Hz). MS (ESI): m/z 441 (M+H)⁺.

Example 22

(1S,2S)-N-((1R)-1-{3-(Hydroxymethyl)-4-[(methylsulfonyl)amino]phenyl}ethyl)-2-methyl-2-[4-(trifluoromethyl)phenyl]cyclopropanecarboxamide;

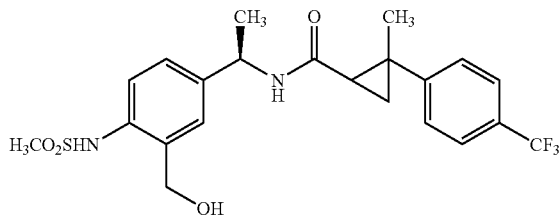

22A) Ethyl 2-[(methylsulfonyl)amino]-5-{(1R)-1-[({(1S,2S)-2-methyl-2-[4-(trifluoromethyl)phenyl]cyclopropyl}carbonyl)amino]ethyl}benzoate The procedure described in Example 14D was followed using a DMF (3 ml) solution of the carboxylic acid of Example 14C (80 mg, 0.328 mmol), HBTU (149 mg, 0.394 mmol), triethylamine (0.137 ml) and the amine of Example 17B (106 mg, 0.328 mmol). The crude residue was applied to a silica gel chromatography column and eluted with a volume mixture of hexane and EtOAc (1/1) to afford 154 mg (92% yield) of the title compound as white solids.

¹H NMR (270 MHz CDCl₃) δ ppm 1.25-1.74 (12H, m), 3.05 (3H, s), 4.39 (2H, t, J=7.3 Hz), 5.06-5.19 (1H, m), 5.93 (1H, d, J=7.3 Hz), 7.37 (2H, d, J=7.9 Hz), 7.48-7.58 (1H, m), 7.57 (2H, d, J=7.9 Hz), 7.72 (1H, d, J=8.6 Hz), 7.95-8.07 (1H, m), 10.43-10.55 (1H, m), MS (ESI): m/z 513 (M+H)⁺.

22B) (1S,2S)-N-((1R)-1-{3-(Hydroxymethyl)-4-[(methylsulfonyl)amino]phenyl}ethyl)-2-methyl-2-[4-(trifluoromethyl)phenyl]cyclopropanecarboxamide The procedure described in Example 17D was followed using a THF (3 ml) mixture of the compound of Example 22A (154 mg, 0.30 mmol) and lithium aluminium hydride (23 mg, 0.60 mmol). The crude residue was applied to a silica gel chromatography column and eluted with a volume mixture of hexane and EtOAc (2/3) to afford 88 mg (63% yield) of the title compound as white solids.

¹H NMR (CDCl₃, 270 MHz) δ ppm 1.35-1.40 (1H, m), 1.49 (3H, d, J=7.3 Hz), 1.58 (3H, s), 1.66-1.71 (1H, m), 2.44 (1H, t, J=5.6 Hz), 3.04 (3H, s), 4.74 (2H, d, J=5.3 Hz), 5.05-5.15 (1H, m), 5.96 (1H, d, J=7.3 Hz), 7.19-7.21 (1H, m), 7.25-7.33 (2H, m), 7.35 (2H, d, J=8.6 Hz), 7.51 (1H, d, J=7.9 Hz), 7.56 (2H, d, J=8.6 Hz), 7.44 (1H, s). MS (ESI): m/z 471 (M+H)⁺.

Example 23

(1S,2S)-N-((1R)-1-{3-Fluoro-4-[(methylsulfonyl)amino]phenyl}ethyl)-2-methyl-2-[4-(trifluoromethyl)phenyl]cyclopropanecarboxamide

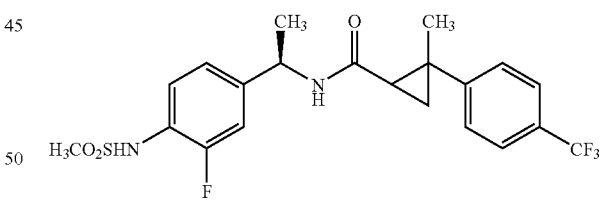

The procedure described in Example 14D was followed using a DMF (4 ml) solution of the carboxylic acid of Example 14C (98 mg, 0.402 mmol), HBTU (183 mg, 0.482 mmol), triethylamine (0.168 ml) and the amine compound of Example 8 (108 mg, 0.402 mmol). The crude residue was applied to a silica gel chromatography column and eluted with a volume mixture of hexane and EtOAc (1/1) to afford 157 mg (85% yield) of the title compound as white solids.

¹H NMR (CDCl₃, 300 MHz) δ ppm 1.40-1.44 (1H, m), 1.50 (3H, d, J=6.6 Hz), 1.58 (3H, s), 1.68-1.73 (2H, m), 3.03 (3H, s), 5.10-5.19 (1H, m), 5.90 (1H, d, J=6.6 Hz), 6.48 (1H, s), 7.10-7.19 (2H, m), 7.37(2H, d, J=8.1 Hz), 7.52 (1H, d, J=8.8 Hz), 7.57 (2H, d, J=8.1 Hz), MS (ESI): m/z 459 (M+H)⁺.

Example 24

2-Methyl-N-((1R)-1-{3-methyl-4-[(methylsulfonyl)amino]phenyl}ethyl)-2-{4-[(trifluoromethyl)thio]phenyl}cyclopropanecarboxamide

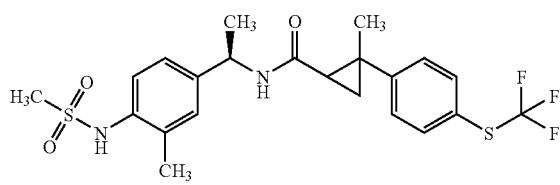

24A) 1-Isopropenyl-4-[(trifluoromethyl)thio]benzene

To a stirred suspension of 60% sodium hydride (363 mg, 9.08 mmol, wash with n-hexane [can you clarify?]) was added DMSO (4 ml) dropwise at 0° C. and the mixture was stirred at 80° C. for 30 minutes. After cooling to 0° C., to this mixture was added a solution of methyltriphenylphosphonium bromide (3.24 g, 9.08 mmol) in DMSO (12 ml) dropwise at 0° C. and stirred at ambient temperature for 45 minutes. Then, to this mixture 1-[4-(trifluoromethyl)thio]phenyl]ethanone (1 g, 4.54 mmol) was added dropwise at ambient temperature and the mixture stirred at ambient temperature for 1hour. The reaction was quenched with a small amount of acetone and diluted with hexane and water. The resulting precipitates were filtered and the organic layer was separated. After evaporation of the solvent, the residue was washed with hexane and concentrated in vacuo to afford 520 mg (52% yield) of the title compound as colorless oil.

$^1$H NMR (300 MHz CDCl$_3$) δ ppm 7.61 (2H, d, J=8.8 Hz), 7.50 (2H, d, J=8.8 Hz), 5.44 (1H, s), 5.19 (1H, s), 2.16 (3H, s)

24B) Ethyl 2-methyl-2-{4-[(trifluoromethyl)thio]phenyl}cyclopropanecarboxylate

To a toluene (12 ml) solution of the compound of Example 24A (1.23 g, 5.67 mmol), Co(TPP) (114 mg, 0.170 mmol) and 1-methyl-1H-imidazole (1.4 g, 17.0 mmol), ethyl diazoacetate (905 mg, 7.93 mmol) was added in the same procedure as described in Example 2H. The crude residue was applied to a silica gel chromatography column and eluted with a volume mixture of hexane and EtOAc (25/1) to afford 1.3 g (75% yield, trans) of the title compound as a purple oil.

$^1$H NMR (270 MHz CDCl$_3$) δ ppm 1.30 (3H, t, J=6.9 Hz), 1.41-1.52 (2H, m), 1.54 (3H, s), 1.97 (1H, dd, J=5.9, 8.6 Hz), 4.15-4.25 (2H, m), 7.34 (2H, d, J=8.6 Hz), 7.88 (2H, d, J=8.6 Hz)

24C) 2-Methyl-2-{4-[(trifluoromethyl)thio]phenyl}cyclopropanecarboxylic acid

The procedure described in Example 2I was followed using a THF (5 ml) solution of the compound of Example 24B (343 mg, 1.12 mmol), 2M sodium hydroxide aqueous solution (1.5 ml) and MeOH (5 ml) to afford 320 mg (quant.) of the title compound as pale yellow solids.

$^1$H NMR (270 MHz CDCl$_3$) δ ppm 1.50-1.57 (2H, m), 1.60 (3H, s), 2.00 (1H, dd, J=6.6, 7.9 Hz), 7.39 (2H, d, J=8.1 Hz), 7.60 (2H, d, J=7.9 Hz), MS (ESI): m/z 275 (M+H)$^-$.

24D) 2-Methyl-N-((1R)-1-{3-methyl-4-[(methylsulfonyl)amino]phenyl}ethyl)-2-{4-[(trifluoromethyl)thio]phenyl}cyclopropanecarboxamide The procedure described in Example 14D was followed using a DMF (4 ml) solution of the carboxylic acid of Example 24C (66 mg, 0.238 mmol), triethylamine (0.1 ml) and HBTU (108 mg, 0.286 mmol) and the compound of Example 2D (63 mg, 0.238 mmol). The crude residue was applied to a silica gel chromatography column and eluted with a volume mixture of hexane and EtOAc (1/1) to afford 80 mg (69% yield) of the title compound as white solids.

$^1$H NMR (300 MHz CDCl$_3$) δ ppm 1.35-1.80 (9H, m), 2.31-2.38 (3H, m), 3.01-3.15 (3H, m), 5.07-5.22 (1H, m), 5.82-5.99 (1H, m), 6.17-6.25 (1H, m), 7.18-7.47 (5H, m), 7.56-7.65 (2H, m). MS (ESI): m/z 487 (M+H)$^+$.

Example 25

N-((1R)-1-{3-(Hydroxymethyl)-4-[(methylsulfonyl)amino]phenyl}ethyl)-2-methyl-2-{4-[(trifluoromethyl)thio]phenyl}cyclopropanecarboxamide

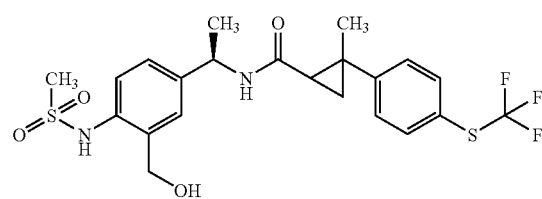

25A) Ethyl 2-[(methylsulfonyl)amino]-5-((1R)-1-{[(2-methyl-2-{4-[(trifluoromethyl)thio]phenyl}cyclopropyl)carbonyl]amino}ethyl)benzoate The procedure described in Example 14D was followed using a DMF (10 ml) solution of the carboxylic acid of Example 24C (253 mg, 0.92 mmol), triethylamine (0.38 ml) and HBTU (417 mg, 1.10 mmol) and the amine of Example 17B (310 mg, 0.96 mmol). The crude residue was applied to a silica gel chromatography column and eluted with a volume mixture of hexane and EtOAc (1/1) to afford 500 mg (quant.) of the title compound as pale purple solids.

$^1$H NMR (300 MHz CDCl$_3$) δ ppm 1.36-1.68 (10H, m), 1.70-1.80 (2H, m), 3.05 (3H, s), 4.39 (2H, t, J=7.3 Hz), 5.07-5.32 (1H, m), 5.96-6.05 (1H, m), 7.25-7.35 (2H, m), 7.48-7.70 (3H, m), 7.71 (1H, d, J=9.5 Hz), 7.98-8.05 (1H, m), 10.44-10.55 (1H, m), MS (ESI): m/z 545 (M+H)$^+$.

25B) N-((1R)-1-{3-(hydroxymethyl)-4-[(methylsulfonyl)amino]phenyl}ethyl)-2-methyl-2-{4-[(trifluoromethyl)thio]phenyl}cyclopropanecarboxamide The procedure described in Example 17C was followed using a THF (2.5 ml) and diethyl ether (10 ml) mixture of the compound of Example 25A (250 mg, 0.459 mmol) and LiAlH$_4$ (35 mg, 0.918 mmol). The crude residue was applied to a silica gel chromatography column and eluted with a volume mixture of hexane and EtOAc (1/2) to afford 145 mg (63% yield) of the title compound as white solids.

$^1$H NMR (300 MHz CDCl$_3$) δ ppm 1.32-1.82 (8H, m), 2.50-2.64 (1H, m), 3.03 (3H, s), 4.73 (2H, s), 5.05-5.18 (1H, m), 5.96-6.05 (1H, m), 7.10-7.36 (4H, m), 7.48-7.52 (1H, m), 7.55-7.64 (2H, m), 7.78 (1H, d, J=5.1 Hz). MS (ESI): m/z 503 (M+H)$^+$.

Example 26

2-Methyl-N-((1R)-1-{3-methyl-4-[(methylsulfonyl)amino]phenyl}ethyl)-2-{4-[(trifluoromethyl)sulfonyl]phenyl}cyclopropanecarboxamide

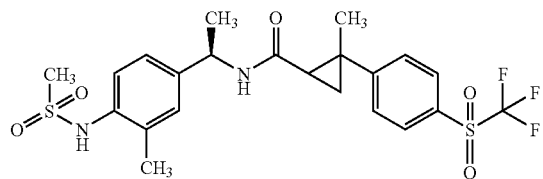

26A) Ethyl 2-methyl-2-{4-[(trifluoromethyl)sulfonyl]phenyl}cyclopropanecarboxylate To a solution of the compound of Example 24B (304 mg, 1 mmol), sodium metaperiodate (642 mg, 3 mmol), tetrachloromethane (2 ml), and acetonitrile (2 ml) in water (4 ml) was added ruthenium trichloride hydrate (0.1 mg) and the mixture was stirred for 16 hours at room temperature. The reaction was quenched with 1N-HCl aqueous solution and the whole was extracted with EtOAc. Then, evaporation and purification gave the title compound (347 mg, quant., trans) as a colorless oil.

$^1$H NMR (270 MHz CDCl$_3$) δ 1.31 (3H, t, J=6.9 Hz), 1.47-1.62 (2H, m), 1.59 (3H, s), 2.00-2.04 (1H, m), 4.18-4.25 (2H, m), 7.57 (2H, d, J=8.6 Hz), 7.97 (2H, d, J=8.6 Hz)

26B) 2-Methyl-2-{4-[(trifluoromethyl)sulfonyl]phenyl}cyclopropanecarboxylic acid The procedure described in Example 10D was followed using a a THF (5 ml) solution of the compound of Example 26A (336 mg, 1 mmol), 2M sodium hydroxide aqueous solution (1 ml) and MeOH (5 ml) to afford the title compound (62 mg, 85% yield) as white solids.

$^1$H NMR (270 MHz CDCl$_3$) δ 1.57-1.65 (2H, m), 1.65 (3H, s), 2.03-2.09 (1H, m), 7.60 (2H, d, J=8.6 Hz), 7.99 (2H, d, J=8.6 Hz) MS (ESI) m/z 307 (M–H)$^-$.

26C) 2-Methyl-N-((1R)-1-{3-methyl-4-[(methylsulfonyl)amino]phenyl}ethyl)-2-{4-[(trifluoromethyl)sulfonyl]phenyl}cyclopropanecarboxamide To a DMF (2 ml) solution of the compound of Example 26B (38 mg, 0.125 mmol), the compound of Example 2D (33 mg, 0.125 mmol), triethylamine (38 mg, 0.375 mmol) and HBTU (57 mg, 0.15 mmol) were added in the same procedure as described in Example 14D. Then, the reaction was quenched with water and the whole was extracted with EtOAc/hexane (3:1) which was dried over sodium sulfate. Then, filtration, evaporation, and purification by silica gel column chromatography, eluting with hexane/EtOAc (1:1), gave the title compound (64 mg, 99% yield, white solids) as a mixture of diastereomeric products (1:1).

$^1$H NMR (270 MHz CDCl$_3$) δ 1.30-1.85 (9H, m), 2.32 (3H, s), 3.02-3.03 (3H, m), 5.10-5.16 (1H, m), 5.88-5.93 (1H, m), 6.15 (1H, brs), 7.17-7.22 (2H, m), 7.42 (1H, d, J=8.6 Hz), 7.49-7.54 (2H, m), 7.93-7.99 (2H, m). MS (ESI): m/z 519 (M+H)$^+$.

Example 27

2-Methyl-N-((1R)-1-{3-methyl-4-[(methylsulfonyl)amino]phenyl}ethyl)-2-[4-(2,2,2-trifluoro-1,1-dimethylethyl)phenyl]cyclopropanecarboxamide

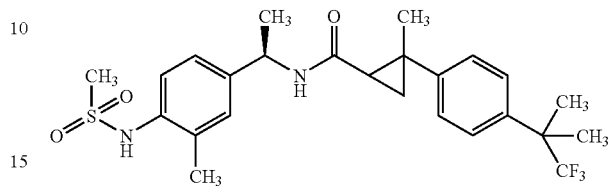

To a DMF (0.5 ml) solution of the compound of Example 13C (29 mg, 0.10 mmol), EDC (29 mg, 0.15 mmol), HOBt (17 mg, 0.11 mmol), triethylamine (0.042 ml) and the compound of Example 2D (30 mg, 0.11 mmol) were added in the same procedure as described in Example 1. Then, the reaction was quenched with 1N-HCl aqueous solution and the whole was extracted with EtOAc/hexane (3:1) which was dried over sodium sulfate. Then, filtration, evaporation, and purification by silica gel column, chromatography eluting with hexane/EtOAc (1:2,) gave the title compound (14 mg, 29% yield, white solids) as a mixture of diastereomeric products (1:1).

$^1$H NMR (300 MHz, CDCl$_3$) δ 1.20-1.89 (15H, m), 2.31 (3H, s), 3.00 (3H, s), 5.09-5.20 (1H, m), 5.88-5.97 (1H, m), 6.31 (1H, brs), 7.10-7.30 (4H, m), 7.39-7.47 (3H, m). MS (ESI): m/z 497 (M+H)$^+$.

Example 28

2-Methyl-N-((1R)-1-{3-methyl-4-[(methylsulfonyl)amino]phenyl}ethyl)-2-{4-[(trifluoromethyl)oxy]phenyl}cyclopropanecarboxamide(single isomer)

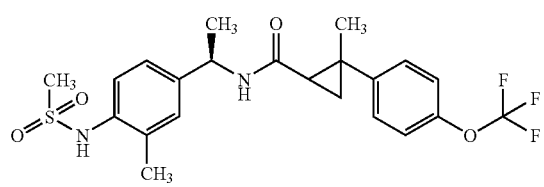

The diastereomer mixture of the compound of Example 16D was separated by Daicel Chiralpal AS-H (20×250 mm), eluting with n-hexane/i-propanol/diethylamine=80/20/0.1 at column temperatute of 40° C. The title compound was given as an earlier fraction (single isomer; retention time was 10 minutes; white solids).

$^1$H NMR (270 MHz, CDCl$_3$) δ 1.33-1.74 (9H, m), 2.32 (3H, s), 3.01 (3H, s), 5.08-5.17 (1H, m), 5.91 (1H, d, J=7.3 Hz), 6.33 (1H, s), 7.13-7.29 (6H, m), 7.42 (1H, d, J=8.1 Hz). MS (ESI): m/z 471 (M+H)$^+$.

Example 29

N-((1R)-1-{3-Ethyl-4-[(methylsulfonyl)amino]phenyl}ethyl)-2-methyl-2-{4-[(trifluoromethyl)oxy]phenyl}cyclopropanecarboxamide (diastereomeric mixture)

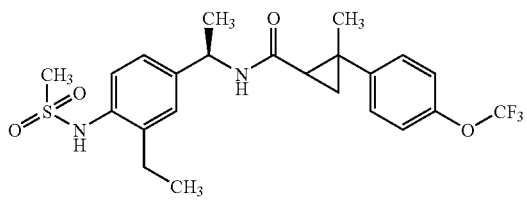

The procedure described in Example 14D was followed using a DMF (5 ml) solution of the compound of Example 16C (321 mg, 1.15 mmol), HBTU (523 mg, 1.38 mmol), triethylamine (0.48 ml) and the compound of Example 32C (300 mg, 1.15 mmol). The crude residue was applied to a silica gel chromatography column and eluted with a volume mixture of hexane and EtOAc (1:1) to afford the title compound (490 mg, 89% yield, white solids) as a mixture of diastereomer products (1:1).

$^1$H NMR (300 MHz, CDCl$_3$) δ 1.25 (3H, t, J=7.7 Hz), 1.34-1.73 (9H, m), 2.66 (2H, q, J=7.7 Hz), 3.02-3.03 (3H, m), 5.10-5.20 (1H, m), 5.83-5.90 (1H, m), 6.18 (1H, s), 7.14-7.47 (7H, m) MS (ESI): m/z 485 (M+H)+.

Example 30

2-[3,5-Difluoro-4-(2,2,2-trifluoro-1,1-dimethylethyl)phenyl]-N-((1R)-1-{3-methyl-4-[(methylsulfonyl)amino]phenyl}ethyl)cyclopropanecarboxamide (single isomer)

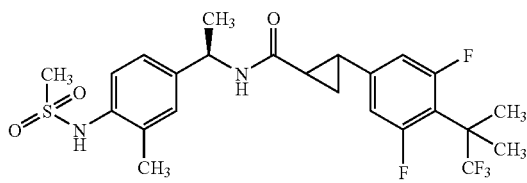

30A) 2-(2,6-Difluoro-4-methoxyphenyl)-1,1,1-trifluoropropan-2-ol

To a THF (100 ml) solution of 1,3-difluoro-5-methoxybenzene (7 g, 48.6 mmol) was added dropwise 1.6 M hexane solution of n-butyllithium (30 ml, 48.6 mmol) at −78° C. over 30 minutes and the mixture was stirred for 2 hours at −78 °C. Then 1,1,1-Trifluoroacetone (6.5 g, 58.3 mmol) was added at −78° C. and the mixture was stirred for 2 hours at −78° C. After stirring at room temperature for an additional 1 hour, the reaction was quenched with water. The whole was extracted with EtOAc and the organic layer was dried over sodium sulfate, filterd, and concentrated in vacuo. Purification by silica gel column chromatography eluting with hexane/EtOAc (10:1) gave the title compound (9.7 g, 78% yield) as a colorless oil.

$^1$H NMR (270 MHz, CDCl$_3$) δ 1.83-1.85 (3H, m), 3.94 (3H, s), 6.17 (1H, s), 6.49-6.60 (2H, m)

30B) 2-(1-Chloro-2,2,2-trifluoro-1-methylethyl)-1,3-difluoro-5-methoxybenzene

A thionyl chloride (25 ml) solution of the compound of Example 30A (8.7 g, 34.1 mmol) and pyridine (26 mg, 0.34 mmol) were stirred at 70° C. for 3 hours. Then the reaction was concentrated in vacuo and quenched with water. The whole was extracted with hexane and the extract was dried over sodium sulfate. After filtration and evaporation, the title compound (8.84 g, 94% yield) was obtained as a colorless oil.

$^1$H NMR (270 MHz, CDCl$_3$) δ 2.24-2.29 (3H, m), 3.81 (3H, s), 6.44-6.54 (2H, m)

30C) 1,3-Difluoro-5-methoxy-2-(2,2,2-trifluoro-1,1-dimethylethyl)benzene

To a cyclohexane (100 ml) solution of the compound of Example 30B (8.84 g, 32.2 mmol) was added a 1.0 M hexane solution of trimethyl aluminum (129 ml, 129 mmol) at room temperature and the mixture was stirred at reflux for 4 hours. Then the reaction was quenched with 2N-HCl aqueous solution and the whole was extracted with hexane. The extract was dried over sodium sulfate, filterd and concentrated to give the title compound (7.93 g, 97% yield) as a colorless oil.

$^1$H NMR (300 MHz, CDCl$_3$) δ 1.71 (6H, s), 3.78 (3H, s), 6.39-6.49 (2H, m)

30D) 3,5-Difluoro-4-(2,2,2-trifluoro-1,1-dimethylethyl)phenol

A mixture of the compound of Example 30C (7.93 g, 31.2 mmol) and 1 M DCM solution of boron tribromide (150 ml, 150 mmol) was stirred at room temperature for 16 hours. Then, the reaction was cautiously quenched with water and the whole was extracted with EtOAc. The extract was dried over sodium sulfate, filtered, and concentrated in vacuo. Purification by silica gel column chromatography,eluting with hexane/EtOAc (10:1) gave the title compound (7.79 g, quant.) as brown solids.

$^1$H NMR (270 MHz, CDCl$_3$) δ 1.71 (6H, s), 5.27 (1H, brs), 6.36-6.50 (2H, m)

30E) 3,5-Difluoro-4-(2,2,2-trifluoro-1,1-dimethylethyl)phenyl trifluoromethanesulfonate The procedure described in Example 2G was followed using a pyridine (5 ml) and DCM (10 ml) solution of the compound of Example 30D (456 mg, 1.9 mmol), trifluoromethane sulfonic acid anhydride (643 mg, 2.28 mmol) and 4-(dimethylamino)pyridine (2 mg, 0.02 mmol). The crude residue was applied to a silica gel chromatography column and eluted with a volume mixture of hexane and ethylacetate (9:1) to afford the title compound (440 mg, 62% yield) as a colorless oil.

$^1$H NMR (300 MHz, CDCl$_3$) δ 1.75-1.77 (6H, m), 6.86-6.95 (2H, m)

30F) 5-Ethenyl-1,3-difluoro-2-(2,2,2-trifluoro-1,1-dimethylethyl)benzene

The procedure described in Example 2G was followed using a DMF (5 ml) solution of the compound of Example 30E (440 mg, 1.18 mmol), vinyltributylstannane (450 mg, 1.42 mmol), lithium chloride (500 mg, 11.8 mmol) and bis(triphenylphosphine)palladium chloride (41 mg, 0.059 mmol). The crude residue was applied to a silica gel chromatography column and eluted with hexane to afford the title compound as a crude product including vinyltributylstannane (crude 829 mg) as a colorless oil.

$^1$H NMR (270 MHz, CDCl$_3$) δ 5.66 (1H, d, J=10.6Hz), 6.05 (1H, d, J=17.8Hz), 6.86 (1H, dd, J=10.6, 17.8 Hz), 7.14-7.22 (2H, m)

30G) Ethyl 2-[3,5-difluoro-4-(2,2,2-trifluoro-1,1-dimethylethyl)phenyl]cyclopropanecarboxylate The procedure described in Example 2H was followed using a toluene (3 ml) solution of the crude compound of Example 30F (829 mg), Co(TPP) (24 mg, 0.035 mmol), 1-methyl-1H-imidazole (484 mg, 5.9 mmol) and ethyl diazoacetate (262 mg, 2.6 mmol). The crude residue was applied to a silica gel chromatography column and eluted with gradually from hexane to hexane/ethylacetate (10:1) to afford the crude product of the title compound (trans) including vinyltributylstannane as a black oil.

$^1$H NMR (270 MHz, CDCl$_3$) δ 0.88-1.93 (12H, m), 2.40-2.47 (1H, m), 4.14-4.20 (2H, m), 6.57-6.66 (2H, m)

30H) 2-[3,5-Difluoro-4-(2,2,2-trifluoro-1,1-dimethylethyl)phenyl]cyclopropanecarboxylic acid The procedure described in Example 10D was followed using a THF (5 ml) solution of the crude compound of Example 30G, 2M sodium hydroxide aqueous solution (2 ml) and MeOH (5 ml) to afford the title compound (198 mg, 54% yield in 3 steps) as white solids. MS (ESI) m/z 307 (M−H)$^-$.

30I) 2-[3,5-Difluoro-4-(2,2,2-trifluoro-1,1-dimethylethyl)phenyl]-N-((1R)-1-{3-methyl-4-[(methylsulfonyl)amino]phenyl}ethyl)cyclopropanecarboxamide (single isomer)

The procedure described in Example 14D was followed using a DMF (2 ml) solution of the compound of Example 30H (60 mg, 0.195 mmol), HBTU (89 mg, 0.234 mmol), triethylamine (0.082 ml) and the compound of Example 2D (52 mg, 0.195 mmol). The crude residue was applied to a silica gel chromatography column and eluted with a volume mixture of hexane and EtOAc (1:1) and HPLC (XTerra MS C18, 5 um, 30×50 mm) to separate the diastereomers, eluting with acetonitrile/0.05% formic acid aqueous solution (32:68 to 68:32, later fraction as the title compound), to afford the title compound (16 mg, 16% yield) as white solids.

$^1$H NMR (300 MHz, CDCl$_3$) δ 1.15-1.24 (1H, m), 1.47 (3H, d, J=6.6 Hz), 1.57-1.70 (2H, m), 1.70-1.75 (6H, m), 2.32 (3H, s), 2.39-2.46 (1H, m), 3.02 (3H, s), 5.03-5.12 (1H, m), 5.90 (1H, d, J=7.3 Hz), 6.21 (1H, s), 6.54-6.62 (2H, m), 7.15-7.20 (2H, m), 7.41 (1H, d, J=8.8 Hz) MS (ESI): m/z 519 (M+H)+.

Example 31

(1S,2S)-2-Methyl-N-((1R)-1-{4-[(methylsulfonyl)amino]phenyl}propyl)-2-[4-(trifluoromethyl)phenyl]cyclopropanecarboxamide

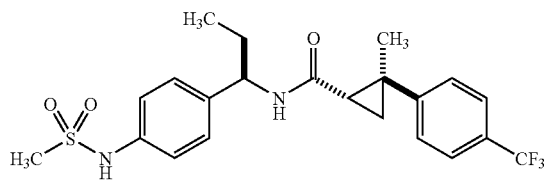

31A) N-[4-((1R)-1-{[(R)-tert-butylsulfinyl]amino}propyl)phenyl]methanesulfonamide To a solution of titanium(IV) ethoxide (2.0 ml) and N-(4-propanoylphenyl)methanesulfonamide (280 mg, 1.2 mmol, Bioorganic & Medicinal Chemistry Letters, 2004, 14(7), 1751-1755) in THF (5.0 ml) was added (R)-(+)-2-methyl-2-propanesulfininamide (149 mg, 1.2 mmol) and the mixture was stirred for 16 hours at 70° C. Upon completion, as determined by TLC, the mixture was cooled to room temperature and then to 0° C. before the reaction mixture was added dropwise to a suspension of sodium borohydride (185 mg, 4.9 mmol) in THF (12 ml) at 0° C. The procedure described in Example 2C was performed to give the title compound (240 mg, 72%) as a yellow oil. MS (ESI) m/z 333 (M+H)$^+$.

31B) N-{4-[(1R)-1-Aminopropyl]phenyl}methanesulfonamide hydrochloride

To a solution of the compound of Example 31A (280 mg, 1.60 mmol) in MeOH (5.0 ml) was added HCl-MeOH (2.0 M, 5.0 ml) and 1,4-dioxane (5.0 ml). The same procedure as described in Example 2D was performed to give the title compound (180 mg, 89%) as white solids. MS (ESI) m/z 227 (M−H)$^-$.

31C) (1S,2S)-2-Methyl-N-((1R)-1-{4-[(methylsulfonyl)amino]phenyl}propyl)-2-[4(trifluoromethyl)phenyl]cyclopropanecarboxamide To a DMF (2.0 ml) solution of the compound of Example 14C (40 mg, 0.15 mmol), HBTU (68 mg, 0.18 mmol), triethylamine (0.1 ml) and the compound of Example 31B (40 mg, 0.15 mmol) were added and the mixture was stirred for 16 hours at room temperature. The same procedure as described in Example 14D was performed to give the title compound (40 mg, 22% yield) as white solids.

$^1$H NMR (300 MHz, DMSO-d$_6$) δ 0.84 (3H, t, J=7.3 Hz), 1.32 (2H, d, J=7.3 Hz), 1.43 (3H, s), 1.60-1.70 (2H, m), 2.01 (1H, t, J=7.3 Hz), 2.95 (3H, s), 4.73 (1H, q, J=7.3 Hz), 7.14 (2H, d, J=8.1 Hz), 7.26 (2H, d, J=8.1 Hz), 7.54 (2H, d, J=8.1 Hz), 7.69 (2H, d, J=8.1 Hz), 8.55 (1H, d, J=8.8Hz), 9.68 (1H, brs). MS (ESI) m/z 513 (M+H)$^+$, 511 (M−H)$^-$ Example 32

(1S,2S)-N-((1R)-1-{3-Ethyl-4-[(methylsulfonyl)amino]phenyl}ethyl)-2-methyl-2-[4-(trifluoromethyl)phenyl]cyclopropanecarboxamide

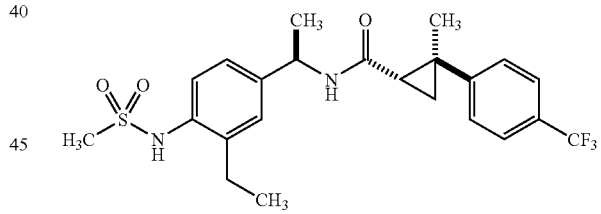

32A) N-(4-Acetyl-2-ethylphenyl)methanesulfonamide

To a solution of 2-amino-1-ethylbenzene (purchased from TCI, 12.1 g, 100 mmol) in pyridine (8.5 mL) and DCM (20 ml), methanesulfonyl chloride (7.74 ml, 11.4 g, 105 mmol) was added dropwise over 10 minutes at 0° C. The reaction mixture was stirred at room temperature for 1 hour. After cooling to 0° C., aluminum trichloride (33.3 g, 250 mmol) was added to the reaction mixture carefully. Then acetyl chloride (11 ml, 12 g, 150 mmol) was added dropwise over 15 minutes. The reaction mixture was diluted with toluene (50 ml) and poured into 2 M HCl aqueous solution (100 ml) with stirring at 0° C. The precipitates were filtered, washed with water and dried in vacuo to give the title compound (18 g, 75%) as yellow solids.

$^1$H NMR (300 MHz, DMSO-d$_6$) δ 1.17 (3H, t, J=7.3 Hz), 2.55 (3H, s), 2.75 (2H, q, J=703 Hz), 3.09 (3H, s), 7.46 (1H, d, J=8.1 Hz), 7.82 (2H, m), 9.36 (1H, s). MS (ESI) m/z 243 (M+H)$^+$, 241 (M−H)$^-$.

32B) N-[4-((1R)-1-{[(R)-tert-Butylsulfinyl]amino}ethyl)-2-ethylphenyl]methanesulfonamide To a solution of titanium(IV) ethoxide (20 ml) and the compound of Example 32A (2.4 g, 10 mmol) in THF (20 ml) was added (R)-(+)-2-methyl-2-propanesulfininamide (1.2 g, 10 mmol) and the mixture was stirred for 16 hours at 80° C. Upon completion, as determined by LC-MS, the mixture was cooled to room temperature and then to 0° C. before the reaction mixture was added dropwise to a suspension of sodium borohydride (1.5 g, 24 mmol) in THF (20 ml) at 0° C. The same procedure as described in Example 2C was performed to give the title compound (1.35 g, 48%) a yellow oil. MS (ESI) m/z 347 (M+H)$^+$, 345 (M–H)$^-$.

32C) N-{4-[(1R)-1-Aminoethyl]-2-ethylphenyl}methanesulfonamide hydrochloride

To a solution of the compound of Example 32B (1.65 g, 4.76 mmol) in MeOH (30 ml) was added HCl-MeOH (2.0 M, 30 ml). The same procedure as described in Example 2D was performed to give the title compound (1.2 g, 90%) as white solids. MS (ESI) m/z 241 (M–H)$^-$.

32D) (1S,2S)-N-((1R)-1-{3-Ethyl-4-[(methylsulfonyl)amino]phenyl}ethyl)-2-methyl-2-[4-(trifluoromethyl)phenyl]cyclopropanecarboxamide To a DMF (1.0 ml) solution of the compound of Example 14C (50 mg, 0.21 mmol), HBTU (93 mg, 0.25 mmol), triethylamine (0.1 ml) and the compound of Example 32C (57 mg, 0.21 mmol) were added and the mixture was stirred for 16 hours at room temperature. The same procedure as described in Example 14D was performed to give the title compound (67 mg, 70% yield) as white solids.

$^1$H NMR (300 MHz, DMSO-d$_6$) δ 1.15 (3H, t, J=7.3 Hz), 1.30-1.35 (5H, m), 1.45 (3H, s), 2.01 (1H, t, J=7.3 Hz), 2.69 (2H, q, J=7.3 Hz), 2.96 (3H, s), 4.95 (1H, m), 7.14 (1H, d, J=8.1 Hz), 7.20-7.21 (2H, m), 7.54 (2H, d, J=8.1 Hz), 7.68 (2H, d, J=8.1 Hz), 8.63 (1H, d, J=8.1 Hz), 9.04 (1H, brs). MS (ESI) m/z 467 (M+H)$^+$, 469 (M–H)$^-$ Example 33

N-((1R)-1-{3-Ethyl-4-[(methylsulfonyl)amino]phenyl}ethyl)-2-[4-(trifluoromethyl)phenyl]cyclopropanecarboxamide

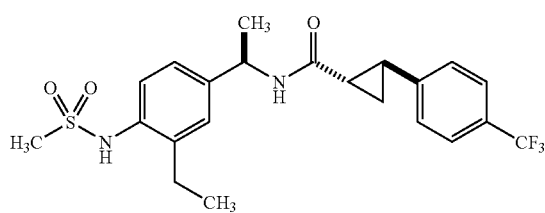

33A) trans-2-[4-(Trifluoromethyl)phenyl]cyclopropanecarboxylic acid

The racemic title compound (4.0 g) [Journal of Organic Chemistry, vol. 62 (No. 26) 9114-9122 (1997)] was separated with DAICEL CHIRALCEL OJ-H (column size: 2×25 cm, Mobile Phase: Hexane/2-propanol/TFA=97/3/0.1, column temperature: 40° C., flow rate: 20 ml/min, detection: 230 nm, Run time: 13.5 minutes, Retention time: 8 minutes and 10 minutes). The later fraction was collected as white solids (1.81 g).

[α]$_D$=+246.4 (c=0.46, methanol, cell temperature=21.0° C.)

33B) N-((1R)-1-{3-Ethyl-4-[(methylsulfonyl)amino]phenyl}ethyl)-2-[4-(trifluoromethyl)phenyl]cyclopropanecarboxamide To a DMF (1.0 ml) solution of the compound of Example 33A (50 mg, 0.22 mmol), HBTU (99 mg, 0.26 mmol), triethylamine (0.1 ml) and the amine compound of Example 32C (60 mg, 0.22 mmol) were added and the mixture was stirred for 16 hours at room temperature. The same procedure as Example 14D was performed to give the title compound (69 mg, 70% yield) as white solids.

$^1$H NMR (300 MHz, DMSO-d$_6$) δ 1.15 (3H, t, J=7.3 Hz), 1.24-1.41 (2H, m), 1.33 (2H, d, J=7.3 Hz), 1.99-2.05 (1H, m), 2.32-2.39 (1H, m), 2.68 (2H, q, J=7.3 Hz), 2.95 (3H, s), 4.91 (1H, m), 7.11 (1H, m), 7.18-7.23 (2H, m), 7.37 (2H, d, J=8.1 Hz), 7.63 (2H, d, J=8.1 Hz), 8.60 (1H, d, J=7.3 Hz). MS (ESI) m/z 455 (M+H)$^+$, 453 (M–H)$^-$

Example 34

(1S,2S)-2-Methyl-N-((1R)-1-{3-methyl-4-[(methylsulfonyl)amino]phenyl}propyl)-2-[4-(trifluoromethyl)phenyl]cyclopropanecarboxamide

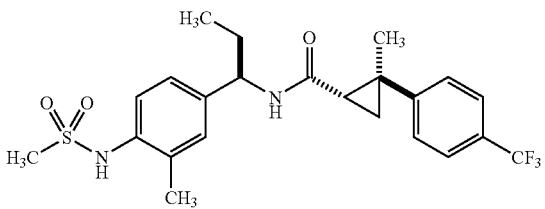

34A) N-(2-Methyl-4-propanoylphenyl)methanesulfonamide

To a solution of 2-methylaniline (2.2 g, 20 mmol, purchased from TCI) in pyridine (1.7 ml. 1.7 g, 21.4 mmol) and DCM (85 ml), methanesulfonyl chloride (1.6 ml, 2.3 g, 20 mmol) was added dropwise over 10 minutes at 0° C. The reaction mixture was stirred at room temperature for 1 hour. After cooling to 0° C., aluminum trichloride (6.8 g, 51 mmol) was added to the reaction mixture carefully. Then acetyl chloride (1.9 g, 20 mmol) was added dropwise over 15 minutes. The reaction mixture was diluted with toluene (25 ml) and poured into 2 M HCl aqueous solution (500 ml) with stirring at 0° C. The precipitates were filtered, washed with water and dried in vacuo to afford the title compound (2.1 g, 43%) as yellow solids.

MS (ESI) m/z 240 (M+H)$^+$, 242 (M–H)$^-$.

34B) N-[4-((1R)-1-{[(R)-tert-butylsulfinyl]amino}propyl)-2-methylphenyl]methanesulfonamide To a solution of titanium(IV) ethoxide (20 ml) and the compound of Example 34A (1.5 g, 6.2 mmol) in THF (20 ml) was added (R)-(+)-2-methyl-2-propanesulfininamide (753 mg, 6.2 mmol) and the mixture was stirred for 16 hours at 80° C. Upon completion, as determined by LC-MS, the mixture was cooled to room temperature and then to 0° C. before it was added dropwise to a suspension of sodium borohydride (941 mg, 25 mmol) in THF (20 ml) at 0° C. The same procedure as described in Example 2C was performed to give the title compound (1.13 g, 53%) as a yellow oil.

$^1$H NMR (300 MHz, DMSO-d$_6$) δ 0.81 (3H, t, J=7.3 Hz), 1.23 (9H, s), 1.73-1.78 (1H, m), 1.97-2.05 (1H, m), 2.32 (3H, s), 3.03 (3H, d, J=3.0 Hz), 3.35 (1H, m), 4.20 (1H, m), 6.36 (1H, brs), 7.17 (2H, m), 7.43 (1H, dd, J=3.0, 8.8 Hz). MS (ESI) m/z 347 (M+H)⁺, 345 (M−H)⁻

34C) N-{4-[(1R)-1-Aminopropyl]-2-methylphenyl}methanesulfonamide

To a solution of the compound of Example 34B (1.13 g, 3.3 mmol) in MeOH (20 ml) was added HCl-MeOH (2.0 M, 20 ml). The same procedure as described in Example 2D was performed to give the title compound (610 mg, 67%) as white solids.

¹H NMR (300 MHz, DMSO-d₆) δ 0.76 (3H, t, J=7.3 Hz), 1.72-1.96 (2H, m), 2.31 (3H, s), 2.99 (3H, s), 4.06 (1H, m), 7.28-7.35 (3H, m), 8.53 (3H, brs). MS (ESI) m/z 242 (M−H)⁻.

34D) (1S,2S)-2-Methyl-N-((1R)-1-{3-methyl-4-[(methylsulfonyl)amino]phenyl}propyl)-2-[4-(trifluoromethyl)phenyl]cyclopropanecarboxamide To a DMF (2.0 ml) solution of the compound of Example 14C (55 mg, 0.23 mmol), HBTU (102 mg, 0.27 mmol), triethylamine (0.1 ml) and the compound of Example 34C (63 mg, 0.23 mmol) were added and the mixture was stirred for 16 hours at room temperature. The same procedure as described in Example 14D was performed to give the title compound (70 mg, 60%) as white solids.

¹H NMR (300 MHz, DMSO-d₆) δ 0.85 (3H, t, J=6.6 Hz), 1.32 (2H, d, J=6.6 Hz), 1.59-1.70 (2H, m), 2.02 (1H, t, J=6.6 Hz), 2.28 (3H, s), 2.94 (3H, s), 4.72 (1H, m), 7.10-7.22 (3H, m), 7.54 (2H, d, J=8.1 Hz), 7.69 (2H, d, J=8.1 Hz), 8.55 (1H, d, J=8.8 Hz), 9.05 (1H, brs). MS (ESI) m/z 469 (M+H)⁺, 467 (M−H)⁻

Example 35

N-((1R)-1-{6-Ethyl-5-[(methylsulfonyl)amino]pyridin-2-yl}ethyl)-2-methyl-2-[4-(2,2,2,-trifluoro-1,1-dimethylethyl)phenyl]cyclopropanecarboxamide

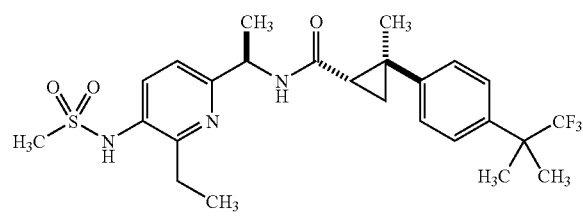

35A) 6-Chloro-2-ethylpyridin-3-ylamine

To a solution of 3-amino-2,6-dichloropyridine (8.1 g, 50 mmol, purchased from TCI) in 1,4-dioxane (248 ml) was added tetrakis(triphenylphosphine)palladium(0) (920 mg, 0.80 mmol) and triethylaluminum (52 mmol, 0.94 M in hexane) at room temperature, and the mixture was stirred for 3 hours at 100° C. The mixture was quenched with 2 M HCl aqueous solution after cooling, and then it was separated between the aqueous and organic phases. The aqueous phase was extracted with EtOAc. The combined organic phases were dried over magnesium sulfate and concentrated. The crude product was purified by silica gel column chromatography, eluting with hexane/EtOAc (2:1), to give the title compound (2.73 g, 35%).

¹H NMR (300 MHz, DMSO-d₆) δ 1.13 (3H, t, J=7.3 Hz), 2.55 (2H, q, J=7.3 Hz), 5.24 (2H, brs.), 6.97 (2H, s). MS (ESI) m/z 157 (M+H)⁺.

35B) N-(6-Chloro-2-ethylpyridin-3-yl)methanesulfonamide

To a solution of the compound of Example 35A (4.76 g, 30.4 mmol) in DCM (122 mL) were added pyridine (2.88 g, 36.5 mmol) and methanesulfonyl chloride (3.83 g, 33.4 mmol) at room temperature. After 16 hours, additional methanesulfonyl chloride (0.37 g, 3.2 mmol) was added and the reaction mixture was stirred for 5 hours. Further additional methanesulfonyl chloride (0.37 g, 3.2 mmol) was added. After 95 hours, the mixture was washed with brine, and then the separated organic phase was dried over magnesium sulfate and concentrated. The residue was purified by silica gel column chromatography, eluting with hexane/EtOAc (1:1,) to give the title compound (5.55 g, 78%) as pale yellow solids.

¹H NMR (300 MHz, DMSO-d₆) δ 1.18 (3H, t, J=7.3 Hz), 2.83 (2H, q, J=7.3 Hz), 3.05 (3H, s), 7.36 (1H, d, J=8.8 Hz), 7.72 (1H, d, J=8.8 Hz), 9.45 (1H, s). MS (ESI) m/z 235 (M+H)⁺, 233 (M−H)⁻.

35C) N-(6-Cyano-2-ethylpyridin-3-yl)methanesulfonamide

A test tube suitable for microwave use was charged with the compound of Example 35B (3.54 g, 15 mmol), zinc cyanide (2.19 g, 19 mmol) and tetrakis(triphenylphosphine)palladium(0) (1.73 g, 1.5 mmol) in N,N'-dimethylformamide (15 ml). The same procedure as described in Example 9B was performed to give the title compound (3.18 g, quant) as pale yellow solids.

MS (ESI) m/z 226 (M+H)⁺, 224 (M−H)⁻.

35D) N-(6-Acetyl-2-ethylpyridin-3-yl)methanesulfonamide

To a solution of the compound of Example 35C (1.1 g, 4.9 mmol) in THF (20 ml) was added dropwise THF solution of methyl magnesium bromide (18 ml, 14.7 mmol) at 0° C. with stirring. The same procedure as described in Example 9C was performed to give the title compound (720 mg, 61% yield) as brown solids.

¹H NMR (300 MHz, DMSO-d₆) δ 1.41 (2H, t, J=7.3 Hz), 2.70 (3H, s), 2.83 (2H, q, J=7.3 Hz), 3.11 (3H, s), 6.57 (1H, brs), 7.93 (2H, d, J=2.0 Hz). MS (ESI) m/z 243 (M+H)⁺, 241 (M−H)⁻.

35E) N-[6-((1R)-1-{[(R)-tert-butylsulfinyl]amino}ethyl)-2-ethylpyridin-3-yl]methanesulfonamide To a solution of titanium(IV) ethoxide (6.0 ml) and the compound of Example 35D (330 mg, 1.3 mmol) in THF (6.0 ml) was added (R)-(+)-2-methyl-2-propanesulfininamide (157 mg, 1.3 mmol) under a nitrogen atmosphere and the mixture was stirred for 16 hours at 80° C. Upon completion, as determined by TLC, the mixture was cooled to room temperature and then to 0° C. before it was added dropwise to a suspension of sodium borohydride (197 mg, 5.2 mmol) in THF (12 ml) at 0° C. The same procedure as described in Example 2C was performed to give the title compound (280 mg, 62%) as a yellow oil.

¹H-NMR (CDCl₃) δ 1.28 (9H, s), 1.30 (3H, s, J=7.3 Hz), 1.48 (3H, d, J=6.6 Hz), 2.79 (2H, q, J=7.3 Hz), 3.00 (3H, s), 4.58 (1H, m), 5.21 (1H, m), 6.73 (1H, m), 7.13 (1H, d, J=8.6Hz), 7.72 (1H, d, J=7.9 Hz). MS (ESI) m/z 348 (M+H)⁺, 346 (M−H)⁻.

35F) N-{6-[(1R)-1-Aminoethyl]-2-ethylpyridin-3-yl}methanesulfonamide hydrochloride To a solution of the compound of Example 35E (280 mg, 0.81 mmol) in MeOH (5.0 ml) was added HCl-MeOH (2.0 M, 5.0 ml). The same procedure as described in Example 2D was performed to give the title compound (170 mg, 54%) as yellow solids.

MS (ESI) m/z 244 (M+H)⁺.

35G) N-((1R)-1-{6-Ethyl-5-[(methylsulfonyl)amino]pyridin-2-yl}ethyl)-2-methyl-2-[4-(2,2,2-trifluoro-1,1-dimethylethyl)phenyl]cyclopropanecarboxamide To a DMF (2.0 ml) solution of the compound of Example 13D (82 mg, 0.29 mmol), HBTU (133 mg, 0.35 mmol), triethylamine (0.12 ml, 0.87 mmol) and the compound of Example 35F (70 mg, 0.29 mmol) were added and the mixture was stirred for 16 hours at room temperature. The same procedure as described in Example 14D was performed to give the title compound (33 mg, 22% yield) as white solids.

$^1$H-NMR (CDCl$_3$) δ 1.33 (3H, s, J=7.9 Hz), 1.47 (3H, d, J=6.6 Hz), 1.51 (2H, m), 1.55 (3H, s), 1.57 (6H, s), 1.79 (1H, m), 2.85 (2H, q, J=7.9Hz), 3.04 (3H, s), 5.18 (1H, m), 6.97 (1H, m), 7.14 (1H, d, J=8.6 Hz), 7.30 (1H, d, J=8.6 Hz), 7.46 (1H, d, J=8.6 Hz), 7.76 (1H, d, J=8.6 Hz). MS (ESI) m/z 429 (M+H)$^+$ 512, (M−H)$^-$.510

Example 36

2-[4-tert-Butyl-3-fluorophenyl]-N-((1R)-1-{3-(hydroxymethyl)-4-[(methylsulfonyl)amino]phenyl}ethyl)cyclopropanecarboxamide

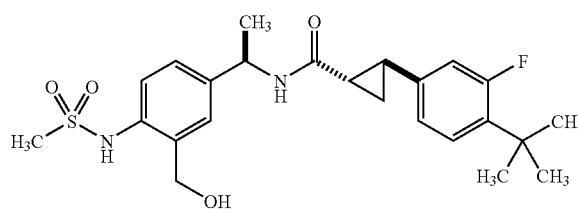

To a solution of the compound of Exmaple 20B (40 mg, 0.14 mmol) in DMF (2 ml), the compound of Example 21 (33 mg, 0.14 mmol), EDC (40 mg), and DMAP (0.5 mg, 0.004 mmol) were added. The solution was stirred at room temperature for 16 hours and then partitioned between EtOAc and water. The same procedure as described in Example 1 was performed to give the title compound (32 mg, 49%) as white solids.

$^1$H NMR (270 MHz, DMSO-d6) δ ppm 1.08-1.14 (1H, m), 1.34 (9H, s), 1.41 (3H, d, J=6.6 Hz), 1.48-1.52 (1H, m), 1.59-1.65 (1H, m), 1.88 (1H, brs), 2.36-2.45 (1H, m), 2.99 (3H, s), 4.66 (2H, s), 4.95-5.04 (1H, m), 6.43 (1H, d, J=8.1 Hz), 6.68 (1H, dd, J=2.2, 13.2 Hz), 6.81 (1H, dd, J=2.2, 8.1 Hz), 7.15-7.27 (3H, m), 7.46 (1H, d, J=8.1 Hz), 7.98 (1H, s). MS (ESI) m/z 463 [M+H]$^+$. 461 [M−H]$^-$.

Example 37

2-Methyl-N-((1R)-1-{4-methyl-5-[(methylsulfonyl)amino]pyridin-2-yl}ethyl)-2-[4-(2,2,2-trifluoro-1,1-dimethylethyl)phenyl]cyclopropanecarboxamide

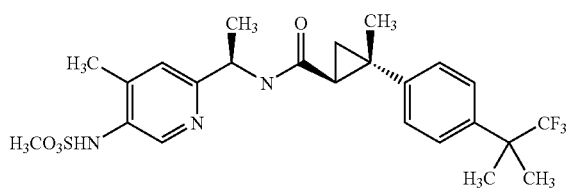

To a solution of the compound of Example 9E and the compound of Example 13D (124 mg, 0.434 mmol in DMC (4.3 ml) was added triethylamine (0.18 ml, 132 mg, 1.30 mmol) and HBTU (198 mg, 0.521 mmol) at room temperature. After 2 hours, the mixture was quenched with saturated aqueous sodium bicarbonate and washed with brine. The separated aqueous layer was dried over magnesium sulfate and concentrated. The same procedure as described in Example 14D was performed to give the title compound (97.7 mg, 45%) as white solids.

$^1$H NMR (270 MHz, CDCl$_3$) δ 1.36 (1H, dd, J=4.6, 7.9 Hz), 1.47 (3H, d, J=6.6 Hz), 1.50-1.64 (10H, m), 1.80 (1H, dd, J=5.9, 7.9 Hz), 2.38 (3H, s), 3.08 (3H, s), 5.08-5.24 (1H, m), 6.33 (1H, s), 6.87 (1H, d, J=7.3 Hz), 7.17 (1H, s), 7.27 (2H, d, J=8.6 Hz), 7.45 (2H, d, J=8.6 Hz), 8.51 (1H, s). MS (ESI) m/z 498 (M+H)$^+$, 496 (M−H)$^-$.

Example 38

2-[4-tert-Butyl-3,5-difluorophenyl]-N-((1R)-1-{4-[(methylsulfonyl)amino]phenyl}ethyl)cyclopropanecarboxamide

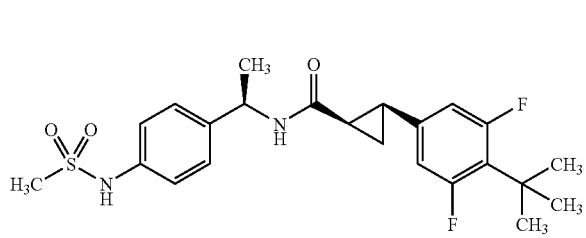

38A) 4-tert-Butyl-3,5-difluorophenol

A mixture of 3,5-difluorophenol (TCl, 14 g, 107 mmol), tert-butyl methyl ether (12.8 ml, 108 mmol) and zirconium (IV) chloride (25 g, 107 mmol) was stirred for 12 hours at 55° C., followed by addition of tert-butyl methyl ether (6.4 ml, 54 mmol). The additional injection of tert-butyl methyl ether (6.4 ml, 54 mmol), was repeated 8 times at intervals of 24 hours and then the reaction was quenched with saturated ammonium chloride aqueous solution and 2 M HCl aqueous solution. The whole was extracted with DCM, washed with brine, and dried over magnesium sulfate. The organic layer was evaporated to give a crude residue which was purified by silica gel column chromatography, eluting with gradually from hexane only to hexane/EtOAc (10:1), to give the title compound (10.8 g, 54%) as white solids.

$^1$H NMR (270 MHz, CDCl$_3$) δ 1.42 (9H, t, J=2.3 Hz), 5.16 (1H, brs), 6.26-6.37 (2H, m). MS (ESI) m/z 185 (M−H)$^-$.

38B) 4-tert-Butyl-3,5-difluorophenyl trifluoromethanesulfonate

To a pyridine (30 ml) and DCM (44 ml) solution of the compound of Example 38A (5.0 g, 26.9 mmol), trifluoromethane sulfonic acid anhydride (11.4 g, 54 mmol) and 4-dimethylaminopyridine (55 mg, 0.4 mmol) were added and the mixture was stirred for 2 hours at 0° C. After being quenched with water, the whole was extracted with hexane, evaporated, and purified by silica gel column chromatography, eluting with hexane/EtOAc (10:1), to give the title compound (6.6 g, 77%) as a colorless oil.

$^1$H NMR (CDCl$_3$) δ 2.57 (300 MHz, 9H, t, J=2.6 Hz), 6.76-6.86 (2H, m)

38C) 2-tert-Butyl-5-ethenyl-1,3-difluorobenzene

To a DMF (230 ml) solution of the compound of Example 38B (6.5 g, 20.4 mmol), yinyltributylstannane (13.0 g, 40.8 mmol), lithium chloride (18.7 g, 204 mmol) and bis(triphenylphosphine)palladium chloride (716 mg, 1.02 mmol) were added and the mixture was stirred for 2 hours at 80° C. The reaction was quenched with water and the whole was extracted with hexane. Then, evaporation and purification by silica gel column chromatography, eluting with hexane, gave the title compound (4.0 g, 99%) as a colorless oil.

$^1$H NMR (270 MHz, CDCl$_3$) δ 1.45-1.46 (9H, m), 5.30 (1H, d, J=10.6 Hz), 5.71 (1H, d, J=17.8 Hz), 6.56 (1H, dd, J=17.5, 10.9 Hz), 6.79-6.89 (2H, m).

38D) 2-[4-tert-Butyl-3,5-difluorophenyl]cyclopropanecarboxylic acid

To a toluene (50 ml) solution of the compound of Example 38C (4.0 g, 20.4 mmol), Co(TPP) (411 mg, 0.61 mmol) and 1-methyl-1H-imidazole (5.0 g, 61.2 mmol), ethyl diazoacetate (3.5 g, 30.6 mmol) was added and the mixture was stirred for 5 minutes at room temperature followed by additional stirring for 2 hours at 80° C. Then, evaporation and purification by silica gel column chromatography, eluting with gradually from hexane to hexane/EtOAc (20:1), gave ethyl 2-(4-tert-butyl-3,5-difluorophenyl)cyclopropanecarboxylate (4.4 g, 76%, trans). To a THF (5 ml) solution of ethyl 2-(4-tert-butyl-3,5-difluorophenyl)cyclopropanecarboxylate (4.4 g, 15.5 mmol), 2M sodium hydroxide aqueous solution (30 ml) and MeOH (30 ml) were added and the mixture was stirred for 1 hour at room temperature. After the reaction was completed, the aqueous layer was extracted, and then acidified with 2M HCl aqueous solution and the whole was extracted with EtOAc, followed by evaporation, to give the title compound (3.48 g, 88%) as white solids.

MS (ESI) m/z 253 (M−H)$^-$.

38E) 2-[4-tert-Butyl-3,5-difluorophenyl]-N-((1R)-1-{4-[(methylsulfonyl)amino]phenyl}ethyl)cyclopropanecarboxamide To a DMF (10 ml) solution of the amine compound of Example 21 (200 mg, 0.8 mmol), the compound of Example 38D (203 mg, 0.8 mmol), HBTU (394 mg, 1.0 mmol) and triethylamine (0.33 ml, 2.4 mmol) were added and the mixture was stirred for 2 hours at room temperature. The reaction was quenched with water and the whole was extracted with EtOAc. Then, evaporation and purification by HPLC (the used column was MS C 30×50 mm, and the condition was acetonitrile/0.01% aqueous ammonia eluting with 32 to 68 ) gave the title compound (81 mg, 22%) as white solids. The fraction time for the desired product was 4.61 min.

$^1$H NMR (300 MHz, DMSO-d$_6$) δ 1.15-1.48 (14H, m), 1.90-1.96(1H, m), 2.20-2.26 (1H, m), 2.96 (3H, s), 4.86-4.95 (1H, m), 6.82 (2H, d, J=12.5 Hz), 7.15-7.28 (4H, m), 8.53 (1H, d, J=7.3 Hz), 9.69 (1H, brs). MS (ESI) m/z 449 (M−H)$^-$, 451 (M+H)$^+$ Example 39

2-(4-tert-Butyl-3,5-difluorophenyl)-N-((1R)-1-{3-methyl-4-[(methylsulfonyl)amino]phenyl}ethyl)cyclopropanecarboxamide

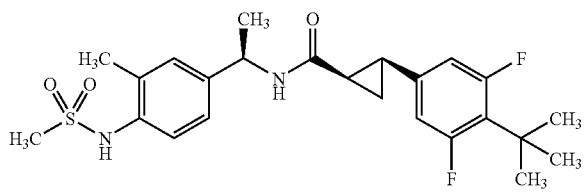

To a DMF (10 ml) solution of the compound of Example 2D (200 mg, 0.8 mmol), the compound of Example 38D (192 mg, 0.8 mmol), HBTU (375 mg, 1.0 mmol) and triethylamine (0.32 ml, 2.3 mmol) were added and the mixture was stirred for 2 hours at room temperature. The same procedure as described in Example 38E was performed to give the title compound (105 mg, 30%). The fraction time for the desired product was 4.8 min.

$^1$H NMR (270 MHz, DMSO-d$_6$) δ 1.18-1.51 (14H, m), 1.87-2.02(1H, m), 2.15-2.37 (4H, m), 2.96 (3H, s), 4.81-4.97 (1H, m), 6.82 (2H, d, J=11.9 Hz), 7.11-7.24 (3H, m), 8.53 (1H, d, J=7.3 Hz), 9.04 (1H, brs). MS (ESI) m/z 463 (M−H)$^-$, 465 (M+H)$^+$ Example 40

2-(4-tert-Butyl-3,5-difluorophenyl)-N-((1R)-1-{3-fluoro-4-[(methylsulfonyl)amino]phenyl}ethyl)cyclopropanecarboxamide

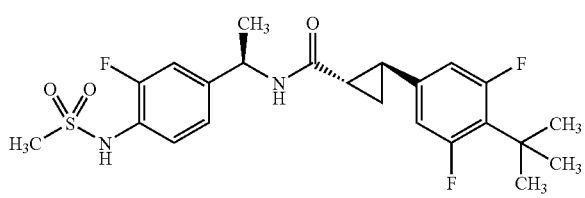

To a DMF (10 ml) solution of the amine compound of Example 8 (210 mg, 0.8 mmol), the compound of Example 38D (200 mg, 0.8 mmol), HBTU (394 mg, 1.0 mmol) and triethylamine (0.33 ml, 2.4 mmol) were added and the mixture was stirred for 2 hours at room temperature. The same procedure as described in Example 38E was followed, but using HPLC condition of acetonitrile/0.05% aqueous formic acid 32 to 68, to give the title compound (33 mg, 9%). The fraction time for the desired product was 4.7 min.

$^1$H NMR (300 MHz, DMSO-d$_6$) δ 1.22-1.50 (14H, m), 1.86-1.97 (1H, m), 2.18-2.30 (1H, m), 3.00 (3H, s), 4.86-4.99 (1H, m), 6.82 (2H, d, J=11.7 Hz), 7.07-7.24 (2H, m), 7.33 (1H, t, J=8.4 Hz), 8.60 (1H, d, J=8.0 Hz), 9.58 (1H, brs). MS (ESI) m/z 467 (M−H)$^-$, 469 (M+H)$^+$

Example 41

(1S,2S)-N-((1R)-1-{2-Fluoro-5-methyl-4-[(methylsulfonyl)amino]phenyl}ethyl)-2-methyl-2-[4-(trifluoromethyl)phenyl]cyclopropanecarboxamide

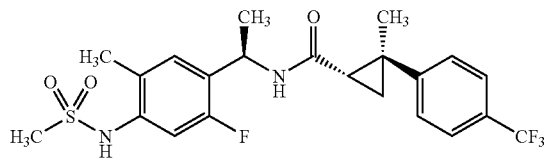

41A) N-(5-fluoro-2-methylphenyl)methanesulfonamide

To a pyridine (20 ml) and DCM (40 ml) solution of 2-fluoro-5-methylaniline (purchased from ACROS, 3.5 g, 28 mmol), methanesulfonyl chloride (purchased from WAKO, 4.3 ml, 56 mmol) was added at room temperature and the mixture was stirred for 20 hours. The reaction was quenched with 2M sodium hydroxide aqueous solution and the aqueous layer was separated and washed with DCM. The layer was cooled to 0° C. and acidified to pH 2.0 using 2M HCl aqueous solution. The precipitates were collected, and the solvent evaporated in vacuo, to give the title compound (5.1 g, 90%). MS (ESI) m/z 202 (M−H)⁻

41 B) N-(4-Acetyl-5-fluoro-2-methylphenyl)methanesulfonamide

To a DCM (45 ml) suspension of aluminum trichloride (WAKO, 4.9 g, 36.9 mmol), acetyl chloride (purchased from WAKO, 1.9 g, 24.6 mmol) was slowly added at room temperature and the mixture wasstirred for 20 minutes, then a dichloromethane (15 ml) solution of the compound of Example 41A (2.5 g, 12.3 mmol) was added to the mixture and the reaction was stirred for 2.5 hours at room temperature. The reaction mixture was poured into ice-water and the whole was extracted with DCM. The organic layer was dried over magnesium sulfate and the solvent evaporated to give the title compound (1.4 g, 46%).

$^1$H NMR (270 MHz, DMSO-d$_6$) δ 2.24-2.31 (3H, m), 2.54 (3H, d, J=4.6 Hz), 3.15 (3.15 (3H, s), 7.27 (1H, d, J=13.2 Hz), 7.28 (1H, d, J=7.9 Hz), 9.54 (1H, brs).

41C) N-[4-((1R)-1-{[(R)-tert-Butylsulfinyl]amino}ethyl)-5-fluoro-2-methylphenyl]methanesulfonamide To a THF (5 ml) solution of the compound of Example 41 B (1.4 g, 5.5 mmol) and (R)-(+)-2-methyl-2-propanesulfinylamide (1.0 g, 8.26 mmol), titanium(IV) ethoxide (5.0 ml, 21.9 mmol) was added under a nitrogen atmosphere and the mixture was subjected to microwave irradiation at at 70° C. with stirring for 2.5 hours. After imine formation was confirmed with LC-MS (MS (ESI) m/z 347 (M−H)⁻, 349 (M+H)⁺), the mixture was cooled to 0° C. and sodium borohydride (707 mg, 18.7 mmol) was added and the reaction mixture was stirred for 2 hours at 0° C. The reaction mixture was partitioned with water and ethanol, then the mixture was stirred for 1 hour at room temperature. The mixture was filtrated through a Celite pad, and the filtrate was evaporated and concentrated in vacuo to give the title compound (1.9 g, 99%).

MS (ESI) m/z 349 (M−H)⁻, 351 (M+H)⁺

41D) N-{4-[(1R)-1-Aminoethyl]-5-fluoro-2-methylphenyl}methanesulfonamide hydrochloride To the compound of Example 41C (1.9 g, 5.5 mmol) was added HCl-MeOH (2.0 M, 15.0 ml) and 1,4-dioxane (15.0 ml). The same procedure as describe in Example 2D was performed to give the title compound (1.2 g, 74%) as white solids.

MS (ESI) m/z 245 (M−H)⁻.

41E) (1S,2S)-N-((1R)-1-{2-Fluoro-5-methyl-4-[(methylsulfonyl)amino]phenyl}ethyl)-2-methyl-2-[4-(trifluoromethyl)phenyl]cyclopropanecarboxamide To a DMF (8 ml) solution of the compound of Example 41D (115 mg, 0.4 mmol), the compound of Example 14C (100 mg, 0.4 mmol), HBTU (202 mg, 0.5 mmol) and triethylamine (0.2 ml, 1.2 mmol) were added and the mixture was stirred for 2 hours at room temperature. The same procedure as described in Example 38E was performed to give the title compound (54 mg, 28%). The fraction time for the desired product was 4.0 min.

$^1$H NMR (300 MHz, DMSO-d$_6$) δ 1.27-1.37 (5H, m), 1.44 (3H, s), 1.98-2.07 (1H, m), 2.25 (3H, s), 3.01 (3H, s), 5.09-5.20 (1H, m), 7.07 (1H, d, J=11.0 Hz), 7.24 (1H, d, J=8.8 Hz), 7.54 (2H, d, J=8.1 Hz), 7.68 (2H, d, J=8.1 Hz), 9.20 (1H, brs). MS (ESI) m/z 471 (M−H)⁻, 473 (M+H)⁺

Example 42

N-((1R)-1-{2-Fluoro-5-methyl-4-[(methylsulfonyl)amino]phenyl}ethyl)-2-[3-fluoro-4-(trifluoromethyl)phenyl]-2-methylcyclopropanecarboxamide

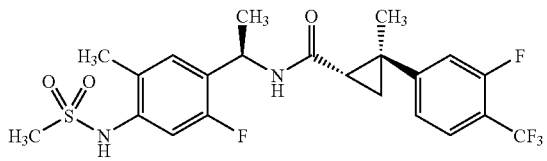

To a DMF (8 ml) solution of the compound of Example 41D (129 mg, 0.5 mmol), the compound of Example 66C (120 mg, 0.5 mmol), HBTU (227 mg, 0.6 mmol) and triethylamine (0.2 ml, 1.4 mmol) were added and the mixture was stirred for 2 hours at room temperature. The same procedure as described in Example 38E was performed to give the title compound (23 mg, 10%). The fraction time for the desired product was 3.9 min.

$^1$H NMR (300 MHz, DMSO-d$_6$) δ 1.26-1.49 (8H, m), 2.01-2.12 (1H, m), 2.24 (3H, s), 3.01 (3H, s), 5.06-5.20 (1H, m), 7.07 (1H, d, J=11.7 Hz), 7.23 (1H, d, J=8.1 Hz), 7.36(1H, d, J=8.1 Hz), 7.45 (1H, d, J=12.5 Hz), 7.72 (1H, t, J=7.7 Hz), 8.68 (1H, d, J=8.1 Hz), 9.22 (1H, brs). MS (ESI) m/z 489 (M−H)⁻, 491 (M+H)⁺

Example 43

2-(4-tert-Butyl-3,5-difluorophenyl)-2-methyl-N-((1R)-1-{4-[(methylsulfonyl)amino]phenyl}ethyl)cyclopropanecarboxamide

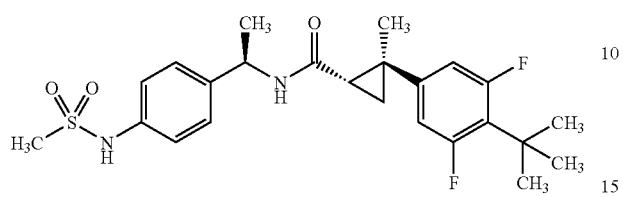

43A) 2-tert-Butyl-1,3-difluoro-5-isopropenylbenzene

A mixture of the compound of Example 38B (2.7 g, 8.5 mmol), potassium isopropenyltrifluoroborate (1.5 g, 10.2 mmol, Org. Lett. 2002, 4,107), 1,1'-bis(diphenylphospino)ferrocene palladium (II) dichloride (350 mg, 0.4 mmol) and triethylamine (1.2 ml, 8.5 mmol) in 2-propanol (86 ml) was stirred at 80° C. for 2 hours. The reaction mixture was cooled to room temperature and evaporated. The whole was extracted with hexane, dried over magnesium sulfate, and the solvent evaporated. The crude residue was purified by silica gel column chromatography, eluting with hexane, to give the title compound (1.1 g, 63%) as a colorless oil.

$^1$H NMR (300 MHz, CDCl$_3$) δ 1.46 (9H, t, J=1.8 Hz), 2.08 (3H, s), 5.11 (1H, s), 5.38 (1H, s), 6.84-6.95 (2H, m).

43B) Ethyl 2-(4-tert-butyl-3,5-difluorophenyl)-2-methylcyclopropanecarboxylate

To a toluene (50 ml) solution of the compound of Example 43A (1.1 g, 5.3 mmol), Co(TPP) (107 mg, 0.16 mmol) and 1-methyl-1H-imidazole (1.31 ml, 16.0 mmol), ethyldiazoacetate (0.9 ml, 8.0 mmol) was added and the mixture was stirred for 5 minutes at room temperature followed by additional stirring for 2 hours at 80° C. Then, evaporation and purification by silica gel column chromatography with graduate elution from hexane to hexane/EtOAc (20:1), gave the title compound (912 mg, 58%, trans).

$^1$H NMR (300 MHz, CDCl$_3$) δ 1.24-1.52 (17H, m), 1.85-1.94 (1H, m), 4.09-4.28 (2H, m), 6.64-6.78 (2H, m).

43C) 2-(4-tert-Butyl-3,5-difluorophenyl)-2-methylcyclopropanecarboxylic acid

To a THF (5 ml) solution of the compound of Example 43B (900 mg, 3.0 mmol), 2M sodium hydroxide aqueous solution (10 ml) and MeOH (10 ml) were added and the mixture was stirred for 2 hours at room temperature. After the reaction was completed, the aqueous layer was extracted and acidified with 2M HCl aqueous solution. The whole was extracted with EtOAc followed by evaporation of the solvent to give the title compound (516 mg, 63%).

MS (ESI) m/z 267 (M−H)$^−$ 43D) 2-(4-tert-Butyl-3,5-difluorophenyl)-2-methyl-N-((1R)-1-{4-[(methylsulfonyl)amino]phenyl}ethyl)cyclopropanecarboxamide To a DMF (10 ml) solution of the amine compound of Example 21 (140 mg, 0.6 mmol), the compound of Example 43C (150 mg, 0.6 mmol), HBTU (276 mg, 0.7 mmol) and triethylamine (0.2 ml, 1.7 mmol) were added and the mixture was stirred for 2 hours at room temperature. The same procedure as described in Example 38E was performed to give the title compound (70 mg, 27%). The fraction time for the desired product was 5.1 min.

$^1$H NMR (300 MHz, DMSO-d$_6$) δ 1.16-1.62 (17H, m), 1.88-2.05 (1H, m), 2.95 (3H, s), 4.83-5.00 (1H, m), 6.93 (2H, d, J=12.5 Hz), 7.15 (2H, d, J=8.1 Hz), 7.27 (2H, d, J=8.1 Hz), 8.56 (1H, d, J=7.3 Hz), 9.66 (1H, brs). MS (ESI) m/z 463 (M−H)$^−$, 465 (M+H)$^{+ [α]}{_D}$=+95.8 (c=0.5, methanol, cell temperature=21.6° C.)

Example 44

2-(4-tert-Butyl-3,5-difluorophenyl)-2-methyl-N-((1R)-1-{3-methyl-4-[(methylsulfonyl)amino]phenyl}ethyl)cyclopropanecarboxamide

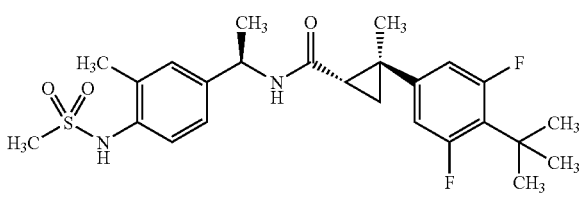

To a DMF (10 ml) solution of the compound of Example 2D (140 mg, 0.5 mmol), the compound of Example 43C (142 mg, 0.5 mmol), HBTU (261 mg, 0.7 mmol) and trimethylamine (0.2 ml, 1.6 mmol) were added and the mixture was stirred for 2 hours at room temperature. The same procedure as described in Example 38E was performed to give the title compound (76 mg, 30%).

$^1$H NMR (300 MHz, DMSO-d$_6$) δ 1.17-1.57 (17H, m), 1.89-2.04 (1H, m), 2.30 (3H, s), 2.96 (3H, s), 4.84-4.99 (1H, m), 6.93 (2H, d, J=12.5 Hz), 7.08-7.32 (3H, m), 8.57 (1H, d, J=7.3 Hz), 9.04 (1H, brs). MS (ESI) m/z 477 (M−H)$^−$, 479 (M+H)$^+$

Example 45

2-(4-tert-Butyl-3,5-difluorophenyl)-N-((1R)-1-{3-fluoro-4-[(methylsulfonyl)amino]phenyl}ethyl)-2-methylcyclopropanecarboxamide

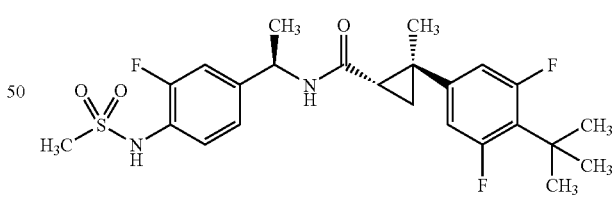

To a DMF (10 ml) solution of the amine compound of Example 8 (140 mg, 0.5 mmol), the compound of Example 43C (142 mg, 0.5 mmol), HBTU (261 mg, 0.7 mmol) and triethylamine (0.2 ml, 1.6 mmol) were added and the mixture was stirred for 2 hours at room temperature. The same procedure as described in Example 40 was performed to give the title compound (76 mg, 30%). The fraction time for the desired product was 5.3 min.

$^1$H NMR (300 MHz, DMSO-d$_6$) δ 1.16-1.54 (17H, m), 1.90-2.05 (1H, m), 3.00 (3H, s), 4.87-5.04 (1H, m), 6.93 (2H, d, J=12.5 Hz), 7.07-7.41 (3H, m), 8.62 (1H, d, J=6.6 Hz), 9.60

(1H, brs). MS (ESI) m/z 481 (M−H)⁻, 483 (M+H)⁺ [α]_D=+85.1 (c=0.5, methanol, cell temperature=21.3° C.)

Example 46

N-((1R)-1-{3-Methyl-4-[(methylsulfonyl)amino]phenyl}ethyl)-2-[2-pyrrolidin-1-yl-6-(trifluoromethyl)pyridin-3-yl]cyclopropanecarboxamide

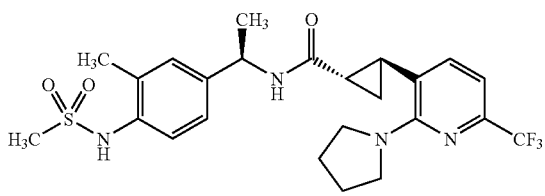

46A) 2-Pyrrolidin-1-yl-6-(trifluoromethyl)nicotinic acid

A mixture of 2-chloro-6-(trifluoromethyl)nicotinic acid (purchased from APOLLO, 5.0 g, 22.2 mmol) and pyrrolidine (40 ml, 562 mmol) was stirred for 24 hours at room temperature according to *J. Med. Chem.*, 2005, 48, 71-90). Then the reaction mixture was evaporated in vacuo to give the title compound (5.5 g, 95%).

MS (ESI) m/z 259 (M−H)⁻, 260 (M+H)⁺

46B) 2-Pyrrolidin-1-yl-6-(trifluoromethyl)pyridin-3-yl]methanol

To a THF (50 ml) of lithium aluminum tetrahydride (1.6 g, 42.3 mmol), a THF (40 ml) solution of the compound of Example 46A (5.5 g, 21.1 mmol) was added at 0° C. and the mixture was stirred for 5 minutes 0° C. followed by additional stirring for 24 hours at 65° C. The reaction mixture was cooled to 0° C. and partitioned with 10% potassium sodium tartrate tetrahydrate aqueous solution and EtOAc, and the mixture was stirred for 2 hours at room temperature. To the mixture was added water and the organic layer was extracted, washed with 2M sodium hydroxide aqueous solution and brine, and evaporated. The residue was purified by silica gel column chromatography, eluting with hexane/EtOAc (7:1), to give the title compound (2.6 g, 51%). MS (ESI) m/z 247 (M+H)⁺

46C) 2-Pyrrolidin-1-yl-6-(trifluoromethyl)nicotinaldehyde

To a DCM (35 ml) solution of ethanedioyl dichloride (2.7 ml, 21.1 mmol) was added dimethyl sulfoxide (2.5 ml, 31.8 mmol) at −78° C. and the mixture was stirred for 15 minutes at temperature. Then to the mixture was slowly added a DCM solution of the compound of Example 46B (2.6 g, 10.6 mmol) at −78° C. and the mixture was stirred for 30 minutes followed by addition of triethylamine (10 ml, 106 mmol) and stirring for 30 minutes −78° C. The reaction was allowed to warm to room temperature and stirred for 1 hour. Then the reaction mixture was quenched with water and extracted with EtOAc, dried over magnesium sulfate, and evaporated. The crude residue was purified by silica gel column chromatography, eluting with hexane/EtOAc (10:1), to give the title compound (1.3 g, 51%).

MS (ESI) m/z 245 (M+H)⁺

46D) 2-[2-Pyrrolidin-1-yl-6-(trifluoromethyl)pyridin-3-yl]cyclopropanecarboxylic acid To a THF (25 ml) suspension of methyltriphenylphosphonium bromide (3.8 g, 10.6 mmol) was added 1.60 M n-butyllithium in hexane solution (6.7 ml, 10.6 mmol) at 0° C. and the reaction was stirred for 30 minutes. Then the THF (5 ml) solution of the compound of Example 46C (1.3 g, 5.3 mmol) was added to at room temperature and stirred for 1 hour at room temperature. The reaction was quenched with saturated ammonium chloride aqueous solution, and the whole was extracted with EtOAc, dried over magnesium sulfate, and evaporated. The crude residue was purified by silica gel column chromatography, eluting with hexane/EtOAc (10:1), to give 2-pyrrolidin-1-yl-6-(trifluoromethyl)-3-vinylpyridine (1.03 g, 80%, trans). To a toluene (15 ml) solution of 2-pyrrolidin-1-yl-6-(trifluoromethyl)-3-vinylpyridine (1.03 g, 4.3 mmol), Co(TPP) (142 mg, 0.2 mmol) and 1-methyl-1H-imidazole (1.22 ml, 14.9 mmol), ethyldiazoacetate (1.0 ml, 8.5 mmol) was added and the mixture was stirred for 5 minutes at room temperature followed by additional stirring for 2 hour at 80° C. Then, evaporation and purification by silica gel column chromatography, eluting with hexane/EtOAc (20:1), gave ethyl 2-[2-pyrrolidin-1-yl-6-(trifluoromethyl)pyridin-3-yl]cyclopropanecarboxylate (1.3 g, 93%). To a THF (10 ml) solution of this compound (1.3 g, 4.0 mmol), 2M sodium hydroxide aqueous solution (15 ml) and MeOH (15 ml) were added and the mixture was stirred for 2 hours at room temperature. After the reaction was completed, the aqueous layer was extracted and then acidified with 2M HCl aqueous solution. The whole was extracted with EtOAc followed by evaporation to give the title compound (1.1 g, 92%).

MS (ESI) m/z 299 (M−H)⁻, 301 (M+H)⁺

46E) N-((1R)-1-{3-Methyl-4-[(methylsulfonyl)amino]phenyl}ethyl)-2-[2-pyrrolidin-1-yl-6-(trifluoromethyl)pyridin-3-yl]cyclopropanecarboxamide To a stirred solution of the compound of Example 46D (200 mg, 0.7 mmol) in DCM (10 ml) was added oxalyl chloride (0.2 ml, 1.3 mmol) and DMAP (1 drop) at 0° C. After being stirred for 45 minutes at room temperature, the mixture was evaporated in vacuo and the residue was dissolved in DCM (5 ml). The above solution was added to a solution of the compound of Example 2D (195 mg, 0.7 mmol) in pyridine (5 ml) at room temperature. After being stirred for 2 hours at room temperature, the mixture was evaporated in vacuo to give the crude product, which was purified by HPLC (MS C 30×50 mm, acetonitrile/0.05% aqueous formic acid 04 to 96) to give the title compound (81 mg, 24%). The fraction time for the desired product was 4.4 min.

¹H-NMR (300 MHz, DMSO-d₆) δ 1.23-1.42 (5H, m), 1.77-1.96 (5H, m), 2.29 (3H, s), 2.35-2.47 (1H, m), 2.96 (3H, s), 3.51-3.66 (4H, m), 4.88-5.03 (1H, m), 7.00 (1H, d, J=8.1 Hz), 7.10-7.30 (3H, m), 7.48 (1H, J=7.3 Hz), 8.62 (1H, J=8.1 Hz), 9.04 (1H, brs) as while solids. MS (ESI) m/z 509 (M−H)⁻, 511 (M+H)⁺

Example 47

N-((1R)-1-{3-(Hydroxymethyl)-4-[(methylsulfonyl)amino]phenyl}ethyl)-2-[2-pyrrolidin-1-yl-6-(trifluoromethyl)pyridin-3-yl]cyclopropanecarboxamide

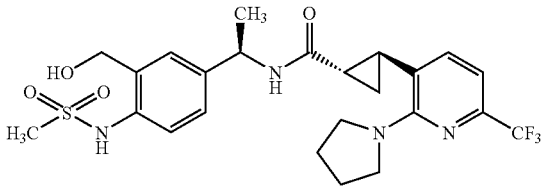

To a DMF (15 ml) solution of the compound of Example 17B (215 mg, 0.7 mmol), the compound of Example 46D (200 mg, 0.7 mmol), HBTU (330 mg, 0.9 mmol) and triethylamine (0.3 ml, 2.0 mmol) were added and the mixture was stirred for 1.5 hours at room temperature. The reaction was quenched with water and the whole was extracted with EtOAc and evaporated in vacuo to give ethyl 2-[(methylsulfonyl)amino]-5-{(1R)-1-[({2-[2-pyrrolidin-1-yl-6-(trifluoromethyl)pyridin-3-yl]cyclopropyl}carbonyl)amino]ethyl}benzoate. (MS (ESI) m/z 567 (M−H)⁻, 569 (M+H)⁺). This product was used in a further reaction without purification. To a THF (10 ml) of lithium aluminum hydride (300 mg, 7.9 mmol), a THF (5 ml) solution of the above compound was added and the reaction stirred for 1 hour at room temperature. The reaction mixture was cooled to 0° C. and quenched with 10% potassium sodium tartrate tetrahydrate aqueous solution and EtOAc. The mixture was stirred for 2 hours at room temperature and quenched with water. The organic layer was extracted and washed with 2M sodium hydroxide aqueous solution and brine. The organic layer was evaporated to give the residue which was purified by HPLC (MS C 30×50 mm, acetonitrile/0.05% aqueous formic acid aqueous solution eluting with 32 to 68) to give the title compound (37 mg, 10%). The fraction time for the desired product was 3.7 min.

¹H-NMR (270 MHz, DMSO-d₆) δ 1.22-1.44 (5H, m), 1.75-1.97 (5H, m), 2.34-2.47 (1H, m), 2.97(3H, s), 3.52-3.63 (4H, m), 4.61 (2H, s), 4.93-5.06 (1H, m), 7.00 (1H, d, J=7.9 Hz), 7.16-7.32 (2H, m), 7.37-7.54 (2H, m), 8.66 (1H, d, J=7.9 Hz). H for OH, NH could not be observed. MS (ESI) m/z 525 (M−H)⁻, 527 (M−H)⁺

Example 48

N-((1R)-1-{3-(Hydroxymethyl)-4-[(methylsulfonyl)amino]phenyl}ethyl)-2-[4-(2,2,2-trifluoro-1,1-dimethylethyl)phenyl]cyclopropanecarboxamide To a DMF (15 ml) solution of the compound of Example 17B (237 mg, 0.7 mmol), the compound of Example 6D (200 mg, 0.7 mmol), HBTU (365 mg, 1.0 mmol) and trimethylamine (0.3 ml, 2.2 mmol) were added and the mixture was stirred for 1.5 hours at room temperature. The reaction was quenched with water and the whole was extracted with EtOAc and evaporated in vacuo to give ethyl 2-[(methylsulfonyl)amino]-5-{(1R)-1-[({2-[4-(2,2,2-trifluoro-1,1-dimethylethyl)phenyl]cyclopropyl}carbonyl)amino]ethyl}benzoate (MS (ESI) m/z 539 (M−H)⁻, 541 (M +H)⁺). The same procedure as described in Example 47 was performed, using HPLC conditions of acetonitrile/0.05% aqueous formic acid 4 to 96, to give the title compound (230 mg, 62%). The fraction time for the desired product was 4.0 min.

¹H-NMR (270 MHz, DMSO-d₆) δ 1.16-1.40 (5H, m), 1.53 (6H, s), 1.88-2.01 (2H, m), 2.18-2.30 (1H, m), 2.99 (3H, s), 4.62 (2H, s), 4.86-5.02 (1H, m), 7.09-7.29 (4H, m), 7.38-7.48 (3H, m), 8.59 (1H, d, J=7.9 Hz). A signal due to NH wasn't observed. MS (ESI) m/z 497 (M−H)⁻, 499 (M+H)⁺

Example 49

2-(6-tert-Butyl-2-piperidin-1-ylpyridin-3-yl)-N-((1R)-1-{3-methyl-4-[(methylsulfonyl)amino]phenyl}ethyl)cyclopropanecarboxamide

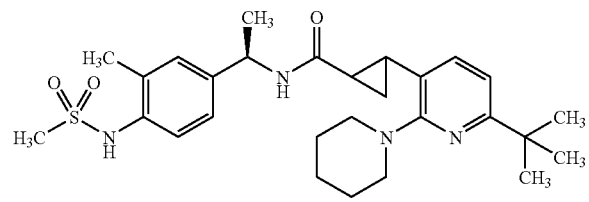

49A) 6-tert-Butyl-2-piperidin-1-ylnicotinonitrile
A mixture of 6-tert-butyl-2-chloronicotinonitrile (*Tetrahedron* 1965, 21, 2453-2467, 1.5 g, 7.7 mmol) and piperidine (15 ml, 176 mmol) was stirred for 20 hours at room temperature. Then the reaction mixture was evaporated to remove piperidine in vacuo to give the title compound (1.8 g, 98%).
MS (ESI) m/z 244 (M+H)⁺

49B) 6-tert-Butyl-2-piperidin-1-ylnicotinaldehyde
To a diethyl ether (17 ml) solution of the compound of Example 49A (1.8 g, 7.6 mmol) was added 0.94 M diisobutylaluminum hydride in toluene solution (12.1 ml, 11.4 mmol) at −78° C. and the mixture was allowed to warm to room temperature for 2 hours with stirring. Then the reaction was quenched with 10% potassium sodium tartrate tetrahydrate aqueous solution and the whole was extracted with EtOAc, and washed with 2M sodium hydroxide aqueous solution and brine. The organic layer was evaporated to give the residue which was purified by silica gel column chromatography, eluting with hexane/EtOAc (5:1), to give the title compound (1.8 g, 97%).
MS (ESI) m/z 247 (M+H)⁺

49C) 6-tert-Butyl-2-piperidin-1-yl-3-vinylpyridine
To a THF (24 ml) suspension of methyltriphenylphosphonium bromide (5.3 g, 14.8 mmol) was added 1.60 M n-butyllithium (9.3 ml, 14.8 mmol) in hexane solution at 0° C. and the reaction was stirred for 30 minutes. Then to this mixture was added a THF (5 ml) solution of the compound of Example 49B (1.8 g, 7.5 mmol) at 0° C. and the mixture was stirred for 2 hours at room temperature. The reaction was quenched withsaturated ammonium chloride aqueous solution, and the whole was extracted with EtOAc, dried overmagnesium sulfate, and the solvent evaporated. The crude residue was purified by silica gel column chromatography, eluting with hexane/EtOAc (10:1), to give the title compound (1.70 g, 93%).
¹H-NMR (270 MHz, CDCl₃) δ 1.31 (9H, s), 1.59-1.75 (6H, m), 3.13-3.24 (4H, m), 5.16-5.24 (1H, m), 5.56-5.67 (1H, m), 6.76 (1H, dd, J=17.8, 10.6 Hz), 6.85 (1H, d, J=7.9 Hz), 7.57 (1H, d, J=7.3 Hz)

49D) 2-(6-tert-Butyl-2-piperidin-1-ylpyridin-3-yl)cyclopropanecarboxylic acid
To a toluene (15 ml) solution of the compound of Example 49C (1.7 g, 6.9 mmol), Co(TPP) (140 mg, 0.2 mmol) and 1-methyl-1H-imidazole (1.7 ml, 21 mmol), ethyldiazoacetate (1.1 ml, 9.7 mmol) was added and the mixture was stirred for 5 minutes at room temperature followed by additional stirring for 2 hours at 80° C. Then, evaporation and purification through silica gel column chromatography, eluting with hexane/EtOAc (20:1), gave ethyl 2-(6-tert-butyl-2-piperidin-1-ylpyridin-3-yl)cyclopropanecarboxylate (2.0 g, 89%, trans). To a THF (6 ml) solution of this compound (1.98 g, 6.0 mmol), 2M sodium hydroxide aqueous solution (6 ml) and MeOH (6 ml) were added and the mixture was stirred for 2 hours at 80° C. After the reaction was completed, ethylacetate was added and the aqueous layer was separated and then acidified with 2M HCl aqueous solution. The whole was extracted with EtOAc followed by evaporation to give the title compound (1.4 g, 76%).

MS (ESI) m/z 301 (M−H)⁻, 303 (M+H)⁺

49E) 2-(6-tert-Butyl-2-piperidin-1-ylpyridin-3-yl)-N-((1R)-1-{3-methyl-4-[(methylsulfonyl)amino]phenyl}ethyl)cyclopropanecarboxamide To a stirred solution of the compound of Example 49D (127 mg, 0.4 mmol) in DCM (7 ml) was added oxalyl chloride (107 mg, 0.84 mmol) and DMAP (1 drop) at 0° C. After being stirred for 30 minutes at room temperature, the mixture was evaporated in vacuo and the residue was dissolved in DCM (2 ml). The above solution was added to a solution of the compound of Example 2D (122 mg, 0.5 mmol) in pyridine (7 ml) at room temperature. After being stirred for 2.5 hours at room temperature, the mixture was evaporated in vacuo, the crude product was purified by silica gel column chromatography, eluting with hexane/EtOAc (2:1), and the obtained product was recrystallized from hexane and ethylacetate cosolvent to give the title compound (95 mg, 19%) as white solids.

¹H-NMR (300 MHz, DMSO-d₆) δ 1.18-1.50 (18H, m), 1.52-1.82 (4H, m), 2.28 (3H, m), 2.89-3.25 (7H, m), 4.85-4.99 (1H, m), 6.82-6.93 (1H, m), 7.05-7.25 (4H, m), 8.53 (1H, d, J=8.1 Hz), 9.02 (1H, brs). MS (ESI) m/z 511 (M−H)⁻, 513 (M+H)⁺

Example 50

2-(6-tert-Butyl-2-piperidin-1-ylpyridin-3-yl)-N-((1R)-1-{3-fluoro-4-[(methylsulfonyl)amino]phenyl}ethyl)cyclopropanecarboxamide

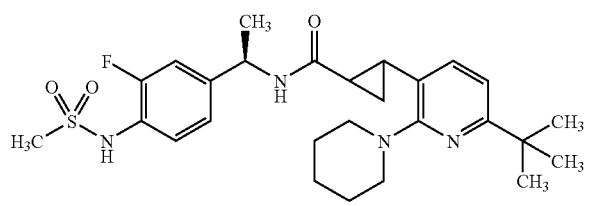

To a stirred solution of the compound of Example 49D (127 mg, 0.4 mmol) in DCM (7 ml) was added oxalyl chloride (100 mg, 0.8 mmol) and DMAP (1 drop) at 0° C. After being stirred for 30 minutes at room temperature, the mixture was evaporated in vacuo and the residue was dissolved in DCM (2 ml). The above solution was added to a solution of the amine compound of Example 8 (124 mg, 0.5 mmol) in pyridine (8 ml) at room temperature. After being stirred for 2.5 hours at room temperature, the mixture was evaporated in vacuo, purified by silica gel column chromatography, eluting with dichloromrtane/EtOAc (10:1), and the product was recrystallized to give the title compound (60 mg, 28%) as white solids.

¹H-NMR (300 MHz, DMSO-d₆) δ 1.17-1.83 (21 H, m), 2.16-2.32 (1H, m), 2.90-3.21 (7H, m), 4.87-5.02 (1H, m), 6.82-6.93 (1H, m), 7.07-7.39 (4H, m), 8.57 (1H, d, J=8.1 Hz), 9.53 (1H, brs). MS (ESI) m/z 515 (M−H)⁻, 517 (M+H)⁺

Example 51

2-(6-tert-Butyl-2-pyrrolidin-1-ylpyridin-3-yl)-N-((1R)-1-{3-methyl-4-[(methylsulfonyl)amino]phenyl}ethyl)cyclopropanecarboxamide

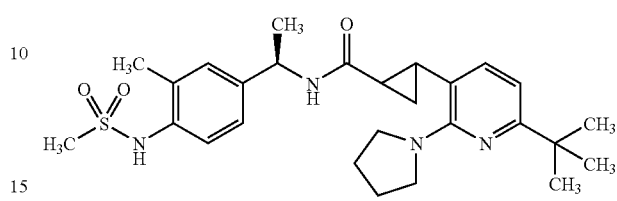

51A) 6-tert-Butyl-2-chloro-3-vinylpyridine

To a diethyl ether (17 ml) solution of 6-tert-butyl-2-chloronicotinonitrile (*Tetrahedron* 1965, 21, 2453-2467, 1.0 g, 5.4 mmol) was added 0.94 M diisobutylaluminum hydride in toluene solution (8.6 ml, 8.0 mmol) at −78° C. and the reaction was allowed to warm to room temperature over 2 hours with stirring. Then the reaction was quenched with 10% potassium sodium tartrate tetrahydrate aqueous solution and the whole was extracted with EtOAc, and washed with 2M sodium hydroxide aqueous solution and brine. The organic layer was evaporated and purified by silica gel column chromatography, eluting with hexane/EtOAc (5:1), to give 6-tert-butyl-2-chloronicotinaldehyde (1.0 g, 95%). To a THF (24 ml) suspension of methyltriphenylphosphonium bromide (5.3 g, 14.8 mmol) was added 1.60 M n-butyllithium (9.3 ml, 14.8 mmol) in hexane solution at 0° C. and the reaction was stirred for 30 minutes. Then to this mixture was added a THF (5 ml) solution of the 6-tert-butyl-2-chloronicotinaldehyde (1.0 g, 5.2 mmol) at 0° C., and the reaction was stirred for 2 hours at room temperature. The reaction was quenched with saturated ammonium chloride aqueous solution, and the whole was extracted with EtOAc, and dried over magnesium sulfate. The organic layer was evaporated and purified by silica gel column chromatography, eluting with hexane/EtOAc (10:1), to give the title compound (735 mg, 71%).

¹H-NMR (270 MHz, DMSO-d₆) δ 1.35 (9H, s), 5.43 (1H, d, J=11.2 Hz), 5.72 (1H, d, J=17.1 Hz), 7.01 (1H, dd, J=17.5, 10.9 Hz), 7.22-7.28 (1H, m), 7.78 (1H, d, J=7.9 Hz).

51B) Ethyl 2-(6-tert-butyl-2-chloropyridin-3-yl)cyclopropanecarboxylate

To a toluene (4 ml) solution of the compound of Example 51A (365 mg, 1.9 mmol), Co(TPP) (38 mg, 0.06 mmol) and 1-methyl-1H-imidazole (461 mg, 5.6 mmol), ethyl diazoacetate (300 mg, 2.6 mmol) was added and the mixture was stirred for 5 minutes at room temperature followed by additional stirring for 2 hours at 80° C. Then, evaporation and purification by silica gel column chromatography, eluting with hexane/EtOAc (20:1), gave the title compound (440 mg, 84%, trans).

MS (ESI) m/z 282 (M+H)⁺

51C) 2-(6-tert-Butyl-2-chloropyridin-3-yl)cyclopropanecarboxylic acid

To a THF (3 ml) solution of the compound of Example 51B (220 mg, 0.8 mmol), 2M sodium hydroxide aqueous solution (3 ml) and MeOH (3 ml) were added and the mixture was stirred for 1.5 hours at 80° C. After the reaction was completed, the aqueous layer was partitioned with EtOAc and the aqueous layer was separated and then acidified with 2M HCl aqueous solution. The whole was extracted with EtOAc followed by evaporation to give the title compound (135 mg, 68%).

MS (ESI) m/z 252 (M−H)⁻, 253 (M+H)⁺

51D) 2-(6-tert-Butyl-2-chloropyridin-3-yl)-N-((1R)-1-{3-methyl-4-[(methylsulfonyl)amino]phenyl}ethyl)cyclopropanecarboxamide To a stirred solution of the compound of Example 51C (30 mg, 0.12 mmol) in DCM (1.5 ml) was added oxalyl chloride (0.03 ml, 0.24 mmol) and DMAP (1 drop) at 0° C. After being stirred for 30 minutes at room temperature, the mixture was evaporated in vacuo and the residue was dissolved in DCM (1 ml). The above solution was added to a solution of the compound of Example 2D (35 mg, 0.13 mmol) in pyridine (2 ml) at room temperature. After being stirred for 2.5 hours at room temperature, the mixture was evaporated in vacuo, purified by silica gel column chromatography, eluting with DCM/EtOAc (4:1), and the product was recrystallized from hexane and EtOAc to give the title compound (45 mg, 80%).

MS (ESI) m/z 462 (M−H)⁻, 464 (M+H)⁺

51E) 2-(6-tert-Butyl-2-pyrrolidin-1-ylpyridin-3-yl)-N-((1R)-1-{3-methyl-4-[(methylsulfonyl)amino]phenyl}ethyl)cyclopropanecarboxamide To a DMSO (1.5 ml) of the compound of Example 51D (45 mg, 0.01 mmol) was added pyrrolidine (0.5 ml, 7.0 mmol) and tetrabutylammonium fluoride (0.5 ml, 1.9 mmol) and the mixture was subjected to irradiation by microwave for 5 hours at 150° C. The whole was extracted with EtOAc, evaporated, and purified by silica gel column chromatography, eluting with DCM/EtOAc (10:1), and the product was recrystallized from hexane and EtOAc to give the title compound (13 mg, 27%).

$^1$H-NMR (300 MHz, CDCl$_3$) δ 1.12-1.78 (17H, m), 1.84-1.97 (2H, m), 2.28-2.38 (3H, m), 2.52-2.65 (1H, m), 2.99-3.03 (3H, m), 3.40-3.72 (4H, m), 5.05-5.22 (1H, m), 5.92 (1H, dd, J=7.3, 2.9 Hz), 6.24 (1H, brs), 6.56 (1H, dd, J=7.3, 5.9 Hz), 7.09-7.24 (3H, m), 7.37-7.47(1H, m). MS (ESI) m/z 497 (M−H)⁻, 499 (M+H)⁺

Example 52

2-[6-tert-Butylpyridin-3-yl]-N-((1R)-1-{3-fluoro-4-[(methylsulfonyl)amino]phenyl}ethyl)cyclopropanecarboxamide

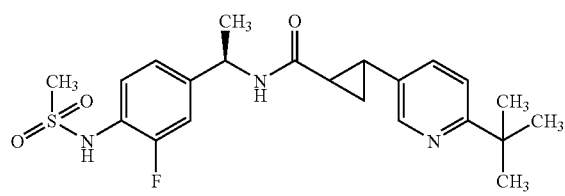

52A) 5-Bromo-2-tert-butylpyridine

To a THF (40 ml) suspension of copper cyanide (1.79 g, 20 mmol) which was dried under reduced pressure for 4 hours was added 1.0 M THF solution of tert-butylmagnesium chloride (40 ml, 40 mmol) dropwise at −78° C. over 30 minutes and the mixture was stirred for 1 hour at −78° C. 5-Bromo-2-iodopyridine (2.83 g, 10 mmol) was added at −78° C. and the mixture was stirred for 1 hour at −78° C., followed by additional stirring for 16 hours at room temperature. Then, the reaction was quenched with 25% aqueous ammonia solution (40 ml) and the precipitates were removed by filtration and washed with EtOAc. The filtrate and washings were combined and concentrated in vacuo. Then, filtration, evaporation, and purification by silica gel column chromatography, eluting with hexane/EtOAc (20:1), gave the title compound (1.07 g, 50% yield) as a colorless oil.

$^1$H NMR (300 MHz, CDCl$_3$) δ 1.35 (9H, s), 7.24 (1H, d, J=8.1 Hz), 7.72 (1H, dd, J=2.2, 8.1 Hz), 8.61-8.62 (1H, m)

52B) 2-tert-Butyl-5-ethenylpyridine

To a DMF (20 ml) solution of the compound of Example 52A (915 mg, 4.27 mmol), vinyltributylstannane (3.14 g, 9.90 mmol), lithium chloride (2.1 g, 49.5 mmol) and bis(triphenylphosphine)palladium chloride (173 mg, 0.25 mmol) were added in the same procedure as described in Example 2G. The crude residue was applied to a silica gel chromatography column and eluted with hexane/EtOAc (20:1) to afford the title compound (766 mg, quant.) as a pale yellow oil.

$^1$H NMR (270 MHz, CDCl$_3$) δ 1.36 (9H, s), 5.32 (1H, d, J=11.2 Hz), 5.77 (1H, d, J=17.8 Hz), 6.69 (1H, dd, J=10.6, 17.8 Hz), 7.30 (1H, d, J=8.6 Hz), 7.67 (1H, dd, J=2.6, 8.6 Hz), 8.56 (1H, d, J=2.6 Hz) MS (ESI): m/z 162 (M+H)+.

52C) Ethyl 2-[6-tert-butylpyridin-3-yl]cyclopropanecarboxylate

To a toluene (7 ml) solution of the title compound of Example 52B (766 mg, 4.27 mmol), Co(TPP) (85 mg, 0.126 mmol) and 1-methyl-1H-imidazole (1.03 g, 12.6 mmol), ethyl diazoacetate (671 mg, 5.88 mmol) was added in the same procedure as described in Example 2H. The crude product was diluted with 2M HCl aqueous solution and washed with diethyl ether. The separated aqueous layer was basified by saturated sodium bicarbonate aqueous solution and the whole was extracted with EtOAc, which was dried over sodium sulfate. Then, filtration and evaporation of the solvent gave the crude product of the title compound (crude 1.11 g) as a black oil.

$^1$H NMR (270 MHz, CDCl$_3$) δ 1.28 (3H, t, J=7.3 Hz), 1.34 (9H, s), 1.58-1.65 (1H, m), 1.86-1.92 (1H, m), 2.45-2.53(1H, m), 4.18 (3H, q, J=7.3 Hz), 7.06 (1H, s), 7.44 (1H, s), 8.39 (1H, s) MS (ESI): m/z 248 (M+H)+.

52D) 2-[6-tert-Butylpyridin-3-yl]cyclopropanecarboxylic acid

A MeOH (10 ml) solution of the crude compound of Example 52C (crude 1.11 g) and 2M sodium hydroxide aqueous solution (4 ml) was stirred at 40° C. for 15 minutes. After the reaction was completed, the basic mixture was washed with diethyl ether, and the separated aqueous layer was neutralized with 2M HCl aqueous solution to pH 5~6 and the whole was extracted with EtOAc followed by evaporation to afford the title compound (785 mg, 84% yield in 2 steps, trans) as white solids.

$^1$H NMR (300 MHz, CDCl$_3$) δ 0.86-1.45 (1H, m), 1.35 (9H, s), 1.65-1.71 (1H, m), 1.88-1.94 (1H, m), 2.54-2.61 (1H, m), 7.24-7.35 (2H, m), 8.44 (1H, s) MS (ESI) m/z 220 (M+H)+.

52E) 2-[6-tert-Butylpyridin-3-yl]-N-((1R)-1-{3-fluoro-4-[(methylsulfonyl)amino]phenyl}ethyl)cyclopropanecarboxamide The procedure desribed in Example 10E was followed using a DMF (1 ml) solution of the compound of Example 52D (117 mg, 0.533 mmol), triethylamine (0.22 ml), EDC (153 mg, 0.80 mmol), HOBt (90 mg, 0.59 mmol) and N-{4-[(1R)-1-aminoethyl]-2-fluorophenyl}methanesulfonamide HCl (143 mg, 0.533 mmol). The crude residue was applied to a silica gel chromatography column and eluted with a volume mixture of hexane and EtOAc (1:1) to afford the title compound (133 mg, 57% yield, white solids) as a mixture of diastereomeric products (1:1).

$^1$H NMR (300 MHz, CDCl$_3$) δ 1.12-1.70 (15H, m), 2.43-2.52 (1H, m), 3.02-3.03 (3H, m), 5.09-5.13 (1H, m), 5.92-5.94 (1H, m), 6.51 (1H, brs), 7.09-7.14 (2H, m), 7.22-7.33 (2H, m), 7.49-7.56 (1H, m), 8.35 (1H, d, J=11.0 Hz) MS (ESI): m/z 434 (M+H)+.

Example 53

2-[6-tert-Butylpyridin-3-yl]-N-((1R)-1-{3-methyl-4-[(methylsulfonyl)amino]phenyl}ethyl)cyclopropanecarboxamide

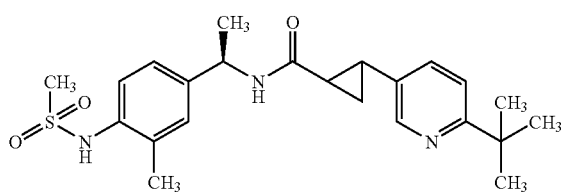

To a DMF (1 ml) solution of the compound of Example 52D (252 mg, 1.15 mmol), triethylamine (0.48 ml), EDC (331 mg, 1.73 mmol), HOBt (194 mg, 1.27 mmol) and the amine compound of Example 2D (304 mg, 1.15 mmol) were added in the same procedure as Example 1. The crude residue was applied to a silica gel chromatography column and eluted with a volume mixture of hexane and EtOAc (1:1) to afford the title compound (302 mg, 61% yield, white solids) as a mixture of diastereomeric products (1:1).

$^1$H NMR (270 MHz, CDCl$_3$) δ 0.86-1.65 (15H, m), 2.31-2.32 (3H, m), 2.45-2.51 (1H, m), 3.01-3.02 (3H, m), 5.05-5.15 (1H, m), 5.90 (1H, d, J=7.3 Hz), 6.20 (1H, s), 7.18-7.25 (4H, m), 7.39-7.43 (1H, m), 8.35-8.37 (1H, m) MS (ESI): m/z 430 (M+H)+.

Example 54

(1S,2S)-2-Methyl-N-((1R)-1-{6-methyl-5-[(methylsulfonyl)amino]pyridin-2-yl}ethyl)-2-(4-trifluoromethyl)phenyl]cyclopropanecarboxamide

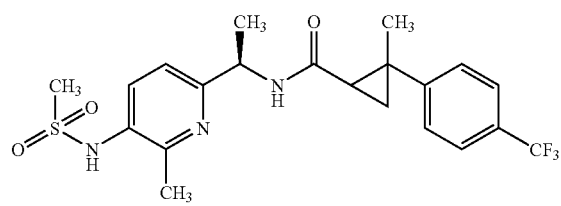

To a DMF (2 ml) solution of the compound of Example 14B (81 mg, 0.33 mmol), triethylamine (0.14 ml), EDC (95 mg, 0.50 mmol), HOBt (56 mg, 0.36 mmol) and the compound of Example 9E (100 mg, 0.33 mmol) were added in the same procedure as described in Example 1. The crude residue was applied to a silica gel chromatography column and eluted with a volume mixture of hexane and EtOAc (1:1) to afford the title compound (44 mg, 29% yield, white solids) as a mixture of diastereomeric products (1:1).

$^1$H NMR (270 MHz, CDCl$_3$) δ 0.86-1.47 (1H, m), 1.46-1.48 (3H, m), 1.50-1.60 (4H, m), 1.78-1.85 (1H, m), 2.56-2.58 (3H, m), 3.04-3.05 (3H, m), 5.12-5.21 (1H, m), 6.93-7.02 (1H, m), 7.14 (1H, d, J=8.1 Hz), 7.25-7.49 (3H, m), 7.55-7.63 (2H, m), 7.72-7.75 (1H, m) MS (ESI): m/z 456 (M+H)+, 454 (M–H)–.

Example 55

2-[4-tert-Butylphenyl]-N-((1R)-1-{6-methyl-5-[(methylsulfonyl)amino]pyridin-2-yl}ethyl)cyclopropanecarboxamide

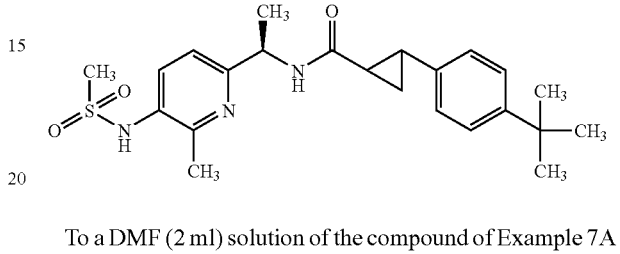

To a DMF (2 ml) solution of the compound of Example 7A (72 mg, 0.33 mmol), triethylamine (0.14 ml), EDC (95 mg, 0.50 mmol), HOBt (56 mg, 0.36 mmol) and the amine compound of Example 9E (100 mg, 0.33 mmol) were added in the same procedure as Example 1. The crude residue was applied to a silica gel chromatography column and eluted with a volume mixture of hexane and EtOAc (1:1) to afford the title compound (single isomer; 44 mg, 31% yield) as white solids.

$^1$H NMR (300 MHz, CDCl$_3$) δ 1.19-1.30 (1H, m), 1.31 (9H, s), 1.43 (3H, d, J=6.6 Hz), 1.52-1.71 (2H, m), 2.46-2.52 (1H, m), 2.56 (3H, s), 3.04 (3H, s), 5.08-5.17 (1H, m), 6.35 (1H, s), 6.96 (1H, d, J=6.6 Hz), 7.06 (2H, d. J=8.1 Hz), 7.12 (1H, d, J=8.3 Hz), 7.32 (2H, d, J=8.1 Hz), 7.72 (1H, d, J=8.3 Hz) MS (ESI): m/z 430 (M+H)+

Example 56

N-((1R)-1-{6-Methyl-5-[(methylsulfonyl)amino]pyridin-2-yl}ethyl)-2-[4-(trifluoromethyl)phenyl]cyclopropanecarboxamide

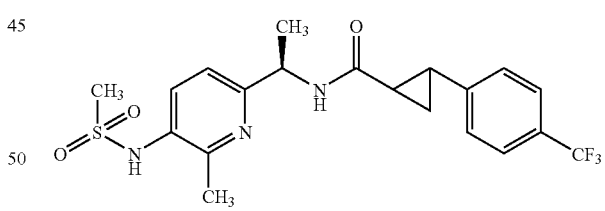

To a DMF (2 ml) solution of 2-[4-(trifluoromethyl)phenyl]cyclopropanecarboxylic acid (racemic) (76 mg, 0.33 mmol) [Journal of Organic Chemistry (1997), 62(26), 9114-9122.], EDC (95 mg, 0.50 mmol), HOBt (56 mg, 0.36 mmol), triethylamine (0.14 ml) and the amine compound of Example 9E (100 mg, 0.33 mmol) were added in the same procedure as described in Example 1. The crude residue was applied toa silica gel chromatography column and eluted with a volume mixture of hexane and EtOAc (1:1) to afford the title compound (13 mg, 9% yield, single diastereomer product) as white solids $^1$H NMR (300 MHz, CDCl$_3$) δ 1.23-1.79 (6H, m), 2.57 (3H, s), 2.55-2.63 (1H, m), 3.05 (3H, s), 5.10-5.18 (1H, m), 6.25 (1H, brs), 7.03 (1H, d, J=5.9 Hz), 7.13 (1H, d, J=8.1 Hz),

Example 57

2-Methyl-N-((1R)-1-{3-methyl-4-[(methylsulfonyl)amino]phenyl}ethyl)-2-[6-(trifluoromethyl)pyridin-3-yl]cyclopropanecarboxamide

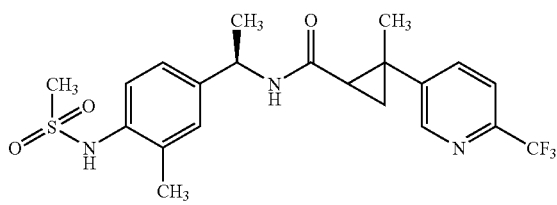

57A) 2-Methyl-2-[6-(trifluoromethyl)pyridin-3-yl]cyclopropanecarboxylic acid The racemic compound of Example 12C was separated by Daicel Chiralpal AD-H (20×250 mm), eluting with 0.1 mM ammonium trifluoroacetate in n-hexane/ethanol (96/4, v/v) (column temperatute 40° C.). The title compound was given as a later fraction(retention time was 20 minutes).

57B) 2-Methyl-N-((1R)-1-{3-methyl-4-[(methylsulfonyl)amino]phenyl}ethyl)-2-[6-(trifluoromethyl)pyridin-3-yl]cyclopropanecarboxamide (single isomer)

To a DMF (4 ml) solution of the compound of Example 57A (112 mg, 0.46 mmol), HBTU (208 mg, 0.55 mmol), triethylamine (0.2 ml) and the amine compound of Example 2D (121 mg, 0.46 mmol) were added in the same procedure as Example 14D. The crude residue was applied to a silica gel chromatography column and eluted with a volume mixture of hexane and EtOAc (1:1) to afford the title compound (single isomer; 166 mg, 78% yield) as white solids.

$^1$H NMR (300 MHz, CDCl$_3$) δ 1.40-1.45 (1H, m), 1.50 (3H, d, J=7.3 Hz), 1.57-1.76 (5H, m), 2.32 (3H, s), 3.02 (3H, s), 5.09-5.17 (1H, m), 5.98 (1H, d, J=7.3 Hz), 6.19 (1H, s), 715-7.25(1H, m), 7.42 (1H, d, J=8.8 Hz), 7.62 (2H, d, J=8.1 Hz), 7.69-7.74 (1H, m), 8.62-8.65 (1H, m) MS (ESI): m/z 456 (M+H)+.

Example 58

2-[4-tert-Butyl-3-Fluorophenyl]-N-((1R)-1-{3-fluoro-4-[(methylsulfonyl)amino]phenyl}ethyl)cyclopropanecarboxamide

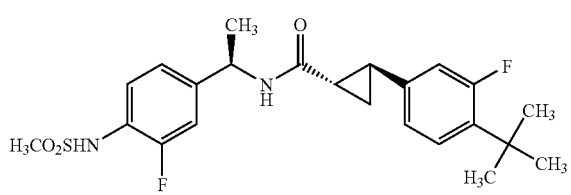

58A) 2-[4-tert-Butyl-3-fluorophenyl]cyclopropanecarboxylic acid

Racemic 2-[(4-tert-Butyl-3-fluorophenyl)cyclopropanecarboxylic acid was separated with Daicel CHIRALPAK AD-H [trademark?] (column size; 2×25 cm, temperature; 40° C., solvent; Hexane/EtOH=1/1). The later fraction (retention time was 7.8 minutes) was used for the next step.

58B) 2-[4-tert-Butyl-3-Fluorophenyl]-N-((1R)-1-{3-fluoro-4-[(methylsulfonyl)amino]phenyl}ethyl)cyclopropanecarboxamide To a THF (1.0 ml) solution of the compound of Example 58A (100 mg, 0.42 mmol) was added 2-chloro-1,3-dimethylimidazolinium chloride (CDI) (68 mg, 0.42 mmol) at room temperature and the mixture was stirred for 1 hour at room temperature and then, to this reaction was added triethylamine (1.0 ml) and the compound of Example 8 (113 mg, 0.42 mmol). The same procedure as described in Example 2J was performed to afford the title compound as white solids.

$^1$H NMR (CDCl$_3$, 270 MHz) δ ppm 1.31 (9H, s), 1.06-1.39 (5H, m), 1.84 (1H, br), 2.23 (1H, br), 2.94 (3H, s), 3.38 (1H, br), 4.86 (1H, t, J=5.4 Hz), 6.78-6.93 (2H, m), 7.02-7.37 (4H, m), 8.54 (1H, d, J=5.4 Hz). MS (ESI): m/z 451 (M+H)$^+$.

Example 59

2-[4-tert-Butylphenyl]-2-(hydroxymethyl)-N-((1R)-1-{3-methyl-4-[(methylsulfonyl)amino]phenyl}ethyl)cyclopropanecarboxamide

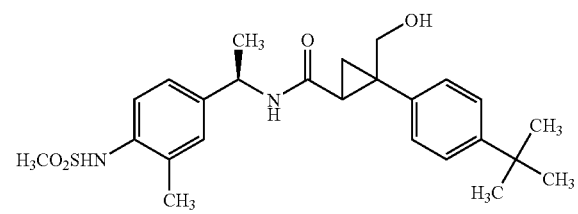

trans diastereo mixture

59A) 2-[4-tert-Butylphenyl]prop-2-en-1-yl acetate

To a stirred suspension of methyltriphenylphosphonium bromide (8.48 g, 23.7 mmol) in THF (75 ml) was added potassium tert-butoxide (2.66 g, 23.7 mmol) at room temperature. The mixture was stirred at 40° C. for 1 hour. After cooling to room temperature, a solution of 2-[4-tert-butylphenyl]-2-oxoethyl acetate (U.S. Pat. No. 3,526,634, 2.78 g, 11.9 mmol) in THF (25 ml) was added to the mixture. The mixture was heated atreflux for 3 hours. The mixture was concentrated, diluted with EtOAc and washed with water and brine.The organic layer was dried over sodium sulfate and concentrated in vacuo. The crude material was purified by silica gel column chromatography, eluting with hexane/EtOAc (9:1), to afford the title compound (2.13 g, 77%) as a yellow oil.

$^1$H NMR (300 MHz, CDCl$_3$) δ 1.33 (9H, s), 2.09 (3H, s), 4.98 (2H, s), 5.33 (1H, s), 5.56 (1H, s), 7.38 (4H, s).

59B) tert-Butyl 2-[(acetyloxy)methyl]-2-[4-tert-butylphenyl]cyclopropanecarboxylate To the toluene (20 ml) solution of the compound of Example 59A (1.0 g, 4.3 mmol), Co(TPP) (86.6 mg, 0.13 mmol) and 1-methyl-1H-imidazole (1.0 ml, 12.9 mmol), tert-butyl diazoacetate (0.83 ml, 6.0 mmol was added and the mixture was stirred for 5 minutes at room temperature followed by additional stirring for 3 hours at 80° C. Then, evaporation and purification by silica gel column chromatography, eluting hexane/EtOAc (20:1), gave the title compound (644 mg, 43%) as a brown oil.

¹H NMR (300 MHz, CDCl₃) δ 1.31 (9H, s), 1.48 (9H, s), 1.35-1.60 (2H, m), 1.98 (3H, s), 2.02-2.07 (1H, m), 4.33 (1H, d, J=11.0 Hz), 4.61 (1H, d, J=11.7 Hz), 7.25 (2H, d, J=8.8 Hz), 7.33 (2H, d, J=8.1 Hz).

59C) (1-[4-tert-Butylphenyl]-2-{[((1R)-1-{3-methyl-4-[(methylsulfonyl)amino]phenyl}ethyl)amino]carbonyl}cyclopropyl)methylacetate(trans diastereo mixture)

To a solution of the compound of Example 59B (280 mg, 0.81 mmol) in DCM (12 ml) was added TFA (3 ml). After being stirred for 4 hours at room temperature, the mixture was evaporated in vacuo and theresidue was dissolved in DMF (5 ml). To the above solution was added the compound of Example 2D (195 mg, 0.74 mmol), EDC (211 mg, 1.1 mmol), HOBt (149 mg, 1.1 mmol) and triethylamine (1.0 ml, 7.35 mmol) at room temperature. After being stirred for 4 days at room temperature, the mixture was concentrated, diluted with EtOAc and washed with water and brine. The organic layer was dried over sodium sulfate and concentrated in vacuo. The crude material was purified by NH₂ silica gel column (YAMAZEN. size 40 μm) chromatography, eluting with hexane/EtOAc (1:2), to afford the title compound (128 mg, 35%) as a yellow oil.

¹H-NMR (CDCl₃) δ 1.30-1.72 (14H, m), 1.81-1.88 (1H, m), 1.99-2.05 (3H, m), 2.32-2.33 (3H, m), 3.01-3.02 (3H, m), 4.31-4.42 (1H, m), 4.53-4.68 (1H, m), 5.07-5.17 (1H, m), 5.92-5.98 (1H, m), 6.22-6.32 (1H, m), 7.18-7.44 (7H, m).

59D) 2-[4-tert-Butylphenyl]-2-(hydroxymethyl)-N-((1R)-1-{3-methyl-4-[(methylsulfonyl)amino]phenyl}ethyl)cyclopropanecarboxamide(trans diastereo mixture)

To a solution of the compound of Example 59C (100 mg, 0.20 mmol) in ethanol (2 ml) was added 2 Msodium hydroxide aqueous solution (0.5 ml) at room temperature. After being stirred for 3 hours at room temperature, the mixture was evaporated in vacuo and the residue was acidified with 2 M HCl aqueous solution, and extracted with DCM. The organic layer was dried over sodium sulfate and concentrated in vacuo. The crude material was purified by NH₂ silica gel column (Biotage) chromatography, eluting with EtOAc, to give white solids. The solids were recrystallized from hexane-EtOAc to afford the title compound (58 mg, 64%) as white solids.

¹H NMR (300 MHz, DMSO-d₆) δ 1.14-1.41 (14H, m), 1.89-1.98 (1H, m), 3.03 (3H, s), 2.96 (3H, s), 3.67-3.69 (1H, m), 3.73-3.81 (1H, m), 4.38-4.47 (1H, m), 4.87-4.97 (1H, m), 7.12-7.22 (3H, m), 7.30-7.32 (4H, m), 8.57 (1H, d, J=8.1 Hz), 8.96 (1H, br s).

Example 60

(1S,2S)-N-((1R)-1-{2,5-Difluoro-4-[(methylsulfonyl)amino]phenyl}ethyl)-2-methyl-2-[4-(trifluoromethyl)phenyl]cyclopropanecarboxamide

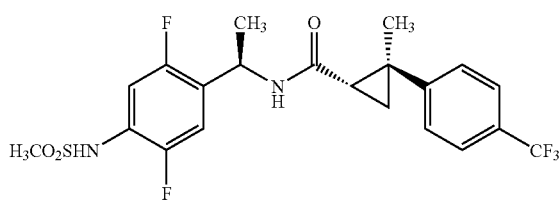

60A) N-(2,5-Difluoro-4-iodophenyl)methanesulfonamide

To a solution of 2,5-difluoro-4-iodoaniline (5.3 g, 19.4 mmol, Can. J. Chem., 2000(78), 1081-1088) in DCM(50 ml) was added methanesulfonyl chloride (1.65 ml, 21.3 mmol) and pyridine (4.7 ml, 58.2 mmol) at 0° C. The mixture was stirred for 24 hours at room temperature. The mixture was partitionedbetween EtOAc and 2 M HCl aqueous solution. The organic layer was separated and washed with 2 M aqueous HCl solution and brine, dried over sodium sulfate and concentrated in vacuo. The crude puroduct was purified by silica gel column chromatography eluting with gradually from hexane/EtOAc (4:1) to hexane/EtOAc (3:1) to give the title compound (5.6 g, 87%) as purple solids.

¹H NMR (270 MHz, CDCl₃) δ 3.09 (3H, s), 6.81 (1H, br s), 7.39 (1H, dd, J=6.9, 8.2 Hz), 7.53 (1H, dd, J=5.3, 9.2 Hz). MS (ESI) m/z 332 (M–H)⁻.

60B) N-(4-Acetyl-2,5-difluorophenyl)methanesulfonamide

A test tube suitable for microwave reaction was charged with palladium (II) acetate (20 mg, 0.09 mmol), 1,3-bis(diphenylphosphino)propane (74 mg, 0.18 mmol), the compound of Example 60A (1000 mg, 3.0 mmol), n-butyl vinyl ether (1.94 ml, 15.0 mmol), and potassium carbonate (622 mg, 4.5 mmol) in DMF (7.5 ml)—water (1.9 ml). The mixture was subjected to microwave irradiation at 100° C. with stirring for 30 minutes. The mixture was diluted with THF, acidified with 2 M aqueous HCl solution and stirred at room temperature for 2 hours. The mixture was extracted with EtOAc and the organic layer was dried over sodium sulfate and then concentrated in vacuo. The crude puroduct was purified by silica gel column chromatography eluting with hexane/EtOAc (3:1) to give the title compound (353 mg, 47% yield) as white solids.

¹H NMR (270 MHz, CDCl₃) δ 2.63 (3H, s), 3.15 (3H, s), 6.95 (1H, br s), 7.45 (1H, dd, J=6.3, 11.5 Hz), 7.71 (1H, dd, J=6.3, 10.9 Hz). MS (ESI) m/z 248 (M–H)⁻.

60C) N-[4-((1R)-1-{[(R)-tert-Butylsulfinyl]amino}ethyl)-2,5-difluorophenyl]methanesulfonamide To a solution of the compound of Example 60B (350 mg, 1.4 mmol) and titanium(IV) ethoxide (2.6 ml) in THF (2.6 ml) was added (R)-(+)-2-methyl-2-propanesulfininamide (170 mg, 1.4 mmol) under a nitrogen atmosphere and the mixture was stirred for 30 hours at 70° C. After cooling to 0° C., sodium borohydrate (159 mg, 4.2 mmol) was added to the mixture. The mixture was warmed to room temperature andstirred for 18 hours, then quenched with MeOH and water. The resuling white precipitates were filtered off and the filtrate was concentrated in vacuo to afford the title compound (882 mg, 100% yield) as yellow solids.

¹H NMR (270 MHz, DMSO-d₆) δ 1.09 (9H, s), 1.32 (3H, d, J=6.6 Hz), 2.54 (3H, s), 4.43-4.50 (1H, m), 6.88-6.97 (2H, m). Signals due to NH were not observed. MS (ESI) m/z 355 (M+H)⁺, 353 (M–H)⁻.

60D) N-{4-[(1R)-1-Aminoethyl]-2,5-difluorophenyl}methanesulfonamide hydrochloride A mixture of the compound of Example 60C (882 mg, 1.4 mmol) and HCl-MeOH (10%, 10 ml) was stirred at room temperature for 24 hours and then concentrated in vacuo. Diethyl ether and MeOH were added to precipitate the amine hydrochloride. The precipitates were then filtered and washed with diethyl ether to afford the title compound (540 mg, 100% yield) as white solids.

¹H NMR (270 MHz, DMSO-d₆) δ 1.53 (3H, d, J=6.6 Hz), 3.12 (3H, s), 4.45 (1H, br s), 7.33 (1H, dd, J=6.9, 10.9 Hz), 7.74-7.80 (1H, m), 8.84 (2H, br s), 10.06 (1H, br s). MS (ESI) m/z 249 (M–H)⁻

60E) (1S,2S)-N-((1R)-1-{2,5-Difluoro-4-[(methylsulfonyl)amino]phenyl}ethyl)-2-methyl-2-[4-(trifluoromethyl)phenyl]cyclopropanecarboxamide To a solution of the compound of Example 60D (176 mg, 0.614 mmol) in DMF (10 ml) was added the compound of Example 14C (100 mg, 0.41 mmol), HBTU (233 mg, 0.61 mmol) and triethylamine (0.23 ml, 1.64 mmol) at room temperature. After being stirred for 14 hours at room temperature, the mixture was concentrated. The crude product was purified by silica gel column chromatography with graduate elution from hexane/EtOAc (2:1) to hexane/EtOAc (1:1) to give pale yellow solids, which was recrystallized from EtOAc-hexane to afford the title compound (102 mg, 53% yield) as white solids.

$^1$H-NMR (270 MHz, DMSO-d$_6$) δ 1.29-1.36 (5H, m), 1.44 (3H, s), 2.00-2.05 (1H, m), 3.08 (3H, s), 5.09-5.19 (1H, m), 7.14-7.30 (2H, m), 7.54 (2H, d, J=8.6 Hz), 7.69 (2H, d, J=8.6 Hz), 8.71 (1H, d, J=7.9 Hz), 9.81 (1H, s). MS (ESI) m/z 477 (M+H)$^+$, 475 (M-H)$^-$

Example 61

(1S,2S)-N-((1R)-1-{3,5-Difluoro-4-[(methylsulfonyl)amino]phenyl}ethyl)-2-methyl-2-[4-(trifluoromethyl)phenyl]cyclopropanecarboxamide

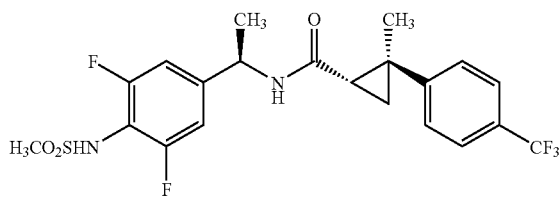

61A) N-(4-Bromo-2,6-difluorophenyl)methanesulfonamide

To a solution of 4-bromo-2,6-difluoroaniline (3.0 g, 14.4 mmol) in pyridine (20 ml) was added methanesulfonyl chloride (2.23 ml, 28.8 mmol) at room temperature. Then the mixture was stirred at 50° C. for 6 hours. After cooing to room temperature, the mixture was concentrated in vacuo. The resulting residue was dissolved in THF (40 ml). To this solution was added 2M aqueous sodium hydroxide solution (40 ml) and the reaction was stirred at room temperature for 4 hours. The mixture was acidified with 2M aqueous HCl solution and the whole was extracted with EtOAc. The organic layer was washed with 2M aqueous HCl solution, brine, and dried over sodium sulfate. After concentration in vacuo, the title compound (4.05 g, 98% yield) was obtained as orange solids.

$^1$H NMR (270 MHz, CDCl$_3$) δ 3.22 (3H, s), 6.08 (1H, br s), 7.17-7.24 (2H, m). MS (ESI) m/z 286 (M+H)$^+$, 284 (M-H)$^-$.

61B) N-(4-Acetyl-2,6-difluorophenyl)methanesulfonamide

A test tube suitable for for microwave reaction was charged with palladium (II) acetate (12 mg, 0.05 mmol), 1,3-bis(diphenylphosphino)propane (43 mg, 0.11 mmol), the compound of Example 61A (500 mg, 1.75 mmol), n-butyl vinyl ether (1.1 ml, 8.75 mmol), and potassium carbonate (290 mg, 2.10 mmol) in DMF (4.8 ml)—water (1.2 ml). The mixture was subjected to microwave irradiation at 100° C. with stirring for 30 minutes. The mixture was diluted with THF, acidified with concentrated HCl and stirred at room temperature for 14 hours. The mixture was partitioned between EtOAc and water. The organic layer was separated, dried over sodium sulfate and concentrated in vacuo. The crude puruduct was purified by silica gel column chromatography with graduate elution from hexane/EtOAc (2:1) to hexane/EtOAc (1:1) to give the title compound (214 mg, 49%) as white solids.

$^1$H NMR (270 MHz, CDCl$_3$) δ 2.59 (3H, s), 3.32 (3H, s), 7.55-7.63 (2H, m). A signal due to NH was not observed. MS (ESI) m/z 248 (M-H)$^-$.

61C) N-[4-((1R)-1-{[(R)-tert-Butylsulfinyl]amino}ethyl)-2,6-difluorophenyl]methanesulfonamide To a solution of the compound of Example 61B (270 mg, 1.1 mmol) and titanium(IV) ethoxide (2 ml) in THF(2 ml) was added (R)-(+)-2-methyl-2-propanesulfininamide (131 mg, 1.1 mmol) under a nitrogen atmosphere and the mixture was stirred for 18 hours at 70° C. After cooling to -20° C., sodium borohydrate (123 mg, 3.2 mmol) was added to the mixture. The mixture was warmed to room temperature and stirred for 16 hours, then quenched with MeOH and water, and the resulting white precipitates were filtered off. The filtrate was concentrated in vacuo to afford the title compound (423 mg, 100%) as yellow solids.

$^1$H NMR (270 MHz, CDCl$_3$) δ 1.18 (9H, s), 1.40 (3H, d, J=6.6 Hz), 2.92 (3H, s), 3.84-3.85 (1H, m), 4.30-4.38 (1H, m), 6.87 (2H, d, J=8.6 Hz). A signal due to NH was not observed.

61D) N-{4-[(1R)-1-Aminoethyl]-2,6-difluorophenyl}methanesulfonamide hydrochloride A mixture of the compound of Example 61C (423 mg, 1.1 mmol) and HCl-MeOH (10%, 10 ml) was stirred at room temperature for 24 hours and then concentrated in vacuo. Diethyl ether and MeOH were added to precipitate the amine hydrochloride. The precipitates were filtered and washed with diethyl ether to afford the title compound (290 mg, 94%) as yellow solids.

$^1$H NMR (270 MHz, DMSO-d$_6$) δ 1.51 (3H, d, J=6.6 Hz), 3.08 (3H, s), 4.44 (1H, br s), 7.44-7.47 (2H, m), 8.67 (2H, br s), 9.67 (1H, s). MS (ESI) m/z 249 (M-H)$^-$.

61E) (1S,2S)-N-((1R)-1-{3,5-Difluoro-4-[(methylsulfonyl)amino]phenyl}ethyl)-2-methyl-2-[4-(trifluoromethyl)phenyl]cyclopropanecarboxamide To a solution of the compound of Example 61D (117 mg, 0.41 mmol) in DMF (5 ml) were added the compound of Example 14C (100 mg, 0.41 mmol), HBTU (233 mg, 0.61 mmol) and triethylamine (0.17 ml, 1.23 mmol) at room temperature. After being stirred for 18 hours at room temperature, the mixture was concentrated, diluted with EtOAc and then washed with water and brine. The organic layer was dried over sodium sulfate and concentrated in vacuo. The crude puruduct was purified by silica gel column chromatography eluting gradually from hexane/EtOAc (3:1) to hexane/EtOAc (2:1) to give pale yellow solids. The solids were purified with XTerra MS C18, 5 μm, (column size; 30×50 mm, ambient temperature, solvent; CH$_3$CN/0.05% HCOOH aq.) to afford white solids, which were triturated with hexane-EtOAc to afford the title compound (59 mg, 30%) as white solids.

$^1$H-NMR (270 MHz, DMSO-d$_6$) δ 1.30-1.38 (5H, m), 1.44 (3H, s), 2.06-2.00 (1H, m), 3.04 (3H, s), 4.92-5.02 (1H, m), 7.14 (2H, d, J=8.6 Hz), 7.54 (2H, d, J=7.5 Hz), 7.69 (2H, d, J=7.9 Hz), 8.69 (1H, d, J=7.9 Hz), 9.50 (1H, br s). MS (ESI) m/z 477 (M+H)$^+$, 475 (M-H)$^-$. [α]$_D$=+111.3 (c=0.50, methanol, cell temperature=21.4° C.)

Example 62

2-[6-tert-Butylpyridin-3-yl]-2-ethyl-N-((1R)-1-{3-methyl-4-[(sulfonyl)amino]phenyl}ethyl)cyclopropanecarboxamide

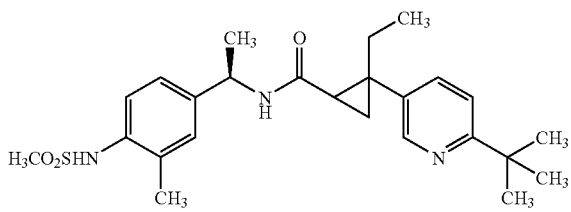

62A) 1-[6-tert-Butylpyridin-3-yl]propan-1-one

To a 10% sulphuric acid aqueous solution (22 ml) of 3-propionylpyridine (Lancaster, 2.70 g, 20 mmol), trimethylacetic acid (10.21 g, 0.1 mol), silver nitrate (0.68 g, 4 mmol) and ammonium persulfate in water (36 ml) were added and the mixture was stirred for 1.5 hours at 70° C. Then, the mixture was basified with 25% ammonia solution (pH=9~10) and extracted with DCM. The organic layer was washed with brine and dried over sodium sulfate. Removal of the solvent gave a residue, which was purified by column chromatography, eluting with hexane/EtOAc (5:1), to give the title compound (3.75 g, 98%) as a yellow oil.

$^1$H NMR (270 MHz, CDCl$_3$) δ 1.24 (3H, t, J=7.3 Hz), 1.39 (9H, s), 3.01 (2H, q, J=7.3 Hz), 7.44 (1H, d, J=7.3 Hz), 8.17 (1H, dd, J=2.2 Hz, 8.1 Hz), 9.12 (1H, d, J=1.5 Hz). MS (ESI) m/z 192.08 (M+H)$^+$.

62B) 2-tert-Butyl-5-(1-methylidenepropyl)pyridine

A mixture of sodium hydride (0.80 g, 20 mmol) and DMSO (10 ml) was stirred for 45 minutes at 80° C. Then, to this reaction was added methyltriphenylphosphonium bromide (7.15 g, 20 mmol) in DMSO (10 ml) and the reaction was stirred for 1 hour at room temperature. Then, to this reaction was added dropwise the compound of Example 62A (1.91 g, 10 mmol) in DMSO (10 ml) and the reaction was stirred for 20 hours at room temperature. After being quenched with saturated aqueous sodium bicarbonate, the resulting product was extracted with diethyl ether, dried over sodium sulfate, filtered and concentrated in vacuo. The crude material was purified by silica gel column chromatography, eluting with hexane/EtOAc (10:1), to afford the title compound (1.89 g, 100%) as a yellow oil.

$^1$H NMR (270 MHz, CDCl$_3$) δ 1.12 (3H, t, J=7.9 Hz), 1.37 (9H, s), 2.50 (2H, q, J=7.3 Hz), 5.10 (1H, br.s), 5.30 (1H, br.s), 7.29 (1H, dd, J=1.3 Hz, 8.6 Hz), 7.62 (1H, dd, J=2.6 Hz, 8.6 Hz), 8.63 (1H, d, J=1.3 Hz). MS (ESI) m/z 190.22 (M+H)$^+$.

62C) Ethyl 2-[6-tert-butylpyridin-3-yl]-2-ethylcyclopropanecarboxylate

To a toluene (100 ml) solution of the compound of example 62B (1.89 g, 10 mmol), Co(TPP) (0.17 g, 0.25 mmol), 1-methyl-1H-imidazole (2.39 ml, 30 mmol), and ethyl diazoacetate (1.58 ml, 15 mmol) were added and the mixture was stirred for 5 minutes at room temperature followed by additional stirring for 1.5 hours at 80° C. The reaction mixture was diluted with EtOAc and washed with saturated aqueous sodium bicarbonate. The organic layer was dried over sodium sulfate and concentrated in vacuo to give the crude product. The crude product was purified by column chromatography on silica gel, eluting with hexane/EtOAc (1:10), to give the title compound (1.34 g, 49%, trans) as a brown oil.

$^1$H NMR (270 MHz, CDCl$_3$) δ 0.79 (3H, t, J=7.3 Hz), 1.31 (3H, dt, J=2.0 Hz, 7.3 Hz), 1.36 (9H, s), 1.82 (1H, dd, J=2.0 Hz, 7.3 Hz), 1.87 (1H, dd, J=2.6 Hz, 7.3 Hz), 1.94 (1H, dd, J=5.9 Hz, 7.9 Hz), 4.21 (2H, q, J=6.6 Hz), 4.28 (2H, q, J=6.6 Hz), 7.27 (1H, d, J=7.9 Hz), 7.53 (1H, dd, J=2.0 Hz, 7.9 Hz), 8.51 (1H, d, J=2.3 Hz). MS (ESI) m/z 276.23 (M+H)$^+$.

62D) 2-[6-tert-Butylpyridin-3-yl]-2-ethylcyclopropanecarboxylic acid

To a ethanol (20 ml) solution of the compound of Example 62C (1.34 g, 4.87 mmol), 2M sodium hydroxide aqueous solution (5 ml) was added and the mixture was stirred for 6 hours at 80° C. After the reaction was completed, basic mixture was washed with diethyl ether. The aqueous layer was acidified with 2M HCl aqueous solution (5 ml, pH=5~6) and the whole was extracted with DCM, followed by evaporation, to give the title compound (0.63 g, 52%) as brown solids.

$^1$H NMR (270 MHz, CDCl$_3$) δ 0.84 (3H, t, J=7.3 Hz), 1.30-1.46 (10H, m, including 9H, s, 1.36 ppm), 1.49 (1H, t, J=5.3 Hz), 1.91 (2H, q, J=7.3 Hz), 1.98 (1H, dd, J=5.9 Hz, 7.9 Hz), 7.29 (1H, d, J=7.9 Hz), 7.55 (1H, dd, J=2.6 Hz, 7.9 Hz), 8.53 (1H, d, J=2.0 Hz). MS (ESI) m/z 248.22 (M+H)$^+$.

62E) 2-[6-tert-Butylpyridin-3-yl]-2-ethyl-N-((1R)-1-{3-methyl-4-[(sulfonyl)amino]phenyl}ethyl)cyclopropanecarboxamide To a DMF (6 ml) solution of the compound of Example 62D (150 mg, 0.61 mmol), HBTU (276 mg, 0.73 mmol), triethylamine (0.25 ml, 1.82 mmol) and the compound of Example 2D (160 mg, 0.61 mmol) were added and the mixture was stirred for 24 hours at room temperature. The same procedure as described in Example 14D was followed to give the title compound (212 mg, 76%) as white solids.

$^1$H-NMR (300 HMz, DMSO-d$_6$) δ 0.54 (1.5H, t, J=7.3 Hz), 0.71 (1.5H, t, J=6.6 Hz), 1.06-1.19 (1H, m), 1.19-1.26 (1H, m), 1.30 (9H, s), 1.36 (3H, d, J=6.6 Hz), 1.67 (1H, q, J=7.3 Hz), 1.79 (1H, q, J=8.1 Hz), 1.91-2.02 (1H, m), 2.29, 2.30 (3H, each s), 2.94, 2.95 (3H, each s), 4.85-5.01 (1H, m), 7.10-7.28 (2H, m), 7.37 (1H, d, J=8.1 Hz), 7.60-7.72 (1H, m), 8.53 (1H, br.s), 8.66 (1H, t, J=7.3 Hz), 9.01 (1H, br.s). MS (ESI) m/z 458.21 (M+H)$^+$. m.p. 209.9° C. (TG/DTA). Anal. Calcd. for C$_{25}$H$_{35}$N$_3$O$_3$S: C, 65.61; H, 7.71; N, 9.18. Found: C, 65.55; H, 7.65; N, 9.16.

Example 63

N-((1R)-1-{3-Methyl-4-[(methylsulfonyl)amino]phenyl}ethyl)-2-(methyloxy)-2-[4-(trifluoromethyl)phenyl]cyclopropanecarboxamide

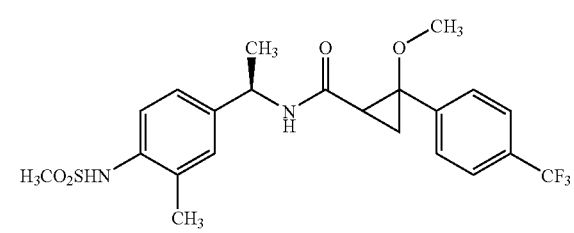

63A) 1-[1,1-bis-(Methyloxy)ethyl]-4-(trifluoromethyl)benzene

To a stirred solution of 4-(trifluoromethyl)acetophenone (purchased from Aldrich, 3.76 g, 20 mmol) in MeOH (3 ml)

was added trimethyl orthoformate (2.33 g, 22 mmol) and tetrabutylammonium tribromide (96.4 mg, 0.2 mmol) successively. The mixture was stirred at room temperature for 24 hours, quenched with saturated aqueous sodium bicarbonate, and extracted with diethyl ether. The organic layer was washed with brine and dried over sodium sulfate. The mixture was filtered and concentrated in vacuo to afford the crude title compound (5.95 g) as a colorless oil.

$^1$H NMR (270 MHz, CDCl$_3$) δ 1.56 (3H, m), 3.19 (6H, s), 7.61 (4H, s). MS (ESI) m/z not observed M$^+$ perk.

63B) 1-[1-(Methoxy)ethenyl]-4-(trifluoromethyl)benzene

To the diglyme (2 ml) solution of the compound of Example 63A (crude 5.95 g, 20 mmol), succinic anhydride (2.20 g, 22 mmol), benzoic acid (61 mg, 0.5 mmol) and pyridine (1.58 g, 20 mmol) were added and the mixture was stirred for 1.5 hours at 110° C. The reaction was quenched with 2M sodium hydroxide aqueous solution and the whole was extracted with diethyl ether. The organic layer was dried over sodium sulfate and concentrated in vacuo to afford the crude title compound (7.80 g) as a brown oil.

$^1$H NMR (300 MHz, CDCl$_3$) δ 3.76 (3H, s). 4.33 (1H, d, J=2.9 Hz), 4.75 (1H, d, J=3.7 Hz), 7.59 (2H, d, J=8.1 Hz), 7.72 (2H, d, J=8.1 Hz). MS (ESI) m/z not observed M$^+$ perk.

63C) Ethyl 2-(methyloxy)-2-[4-(trifluoromethyl)phenyl]cyclopropanecarboxylate

To a toluene (100 ml) solution of the compound of Example 63B (crude 7.80 g, 20 mmol), Co(TPP) (0.34 g, 0.5 mmol), 1-methyl-1H-imidazole (4.78 ml, 60 mmol) and ethyl diazoacetate (3.15 ml, 30 mmol) were added and the mixture was stirred for 5 minutes at room temperature followed by additional stirring for 4 hours at 80° C. The reaction mixture was diluted with EtOAc, washed with 2M HCl solution, saturated aqueous sodium bicarbonate, and brine. The organic layer was dried over sodium sulfate and concentrated in vacuo to give a crude product. The crude product was purified by column chromatography on silica gel, eluting with hexane/EtOAc (1:10), to give the title compound (4.00 g, trans) as a brown oil.

$^1$H NMR (270 MHz, CDCl$_3$) δ 1.31 (3H, t, J=7.3 Hz), 1.45-1.60 (1H, m), 2.02-2.20 (2H, m), 3.19 (3H, s), 4.24 (2H, q, J=7.3 Hz), 7.45 (2H, d, J=8.6 Hz), 7.63 (2H, d, J=7.9 Hz). MS (ESI) m/z not observed M$^+$ perk.

63D) 2-(Methyloxy)-2-[4-(trifluoromethyl)phenyl]cyclopropanecarboxylic acid

To a ethanol (100 ml) solution of the compound of Example 63C (crude 4.00 g, 20 mmol), 2M sodium hydroxide aqueous solution (30 ml) was added and the mixture was stirred for 14 hours at 50° C. After the reaction was completed, the basic mixture was washed with DCM. The aqueous layer was acidified with 2M HCl aqueous solution and the whole was extracted with DCM followed by evaporation to give the crude product. The crude product was purified by column chromatography, eluting with hexane/EtOAc (1:1), to give the title compound (0.40 g, 8% for 4 steps) as brown solids.

$^1$H NMR (270 MHz, CDCl$_3$) δ 1.61 (1H, m), 2.01 (1H, t, J=6.5 Hz), 2.16 (1H, t, J=7.2 Hz), 3.30 (3H, s), 7.47 (2H, d, J=7.9 Hz), 7.65 (2H, d, J=7.9 Hz). MS (ESI) m/z 259.18 (M−H)$^+$.

63E) N-((1R)-1-{3-Methyl-4-[(methylsulfonyl)amino]phenyl}ethyl)-2-(methyloxy)-2-[4-(trifluoromethyl)phenyl]cyclopropanecarboxamide To a DMF (3 ml) solution of the compound of Example 63D (130 mg, 0.50 mmol), HBTU (228 mg, 0.60 mmol), triethylamine (0.21 ml, 1.5 mmol) and the compound of Example 2D (132 mg, 0.50 mmol) were added and the mixture was stirred for 20 hours at room temperature. The same procedure as described in Example 14D was performed to give the title compound (173 mg, 73%). The resulting racemic compound (60 mg was separated with DAICEL CHIRALCEL OJ-H (column size: 2×25 cm, Mobile Phase: 0.1% diethylamine in hexane/ethanol=70/30, column temperature: 40° C., flow rate: 20 ml/min, detection: 230 nm, Retention time: 5 min and 7 min). The later fraction was collected as white solids (25 mg).

$^1$H-NMR (270 HMz, DMSO-) δ 1.32 (3H, t, J=7.3 Hz), 1.43 (1H, dd, J=5.9 Hz, 8.6 Hz), 1.89 (1H, dd, J=5.9 Hz, 7.3 Hz), 2.20 (1H, dd, J=7.9 Hz, 9.2 Hz), 2.28 (3H, s), 2.94 (3H, s), 3.17 (3H, s), 4.90 (1H, m), 7.05-7.25 (3H, m), 7.54 (2H, d, J=7.9 Hz), 7.74 (2H, d, J=8.6 Hz), 8.48 (1H, d, J=7.9 Hz), 8.90 (1H, br.s). MS (ESI) m/z 471.22 (M+H)$^+$.

Example 64

2-[4-tert-Butylphenyl]-N-((1R)-1-{3-methyl-4-[(methylsulfonyl)amino]phenyl}ethyl)-2-(methyloxy)cyclopropanecarboxamide

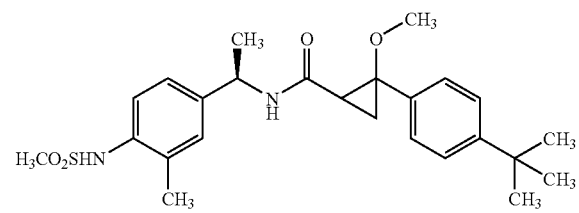

64A) 1-[1,1-Bis(methyloxy)ethyl]-4-tert-butylbenzene

To a stirred solution of 4'-tert-butylacetophenone (purcashed from Aldrich, 1.76 g, 10 mmol) in MeOH (1 mL) was added trimethyl orthoformate (1.97 g, 11 mmol) and tetrabutylammonium tribromide (48.2 mg, 0.1 mmol) successively. The same reaction procedure as described in Example 63A was performed to give the title compound (2.33 g) as a yellow oil.

$^1$H NMR (300 MHz, CDCl$_3$) δ 1.32 (9H, s), 1.54 (3H, s), 3.19 (6H, s), 7.36 (2H, d, J=8.8 Hz), 7.41 (2H, d, J=8.8 Hz).

64B) 4-tert-Butyl-1-[1-(methyloxy)ethenyl]benzene

To a diglyme (1 ml) solution of the compound of Example 64A (crude 2.33 g, 10 mmol), succinic anhydride (1.10 g, 11 mmol), benzoic acid (30.5 mg, 0.25 mmol) and pyridine (0.79 g, 10 mmol) were added successively. The same reaction procedure as described in Example 63B was performed to give the title compound (4.28 g) as a red oil.

$^1$H NMR (300 MHz, CDCl$_3$) δ 1.32 (9H, s), 3.74 (3H, s), 4.18 (1H, d, J=2.9 Hz), 4.62 (1H, d, J=3.0 Hz), 7.36 (2H, d, J=8.0 Hz), 7.55 (2H, d, J=8.0 Hz). MS (ESI) m/z not observed M$^+$ peak.

64C) Ethyl 2-[4-tert-butylphenyl]-2-(methyloxy)cyclopropanecarboxylate

To a toluene (100 ml) solution of the compound of Example 64B (crude 4.28 g, 10 mmol), Co(TPP) (0.34 g, 0.5 mmol), 1-methyl-1H-imidazole (2.39 ml, 30 mmol) and ethyl diazoacetate (1.58 ml, 15 mmol) were added successively. The same procedure as described in Example 63C was performed to give the title compound (0.45 g, 16% for 3 steps) as a red oil.

¹H NMR (300 MHz, CDCl₃) δ 1.29 (3H, t, J=6.6 Hz), 1.32 (9H, s), 1.46 (1H, dd, J=5.7 Hz, 8.7 Hz), 1.90-2.05 (1H, m), 2.05-2.20 (1H, m), 3.23 (3H, s), 4.10-4.30 (2H, m), 7.28 (2H, d, J=8.1 Hz), 7.38 (2H, d, J=8.1 Hz). MS (ESI) m/z 277.25 (M+H)⁺.

64D) 2-[4-tert-Butylphenyl]-2-(methyloxy)cyclopropanecarboxylic acid

To a THF (5 ml) solution of the compound of Example 64C (0.45 g, 1.62 mmol), 2M sodium hydroxide aqueous solution (1 ml) and MeOH (5 ml) were added and the mixture was stirred for 20 hours at room temperature followed by additional stirring for 8 hours at 70° C. The same procedure as described in Example 63D was performed to give the title compound (0.18 g, 45%) as a brown oil.

¹H NMR (300 MHz, CDCl₃) δ 1.32 (9H, s), 1.50-1.70 (1H, m), 1.80-1.96 (1H, m), 2.07-2.17 (1H, m), 3.36 (3H, s), 7.30 (2H, d, J=8.0 Hz), 7.40 (2H, d, J=8.0 Hz). MS (ESI) m/z 247.29 (M−H)⁺.

64E) 2-[4-tert-Butylphenyl]-N-((1R)-1-{3-methyl-4-[(methylsulfonyl)amino]phenyl}ethyl)-2-(methyloxy)cyclopropanecarboxamide To the DMF (2 ml) solution of the compound of Example 64D (105 mg, 0.42 mmol), EDC (122 mg, 0.63 mmol), HOBt (83 mg, 0.63 mmol), triethylamine (0.24 ml, 1.69 mmol) and the compound of Example 2D (112 mg, 0.42 mmol) were added and the mixture was stirred for 24 hours at room temperature. The same procedure as described in Example 10E was performed to give the title compound (123 mg, 63%) as white solids.

¹H-NMR (270 HMz, CDCl₃) δ 1.32 (9H, s), 1.46 (3H, d, J=7.3 Hz), 1.50-1.63 (1H, m), 1.69 (1H, t, J=5.9 Hz), 1.92 (1H, dd, J=7.3 Hz, 9.9 Hz), 2.31 (3H, s), 3.01 (3H, s), 3.23 (3H, s), 5.10 (1H, m), 6.12 (1H, br.s), 6.47 (1H, br.d, J=7.9 Hz), 7.14-7.30 (4H, m), 7.33-7.45 (3H, m). MS (ESI) m/z 459.28 (M+H)⁺. m.p. 230.8° C. (TG/DTA). Anal. Calcd. for C₂₅H₃₄N₂O₄S.0.2H₂O: C, 64.96; H, 7.50; N, 6.06. Found: C, 64.74; H, 7.38; N, 5.99.

Example 65

2-[4-tert-Butyl-2-pyridin-4-ylphenyl]-N-((1R)-1-{3-methyl-4-[(methylsulfonyl)amino]phenyl}ethyl)cyclopropanecarboxamide

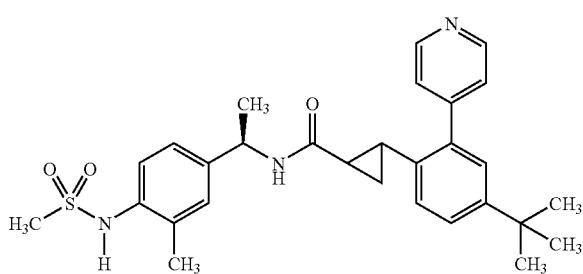

65A) 2-Bromo-4-tert-butyl-1-ethenylbenzene

To a stirred suspension of methyltriphenylphosphonium bromide (12.3 g, 33.7 mmol) in anhydrous THF (40 ml) was added n-butyl lithium (1.60 mol/l, hexane solution) (33.7 mmol, 21.1 ml) at 0° C. After 30 minutes at 0° C., to this was added 2-bromo-4-tert-butylbenzaldehyde (4.06 g, 16.8 mmol)(prepared according to J. Med. Chem. 2005, 48, 71-90) in anhydrous THF (10 ml) at 0° C. The reaction mixture was stirred at ambient temperature for 3 hours. The mixture was quenched with saturated ammonium chloride solution and extracted with EtOAc. The combined solution was washed with brine, dried over sodium sulfate and concentrated in vacuo to give the crude product. The crude product was purified by column chromatography on silica gel, eluting with hexane, to afford the title compound (3.27 g, 81%) as a colorless oil.

¹H NMR (270 MHz, CDCl₃) δ 1.31 (9H, s), 5.28-5.35 (1H, m), 5.62-5.72 (1H, m), 6.96-7.10 (1H, m), 7.28-7.34 (1H, m), 7.47-7.52 (1H, m), 7.54-7.56 (1H, m).

65B) Ethyl 2-[2-bromo-4-tert-butylphenyl]cyclopropanecarboxylate

To a stirred solution of the compound of Example 65A (3.27 g, 13.7 mmol), N-methylimidazole (3.27 ml, 41.0 mmol) and Co(TPP) (276 mg, 0.41 mmol) in toluene (25 ml) was added ethyl diazoacetate (2.01 ml, 19.2 mmol) in one portion at ambient temperature. The same procedure as described in Example 2H was performed to give the title compound (3.46 g, 78%, trams) as a dark yellow oil.

¹H NMR (270 MHz, CDCl₃) δ 1.25-1.36 (13H, m), 1.55-1.65 (1H, m), 1.73-1.82 (1H, m), 2.62-2.72 (1H, m), 4.12-4.30 (2H, m), 6.91-6.97 (1H, m), 7.21-7.28 (1H, m) 7.58-7.56 (1H, m).

65C) Phenylmethyl 2-[2-bromo-4-tert-butylphenyl]cyclopropanecarboxylate

A mixture of the compound of Example 65B (3.46 g, 10.6 mmol) in 2M sodium hydroxide aqueous solution (10.6 ml, 21.3 mmol) and MeOH (50 ml) was heated at 45° C. for 5 hours. After cooling to ambient temperature, the solvent was evaporated in vacuo and the residue was diluted with water. The aqueous solution was washed with diethyl ether, acidified to pH 3 with 2M HCl aqueous solution, and extracted with DCM. The combined solution was washed with brine, dried over sodium sulfate and concentrated in vacuo to give the crude acid compound (2.93 g) as pale purple solids. A mixture of the crude acid (2.91 g, 9.78 mmol), benzyl chloroformate (1.76 g, 9.78 mmol), triethylamine (1.09 g, 10.8 mmol) and 4-(dimethylamino)pyridine (120 mg, 0.98 mmol) in anhydrous DCM (40 ml) was stirred at 0° C. for 1 hour. The resulting mixture was diluted with DCM and saturated ammonium chloride aqueous solution. The organic layer was separated and the aqueous solution was extracted with DCM. The combined solution was washed with brine, dried over sodium sulfate and concentrated in vacuo to give the crude product, which was purified by column chromatography on silica gel, eluting with hexane/EtOAc (50:1-30:1), to afford the title compound (3.21 g, 78%) as a colorless oil.

¹H NMR (270 MHz, CDCl₃) δ 1.28 (9H, s), 1.25-1.40 (1H, m), 1.60-1.69 (1H, m), 1.79-1.87 (1H, m), 2.65-2.76 (1H, m), 5.13-5.26 (2H, m), 6.91-6.96 (1H, m), 7.21-7.26 (1H, m), 7.30-7.42 (5H, m), 7.55-7.58 (1H, m).

65D) Phenylmethyl 2-[4-tert-butyl-2-pyridin-4-ylphenyl]cyclopropanecarboxylate

A mixture of the compound of Example 65C (1.00 g, 2.58 mmol), 4-pyridinylboronic acid (381 mg, 3.10 mmol), tetrakis(triphenylphosphine)palladium(0) (298 mg, 0.26 mmol) in 2M sodium carbonate aqueous solution (3.87 ml, 7.74 mmol), toluene (15 ml) and ethanol (4 ml) was heated at 100° C. for 12 hours. After cooling to ambient temperature, the mixture was diluted with EtOAc and water. The organic layer was separated and the aqueous layer was extracted with EtOAc. The combined organic layers were washed with brine, dried over sodium sulfate and concentrated in vacuo to give the crude product, which was purified by column chromatography on silica gel, eluting with hexane/EtOAc (5:1), to afford the title compound (873 mg, 88%) as a yellow viscous oil.

$^1$H NMR (270 MHz, CDCl$_3$) δ 1.32 (9H, s), 1.22-1.37 (1H, m), 1.46-1.56 (1H, m), 1.72-1.81 (1H, m), 2.42-2.52 (1H, m), 4.97-5.13 (2H, m), 7.01-7.06 (1H, m), 7.21-7.43 (9H, m), 8.54-8.59 (2H, m).

65E) 2-[4-tert-Butyl-2-pyridin-4-ylphenyl]cyclopropanecarboxylic acid

A mixture of the compound of Example 65D (870 mg, 2.26 mmol) in MeOH (30 ml) was hydrogenated over 10% Pd—C (100 mg) under balloon pressure for 5 hours. The catalyst was filtered through a celite pad and the filter cake was washed with MeOH. After the filtrate was evaporated in vacuo, the residue was recrystallized from EtOAc—hexane to afford the title compound (591 mg, 89%) as white solids.

$^1$H NMR (270 MHz, CDCl$_3$) δ 1.34 (9H, s), 1.40-1.59 (3H, m), 2.28-2.38 (1H, m), 7.13-7.18 (1H, m), 7.24-7.27 (1H, m), 7.37-7.48 (3H, m), 8.55-8.60 (2H, m).

65F) 2-[4-tert-Butyl-2-pyridin-4-ylphenyl]-N-((1R)-1-{3-methyl-4-[(methylsulfonyl)amino]phenyl}ethyl)cyclopropanecarboxamide To a stirred solution of the amine compound of Example 2D (122 mg, 0.46 mmol), the compound of Example 65E (136 mg, 0.46 mmol), HOBt (70 mg, 0.46 mmol) and EDC (159 mg, 0.83 mmol) in anhydrous DMF (5 ml) was added triethylamine (106 mg, 1.84 mmol) at ambient temperature. The same procedure as described in Example 1 was performed to give the title compound (182 mg, 78%, mixture of diastereomer products (1:1)) as pale yellow amorphous solids.

$^1$H NMR (270 MHz, CDCl$_3$) δ 1.05-1.30 (2H, m), 1.32 and 1.33 (total 9H, each s), 1.38-1.55 (4H, m), 2.30 and 2.35 (total 3H, each s), 2.38-2.58 (1H, m), 3.00 and 3.06 (total 3H, each s), 4.86-5.10 (1H, m), 5.37-5.45 and 5.64-5.71 (total 1H, each m), 6.20-6.50 (1H, br.s), 6.98-7.48 (8H, m), 8.37-8.42 (1H, m), 8.65-8.69 (1H, m) MS (ESI): m/z 504 (M−H)$^−$, m/z 506 (M+H)$^+$.

Example 66

2-[3-Fluoro-4-(trifluoromethyl)phenyl]-2-methyl-N-((1R)-1-{3-methyl-4-[(methylsulfonyl)amino]phenyl}ethyl)cyclopropanecarboxamide

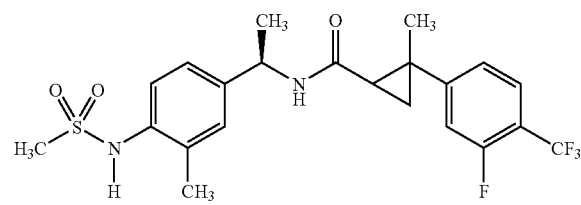

66A) 2-Fluoro-4-(1-methylethenyl)-1-(trifluoromethyl)benzene

To a suspension of 60% sodium hydride (1.96 g, 49.0 mmol) was added DMSO (40 ml) in one portion at 0° C. and the reaction mixture was heated at 80° C. for 40 minutes. After cooling to ambient temperature, to this was added a solution of methyltriphenylphosphonium bromide (17.5 g, 49.0 mmol) in anhydrous DMSO (50 ml) dropwise at 0° C. After being stirred for 1 hour at ambient temperature, to this was added a solution of 1-[3-fluoro-4-(trifluoromethyl)phenyl]ethanone (5.04 g, 24.5 mmol) in anhydrous DMSO (40 ml) dropwise at 0° C. and the reaction was stirred at ambient temperature for 1.5 hours. The mixture was quenched with water (150 ml) and extracted with hexane. The combined solution was washed with water then brine, dried over sodium sulfate and concentrated in vacuo to give the crude title compound (3.20 g containing hexane) as a yellow oil.

$^1$H NMR (270 MHz, CDCl$_3$) δ 2.15 (3H, s), 5.24 (1H, s), 5.47 (1H, s), 7.22-7.35 (2H, m), 7.51-7.59 (1H, m).

66B) Ethyl 2-[3-fluoro-4-(trifluoromethyl)phenyl]-2-methylcyclopropanecarboxylate To a stirred solution of the compound of Example 66A (3.20 g, 15.7 mmol), N-methylimidazole (3.86 ml, 47.0 mmol) and Co(TPP) (316 mg, 0.47 mmol) in toluene (30 ml) was added ethyl diazoacetate (2.50 g, 21.9 mmol) in one portion at ambient temperature. The same procedure as described in Example 2H was performed to give the title compound (1.40 g, 31%, trans) as a dark purple oil.

$^1$H NMR (270 MHz, CDCl$_3$) δ 1.31 (3H, t, J=7.3 Hz), 1.39-1.47 (1H, m), 1.54 (3H, s), 1.49-1.57 (1H, m), 1.93-2.00 (1H, m), 4.13-4.31 (2H, m), 7.06-7.19 (2H, m), 7.49-7.58 (1H, m).

66C) 2-[3-Fluoro-4-(trifluoromethyl)phenyl]-2-methylcyclopropanecarboxylic acid

A mixture of the compound of Example 66B (1.40 g, 4.82 mmol) in 2M sodium hydroxide aqueous solution (10 ml) and MeOH (30 ml) was heated at 80° C. for 6 hours. After cooling to ambient temperature, the solvent was evaporated in vacuo and the residue was diluted with water. The aqueous layer was washed with diethyl ether and acidified to pH<2 with 2M HCl aqueous solution. The mixture was extracted with DCM and the combined organic layer was washed with water then brine, dried over sodium sulfate and concentrated in vacuo to give the title compound (1.19 g, 94%) as pale brown solids.

$^1$H NMR (270 MHz, CDCl$_3$) δ 1.49-1.62 (2H, m), 1.60 (3H, s), 1.96-2.04 (1H, m), 7.10-7.22 (2H, m), 7.51-7.60 (1H, m).

66D) 2-[3-Fluoro-4-(trifluoromethyl)phenyl]-2-methyl-N-((1R)-1-{3-methyl-4-[(methylsulfonyl)amino]phenyl}ethyl)cyclopropanecarboxamide To a stirred solution of the compound of Example 2D (200 mg, 0.76 mmol), the compound of Example 66C (198 mg, 0.76 mmol) and HBTU (344 mg, 0.91 mmol) in anhydrous DMF (10 ml) was added triethylamine (229 mg, 2.27 mmol) at ambient temperature. The same procedure as described in Example 14D was performed to give the title compound (333 mg, 94%, mixture of diastereomer products (1:1)) as white solids.

$^1$H NMR (270 MHz, CDCl$_3$) δ 1.33-1.80 (9H, m), 2.32 (3H, s), 3.00-3.03 (3H, m), 5.04-5.18 (1H, m), 5.87-5.97 (1H, m), 6.24 (1H, br.s), 7.01-7.22 (4H, m), 7.38-7.44 (1H, m), 7.48-7.57 (1H, m) MS (ESI) : m/z 471 (M−H)$^−$, m/z 473 (M+H)$^+$.

Example 67

N-((1R)-1-{3-Fluoro-4-[(methylsulfonyl)amino]phenyl}ethyl)-2-[3-fluoro-4-(trifluoromethyl)phenyl]-2-methylcyclopropanecarboxamide

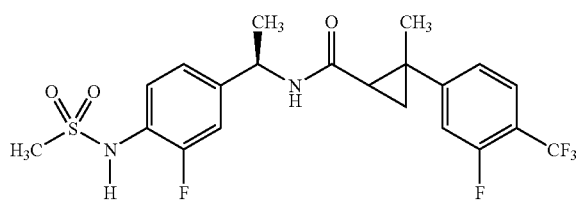

To a stirred solution of the amine compound of Example 8 (200 mg, 0.74 mmol), the compound of Example 66C (195 mg, 0.74 mmol) and HBTU (339 mg, 0.89 mmol) in anhydrous DMF (10 ml) was added triethylamine (226 mg, 2.23 mmol) at ambient temperature. The same procedure as described in Example 14D was performed to give the title compound (256 mg, 72%, mixture of diastereomer products (1:1)) as white solids.

$^1$H NMR (270 MHz, CDCl$_3$) δ 1.36-1.80 (9H, m), 3.01-3.04 (3H, m), 5.05-5.20 (1H, m), 5.89-5.99 (1H, m), 7.03-7.17 (4H, m), 7.48-7.58 (1H, m) (A signal due to NH was not observed) MS (ESI) : m/z 475 (M−H)$^-$, m/z 477 (M+H)$^+$.

Example 68

2-[4-tert-Butyl-2-(hydroxymethyl)phenyl]-N-((1R)-1-{3-methyl-4-[(methylsulfonyl)amino]phenyl}ethyl)cyclopropanecarboxamide

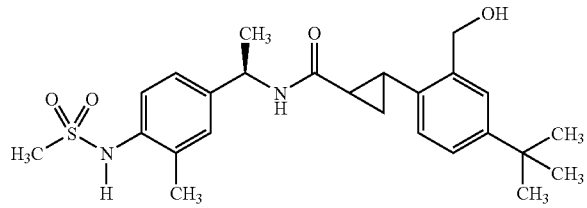

68A) Methyl 5-tert-butyl-2-(2-{[(phenylmethyl)oxy]carbonyl}cyclopropyl)benzoate

A mixture of the compound of Example 65C (1.63 g, 4.20 mmol), palladium acetate (94 mg, 0.42 mmol), 1,3-bis(diphenylphosphino)propane (173 mg, 0.42 mmol), triethylamine (1.27 g, 12.6 mmol) and MeOH (5.38 g, 168 mmol) in anhydrous DMF (10 ml) was heated at 80° C. under carbon monoxide balloon for 15 hours. After cooling to ambient temperature, the mixture was diluted with EtOAc-toluene (8:1) and washed with water then brine, dried over sodium sulfate and concentrated in vacuo to give the crude product. The crude product was purified by column chromatography on silica gel, eluting with hexane/EtOAc (10:1), to afford the title compound (1.21 g, 79%) as a colorless oil.

$^1$H NMR (270 MHz, CDCl$_3$) δ 1.31 (9H, s), 1.29-1.41 (1H, m), 1.55-1.67 (1H, m), 1.75-1.84 (1H, m), 3.06-3.16 (1H, m), 3.79 (3H, s), 5.14-5.25 (2H, m), 7.03-7.09 (1H, m), 7.30-7.47 (6H, m), 7.88-7.90 (1H, m).

68B) 2-{4-tert-Butyl-2-[(methyloxy)carbonyl]phenyl}cyclopropanecarboxylic acid

A mixture of the compound of Example 68A (1.20 g, 3.27 mmol) in MeOH (40 ml) was hydrogenated over 10% Pd—C (150 mg) under balloon pressure. The same procedure as described in Example 65E was performed to give the title compound (882 mg, 98%) as pale purple solids.

$^1$H NMR (270 MHz, CDCl$_3$) δ 1.32 (9H, s), 1.35-1.46 (1H, m), 1.60-1.78 (2H, m), 3.07-3.20 (1H, m), 3.91 (3H, s), 7.05-7.11 (1H, m), 7.43-7.49 (1H, m), 7.91-7.94 (1H, m).

68C) Methyl 5-tert-butyl-2-(2-{[((1R)-1-{3-methyl-4-[(methylsulfonyl)amino]phenyl}ethyl)amino]carbonyl}cyclopropyl)benzoate To a stirred solution of the amine compound of Example 2D (370 mg, 1.39 mmol), the compound of Example 68B (350 mg, 1.27 mmol), HOBt (194 mg, 1.27 mmol) and EDC (438 mg, 2.29 mmol) in anhydrous DMF (10 ml) was added triethylamine (514 mg, 5.08 mmol) at ambient temperature. The same procedure as described in Example 1 was performed to give the title compound (503 mg, 81%) as white solids (a mixture of diastereomeric products (1:1)).

$^1$H NMR (270 MHz, CDCl$_3$) δ 1.22-1.35(10H, m), 1.41-1.60 (5H, m), 2.30-2.34 (3H, m), 2.86-3.00 (1H, m), 3.01 (3H, s), 3.72 and 3.91 (total 3H, each s), 5.05-5.20 (1H, m), 6.04-6.11 (1H, m), 6.19 (1H, br s), 7.02-7.08 (1H, m), 7.15-7.30 (2H, m), 7.37-7.48 (2H, m), 7.82-7.87 (1H, m). MS (ESI) : m/z 485 (M−H)$^-$, m/z 487 (M+H)$^+$.

68D) 2-[4-tert-Butyl-2-(hydroxymethyl)phenyl]-N-((1R)-1-{3-methyl-4-[(methylsulfonyl)amino]phenyl}ethyl)cyclopropanecarboxamide To a stirred suspension of lithium aluminum hydride (85 mg, 1.80 mmol) in anhydrous THF (5 ml) was added a solution of the compound of Example 68C (437 mg, 0.90 mmol) in anhydrous THF (10 ml) dropwise at 0° C. After being stirred for 3 hours at ambient temperature, the mixture was quenched with 2M HCl aqueous solution (10 ml) at 0° C. and extracted with EtOAc. The combined solution was washed with brine, dried over sodium sulfate and concentrated in vacuo to give the crude product, which was purified by column chromatography on amino bounded silica gel, eluting with DCM/MeOH (40:1), to afford the title compound (360 mg, 87%) as yellow amorphous solids (a mixture of diastereomer products (1:1)).

$^1$H NMR (270 MHz, CDCl$_3$) δ 1.20-1.30 (1H, m), 1.30 and 1.31 (total 9H, each s), 1.44-1.60 (5H, m), 2.13 (1H, br s), 2.29-2.32 (3H, m), 2.38-2.57 (1H, m), 2.98-3.00 (3H, m), 4.61-4.91 (2H, m), 5.02-5.16 (1H, m), 6.18-6.30 (1H, m), 6.92-6.99 (1H, m), 7.08-7.30 (3H, m), 7.33-7.43 (2H, m). MS (ESI) : m/z 457 (M−H)$^-$, m/z 459 (M+H)$^+$.

Example 69

N-((1R)-1-{3-(Hydroxymethyl)-4-[(methylsulfonyl)amino]phenyl}ethyl)-2-methyl-2-{4-[(trifluoromethyl)sulfonyl]phenyl}cyclopropanecarboxamide

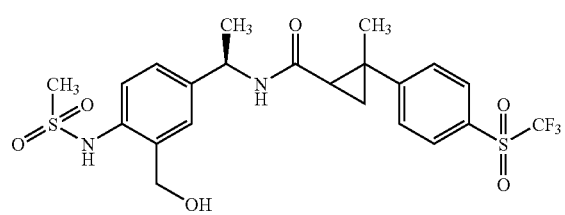

69A) [2-[(Methylsulfonyl)amino]-5-((1R)-1-{[(2-methyl-2-{4-[(trifluoromethyl)thio]phenyl}cyclopropyl)carbonyl]amino}ethyl)phenyl]methylacetate To a THF (1 ml) solution of the compound of Example 25B (113 mg, 0.224 mmol), pyridine (0.2 ml), DMAP (1 mg) was added acetic anhydride (23 mg, 0.224 mmol) at 0° C. and the mixture was stirred at 0° C. for 3 hours. Then the reaction was quenched with 1M-HCl aqueous solution and extracted with. EtOAc. The organic layer was dried over sodium sulfate and concentrated in vacuo to give the crude title compound.

MS (ESI): m/z 545 (M+H)$^+$.

69B) [2-[(Methylsulfonyl)amino]-5-((1R)-1-{[(2-methyl-2-{4-[(trifluoromethyl)sulfonyl]phenyl}cyclopropyl)carbonyl]amino}ethyl)phenyl]methylacetate To a solution of the crude compound of Example 69A, sodium metaperiodate (144 mg, 0.672 mmol), tetrachloromethane (1 ml), acetonitrile (1 ml) in water (2 ml) was added ruthenium trichloride hydrate (0.1 mg) and the mixture was stirred for 16 hours at room temperature. The reaction was quenched with saturated sodium bicarbonate aqueous solution and the whole was extracted with EtOAc, which was dried over sodium sulfate. Then, filtration and evaporation gave the crude title compound.

MS (ESI): m/z 575 (M−H)$^−$.

69C) N-((1R)-1-{3-(Hydroxymethyl)-4-[(methylsulfonyl)amino]phenyl}ethyl)-2-methyl-2-{4-[(trifluoromethyl)sulfonyl]phenyl}cyclopropanecarboxamide A MeOH (4 ml) solution of the crude compound of Example 69B and 2M-sodium hydroxide aqueous solution (1 ml) was stirred at room temperature for 4 hours. After the reaction was completed, the mixture was quenched with 1M HCl aqueous solution and extracted with EtOAc. The organic layer was dried over sodium sulfate. Then filtration, evaporation, and purification by silica gel column chromatography, eluting with hexane/EtOAc (1:2), gave the title compound (50 mg, 42% yield in 3 steps.) as white solids (mixture of diastereomeric products (1:1)).

$^1$H NMR (300 MHz, CDCl$_3$) δ 1.35-1.92 (9H, m), 2.99-3.00 (3H, m), 4.65-4.69 (2H, m), 5.02-5.11 (1H, m), 6.30-6.43 (1H, m), 7.18-7.27 (2H, m), 7.42-7.53 (3H, m), 7.82-7.97 (3H, m). MS (ESI): m/z 535 (M+H)$^+$.

Example 70

(1S,2S)-2-Methyl-N-((1R)-1-{3-methyl-4-[(methylsulfonyl)amino]phenyl}ethyl)-2-[4-(trifluoromethyl)phenyl]cyclopropanecarboxamide

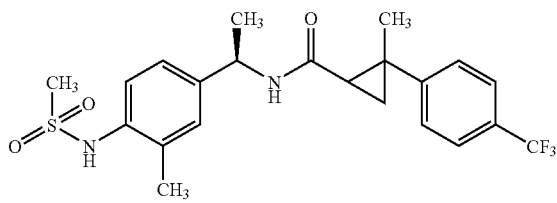

To a DMF (1 ml) solution of the compound of Example 14B (63 mg, 0.258 mmol), triethylamine (0.11 ml) and EDC (71 mg, 0.387 mmol), HOBt (43 mg, 0.284 mmol), and the amine compound of Example 2D (68 mg, 0.258 mmol) were added in the same procedure as described in Example 10E. The crude residue was applied to a silica gel chromatography column and eluted with a volume mixture of hexane and EtOAc (1:1) to afford the title compound (70 mg, 60% yield) as white solids (mixture of diastereomer products (1:1)).

$^1$H NMR (300 MHz, CDCl$_3$) δ 1.30-1.77 (9H, m), 2.32 (3H, s), 3.01-3.02 (3H, m), 5.10-5.20 (1H, m), 5.85-5.91 (1H, m), 6.19 (1H, s), 7.18-7.23 (2H, m), 7.35-7.45 (3H, m), 7.56 (2H, d, J=7.6 Hz). MS (ESI): m/z 455 (M+H)$^+$.

Example 71

2-[3,5-Difluoro-4-(2,2,2-trifluoro-1,1-dimethylethyl)phenyl]-2-methyl-N-((1R)-1-{3-methyl-4-[(methylsulfonyl)amino]phenyl}ethyl)cyclopropanecarboxamide

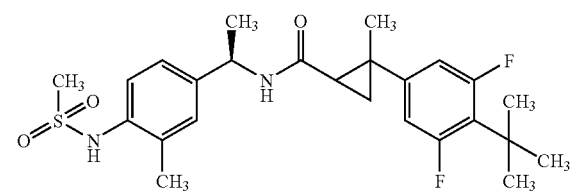

71A) 1,3-Difluoro-5-isopropenyl-2-(2,2,2-trifluoro-1,1-dimethylethyl)benzene

The procedure described in Example 10B was followed using a mixture of the compound of Example 30E (3.37 g, 9.05 mmol), potassium isopropenyltrifluoroborate (2.0 g, 13.6 mmol, Org. Lett. 2002, 4, 107), PdCl$_2$(dppf)·CH$_2$Cl$_2$ (370 mg, 0.45 mmol) and triethylamine (1.9 ml, 13.6 mmol) in n-propanol (90 ml). The crude residue was applied to a silica gel chromatography column and eluted with a volume mixture of hexane and ethylacetate (30:1) to afford the title compound (1.67 g, 70% yield) as a colorless oil.

$^1$H NMR (300 MHz, CDCl$_3$) δ 1.72-1.78 (6H, m), 2.10 (3H, s), 5.19 (1H, s), 5.43 (1H, s), 6.93-6.72 (2H, m).

71B) Ethyl 2-[3,5-difluoro-4-(2,2,2-trifluoro-1,1-dimethylethyl)phenyl]-2-methylcyclopropanecarboxylate To a solution of the compound of Example 71A (1.67 g, 6.32 mmol) in toluene (10 ml), Co(TPP) (127 mg, 0.19 mmol) and 1-methyl-1H-imidazole (2.6 g, 31.6 mmol), ethyl diazoacetate (1.0 g, 8.85 mmol) were added according to the procedure described in Example 2H. The reaction was quenched with 1M aqueous HCl solution and extracted with hexane. The organic layer was dried over sodium sulfate. Then filtration and evaporation gave the crude residue, which was dissolved in small amount of hexane and cooled to 0° C. The resulting precipitates were removed by filtration and the filtrate was concentrated under reduced pressure to afford the title compound (crude 1.95 g) as a black oil.

$^1$H NMR (300 MHz, CDCl$_3$) δ 0.89-1.96 (15H, m), 4.15-4.25 (2H, m), 6.75-6.84 (2H, m).

71C) 2-[3,5-Difluoro-4-(2,2,2-trifluoro-1,1-dimethylethyl)phenyl]-2-methylcyclopropanecarboxylic acid The procedure described in example 21 was followed using a solution of the crude compound of Example 71B (1.95 g) in THF (6 ml)—MeOH (6 ml) and 2M aqueous sodium hydroxide solution (6 ml) to afford the title compound (886 mg, 44% yield in 2 steps, trans) as grey solids.

$^1$H NMR (300 MHz, CDCl$_3$) δ 0.85-2.00 (12H, m), 6.77-6.84 (2H, m). MS (ESI) m/z 321 (M−H)$^−$.

71D) 2-[3,5-Difluoro-4-(2,2,2-trifluoro-1,1-dimethylethyl) phenyl]-2-methyl-N-((1R)-1-{3-methyl-4-[(methylsulfonyl) amino]phenyl}ethyl)cyclopropanecarboxamide (single isomer)

The procedure described in Example 14D was followed using a DMF (2 ml) solution of the compound of Example 71C (100 mg, 0.31 mmol), HBTU (141 mg, 0.37 mmol), triethylamine (0.13 ml) and the compound of Example 2D (82 mg, 0.31 mmol). The crude residue was applied to a silica gel chromatography column and eluted with a volume mixture of hexane and EtOAc (1:1). HPLC (used column was XTerra MS C18, 5 um, 30×50 mm) to separate the diastereomers eluting with acetonitrile/0.05% formic acid aqueous solution (32:68 to 68:32, later fraction as the title compound) gave the title compound (single isomer; 45 mg, 27% yield) as white solids.

$^1$H NMR (300 MHz, CDCl$_3$) δ 1.34 (1H, dd, J=5.0, 8.3 Hz), 1.48 (3H, d, J=7.3 Hz), 1.51 (3H, s), 1.50-1.68 (2H, m), 1.70-1.75 (6H, m), 2.31 (3H, s), 3.01 (3H, s), 5.05-5.15 (1H, m), 5.87 (1H, d, J=7.3 Hz), 6.15 (1H, s), 6.69-6.77 (2H, m), 7.17-7.21 (2H, m), 7.41 (1H, d, J=8.6 Hz) MS (ESI): m/z 533 (M+H)+.

Example 72

2-[3,5-Difluoro-4-(2,2,2-trifluoro-1,1-dimethylethyl) phenyl]-N-((1R)-1-{3-ethyl-4-[(methylsulfonyl) amino]phenyl}ethyl)-2-methylcyclopropanecarboxamide (single isomer)

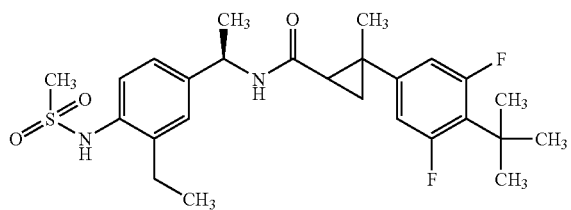

To a DMF (2 ml) solution of the compound of Example 71C (100 mg, 0.31 mmol), HBTU (141 mg, 0.37 mmol), triethylamine (0.13 ml) and the compound of Example 32C (86 mg, 0.31 mmol) were added in the same procedure as described in Example 14D. The crude residue was applied to a silica gel chromatography column and eluted with a volume mixture of hexane and EtOAc (1:1) and HPLC (XTerra MS C18, 5 um, 30×50 mm) to separate the diastereomer, eluting with acetonitrile/0.05% formic acid aqueous solution (32:68 to 68:32, later fraction as the title compound), to afford the title compound (single isomer; 48 mg, 29% yield) as white solids.

$^1$H NMR (270 MHz, CDCl$_3$) δ 1.25 (3H, t, J=7.6 Hz), 1.34 (1H, dd, J=5.0, 8.3 Hz), 1.49 (3H, d, J=7.3 Hz), 1.52 (3H, s), 1.50-1.69 (2H, m), 1.70-1.75 (6H, m), 2.65 (2H, q, J=7.6 Hz), 3.02 (3H, s), 5.08-5.18 (1H, m), 5.84 (1H, d, J=7.9Hz), 6.14 (1H, s), 6.70-6.77 (2H, m), 7.16-7.22 (2H, m), 7.44 (1H, d, J=8.6 Hz). MS (ESI): m/z 547 (M+H)+.

Example 73

N-((1R)-1-{3,5-Difluoro-4-[(methylsulfonyl)amino] phenyl}ethyl)-2-[3-fluoro-4-(trifluoromethyl)phenyl]-2-methylcyclopropanecarboxamide

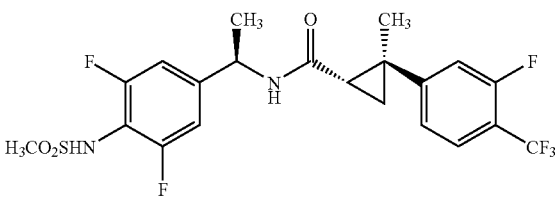

To a solution of the compound of Example 61D (170 mg, 0.59 mmol) in DMF (10 ml) were added the compound of Example 66C (155 mg, 0.591 mmol), HBTU (338 mg, 0.89 mmol) and triethylamine (0.25 ml, 1.78 mmol) at room temperature. The same procedure as described in Example 60E was performed to afford the title compound (50 mg, 17%) as white solids.

$^1$H-NMR (270 MHz, DMSO-d$_6$) δ 1.33-1.43 (8H, m), 2.04-2.10 (1H, m), 3.05 (3H, s), 4.93-4.99 (1H, m), 7.15 (2H, d, J=8.6 Hz), 7.36 (1H, d, J=7.9 Hz), 7.46 (1H, d, J=12.5 Hz), 7.73 (1H, t, J=8.2 Hz), 8.70 (1H, d, J=7.3 Hz), 9.50 (1H, s). MS (ESI) m/z 495 (M+H)+, 493 (M−H)−. [α]$_D$=+89.5 (c=0.50, methanol, cell temperature=21.4° C.)

Example 74

N-((1R)-1-{3,5-Difluoro-4-[(methylsulfonyl)amino] phenyl}ethyl)-2-[3-fluoro-4-(trifluoromethyl)phenyl]-2-methylcyclopropanecarboxamide

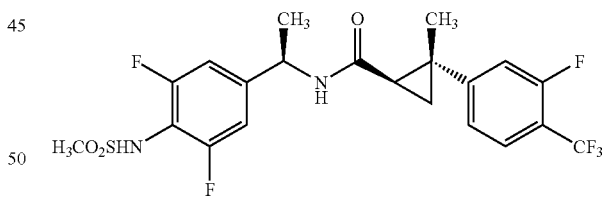

To a solution of the compound of Example 61D (170 mg, 0.59 mmol) in DMF (10 ml) were added the compound of Example 66C (155 mg, 0.591 mmol), HBTU (338 mg, 0.89 mmol) and triethylamine (0.25 ml, 1.78 mmol) at room temperature. The same procedure as described in Example 60E was performed to afford the title compound (45 mg, 15%) as white solids.

$^1$H-NMR (270 MHz, DMSO-d$_6$) δ 1.32-1.43 (8H, m), 2.07-2.12 (1H, m), 3.05 (3H, s), 4.91-4.97 (1H, m), 7.14 (2H, d, J=8.6Hz), 7.38 (1H, d, J=7.3Hz), 7.49 (1H, d, J=13.2Hz), 7.74 (1H, t, J=7.9Hz), 8.73 (1H, d, J=7.3 Hz), 9.48 (1H, s). MS (ESI) m/z 495 (M+H)+, 493 (M−H)−. [α]$_D$=−138.7 (c=0.50, methanol, cell temperature=21.4° C.)

Example 75

N-((1R)-1-{3-Ethyl-4-[(methylsulfonyl)amino]phenyl}ethyl)-2-methyl-2-[4-(trifluoromethoxy)phenyl]cyclopropanecarboxamide (single isomer)

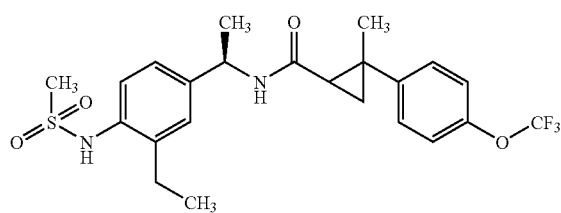

The mixture of diastereomer compounds of Example 29 were separated by HPLC (XTerra MS C18, 5 um, 30×50 mm), eluting with acetonitrile/0.05% formic acid aqueous solution (32:68 to 68:32, later fraction as the title compound), to afford the title compound (single isomer) as white solids.

$^1$H NMR (270 MHz, CDCl$_3$) δ 1.25 (3H, t, J=7.6 Hz), 1.35 (1H, dd, J=4.9, 8.2 Hz), 1.51 (3H, d, J=6.6 Hz), 1.54 (3H ,s), 1.51-1.58 (1H, m), 1.67 (1H, dd, J=5.9, 8.6 Hz), 2.65 (2H, q, J=7.6 Hz), 3.02 (3H, s), 5.10-5.20 (1H, m), 5.87 (1H, d, J=7.9 Hz), 6.18 (1H, s), 7.14-7.30 (6H, m), 7.44 (1H, d, J=7.9 Hz). MS (ESI) : m/z 485 (M+H)+.

Example 76

2-(4-tert-Butyl-3,5-difluorophenyl)-N-((1R)-1-{3-methyl-4-[(methylsulfonyl)amino]phenyl}propyl)cyclopropanecarboxamide

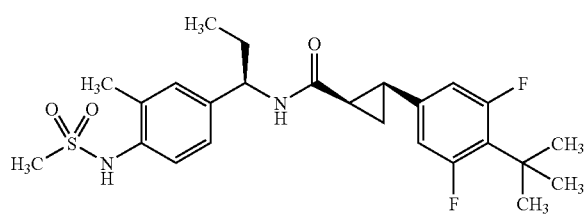

To a DMF (10 ml) solution of the compound of Example 34C (219 mg, 0.8 mmol), the compound of Example 38D (200 mg, 0.8 mmol), HBTU (390 mg, 1.0 mmol) and triethylamine (0.3 ml, 2.4 mmol) were added and the mixture was stirred for 2 hours at room temperature. The same procedure as described in Example 38E was performed to give the title compound (101 mg, 27%). The fraction time for the desired product was 5.1 min.

$^1$H NMR (300 MHz, DMSO-d$_6$) δ 1.11-1.76 (15H, m), 1.88-2.39 (6H, m), 2.96 (3H, s), 4.54-4.83 (1H, m), 6.72-6.93 (2H, m), 7.03-7.28 (3H, m), 8.41-8.59 (1H, m), 9.03 (1H, brs). MS (ESI) m/z 477 (M−H)−, 479 (M+H)+.

Example 77

N-((1R)-1-{3-Fluoro-4-[(methylsulfonyl)amino]phenyl}ethyl)-2-methyl-2-[4-(2,2,2-trifluoro-1,1-dimethylethyl)phenyl]cyclopropanecarboxamide (single isomer)

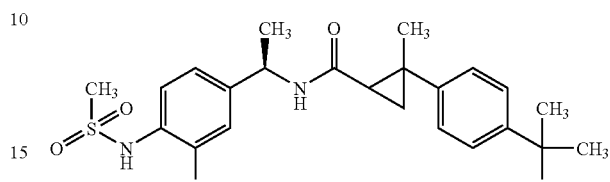

To a DMF (3 ml) solution of the compound of Example 13D (200 mg, 0.7 mmol), HBTU (319 mg, 0.84 mmol), triethylamine (0.29 ml) and N-{4-[(1R)-1-aminoethyl]-2-fluorophenyl}methanesulfonamide hydrochloride (188 mg, 0.7 mmol) were added in the same procedure as described in Example 14D. The crude residue was applied to a silica gel chromatography column and eluted with a volume mixture of hexane and EtOAc (1:1) to afford the title compound (single isomer; 176 mg, 50% yield) as white solids.

$^1$H NMR (270 MHz, CDCl$_3$) δ 1.40 (1H, dd, J=4.6, 7.9 Hz), 1.48 (3H, d, J=7.3 Hz), 1.49-1.60 (10H ,m), 1.70 (1H, dd, J=5.9, 7.9 Hz), 3.02 (3H, s), 5.07-5.17 (1H, m), 5.87 (1H, d, J=7.3 Hz), 6.47 (1H, s), 7.10-7.16 (2H, m), 7.21-7.26 (2H, m), 7.44 (2H, d, J=8.6 Hz), 7.50-7.56 (1H, m). MS (ESI): m/z 501 (M+H)+.

Example 78

2-(4-tert-Butyl-3,5-difluorophenyl)-N-((1R)-1-{2-fluoro-5-methyl-4-[(methylsulfonyl)amino]phenyl}ethyl)-2-methylcyclopropanecarboxamide

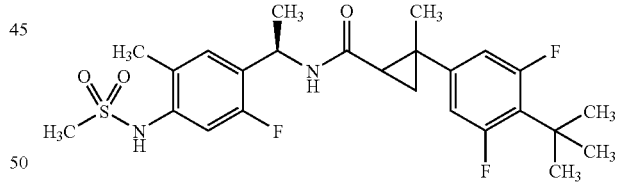

To a DMF (7 ml) solution of the compound of Example 41D (100 mg, 0.4 mmol), the compound of Example 43C (95 mg, 0.4 mmol), HBTU (173 mg, 0.5 mmol) and trimethylamine (0.2 ml, 1.1 mmol) were added and the mixture was stirred for 2 hours at room temperature. The whole was extracted with ethyl acetate, evaporated, and purified through silica gel column chromatography eluting with dichloromethane/ethyl acetate (1:1) to give the title compound (56 mg, 32%).

$^1$H NMR (300 MHz, DMSO-d$_6$) δ 1.19-1.47 (17H, m), 1.80-2.08 (1H, m), 2.20-2.31 (3H, m), 2.96-3.08 (3H, m), 4.80-5.20 (1H, m), 6.64-7.28 (4H, m), 7.37 (0.5H, brs), 8.64 (1H, d, J=7.3 Hz), 9.22 (0.5H, brs). MS (ESI) m/z 495 (M−H)−, 497 (M+H)+.

Example 79

2-[2-(Dimethylamino)-6-(trifluoromethyl)pyridin-3-yl]-N-((1R)-1-{2-fluoro-5-methyl-4-[(methylsulfonyl)amino]phenyl}ethyl)cyclopropanecarboxamide

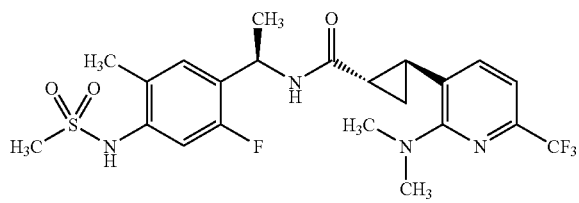

79A) 2-(Dimethylamino)-6-(trifluoromethyl)nicotinic acid

A mixture of 2-chloro-6-(trifluoromethyl)nicotinic acid (APOLLO, 2.5 g, 11.1 mmol) and 2M N-methylmethanamine in THF solvent (50 ml, 25 mmol) was stirred for 24 hours at room temperature according to J. Med. Chem., 2005, 48, 71. Then the reaction mixture was evaporated in vacuo to give the title compound (2.5 g, 96%).

$^1$H NMR (270 MHz, DMSO-d$_6$) δ 2.99 (6H, s), 7.07 (1H, d, J=7.3 Hz), 8.03 (1H, d, J=7.3 Hz). MS (ESI) m/z 233 (M−H)$^−$, 235 (M+H)$^+$.

79B) [2-(Dimethylamino)-6-(trifluoromethyl)pyridin-3-yl]methanol

To a THF (40 ml) of lithium aluminum tetrahydroride [spelling?] (1.0 g, 26.8 mmol), a THF (10 ml) solution of the compound of Example 79A (2.5 g, 10.7 mmol) was added at 0° C. and the mixture was stirred for 5 minutes at 0° C. followed by additional stirring for 4.5 hours at 65° C. The reaction mixture was cooled to 0° C. and partitioned with 10% potassium sodium tartrate tetrahydrate aqueous solution and EtOAc, and the mixture was stirred for 2 hours at room temperature. To the mixture was added water and the organic layer was extracted, washed with 2M sodium hydroxide aqueous solution and brine, and evaporated. The residue was purified by silica gel column chromatography, eluting with hexane/EtOAc (4:1), to give the title compound (1.26 g, 54%).

$^1$H NMR (300 MHz, CDCl$_3$) δ 2.92 (6H, s), 4.26 (2H, s), 7.23 (1H, d, J=8.1 Hz), 7.76 (1H, d, J=8.1 Hz). MS (ESI) m/z 221 (M+H)$^+$.

79C) 2-(Dimethylamino)-6-(trifluoromethyl)nicotinaldehyde

To a DCM (17 ml) solution of ethanedioyl dichloride (1.5 ml, 11.4 ml) was added dimethyl sulfoxide (1.3 ml, 17.2 mmol) at −78° C. and the mixture was stirred for 15 minutes at −78° C. Then to the mixture was slowly added a DCM solution of the compound of Example 79B (1.3 g, 5.7 mmol) at −78° C. and the mixture was stirred for 30 minutes followed by addition of triethylamine (5.8 ml, 57.2 mmol) and stirring for 30 minutes at −78° C. The reaction temperature was allowed to warm to room temperature and stirred for 1 hour. Then the reaction was quenched with water and extracted with EtOAc, dried over magnesium sulfate, and the solvent evaporated. The crude residue was purified by silica gel column chromatography, eluting with hexane/EtOAc (7:1), to give the title compound (1.0 g, 83%).

$^1$H NMR (300 MHz, CDCl$_3$) δ 3.14-3.19 (6H, m), 7.02-7.11 (1H, m), 8.03-8.12 (1H, m), 8.03-8.12 (1H, m), 9.97-10.0 (1H, m).

79D) 2-[2-(Dimethylamino)-6-(trifluoromethyl)pyridin-3-yl]cyclopropanecarboxylic acid To a THF (20 ml) suspension of methyltriphenylphosphonium bromide (3.3 g, 9.2 mmol) was added 1.60 M n-butyllithium in hexane solution (5.7 ml, 9.2 mmol) at 0° C. and the reaction was stirred for 30 minutes. Then to the mixture was added a THF (5 ml) solution of the compound of Example 79C (1.0 g, 4.6 mmol) at room temperature, and the reaction was stirred for 1 hour at room temperature. The reaction was quenched with saturated ammonium chloride aqueous solution, and the whole was extracted with EtOAc, dried over magnesium sulfate, and evaporated. The crude residue was purified by silica gel column chromatography, eluting with hexane/EtOAc (10:1), to give N,N-dimethyl-6-(trifluoromethyl)-3-vinylpyridin-2-amine (847 mg, 86%, trans). To a toluene (15 ml) solution of this (840 mg, 3.9 mmol), Co(TPP) (78 mg, 0.1 mmol) and 1-methyl-1H-imidazole (1.00 ml, 11.7 mmol), ethyl diazoacetate (0.7 ml, 5.8 mmol) was added and the mixture was stirred for 5 minutes at room temperature followed by additional stirring for 2 hours at 80° C. Then, evaporation and purification by silica gel column chromatography, eluting with hexane/EtOAc (20:1), gave ethyl 2-[2-(dimethylamino)-6-(trifluoromethyl)pyridin-3-yl]cyclopropanecarboxylate (427 mg, 36%). To a THF (5 ml) solution of this compound (427 mg, 1.4 mmol), 2M sodium hydroxide aqueous solution (7 ml) and MeOH (7 ml) were added and the mixture was stirred for 2 hours at room temperature. After the reaction was completed, the aqueous layer was extracted and acidified with 2M HCl aqueous solution. The whole was extracted with EtOAc followed by evaporation of the solvent to give the title compound (260 mg, 67%).

MS (ESI) m/z 273 (M−H)$^−$, 275 (M+H)$^+$.

79E) 2-[2-(Dimethylamino)-6-(trifluoromethyl)pyridin-3-yl]-N-((1R)-1-{2-fluoro-5-methyl-4-[(methylsulfonyl)amino]phenyl}ethyl)cyclopropanecarboxamide To a DMF (10 ml) solution of the compound of Example 41D (130 mg, 0.5 mmol), the compound of Example 79D (226 mg, 0.5 mmol), HBTU (227 mg, 0.6 mmol) and trimethylamine (0.3 ml, 1.4 mmol) were added and the mixture was stirred for 2 hours at room temperature. The same procedure as described in Example 38E was followed, but using HPLC conditions of acetonitrile/0.05% aqueous formic acid 4 to 96, to give the title compound (10 mg, 4%). The fraction time for the desired product was 4.2 min.

$^1$H NMR (300 MHz, DMSO-d$_6$) δ 1.26-1.43 (5H, m), 1.93-2.04 (1H, m), 2.18-2.35 (4H, m), 2.92 (6H, s), 2.96 (3H, s), 5.06-5.21 (1H, m), 7.05 (1H, d, J=12.5 Hz), 7.23 (2H, dd, J=15.8, 7.7 Hz), 7.50 (1H, d, J=7.3 Hz), 8.67 (1H, d, J=7.3 Hz). H for OH could not be observed. MS (ESI) m/z 501 (M−H)$^−$, 503 (M+H)$^+$.

Example 80

N-((1R)-1-{3,5-Difluoro-4-[(methylsulfonyl)amino]phenyl}ethyl)-2-[3,5-difluoro-4-(2,2,2-trifluoro-1,1-dimethylethyl)phenyl]-2-methylcyclopropanecarboxamide

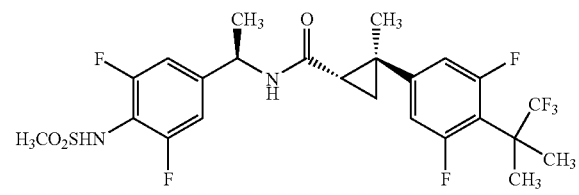

To a solution of the compound of Example 61D (170 mg, 0.59 mmol) in DMF (10 ml) was added the compound of Example 71C (155 mg, 0.591 mmol), HBTU (338 mg, 0.89 mmol) and triethylamine (0.25 ml, 1.78 mmol) at room temperature. The same procedure described in Example 60E was performed to afford the title compound (50 mg, 17% yield) as white solids.

$^1$H-NMR (270 MHz, DMSO-$d_6$) δ 1.33-1.43 (8H, m), 2.04-2.10 (1H, m), 3.05 (3H, s), 4.93-4.99 (1H, m), 7.15 (2H, d, J=8.6Hz), 7.36 (1H, d, J=7.9Hz), 7.46 (1H, d, J=12.5Hz), 7.73 (1H, t, J=8.2Hz), 8.70 (1H, d, J=7.3 Hz), 9.50 (1H, s). MS (ESI) m/z 495 (M+H)$^+$, 493 (M−H)$^−$. [α]$_D$=+78.2 (c=0.56, methanol, cell temperature=21.4° C.)

Example 81

N-((1R)-1-{3,5-Difluoro-4-[(methylsulfonyl)amino] phenyl}ethyl)-2-methyl-2-{4-[(trifluoromethyl)oxy] phenyl}cyclopropanecarboxamide

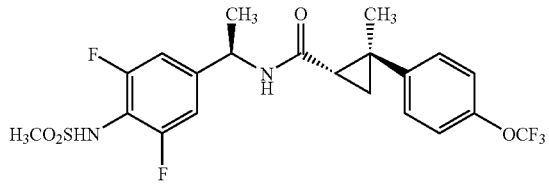

To a solution of the compound of Example 61D (170 mg, 0.59 mmol) in DMF (10 ml) were added the compound of Example 16C (154 mg, 0.59 mmol), HBTU (338 mg, 0.89 mmol) and triethylamine (0.25 ml, 1.78 mmol) at room temperature. The same procedure as described in Example 60E was performed to give the title compound (22 mg, 8%) as white solids.

$^1$H-NMR (270 MHz, DMSO-$d_6$) δ 1.25-1.41 (8H, m), 1.95-2.010 (1H, m), 3.05 (3H, s), 4.92-5.01 (1H, m), 7.15 (2H, d, J=8.6 Hz), 7.32 (2H, d, J=7.9 Hz), 7.45 (2H, d, J=8.6 Hz), 7.45 (2H, d, J=8.6 Hz), 8.69 (1H, d, J=7.9 Hz), 9.49 (1H, s). MS (ESI) m/z 493 (M+H)$^+$, 491 (M−H)$^−$. [α]$_D$=+81.6 (c=0.50, methanol, cell temperature=21.4° C.)

Example 82

(1S,2S)-2-Methyl-N-((1S)-1-{3-methyl-4-[(methylsulfonyl)amino]phenyl}ethyl)-2-[4-(trifluoromethyl) phenyl]cyclopropanecarboxamide

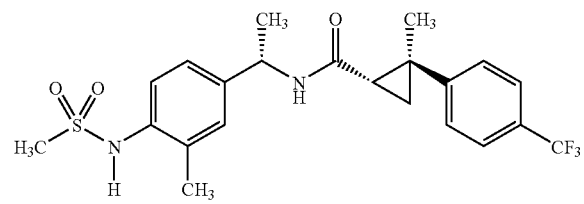

82A) N-[4-((1S)-1-{[(S)-tert-Butylsulfinyl]amino}ethyl)-2-methylphenyl]methanesulfonamide To a mixture of the compound of Example 2B (1.6 g, 7.0 mmol), titanium (IV) ethoxide (10 ml) and THF (10 ml) was added (S)-(−)-2-methylpropane-2-sulfinamide (846 mg, 7.0 mmol, purchased from Advanced Asymmmetry) and the mixture was stirred for 16 hours at 80° C. The mixture was cooled to room temperature and then to 0° C. before it was added dropwise into a 0° C. solution of sodium borohydride (1.1 g, 28 mmol). The mixture was stirred at 0° C. for 3 hours and then warmed to room temperature. The reaction was quenched with MeOH and stirred for 30 minutes. Water was added and the mixture was stirred for 10 minutes. The resulting suspension was filtered through a celite pad and the filter cake was washed with EtOAc. The filtrate was concentrated under reduced pressure to give the residue, which was applied to a silica gel chromatography column and eluted with a volume mixture of DCM and EtOAc (1/1) to afford 1.76 g (76% yield) of the title compound as pale yellow solids.

MS (ESI) m/z 391 [M+H]$^+$, 389 [M−H]$^−$.

82B) N-{4-[(1S)-1-Aminoethyl]-2-methylphenyl}methanesulfonamide

To a solution of the compound of Example 82A (1.7 g, 5.3 mmol) in methanol (30 ml) was added 10% hydrogenchloride-MeOH solution (30 ml). The solution was stirred at room temperature for 30 min and then concentrated under reduced pressure. The resulting residue was recrystallized from MeOH—diethyl ether. The precipitates were then filtered, washed with diethyl ether and collected to afford 1.2 g (64% yield) of the title compound as white solids.

MS (ESI) m/z 227 [M−H]$^−$.

82C) (1S,2S)-2-Methyl-N-((1S)-1-{3-methyl-4-[(methylsulfonyl)amino]phenyl}ethyl)-2-[4-(trifluoromethyl)phenyl]cyclopropanecarboxamide To a stirred solution of the compound of Example 82B (76 mg, 0.29 mmol), the compound of Example 14C (70 mg, 0.29 mmol) and HBTU (131 mg, 0.34 mmol) in anhydrous DMF (2 ml) was added triethylamine (87 mg, 0.86 mmol) at ambient temperature. The same procedure as described in Example 14D was performed to give the singleisomer product of the title compound (112 mg, 86%) as white solids.

$^1$H NMR (270 MHz, CDCl$_3$) δ 1.37-1.61 (8H, m), 1.71-1.79 (1H, m), 2.32 (3H, s), 3.02 (3H, s), 5.06-5.19 (1H, m), 5.88-5.96 (1H, m), 6.30 (1H, br.s), 7.15-7.21 (2H, m), 7.32-7.44 (3H, m), 7.53-7.59 (2H, m). MS (ESI): m/z 453 (M−H)$^−$, m/z 455 (M+H)$^+$. [α]$_D$=+151.1 (c=0.48, methanol, cell temperature=21.0° C.)

Example 83

N-((1R)-1-{3,5-Difluoro-4-[(methylsulfonyl)amino] phenyl}ethyl)-2-[3,5-difluoro-4-(2,2,2-trifluoro-1,1-dimethylethyl)phenyl]-2-methylcyclopropanecarboxamide

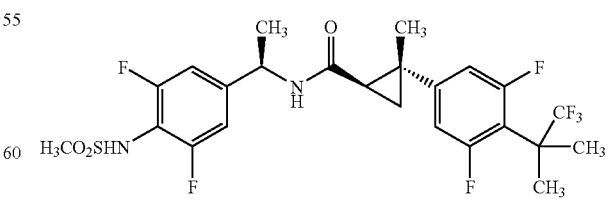

To a solution of the compound of Example 61D (170 mg, 0.59 mmol) in DMF (10 ml) were added the compound of Example 71C (155 mg, 0.591 mmol), HBTU (338 mg, 0.89 mmol) and triethylamine (0.25 ml, 1.78 mmol) at room temperature. The same procedure as described in Example 60E was performed to afford the title compound (45 mg, 15%) as white solids.

$^1$H-NMR (270 MHz, DMSO-$d_6$) δ 1.32-1.43 (8H, m), 2.07-2.12 (1H, m), 3.05 (3H, s), 4.91-4.97 (1H, m), 7.14 (2H, d, J=8.6 Hz), 7.38 (1H, d, J=7.3Hz), 7.49 (1H, d, J=13.2 Hz), 7.74 (1H, t, J=7.9 Hz), 8.73 (1H, d, J=7.3 Hz), 9.48 (1H, s). MS (ESI) m/z 495 (M+H)$^+$, 493 (M−H)$^−$. [α]$_D$=−155.0 (c=0.56, methanol, cell temperature=21.4° C.)

Example 84

2-Methyl-N-((1R)-1-{3-methyl-4-[(methylsulfonyl) amino]phenyl}ethyl)-2-[2-morpholin-4-yl-6-(trifluoromethyl)pyridin-3-yl]cyclopropanecarboxamide

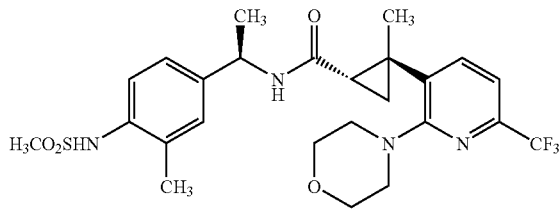

84A) 1-[2-Morpholin-4-yl-6-(trifluoromethyl)pyridin-3-yl] ethanol

To a diethylether (7.0 ml) solution of 2-morpholin-4-yl-6-(trifluoromethyl)pyridine-3-carbaldehyde (Jornal of Medicinal Chemistry, 2005, 48, p 71-90, 0.88 g, 3.4 mmol) was added THF solution of methylmagnesiumchloride (3.0M, 1.36 ml) at 0° C. and the mixture was stirred for 0.5 h. The same procedure as described in Example 9C was performed to give the title compound as a colorless oil (quant. 0.9 g).

84B) 1-[2-Morpholin-4-yl-6-(trifluoromethyl)pyridin-3-yl] ethanone

To a methylene chloride (15 ml) solution of oxalyl chloride (647 mg, 5.1 mmol) was added DMSO (797 mg, 10.2 mmol) at −78° C. and the mixture was stirred for 15 minutes at −78° C. and then, to this reaction was added the compound of Example 84A (1.3 g, 12.6 mmol). The mixture was stirred for 1 hour at room temperature and the reaction was quenched with water. The crude residue was extracted with methylene dichloride and the organic layer was dried over magnesium sulfate. Then, filtration and purification by silica-gel column chromatography column and eluted with hexame/EtOAc (4:1) gave the title compound as a colorless oil (700 mg, 75%).

$^1$H NMR (CDCl$_3$, 270 MHz) δ ppm 2.59 (3H, s), 3.41-3.45 (4H, m), 3.78-3.84 (4H, m), 7.17 (1H, d, J=8.1 Hz), 7.84 (1H, d, J=8.1 Hz). MS (ESI): m/z 275 (M+H)$^+$.

84C) 4-[3-(1-Methylethenyl)-6-(trifluoromethyl)pyridin-2-yl]morpholine

To a THF (5 ml) solution of the compound of Example 84B (650 mg, 2.37 mmol) was added a toluene solution of μ-chlorobis(cyclopentadienyl)(dimethylaluminum)-μ-methylenetitanium (0.5N, 4.8 ml) at 0° C. and the mixture was stirred for 1 hour at 0° C. and then, to this reaction was added water (0.1 ml) and 2N sodium hydroxide aqueous solution (0.2 ml). Magnesium sulfate was added to the reaction and the mixture was filtered. The solvent was evaporated to give the crude residue which was purified by silica gel chromatography column and eluted with hexame/EtOAc (6:1) to give the title compound as a colorless oil (160 mg, 24%).

$^1$H NMR (CDCl$_3$, 270 MHz) δ ppm 2.11 (3H, s), 3.32-3.45 (4H, m), 3.76-3.84 (4H, m), 5.17-5.22 (2H, m), 7.15 (1H, d, J=8.1 Hz), 7.48 (1H, d, J=8.1 Hz).

84D) Ethyl 2-methyl-2-[2-morpholin-4-yl-6-(trifluoromethyl)pyridin-3-yl]cyclopropanecarboxylate The same procedure as described in Example 2H was performed, using the compound of Example 84C (280 mg, 1.0 mmol) instead of the compound of Example 2G, to give the title compound as a colorless oil (76 mg, 21%).

$^1$H NMR (CDCl$_3$, 270 MHz) δ ppm 1.33 (3H, t, J=8.1 Hz), 1.46-1.53 (1H, m), 1.58-1.64 (5H, m), 3.32-3.52 (4H, m), 3.84-3.89 (4H, m), 4.23 (2H, q, J=8.1 Hz), 7.20 (1H, d, J=8.1 Hz), 7.75 (1H, d, J=8.1 Hz). MS (ESI): m/z 359 (M+H)$^+$.

84E) 2-Methyl-2-[2-morpholin-4-yl-6-(trifluoromethyl)pyridin-3-yl]cyclopropanecarboxylic acid The same procedure as described in Example 2H was performed, using the compound of Example 84D (76 mg, 0.2 mmol) instead of that of Example 2H, to give the title compound as white solids (60 mg, 86%).

MS (ESI) : m/z 331 (M+H)$^+$.

84F) 2-Methyl-N-((1R)-1-{3-methyl-4-[(methylsulfonyl) amino]phenyl}ethyl)-2-[2-morpholin-4-yl-6-(trifluoromethyl)pyridin-3-yl]cyclopropanecarboxamide The same procedure as described in Example 7B was performed, using the compound of Example 84E (60 mg, 0.18 mmol) instead of that of Example 7A, to give the title compound as a white oil (17 mg, 17%).

$^1$H NMR (CDCl$_3$, 300 MHz) δ ppm 1.26 (1H, t, J=7.4 Hz), 1.44-1.70 (6H, m), 2.33 (3H, d, J=7.3 Hz), 3.03 (3H, d, J=5.9 Hz), 3.33-3.45 (4H, m), 3.72-3.88 (4H, m), 5.13-5.18 (1H, m), 5.93-6.00 (1H, m), 6.32 (1H, d, J=7.4 Hz), 7.17-7.27 (3H, m), 7.40-7.47 (1H, m), 7.68-7.74 (1H, m). MS (ESI): m/z 539 (M−H)$^−$.

Example 85

2-{4-[1,1-Dimethyl-2-(methyloxy)ethyl]-3-fluorophenyl}-2-methyl-N-((1R)-1-{3-methyl-4-[(methylsulfonyl)amino]phenyl}ethyl)cyclopropanecarboxamide

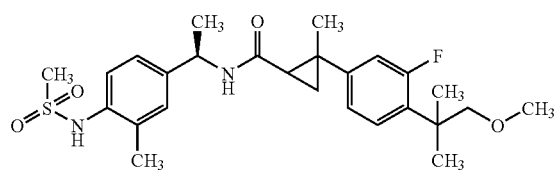

85A) 2-(4-Bromo-2-fluorophenyl)-2-methylpropyl methyl ether

To a DMF (4 ml) solution of 2-(4-bromo-2-fluorophenyl)-2-methylpropan-1-ol (199 mg, 0.8 mmol, WO2004074270A2) was added 60% sodium hydride (35 mg, 0.88 mmol) at 0° C. and the mixture was stirred at 0° C. for 15 minutes followed by additional stirring for 1 hour at room temperature. After the mixture was cooled to 0° C., methyliodide (342 mg, 2.4 mmol) was added and the mixture was stirred for 30 minutes at 0° C. followed by additional stirring for 16 hours at room temperature. Then, the reaction was quenched with water and the whole was extracted with EtOAc, which was dried over sodium sulfate. Then, filtration, evaporation and purification by silica gel column chromatography, eluting with hexane/EtOAc (20:1), gave the title compound (174 mg, 83% yield) as a colorless oil.

$^1$H NMR (300 MHz, CDCl$_3$) δ 1.35 (6H, m), 3.31 (3H, s), 3.51 (2H, s), 7.12-7.25 (3H, m).

85B) 1-[1,1-Dimethyl-2-(methyloxy)ethyl]-2-fluoro-4-(1-methylethenyl)benzene

The procedure described in Example 10B was followed using a mixture of the compound of Example 85A (174 mg, 0.67 mmol), potassium isopropenyltrifluoroborate (118 mg, 0.8 mmol, Org. Lett. 2002, 4, 107), PdCl$_2$(dppf).CH$_2$Cl$_2$ (27 mg, 0.033 mmol) and triethylamine (0.11 ml, 0.8 mmol) in n-propanol (7 ml). The crude residue was applied to a silica gel chromatography column and eluted with a volume mixture of hexane and ethylacetate (30:1) to afford the title compound (58 mg, 39% yield) as a brown oil.

$^1$H NMR (300 MHz, CDCl$_3$) δ 1.37 (6H, m), 2.11 (3H, s), 3.32 (3H, s), 3.54 (2H, s), 5.08 (1H, s), 5.37 (1H, s), 7.08-7.27 (3H, m).

85C) 2-{4-[1,1-Dimethyl-2-(methyloxy)ethyl-3-fluorophenyl}-2-methylcyclopropanecarboxylic acid To a toluene (1 ml) solution of the compound of Example 85B (58 mg, 0.26 mmol), Co(TPP) (14 mg, 0.021 mmol) and 1-methyl-1H-imidazole (172 mg, 2.1 mmol), ethyl diazoacetate (112 mg, 0.98 mmol) was added in the same procedure as described in Example 2H. The reaction mixture was applied to a silica gel chromatography column and eluted with a volume mixture of hexane and EtOAc (30:1) to afford the crude ethyl ester as a black oil, which was diluted in MeOH (3 ml), THF (3 ml) and 2M sodium hydroxide aqueous solution (1 ml) and the mixture was treated with the same procedure as described in Example 21 to afford the title compound (21 mg, 11% yield in 2 steps) as a black oil.

$^1$H NMR (300 MHz, CDCl$_3$) δ 1.36 (6H, s), 1.22-1.58 (5H, m), 1.93-1.98 (1H, m), 3.32 (3H, s), 3.53 (2H, s), 6.90-7.04 (2H, m), 7.16-7.30 (1H, m). MS (ESI) m/z 279 (M−H)$^-$.

85D) 2-{4-[1,1-Dimethyl-2-(methyloxy)ethyl]-3-fluorophenyl}-2-methyl-N-((1R)-1-{3-methyl-4-[(methylsulfonyl)amino]phenyl}ethyl)cyclopropanecarboxamide To a DMF (0.5 ml) solution of the compound of Example 85C (20 mg, 0.07 mmol), triethylamine (0.03 ml), EDC (20 mg, 0.1 mmol), HOBt (12 mg, 0.078 mmol) and the amine compound of Example 2D (19 mg, 0.07 mmol) were added in the same procedure as described in Example 10E. The crude residue was applied to a silica gel chromatography column and eluted with a volume mixture of hexane and EtOAc (1:1) to afford the title compound (10 mg, 29% yield) as white solids (mixture of diastereomer products (1:1)).

$^1$H NMR (300 MHz, CDCl$_3$) δ 1.24-1.72 (15H, m), 2.31 (3H, s), 3.00 (3H, s), 3.30 (3H, s), 3.52 (2H, s), 5.04-5.17 (1H, m), 5.902-5.96 (1H, m), 6.34 (1H, rs), 6.82-6.98 (2H, m), 7.12-7.27 (3H, m), 7.40 (1H, d, J=7.3 Hz). MS (ESI): m/z 491 (M+H)+.

Example 86

(1S,2S)-N-((1R)-1-{3-(2-Hydroxyethyl)-4-[(methylsulfonyl)amino]phenyl}ethyl)-2-methyl-2-[4-(trifluoromethyl)phenyl]cyclopropanecarboxamide

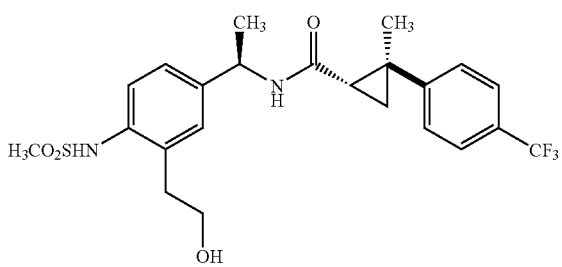

86A) 4-bromo-2-(2-{[(1,1-dimethylethyl)(dimethyl)silyl]oxy}ethyl)aniline

To a DMF (50 ml) solution of 1-Amino-2-[2-(tert-butyldimethylsilyloxy)ethyl]benzene (3.96 g, 0.015 mol) [European journal of organic chemistry, 2001, issue 48, 2447-2462] was added N-bromosuccinimide (2.67 g, 0.015 mol) and the mixture was stirred at ambient temperature for 24 hours. Then, the reaction was poured onto saturated aqueous sodium bicarbonate water and extracted with dichloromethane. The organic layer was dried over sodium sulfate, filtration and evaporation. The crude material was purified through silica gel column chromatography eluting with hexane/ethyl acetate (10:1 to 5:1) to afford 3.62 g (73% yield) of the title compound as brown oil.

$^1$H NMR (300 MHz, CDCl$_3$) δ −0.02 (6H, s), 0.86 (9H, s), 2.71 (2H, t, J=5.9 Hz), 3.85 (2H, t, J=5.9 Hz), 4.01 (2H, br s), 6.54 (1H, d, J=9.5 Hz), 7.08-7.15 (2H, m). MS (ESI) m/z 332 (M+H)$^+$.

86B) N-[4-Bromo-2-(2-{[(1.1-dimethylethyl)(dimethyl)silyl]oxy}ethyl)phenyl]methanesulfonamide To a dichloromethane (10 ml) solution of the compound of Example 86A (3.62 g, 0.011 mol) was added pyridine (2.66 ml, 0.0329 mol) and methanesulfonyl chloride (1.27 ml, 0.0164 mol) at 0° C., and the mixture was stirred at ambient temperature for 2 hours. Then, the reaction was quenched with 2 N HCl aqueous solution and the whole was extracted with ethyl acetate. The organic layer was washed with saturated aqueous sodium bicarbonate water and brine, which was dried over sodium sulfate, filtration and evaporation. The crude material was purified through silica gel column chromatography eluting with hexane/ethyl acetate (2:1 to 1:1) to afford 3.07 g (69% yield) of the title compound as green oil.

$^1$H NMR (300 MHz, CDCl$_3$) δ −0.02 (6H, s), 0.82 (9H, s), 2.85 (2H, t, J=5.3 Hz), 2.93 (3H, s), 3.86 (2H, t, J=5.9 Hz), 7.08-7.53 (3H, m), 8.48 (1H, d, J=4.0 Hz). MS (ESI) m/z 408 (M+H)$^+$.

86C) N-[4-Acetyl-2-(2-{[(1.1-dimethylethyl)(dimethyl)silyl]oxy}ethyl)phenyl]methanesulfonamide A mixture of the compound of Example 86B (3.07 g, 7.52 mmol), palladium (II) acetate (51 mg, 0.23 mmol), 1,3-bis(diphenylphosphino)propane (186 mg, 0.45 mmol), butyl vinyl ether (1.88 g, 18.79 mmol), and potassium carbonate (1.25 g, 9.02 mmol) in DMF (80 ml)—water (10 ml) was stirred at 80° C. for 20 hours. The reaction mixture was cooled to room temperature, diluted with toluene-ethyl acetate (2:1), washed with 2N HCl aqueous solution, water, saturated aqueous sodium bicarbonate water, water, and brine. The organic layer was dried over sodium sulfate, filtered off and the filtrate was concentrated in vacuo. The crude material was purified through silica gel column chromatography eluting with hexane/ethyl acetate (5:1 to 1:1) to afford 0.21 g (8% yield) of the title compound as brown syrup.

$^1$H NMR (270 MHz, CDCl$_3$) δ −0.05 (6H, s), 0.82 (9H, s), 2.54 (3H, s). 2.89 (2H, t, J=5.3 Hz), 2.98 (3H, s), 3.89 (2H, t, J=5.3 Hz), 7.59 (1H, d, J=7.9 Hz), 7.69-7.91 (2H, m), 8.88 (1H, br s). MS (ESI) m/z 372 (M+H)$^+$, 370 (M−H)$^+$.

86D) N-[2-(2-{[(1,1-Dimethylethyl)(dimethyl)silyl]oxy}ethyl)-4-((1R)-1-{[(R)-(1,1-dimethylethyl)sulfinyl]amino}ethyl)phenyl]methanesulfonamide A test tube for microwave was charged with the compound of Example 86C (0.21 g, 0.57 mmol), titanium(IV) ethoxide (2.5 ml), THF (2.5 ml) and (R)-(+)-2-methyl-2-propanesulfininamide (82 mg, 0.68 mmol). The mixture was subjected to microwave irradiation at 80° C. with stirring for 1.5 hours. Upon completion, as determined by LC-MS, the mixture was cooled to room temperature and then to 0° C. before it was added sodium borohydride (86 mg, 2.26 mmol) at 0° C. After stitting for 3 hours at ambient temperature, the reaction mixture was quenched with MeOH carefully, diluted with ethyl acetate, washed with 2N HCl aqueous solution, saturated aqueous sodium bicarbonate water, and brine. The organic layer was dried over sodium sulfate, filtered off and the filtrate was concentrated in vacuo. The crude material was purified through silica gel column chromatography eluting with hexane/ethyl acetate (1:1)-dichloromethane/methanol (10:1) to afford 46 mg (17% yield) of the title compound as brown syrup.

$^1$H NMR (270 MHz, CDCl$_3$) δ −0.02 (6H, s), 0.84 (9H, s), 1.48 (3H, d, J=6.6 Hz), 2.84 (2H, t, J=5.3 Hz), 2.96 (3H, s), 3.87 (2H, t, J=5.3 Hz), 4.40-4.55 (1H, m), 7.08-7.28 (2H, m), 7.47 (1H, d, J=8.6 Hz), 8.58 (1H, br s). MS (ESI) m/z 477 (M+H)$^+$, 475 (M−H)$^−$.

86E) N-[4-[(1R)-1-Aminoethyl]-2-(2-hydroxyethyl)phenyl]methanesulfonamide

To a solution of the compound of Example 86D (46 mg, 0.096 mmol) was added HCl-MeOH (2.0 M, 2 ml). The same procedure as Example 2D was performed to give the title compound (crude, 30 mg) in white solids. MS (ESI) m/z 257 (M−H)$^−$.

86F) (1S,2S)-N-((1R)-1-{3-(2-Hydroxyethyl)-4-[(methylsulfonyl)amino]phenyl}ethyl)-2-methyl-2-[4-(trifluoromethyl)phenyl]cyclopropanecarboxamide To a DMF (2 ml) solution of the carboxylic acid compound of Example 14C (24 mg, 0.096 mmol), HBTU (44 mg, 0.116 mmol), triethylamine (0.054 ml, 0.385 mmol) and the amine compound of Example 86E (crude 30 mg, 0.096 mmol) were added and the mixture was stirred for 4 hours at room temperature. The same procedure as Example 14D was performed to give the title compound (30 mg, 65% yield for 2 steps) as white solids.

$^1$H NMR (300 MHz, CDCl$_3$) δ 1.20-1.35 (1H, m), 1.40-1.60 (7H, m, including 3H, s, 1.52 ppm and 3H, d, J=6.6 Hz, 1.47 ppm), 1.70 (1H, dd, J=5.9 Hz, 8.8 Hz), 2.82 (2H, t, J=5.1 Hz), 2.92 (3H, s), 3.17 (1H, br s), 3.83 (2H, m), 5.00-5.15 (1H, m), 6.33 (1H, d, J=6.0Hz), 7.14 (1H, s), 7.18 (1H, d, J=8.1 Hz), 7.35 (2H, d, J=8.1 Hz), 7.42 (1H, d, J=8.1 Hz), 7.54 (2H, d, J=8.1 Hz), 8.60 (1H, br s). MS (ESI) m/z 485 (M+H)$^+$, 483 (M−H)$^−$.

Example 87

(1S,2S)-N-((1R)-1-{3-ethyl-4-[(methylsulfonyl)amino]phenyl}propyl)-2-methyl-2-[4-(trifluoromethyl)phenyl]cyclopropanecarboxamide

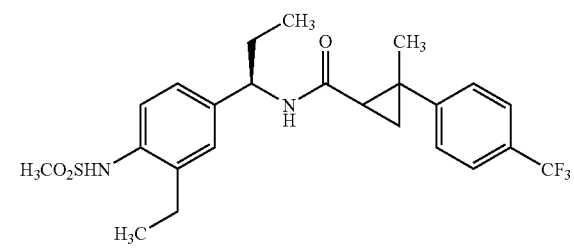

87A) N-(2-ethyl-4-propionylphenyl)methanesulfonamide

To a solution of 2-amino-1-ethylbenzene (5 ml, 5.0 g, 41 mmol) in pyridine (3.5 ml) and dichloromethane (10 ml), methanesulfonyl chloride (3.2 ml. 4.7 g, 41 mmol) was added dropwise over 10 min at 0° C. The reaction mixture was stirred at rt for 1 hour. After cooling to 0° C., aluminum trichloride (13.8 g, 103 mmol) was added to the reaction mixture carefully. Then propionyl chloride (3.6 ml, 3.8 g, 41 mmol) was added dropwise over 15 min. The reaction mixture was diluted with toluene (25 ml) and poured into 2 M hydrogen chloride aquoues solution (50 ml) under stirring at 0° C. The precipitate solids were filtered, washed with water and dried in vacuo to get a desired product (4.5 g, 43% yield) as yellow solids.

$^1$H NMR (DMSO-d$_6$,300 MHz) δ 1.07 (3H, t, J=7.3 Hz), 1.17 (3H, t, J=7.3 Hz), 2.75 (2H, d, J=7.3 Hz), 3.02 (2H, t, J=7.3 Hz), 3.08 (3H, s), 4.64-4.90 (1H, m), 7.45 (1H, d, J=8.0 Hz), 7.82 (2H, m), 9.35 (1H, br s).

87B) N-{4-[(1R)-1-aminopropyl]-2-ethylphenyl}methanesulfonamide

To a stirred solution of N-(2-ethyl-4-propionylphenyl)methanesulfonamide (7.8 mmol) in tetrahydrofuran (15 ml) and titanium (IV) ethoxide (15 ml), (R)-(+)-2-methyl-2-propanesulfinamide (7.8 mmol) was added. The mixure was stirred at 80° C. for 16 hours. Upon completion, as determined by LC-MS, the mixture was cooled to room temperature and then to 0° C. before it was added dropwise into a 0° C. solution of sodium borohydride (1.18 g, 31 mmol) in tetrahydrofuran (15 ml). The mixture was stirred at 0° C. for 3 hours and then quenched with methanol. After stirring at room temperature for 2 hours, Celite pad and water were added to the mixture, filtered thorough Celite, and washed with dichloromethane-ethyl acetate-methanol. The filtration was evaporated under the reduced pressure and the given residue was purified by silica gel eluting with dichloromethane-ethyl acetate (1:1) to afford the title compound as yellow oil. It was dissolved in methanol (30 ml) and hydrogen chloride-methanol (30 ml) was added. The solution was stirred at room temperature for 1 hour. After the solvent was removed under the reduced pressure, the product was recrystalized from diethylether-methanol to afford the desired product as hydrogen chloride salt.

$^1$H NMR (DMSO-d$_6$,300 MHz) δ 0.81 (3H, t, J=7.3 Hz), 1.21 (3H, m), 1.67-1.82 (1H, m), 1.95-2.07 (1H, m), 2.69 (2H, d, J=7.3 Hz), 3.01 (3H, s), 4.21-4.26 (1H, m), 6.96 (1H, s), 7.16-7.19 (2H, m), 7.42 (1H, d, J=8.1 Hz). $NH_2$ was not oabserved.

87C) (1S,2S)-N-((1R)-1-{3-ethyl-4-[(methylsulfonyl)amino]phenyl}propyl)-2-methyl-2-[4-(trifluoromethyl)phenyl]cyclopropanecarboxamide To a DMF (3 ml) solution of the carboxylic acid compound of Example 14C (80 mg, 0.328 mmol), HBTU (149 mg, 0.393 mmol), triethylamine (0.13 ml, 0.983 mmol) and the amine compound of Example 87B (95 mg, 0.328 mmol) were added and the mixture was stirred for 3 hours at room temperature. The same procedure as Example 14D was performed to give the title compound (97 mg, 61% yield) as white solids.

$^1$H NMR (300 MHz, DMSO-$d_6$) δ 0.86 (3H, t, J=6.0 Hz), 1.15 (3H, t, J=6.0 Hz), 1.32 (2H, d, J=6.0 Hz), 1.44 (3H, s), 1.55-1.81 (2H, m), 2.02 (2H, t, J=6.0 Hz), 2.69 (2H, q, J=6.0 Hz), 2.96 (3H, s), 4.64-4.90 (1H, m), 7.02-7.15 (1H, m), 7.15-7.28 (2H, m), 7.55 (2H, d, J=9.0 Hz), 7.70 (2H, d, J=9.0 Hz), 8.57 (1H, d, J=9.0 Hz), 9.03 (1H, br s). MS (ESI) m/z 483 $(M+H)^+$, 481 $(M–H)^-$ Anal. Calcd. for $C_{24}H_{29}F_3N_2O_3S$: C, 59.73; H, 6.06; N, 5.81. Found: C, 59.37; H, 6.03; N, 5.67.

Example 88

2-Ethyl-N-((1R)-1-{3-methyl-4-[(methylsulfonyl)amino]phenyl}ethyl)-2-[4-(trifluoromethyl)phenyl]cyclopropanecarboxamide

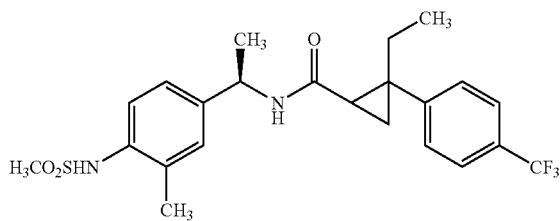

88A) 1-(1-Methylenepropyl)-4-(trifluoromethyl)-benzene

To a stirred suspension of methyltriphenylphosphonium bromide (3.53 g, 9.89 mmol) in THF (30 ml) was added potassium tert-butoxide (1.11 g, 9.89 mmol) in THF (10 ml) dropwise at 0° C. and the mixture was stirred at ambient temperature for 2 hours. Then, to this mixture was added 4-(trifluoromethyl)propiophenone (Aldrich, 1.00 g, 4.95 mmol) in THF (10 ml) at 0° C. and stirred at ambient temperature for 2 hours. The reaction was quenched with small amount of water and evaporated to remove the solvent. The crude mixture was diluted with hexane. The formed precipitates were filtered and the organic layer was separated. After evaporation of solvent, residue was applied to a silica gel chromatography column and eluted with hexane to afford 1.12 g (crude 100%) of the title compound as a red oil.

$^1$H NMR (270 MHz, CDCl$_3$) δ ppm 1.11 (3H, t, J=7.2 Hz), 2.53 (2H, q, J=7.2 Hz), 5.17 (1H, s), 5.34 (1H, s), 7.51 (2H, d, J=8.5 Hz), 7.59 (2H, d, J=8.5 Hz).

88B) Ethyl 2-ethyl-2-[4-(trifluoromethyl)phenyl]cyclopropanecarboxylate

A toluene (10 ml) solution of the compound of example 88A (crude, 1.12 g, 4.95 mmol), Co(TPP) (66 mg, 0.099 mmol) and 1-methyl-1H-imidazole (1.18 ml, 14.84 mmol), ethyl diazoacetate (0.78 ml, 7.42 mmol) were treated in the same procedure as Example 2H. The crude residue was applied to a silica gel chromatography column and eluted with a volume mixture of hexane and EtOAc (10/1) to afford 219 mg (15% yield for 2 steps) of the title compound as brown oil.

$^1$H NMR (270 MHz, CDCl$_3$) δ ppm 0.70-2.05 (11H, m), 3.80-4.30 (2H, m), 7.30-7.60 (4H, m). MS (ESI): not observed $M^+$ peak.

88C) 2-Ethyl-2-[4-(trifluoromethyl)phenyl]cyclopropanecarboxylic acid (Racemic)

An ethanol (3 ml) solution of the compound of Example 88B (219 mg, 0.76 mmol) and 2M sodium hydroxide aqueous solution (0.28 ml, 0.56 mmol) were added and the mixture was stirred at ambient temperature for 20 hours. After the reaction was completed, basic mixture was washed with dichloromethane, acidified with 2M HCl aqueous solution and the whole was extracted with dichloromethane. The organic layer was dried over sodium sulfate, filtered and followed by evaporation to afford 100 mg (69% yield, trans) of the title compound as white solids.

$^1$H NMR (270 MHz, CDCl$_3$) δ ppm 0.82 (3H, t, J=7.3 Hz), 1.43 (1H, dd, J=5.3 Hz, 8.6 Hz), 1.51(1H, t, J=5.3Hz), 1.92 (2H, q, J=7.3Hz), 2.00 (1H, dd, J=5.9Hz, 7.9Hz), 7.43 (2H, d, J=7.9Hz), 7.58 (2H, d, J=8.6 Hz). MS (ESI): m/z 257 $(M–H)^-$.

88D) 2-Ethyl-N-((1R)-1-{3-methyl-4-[(methylsulfonyl)amino]phenyl}ethyl)-2-[4-(trifluoromethyl)phenyl]cyclopropanecarboxamide To a DMF (2 ml) solution of the compound of Example 88C (49 mg, 0.188 mmol), HBTU (85 mg, 0.225 mmol), triethylamine (0.078 ml, 0.563 mmol) and the compound of Example 2D (60 mg, 0.225 mmol) were added and the mixture was stirred for 2 hours at room temperature. The same procedure as Example 14D was performed to give the title compound (59 mg, 67% yield) as white solids.

1H NMR (300 MHz, CDCl$_3$) δ ppm 0.69, 0.80 (3H, each t, J=7.3 Hz), 1.20-1.35 (1H, m), 1.45-1.55 (1H, m), 1.49, 1.52 (3H, each d, J=4.4 Hz), 1.67-2.00 (3H, m), 2.31, 2.32 (3H, each s), 3.00, 3.01 (3H, each s), 5.13 (1H, m), 6.00-6.20 (1H, m), 6.40-6.60 (1H, m), 7.15-7.25 (2H, m), 7.32-7.46 (3H, m), 7.50-7.60 (2H, m). MS (ESI): m/z 469 $(M+H)^+$, 467 $(M–H)^-$. Anal. Calcd. for $C_{23}H_{27}F_3N_2O_3S.0.2H_2O$: C, 58.51; H, 5.85; N, 5.93. Found: C, 58.51; H, 5.74; N, 5.79.

Example 89

2-Ethyl-N-((1R)-1-{3-fluoro-4-[(methylsulfonyl)amino]phenyl}ethyl)-2-[4-(trifluoromethyl)phenyl]cyclopropanecarboxamide

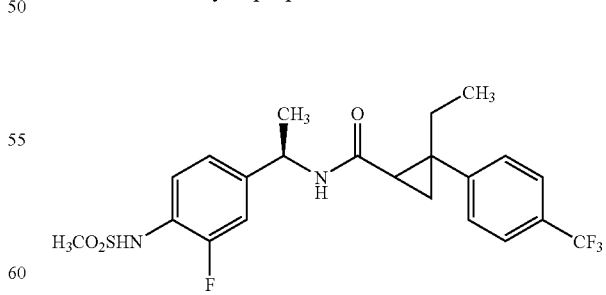

To a DMF (2 ml) solution of the compound of Example 88C (51 mg, 0.196 mmol), HBTU (89 mg, 0.236 mmol), triethylamine (0.082 ml, 0.589 mmol) and the amine compound of Example 8 (63 mg, 0.236 mmol) were added and the mixture was stirred for 2 hours at room temperature. The same procedure as Example 14D was performed to give the title compound (55 mg, 59% yield) as white solids.

$^1$H NMR (300 MHz, CDCl$_3$) δ ppm 0.69, 0.80 (3H, each t, J=7.3 Hz), 1.20-1.40 (1H, m), 1.45-1.57 (1H, m), 1.51, 1.52 (3H, each d, J=2.9 Hz), 1.67-1.96 (3H, m), 3.02 (3H, s), 5.14 (1H, m), 6.00 (1H, br t, J=6.6 Hz), 6.55 (1H, br s), 7.10-7.20 (2H, m), 7.32-7.45 (2H, m), 7.48-7.62 (3H, m). MS (ESI) : m/z 473 (M+H)$^+$, 471 (M−H)$^−$. Anal. Calcd. for C$_{22}$H$_{24}$F$_4$N$_2$O$_3$S.0.5H$_2$O: C, 54.88; H, 5.23; N, 5.82. Found: C, 54.51; H, 5.02; N, 5.70.

Example 90

2-(4-tert-Butyl-3,5-difluorophenyl)-2-methyl-N-((1R)-1-{4-[(methylsulfonyl)amino]phenyl}propyl)cyclopropanecarboxamide

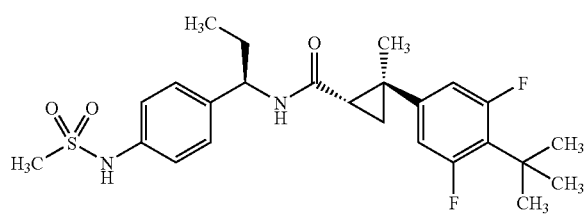

To a DMF (10 ml) solution of the compound of Example 31B (108 mg, 0.4 mmol), the compound of Example 43C (109 mg, 0.4 mmol), HBTU (202 mg, 0.5 mmol) and triethylamine (0.2 ml, 1.2 mmol) were added and the mixture was stirred for 2 hours at room temperature. The same reaction procedure described in Example 38E was performed to give the title compound (101 mg, 24%). The fraction time for the desired product was 5.4 min.

$^1$H NMR (270 MHz, DMSO-d$_6$) δ 0.83 (3H, t, J=7.3 Mz), 1.20-1.31 (2H, m), 1.33-1.49 (12H, m), 1.56-1.72 (2H, m), 1.92-2.01 (1H, m), 2.95 (3H, s), 4.64-4.77 (1H, m), 6.86-7.00 (2H, m), 7.10-7.19 (2H, m), 7.21-7.30 (2H, m), 8.49 (1H, d, J=8.6 Mz), 9.70 (1H, brs). MS (ESI) m/z 477 (M−H)$^−$, 479 (M+H)$^+$.

Example 91

2-(4-tert-butyl-3,5-difluorophenyl)-2-methyl-N-((1R)-1-{3-methyl-4-[(methylsulfonyl)amino]phenyl}propyl)cyclopropanecarboxamide

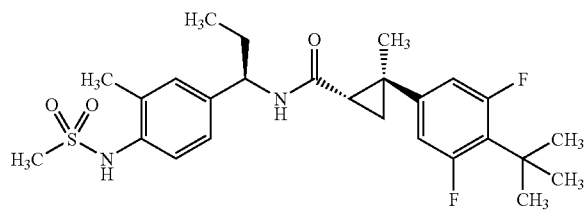

To a DMF (10 ml) solution of the compound of Example 34C (153 mg, 0.6 mmol), the compound of Example 43C (147 mg, 0.6 mmol), HBTU (271 mg, 0.7 mmol) and triethylamine (0.2 ml, 1.7 mmol) were added and the mixture was stirred for 2 hours at room temperature. The same reaction procedure described in Example 38E was performed to give the title compound (101 mg, 27%). The fraction time for the desired product was 5.8 min.

$^1$H NMR (270 MHz, DMSO-d$^6$) δ 0.75-0.90 (3H, m), 1.20-1.31 (2H, m), 1.34-1.46 (12H, m), 1.56-1.75 (2H, m), 1.92-2.02 (1H, m), 2.29 (3H, s), 2.95 (3H, s), 4.63-4.76 (1H, m), 6.86-7.00 (2H, m), 7.07-7.25 (3H, m), 8.50 (1H, d, J=8.6 Mz), 9.03 (1H, brs). MS (ESI) m/z 491 (M−H)$^−$, 493 (M+H)$^+$ The following preparations illustrate two processes for synthesizing of certain intermediates used in the preparation of the preceding Examples.

Preparation 1

1A) N-(4-Acetyl-2-methylphenyl)methanesulfonamide

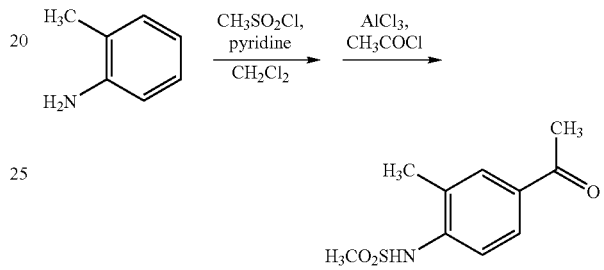

To a solution of o-toluidine (10.7 ml, 100 mmol) and pyridine (8.49 ml, 105 mmol) in dichloromethane (20 mL) was added methanesulfonyl chloride (7.74 ml, 100 mmol) dropwise over 15 minutes at 0° C. The reaction mixture was stirred at room temperature for 1 hour. After cooling to 0° C., aluminum chloride (33.3 g, 250 mmol) was added carefully to the reaction mixture. Then acetyl chloride (10.7 ml, 150 mmol) was added dropwise over 20 minutes at 5~20° C. The reaction mixture was stirred at room temperature for 0.5 hours, the reaction was monitored by using TLC and $^1$H-NMR, and after completion of the reaction, the reaction mixture was diluted with toluene and poured into 2N HCl aqueous solution with stirring at 0° C. The precipitate solid was filtered, washed with H$_2$O and heptane, and dried in vacuo to give the title compound (20.3 g, 89.3 mmol, 89% yield in 2 steps) as a light orange powder.

$^1$H NMR (300 MHz, CDCl$_3$) δ ppm 2.35 (3H, s), 2.58 (3H, s), 3.11 (3H, s), 6.60 (1H, brs), 7.59 (1H, d, J=12.0 Hz), 7.83-7.85 (2H, m). MS (ESI): m/z 228 (M+H)$^+$, 226 (M−H)$^−$.

Preparation 2

N-(4-Acetyl-2-methylphenyl)methanesulfonamide

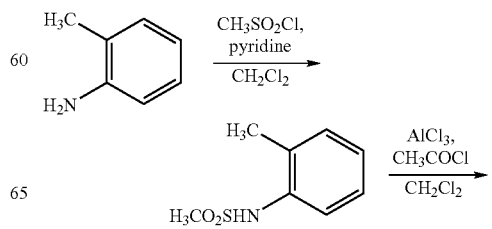

-continued

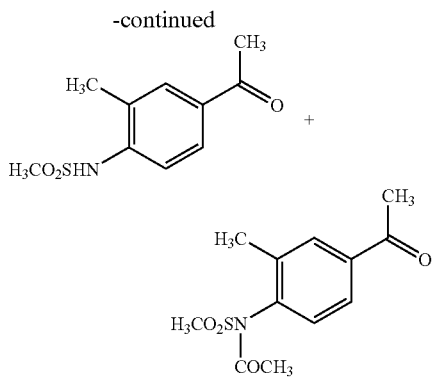

2A) N-(2-methylphenyl)methanesulfonamide

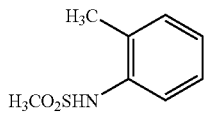

To a solution of o-toluidine (1.07 ml, 10 mmol) and pyridine (0.86 ml, 10.6 mmol) in dichloromethane (2 mL) was added methanesulfonyl chloride (0.81 ml, 10.5 mmol) dropwise at 0° C. The reaction mixture was stirred at room temperature for 1 hour. The reaction mixture was quenched by 1N HCl aqueous solution and extracted with EtOAc. The organic layer was concentrated in vacuo to afford the title compound (1.84 g, 10 mmol, quant.) as an orange solid.

$^1$H NMR (300 MHz, CDCl$_3$) δ ppm 2.38 (3H, s), 3.05 (3H, s), 7.12-7.24 (3H, m), 7.46 (1H, d, J=9.0 Hz).

2B) N-(4-Acetyl-2-methylphenyl)methanesulfonamide

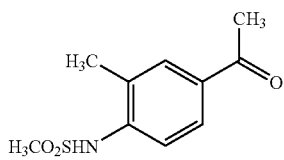

To a solution of N-(2-methylphenyl)methanesulfonamide (1.84 g, 10 mmol) in dichloromethane (2 mL) was added aluminum chloride (3.3 g, 25 mmol) carefully at 0° C. Then acetyl chloride (1.07 ml, 15 mmol) was added dropwise. The reaction mixture was stirred at room temperature for 0.5 hours, the reaction was monitored by using TLC and $^1$H-NMR, and after completion of the reaction, the reaction mixture was diluted with toluene and poured into 2N HCl aqueous solution with stirring at 0° C. The precipitate solid was filtered, washed with H$_2$O, and dried to give a mixture of the title compound and by-product (N-acetylated product) (2.31g, ratio; title compound: by-product=81:19 (ratio was determined by $^1$H-NMR)) as a flesh color powder.

$^1$H NMR (300 MHz, CDCl$_3$) δ ppm 1.92 (0.70H, s), 2.35 (3H, s), 2.45 (0.70H, s), 2.58 (3H, s), 2.64 (0.70H, s), 3.11 (3H, s), 3.53 (0.70H, s), 6.60 (1H, brs), 7.33 (0.23H, d, J=9.0 Hz), 7.59 (1H, d, J=12.0 Hz), 7.83-7.85 (2H, m), 7.89 (0.23H, d, J=9.0 Hz), 7.96 (0.23H, s).

The invention claimed is:

1. A compound of the formula (I):

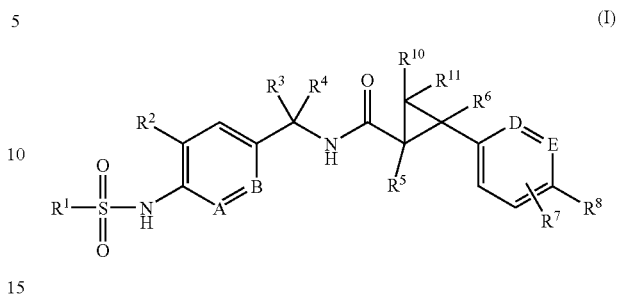

(I)

wherein A and B are independently CR$^{12}$ or N; D and E are each independently CR$^9$ or N; R$^1$ represents (C$_1$-C$_6$)alkyl; R$^2$ represents hydrogen, halogen, hydroxy, (C$_1$-C$_6$) alkyl, halo (C$_1$-C$_6$) alkyl, hydroxy(C$_1$-C$_6$)alkyl, (C$_1$-C$_6$)alkoxy or (C$_1$-C$_6$)alkoxy-(C$_1$-C$_6$)alkyl; R$^3$, R$^4$, R$^5$, R$^6$, R$^{10}$ and R$^{11}$ each independently represent hydrogen, halogen, (C$_1$-C$_6$)alkyl, halo(C$_1$-C$_6$)alkyl, (C$_1$-C$_6$)alkoxy, hydroxy(C$_1$-C$_6$)alkyl or (C$_1$-C$_6$)alkoxy-(C$_1$-C$_6$)alkyl; or R$^3$ and R$^4$ are taken together with the carbon atom to which they are attached to form a 3- to 7-membered carbocyclic ring or heterocyclic ring in which one or two non-adjacent carbon atoms are optionally replaced by an oxygen atom, a sulfur atom or NH; R$^7$ and R$^9$ each independently represent hydrogen, halogen, (C$_1$-C$_6$)alkyl, halo(C$_1$-C$_6$)alkyl, hydroxy(C$_1$-C$_6$)alkyl, (C$_1$-C$_6$)alkoxy, hydroxyl(C$_1$-C$_6$)alkoxy, (C$_1$-C$_6$)alkoxy-(C$_1$-C$_6$)alkyl, (C$_1$-C$_6$)alkoxy-(C$_1$-C$_6$)alkoxy, (C$_1$-C$_6$)alkylthio, (C$_1$-C$_6$)alkylsulfinyl, (C$_1$-C$_6$)alkylsulfonyl, NH$_2$, [(C$_1$-C$_6$)alkyl]NH—, [(C$_1$-C$_6$)alkyl]$_2$N—, H$_2$N—(C$_1$-C$_6$)alkoxy, (C$_1$-C$_6$)alkyl-NH—(C$_1$-C$_6$)alkoxy, [(C$_1$-C$_6$)alkyl]$_2$N(C$_1$-C$_6$)alkoxy; H$_2$N—(C$_1$-C$_6$)alkoxy-(C$_1$-C$_6$)alkyl, (C$_1$-C$_6$)alkyl-NH—(C$_1$-C$_6$)alkoxy-(C$_1$-C$_6$)alkyl, [(C$_1$-C$_6$)alkyl]$_2$N(C$_1$-C$_6$)alkoxy-(C$_1$-C$_6$)alkyl or 5- or 6-membered heterocyclic ring containing at least one nitrogen atom; R$^8$ represents halogen, (C$_1$-C$_6$)alkyl, halo(C$_1$-C$_6$)alkyl, hydroxy(C$_1$-C$_6$)alkyl, (C$_1$-C$_6$)alkoxy, hydroxy(C$_1$-C$_6$)alkoxy, (C$_1$-C$_6$)alkoxy-(C$_1$-C$_6$)alkyl, (C$_1$-C$_6$)alkoxy-(C$_1$-C$_6$)alkoxy, halo(C$_1$-C$_6$)alkylsulfonyl, halo(C$_1$-C$_6$)alkylsulfinyl, halo(C$_1$-C$_6$)alkoxy, halo(C$_1$-C$_6$)alkylthio, [(C$_1$-C$_6$)alkyl]NH— or [(C$_1$-C$_6$)alkyl]$_2$N—; or R$^7$ and R$^8$, when E is CR$^9$, are taken together with the carbon atoms to which they are attached form a 5-8 membered carbocyclic or heterocyclic ring, in which one or two non-adjacent carbon atoms are optionally replaced by oxygen, sulfur, N or NH groups, wherein the carbocyclic ring or the heterocyclic ring is unsubstituted or substituted with one or more substituents each independently selected from the group consisting of hydroxy, (C$_1$-C$_6$)alkyl, (C$_1$-C$_6$)alkoxy and hydroxy (C$_1$-C$_6$)alkyl; and R$^{12}$ represents hydrogen, halogen, (C$_1$-C$_6$) alkyl or hydroxy(C$_1$-C$_6$)alkyl;

with the proviso that one and only one A, B, D, or E is N; or a pharmaceutically acceptable salt thereof.

2. A compound according to claim 1, wherein A represents CR$^{12}$ and D represents CR$^9$; R$^1$ represents (C$_1$-C$_3$)alkyl; R$^3$ and R$^4$ each independently represents hydrogen or (C$_1$-C$_3$) alkyl; R$^5$ represents hydrogen, R$^7$ represents hydrogen, halogen, hydroxy(C$_1$-C$_6$)alkyl, [(C$_1$-C$_6$)alkyl]$_2$N—, pyridyl, piperidino, pyrrolidino or morpholino; R$^8$ represents (C$_1$-C$_6$) alkyl, halo(C$_1$-C$_6$)alkyl, hydroxy(C$_1$-C$_6$)alkyl, (C$_1$-C$_6$) alkoxy-(C$_1$-C$_6$)alkyl, halo(C$_1$-C$_3$)alkoxy, halo(C$_1$-C$_3$) alkylthio or halo(C$_1$-C$_3$)alkylsulfonyl; and R$^{12}$ represents hydrogen, halogen, (C$_1$-C$_3$)alkyl or hydroxymethyl.

3. A compound according to claim 1, wherein R$^{10}$ and R$^{11}$ each independently represents hydrogen.

4. A compound according to claim 1, wherein $R^1$ represents methyl; $R^3$ and $R^4$ each independently represents hydrogen, methyl or ethyl; and $R^8$ represents tert-butyl, trifluoromethyl, 2,2,2-trifluoro-1,1-dimethylethyl, trifluoromethoxy, trifluoromethylthio, trifluoromethylsulfonyl, 2-hydroxy-1,1-dimethylethyl or 2-methoxy-1,1-dimethylethyl.

5. A compound according to claim 1, wherein $R^2$ represents hydrogen, fluoro, methyl, ethyl, hydroxymethyl or hydroxyethyl; $R^4$ and $R^5$ each independently represents hydrogen; $R^6$ represents hydrogen, methyl, ethyl, methoxy or hydroxymethyl; $R^7$ and $R^9$ each independently represents hydrogen or fluoro; and $R^{12}$ represents hydrogen, fluoro, methyl, ethyl, hydroxymethyl or hydroxyethyl.

6. A compound according to claim 1, wherein $R^3$ represents methyl or ethyl; and $R^8$ represents tert-butyl, trifluoromethyl, 2,2,2-trifluoro-1,1-dimethylethyl, trifluoromethoxy or trifluoromethylthio.

7. A compound according to claim 1, wherein $R^6$ represents methyl, ethyl or methoxy.

8. A compound according to claim 1, wherein $R^5$ and $R^6$ are trans.

9. A compound according to claim 1 selected from;

2-Methyl-N-((1R)-1-{6-methyl-5-[(methylsulfonyl)amino]pyridin-2-yl}ethyl)-2-[4-(2,2,2-trifluoro-1,1-dimethylethyl)phenyl]cyclopropanecarboxamide;

2-(6-tert-Butylpyridin-3-yl)-2-methyl-N-((1R)-1-{3-methyl-4-[(methylsulfonyl)amino]phenyl}ethyl)cyclopropanecarboxamide;

2-Methyl-N-((1R)-1-{3-methyl-4-[(methylsulfonyl)amino]phenyl}ethyl)-2-[6-(trifluoromethyl)pyridin-3-yl]cyclopropanecarboxamide;

(1S,2S)-2-Methyl-N-((1R)-1-{6-methyl-5-[(methylsulfonyl)amino]pyridin-2-yl}ethyl)-2-[4-(trifluoromethyl)phenyl]cyclopropanecarboxamide;

N-((1R)-1-{6-Ethyl-5-[(methylsulfonyl)amino]pyridin-2-yl}ethyl)-2-methyl-2-[4-(2,2,2-trifluoro-1,1-dimethylethyl)phenyl]cyclopropanecarboxamide;

2-Methyl-N-((1R)-1-{4-methyl-5-[(methylsulfonyl)amino]pyridin-2-yl}ethyl)-2-[4-(2,2,2-trifluoro-1,1-dimethylethyl)phenyl]cyclopropanecarboxamide;

N-((1R)-1-{3-Methyl-4-[(methylsulfonyl)amino]phenyl}ethyl)-2-[2-pyrrolidin-1-yl-6-(trifluoromethyl)pyridin-3-yl]cyclopropanecarboxamide;

N-((1R)-1-{3-(Hydroxymethyl)-4-[(methylsulfonyl)amino]phenyl}ethyl)-2-[2-pyrrolidin-1-yl-6-(trifluoromethyl)pyridin-3-yl]cyclopropanecarboxamide;

2-(6-tert-Butyl-2-piperidin-1-ylpyridin-3-yl)-N-((1R)-1-{3-methyl-4-[(methylsulfonyl)amino]phenyl}ethyl)cyclopropanecarboxamide;

2-(6-tert-Butyl-2-piperidin-1-ylpyridin-3-yl)-N-((1R)-1-{3-fluoro-4-[(methylsulfonyl)amino]phenyl}ethyl)cyclopropanecarboxamide;

2-(6-tert-Butyl-2-pyrrolidin-1-ylpyridin-3-yl)-N-((1R)-1-{3-methyl-4-[(methylsulfonyl)amino]phenyl}ethyl)cyclopropanecarboxamide;

2-[6-tert-Butylpyridin-3-yl]-N-((1R)-1-{3-fluoro-4-[(methylsulfonyl)amino]phenyl}ethyl)cyclopropanecarboxamide;

2-[6-tert-Butylpyridin-3-yl]-N-((1R)-1-{3-methyl-4-[(methylsulfonyl)amino]phenyl}ethyl)cyclopropanecarboxamide;

(1S,2S)-2-Methyl-N-((1R)-1-{6-methyl-5-[(methylsulfonyl)amino[pyridin-2-yl}ethyl)-2-(4-trifluoromethyl)phenyl]cyclopropanecarboxamide;

2-[4-tert-Butylphenyl]-N-((1R)-1-{6-methyl-5-[(methylsulfonyl)amino]pyridin-2-yl}ethyl)cyclopropanecarboxamide;

N-((1R)-1-{6-Methyl-5-[(methylsulfonyl)amino]pyridin-2-yl}ethyl)-2-[4-(trifluoromethyl)phenyl]cyclopropanecarboxamide;

2-[6-tert-Butylpyridin-3-yl]-2-ethyl-N-((1R)-1-{3-methyl-4-[(sulfonyl)amino]phenyl}ethyl)cyclopropanecarboxamide;

2-[2-(Dimethylamino)-6-(trifluoromethyl)pyridin-3-yl]-N-((1R)-1-{2-fluoro-5-methyl-4-[(methylsulfonyl)amino]phenyl}ethyl)cyclopropanecarboxamide; and 2-Methyl-N-((1R)-1-{3-methyl-4-[(methylsulfonyl)amino]phenyl}ethyl)-2-[2-morpholin-4-yl-6-(trifluoromethyl)pyridin-3-yl]cyclopropanecarboxamide;

or a pharmaceutically acceptable salt thereof.

10. A pharmaceutical composition including a compound of the formula (I) or a pharmaceutically acceptable salt or solvate thereof, as defined in claim 1, together with a pharmaceutically acceptable excipient.

* * * * *